(12) United States Patent
Jensen

(10) Patent No.: US 11,123,369 B2
(45) Date of Patent: Sep. 21, 2021

(54) BISPECIFIC CAR T-CELLS FOR SOLID TUMOR TARGETING

(71) Applicant: Seattle Children's Hospital, Seattle, WA (US)

(72) Inventor: Michael C. Jensen, Bainbridge Island, WA (US)

(73) Assignee: Seattle Children's Hospital, Seattle, WA (US)

( * ) Notice: Subject to any disclaimer, the term of this patent is extended or adjusted under 35 U.S.C. 154(b) by 0 days.

(21) Appl. No.: 17/088,005

(22) Filed: Nov. 3, 2020

(65) Prior Publication Data

US 2021/0085719 A1 Mar. 25, 2021

Related U.S. Application Data

(62) Division of application No. 15/750,708, filed as application No. PCT/US2016/045360 on Aug. 3, 2016.

(60) Provisional application No. 62/202,698, filed on Aug. 7, 2015.

(51) Int. Cl.
| | |
|---|---|
| *A61K 35/17* | (2015.01) |
| *A61P 35/00* | (2006.01) |
| *C07K 14/725* | (2006.01) |
| *C07K 14/705* | (2006.01) |
| *C07K 16/30* | (2006.01) |
| *C07K 16/28* | (2006.01) |

(52) U.S. Cl.
CPC .............. *A61K 35/17* (2013.01); *A61P 35/00* (2018.01); *C07K 14/7051* (2013.01); *C07K 14/70578* (2013.01); *C07K 16/28* (2013.01); *C07K 16/2863* (2013.01); *C07K 16/30* (2013.01)

(58) Field of Classification Search
CPC ...... A61K 35/17; A61K 45/06; A61K 31/138; A61K 31/713; A61K 38/00; A61P 35/00; C07K 14/7051; C07K 14/70578; C07K 16/30; C07K 2319/02; C07K 14/4748; C07K 14/70521; C07K 2319/00; C07K 2317/33; C07K 2317/622; C07K 16/2863; C07K 16/461; C12N 2740/16043; C12N 2510/00; C12N 5/0636; C12N 5/0638
See application file for complete search history.

(56) References Cited

U.S. PATENT DOCUMENTS

| | | | |
|---|---|---|---|
| 5,783,186 A | 7/1998 | Arakawa et al. | |
| 6,040,177 A | 3/2000 | Riddell et al. | |
| 7,070,995 B2 | 7/2006 | Jensen | |
| 7,709,253 B2 | 5/2010 | Gambhir et al. | |
| 7,910,101 B2 | 3/2011 | Cunningham et al. | |
| 8,822,647 B2 | 9/2014 | Jensen | |
| 10,172,885 B2 | 1/2019 | Pule | |
| 10,266,592 B2 | 4/2019 | Jensen | |
| 10,611,837 B2 | 4/2020 | Jensen et al. | |
| 10,865,242 B2 | 12/2020 | Jensen | |
| 2002/0111474 A1 | 8/2002 | Capon et al. | |
| 2003/0148982 A1 | 8/2003 | Brenner et al. | |
| 2005/0060762 A1 | 3/2005 | Bleck | |
| 2005/0129671 A1 | 6/2005 | Cooper et al. | |
| 2006/0160090 A1 | 7/2006 | Anzures et al. | |
| 2006/0246548 A1* | 11/2006 | Jensen ............... | C07K 14/7051 435/69.1 |
| 2007/0087346 A1 | 4/2007 | Ciliberto et al. | |
| 2007/0166318 A1 | 7/2007 | Macina et al. | |
| 2009/0098142 A1 | 4/2009 | Kasaian et al. | |
| 2009/0098604 A1 | 4/2009 | Gallo et al. | |
| 2010/0226901 A1 | 9/2010 | Smolke | |
| 2011/0287020 A1 | 11/2011 | Gruber et al. | |
| 2012/0046645 A1 | 2/2012 | Cal | |
| 2012/0297493 A1 | 11/2012 | Cooper et al. | |
| 2012/0301447 A1 | 11/2012 | Jensen | |
| 2013/0011394 A1 | 1/2013 | Knoetgen | |
| 2013/0143559 A1 | 6/2013 | Nishida et al. | |
| 2013/0280220 A1 | 10/2013 | Ahmed et al. | |
| 2013/0287748 A1 | 10/2013 | June et al. | |
| 2014/0056868 A1 | 2/2014 | Zechiedrich et al. | |
| 2014/0112956 A1 | 4/2014 | Karlsson-Parra et al. | |
| 2014/0271635 A1 | 9/2014 | Brogdon et al. | |
| 2014/0314795 A1 | 10/2014 | Riddell et al. | |
| 2015/0038694 A1 | 2/2015 | Nicotra | |
| 2015/0120622 A1 | 4/2015 | Kobatake | |
| 2015/0299656 A1 | 10/2015 | Gattinoni et al. | |
| 2015/0329640 A1 | 11/2015 | Finer | |
| 2016/0017048 A1 | 1/2016 | Dotti et al. | |
| 2017/0015746 A1 | 1/2017 | Jensen et al. | |
| 2017/0029774 A1 | 2/2017 | Jensen et al. | |
| 2017/0152297 A1 | 6/2017 | Jensen et al. | |
| 2017/0209543 A9 | 7/2017 | Jensen | |
| 2017/0224733 A1 | 8/2017 | Badie et al. | |
| 2017/0267742 A1 | 9/2017 | Jensen et al. | |
| 2018/0009891 A1 | 1/2018 | Jensen et al. | |
| 2018/0028567 A1 | 2/2018 | Li et al. | |
| 2019/0248891 A1 | 8/2019 | Jensen et al. | |

(Continued)

FOREIGN PATENT DOCUMENTS

| | | |
|---|---|---|
| CN | 102227503 A | 10/2011 |
| DE | 102011 118 018 A1 | 4/2013 |

(Continued)

OTHER PUBLICATIONS

Dotti et al., Immunol Rev 257(1): 1-35 (Year: 2014).*

(Continued)

*Primary Examiner* — Phuong Huynh
(74) *Attorney, Agent, or Firm* — Knobbe, Martens, Olson & Bear LLP

(57) ABSTRACT

Disclosed herein are methods of engineering a bi-specific T-cell expressing chimeric antigen receptors for promoting the in vivo expansion and activation of an effector cell and a second chimeric antigen receptor or TcR specific for a ligand on a tumor. Methods of administering to subjects in need, bi-specific chimeric antigen receptor bearing cells are also provided.

16 Claims, 27 Drawing Sheets

Specification includes a Sequence Listing.

(56) References Cited

U.S. PATENT DOCUMENTS

| | | |
|---|---|---|
| 2020/0181624 A1 | 6/2020 | Jensen et al. |
| 2020/0215108 A1 | 7/2020 | Jensen |
| 2021/0002364 A1 | 1/2021 | Jensen et al. |
| 2021/0139583 A1 | 5/2021 | Jensen et al. |

FOREIGN PATENT DOCUMENTS

| | | | |
|---|---|---|---|
| JP | 2006-518753 | 8/2006 | |
| RU | 2003 129 528 A | 4/2005 | |
| WO | WO 92/08796 A1 | 5/1992 | |
| WO | WO 94/00143 A1 | 1/1994 | |
| WO | WO 98/18923 A1 | 5/1998 | |
| WO | WO 00/23573 A2 | 4/2000 | |
| WO | WO-0023573 A2 * | 4/2000 | ......... C07K 16/2887 |
| WO | WO 01/098506 | 12/2001 | |
| WO | WO 02/072605 | 9/2002 | |
| WO | WO 02/097099 A1 | 12/2002 | |
| WO | WO 03/025228 A1 | 3/2003 | |
| WO | WO 03/087338 A2 | 10/2003 | |
| WO | WO 04/029284 | 4/2004 | |
| WO | WO 05/017102 | 2/2005 | |
| WO | WO 2005/040212 A2 | 5/2005 | |
| WO | WO 07/073499 | 6/2007 | |
| WO | WO 07/137267 | 11/2007 | |
| WO | WO 2008/012237 A1 | 1/2008 | |
| WO | WO 2009/013359 A2 | 1/2009 | |
| WO | WO 09/091826 | 7/2009 | |
| WO | WO 2010/036986 A2 | 4/2010 | |
| WO | WO 2010/141543 A1 | 12/2010 | |
| WO | WO 2011/056894 A2 | 5/2011 | |
| WO | WO 2012/031744 A1 | 3/2012 | |
| WO | WO 2012/079000 A1 | 6/2012 | |
| WO | WO 2012/099973 A2 | 7/2012 | |
| WO | WO 2012/129514 A1 | 9/2012 | |
| WO | WO 12/140130 | 10/2012 | |
| WO | WO 12/167192 | 12/2012 | |
| WO | WO 2013/074916 A1 | 5/2013 | |
| WO | WO 13/126733 | 8/2013 | |
| WO | WO 2013/123061 A1 | 8/2013 | |
| WO | WO-2013123061 A1 * | 8/2013 | ....... C07K 14/70517 |
| WO | WO 2013/154760 A1 | 10/2013 | |
| WO | WO 2013/177533 A1 | 11/2013 | |
| WO | WO 2013/178635 A1 | 12/2013 | |
| WO | WO 2014/031687 A1 | 2/2014 | |
| WO | WO 2014/039044 A1 | 3/2014 | |
| WO | WO 14/055657 | 4/2014 | |
| WO | WO 14/055668 | 4/2014 | |
| WO | WO 14/139672 | 9/2014 | |
| WO | WO 14/153270 | 9/2014 | |
| WO | WO 15/066551 | 5/2015 | |
| WO | WO 15/075468 | 5/2015 | |
| WO | WO 15/092024 | 6/2015 | |
| WO | WO 15/105522 | 7/2015 | |
| WO | WO 2015/142675 A2 | 9/2015 | |
| WO | WO 2015/157399 A1 | 10/2015 | |
| WO | WO 2015/157432 A1 | 10/2015 | |

OTHER PUBLICATIONS

Sadelain et al., Current Opinion in Immunology 21: 215-223 (Year: 2009).*
Edwards et al., J Mol Biol 334(1): 103-118 (Year: 2003).*
Lloyd et al., Protein Engineering, Design & Selection 22:159-168 (Year: 2009).*
Aalberse et al., "IgG4 breaking the rules," Immunology (2002) 105:9-19.
Aertgeerts et al., "Structural analysis of the mechanism of inhibition and allosteric activation of the kinase domain of HER2 protein," Journal of Biological Chemistry (2011) vol. 286, No. 21, p. 18756-18765, Becb TeKCT, c.18759-18765.
Ahmed et al., "Regression of experimental medulloblastoma following transfer of HER2-specific T cells," Cancer Res. (Jun. 15, 2007) 67(12):5957-64.
Ahmed, Nabil, "CMV-specific Cytotoxic T Lymphocytes Expressing CAR Targeting HER2 in Patients With GBM (HERT-GBM)," ClinicalTrials.gov Identifier: NCT01109095 (Apr. 22, 2010) pp. 1-8.
Ahmed, Nabil, "Her2 Chimeric Antigen Receptor Expressing T Cells in Advanced Sarcoma," ClinicalTrials.gov Identifier: NCT00902044 (May 14, 2009) pp. 1-11.
Altschul et al., "Local Alignment Statistics, [27] Multiple Alignment and Phylogenetic Trees," Methods in Enzymology (1996) 266:460-480.
Bejcek et al. "Development and Characterization of Three Recombinant Single Chain Antibody Fragments (scFvs) Directed against the CD19 Antigen," Cancer Res (1995) 55:2346-2351.
Berglund et al., "The epitope space of the human proteome," Protein Science (2008) 17:606-613.
Brentjens et al., "CD19-targeted T cells rapidly induce molecular remissions in adults with chemotherapy-refractory acute lymphoblastic leukemia," Science Translational Medicine (Mar. 20, 2013) 5(177).
Budde et al., "Combining a CD20 Chimeric Antigen Receptor and an Inducible Caspase 9 Suicide Switch to Improve the Efficacy and Safety of T Cell Adoptive Immunotherapy for Lymphoma," PLOS ONE (2013) 8(12): e82742. https://doi.org/10.1371/journal.pone.0082742.
Cartellieri et al., "A Novel Ex Vivo Isolation and Expansion Procedure for Chimeric Antigen Receptor Engrafted Human T Cells," PLOS ONE (Apr. 3, 2014) vol. 9, No. 4, e93745, pp. 1-12.
Cha et al., "IL-7 + IL-15 are superior to IL-2 for the ex vivo expansion of4T1 mammary carcinomaspecific T cells with greater efficacy against tumors in vivo," Breast Cancer Research and Treatment, Springer, NY, US (Oct. 14, 2009) vol. 122, No. 2, pp. 359-369.
Chen et al., "Ex vivo expansion of dendritic-cell-activated antigen-specific CD4+ T cells with anti-CD3/CD28, interleukin 7, and interleukin-15: Potential for adoptive T-cell immunotherapy," Clinical Immunology (2006) vol. 119, pp. 21-31.
Chen et al., "Fusion Protein Linkers: Property, Design and Functionality," Adv Drug Deliv Rev (Oct. 15, 2013) vol. 65, pp. 1357-1369.
Chen et al., "Minicircle DNA vectors devoid of bacterial DNA result in persistent and high-level transgene expression in vivo," Mol Ther. (2003) 8(3), 495-500.
Chen et al., Jan. 2007, Generation of a transgenic mouse model with chondrocyte-specific and tamoxifen-inducible expression of CRE recombinase, Genesis, 45:44-50.
Cho et al., "Structure of the extracellular region of HER2 alone and in complex with the Herceptin Fab", Nature (Feb. 13, 2003) 421(6924):756-760.
Circosta et al., "T Cell Receptor (TCR) Gene Transfer with Lentiviral Vectors Allows Efficient Redirection of Tumor Specificity ikn Naïve and Memory T Cells Without Prior Stimulation of Endogenous TCR," Human Gene Therapy (Nov. 18, 2009) vol. 20, No. 12, pp. 1576-1588.
Converse et al., "Counterselection and Co-Delivery of Transposon and Transposase Functions for Sleeping Beauty-Mediated Transposition in Cultured Mammalian Cells," Bioscience Reports, Kluwer Academic Publishers-Plenum Publishers, NE (Dec. 1, 2004) vol. 24, No. 6, pp. 577-594.
Crewe et al., "Metabolism of Tamoxifen by recombinant human cytochrome P-450 enzymes: Formation of the 4-hydroxy, 4'-hydroxy and N-desmethyl metabolites and isomerization of trans-4-hydroxytamoxifen," Drug Metab Dispos (2002) 30(8): 869-874.
Database Geneseq [Online] May 5, 2005 (May 5, 2005), "Human splice variant protein expressed in ovary cells DEX0487 002.orf. 4.", XP002771301, retrieved from EBI accession No. GSP:ADY30515. Database accession No. ADY30515 & WO 2005/017102 A2 (Diadexus Inc [US]; Macina, Roberto A [US]; Turner, Leah R [US]; Sun, Yong) Feb. 24, 2005.
Database UniProt [Online] Oct. 3, 2012 (Oct. 3, 2012), "SubName: Full=Receptor tyrosine-protein kinase erbB-2 {ECO: 00003131 Ensembl:ENSP00000464252}; Flags: Fragment;" XP002771300, retrieved from EBI accession No. UNIPROT:J3QRJ7 Database accession No. J3QRJ7.

(56) References Cited

OTHER PUBLICATIONS

Dotti et al., "Design and development of therapies using chimeric antigen receptor-expressing T cells." Immunological reviews 257.1 (2014): 107-126.
Dotti, Gianpietro, et al. "Design and development of therapies using chimeric antigen receptor-expressing T cells." Immunological reviews 257.1 (2014): 107-126.
Ercikan-Abali et al., "Active Site-Directed Double Mutants of Dihydrofolate Reductase," Cancer Res., (1996) vol. 56, No. 18, pp. 4142-4145.
Frankel et al., "Characterization of diphtheria fusion proteins targeted to the human interleukin-3 receptor," Protein engineering (2000) vol. 13, No. 8, p. 575-581.
Gagnon et al., "IL-6, in Synergy with IL-7 or IL-15, Stimulates TCR-lndependent Proliferation and Functional Differentiation of CD8+ T Lymphocytes," The Journal of Immunology (2008) 180:7958-7968.
Gallinari et al., "A Functionally Orthogonal Estrogen Receptor-Based Transcription Switch Specifically Induced by a Nonsteroid Synthetic Ligand," Chemistry and Biology (Aug. 1, 2005) vol. 12, No. 8, pp. 883-893.
Gargett et al., "Different cytokine and stimulation conditions influence the expansion and immune phenotype of third-generation chimeric antigen receptor T cells specific for tumor antigen GD2," Cytotherapy (2015) 17.4: 487-495.
Garrett et al., "Novel engineered trastuzumab conformational epitopes demonstrate in vitro and in vivo antitumor properties against HER-2/neu," The Journal of Immunology (Jun. 1, 2007) 178:7120-7131.
Ghatar et al., "Epitope Mapping of Human HER2 Specific Mouse Monoclonal Antibodies Using Recombinant Extracellular Subdomains," Asian Pacific Journal of Cancer Prevention (2017) 18(11):3103-3110.
Gianpietro et al., "Design and development of therapies using chimeric antigen receptor-expressing T cells," Immunological Reviews (Dec. 13, 2013) vol. 257, No. 1, pp. 107-126.
Giry-Laterriere et al., "Polyswitch lentivetors: 'all-in-one' lentiviral vectors fordrug-inducible gene expression, live selection, and recombination cloning," Human Gene Therapy (Oct. 2011) 22:1255-1267.
Godiska et al., "Linear plasmid vector for cloning of repectitive or unstable sequences in Excherichia coli," (Dec. 29, 2009) Nuc Acids Res, vol. 38, No. 6, e88, pp. 1-9.
Gottschalk, Stephen, "Her2 and TGFBeta CTLs in Treatment of Her2 Positive Malignancy (HERCREEM)", ClinicalTrials.gov Identifier: NCT00889954 (Apr. 29, 2009) pp. 1-9.
Grada et al., "TanCAR: A Novel Bispecific Chimeric Antigen Receptor for Cancer Immunotherapy", Mol Ther Nucleic Acids, (Jul. 9, 2013) 2:e105. doi: 10.1038/mtna.2013.32.
Han Weidong, "Treatment of Chemotherapy Refractory Human Epidermalgrowth Factor Receptor-2(HER-2) Positive Advanced Solid Tumors (CART-HER-2)," (Sep. 5, 2013) ClinicalTrials.gov Identifier: NCT01935843, pp. 1-7.
Holtkamp et al., "Modification of antigen-encoding RNA increases stability, tgranslational efficacy, and T-cell stimulatory capacity of dendritic cells," Blood (Oct. 28, 2014), 2006/108:509-4017.
Hong et al., "Diverse solid tumors expressing a restricted eptitope of L1-CAM can be targeted by chimeric antigen receptor redirected T lymphocytes," J Immunotherapy (2014) vol. 37, No. 2, pp. 93-104.
Hudecek et al., "Receptor affinity and extracellular domain modifications affect tumor recognition by ROR1-specific chimeric antigen receptor T-cells," Clin Cancer Res. (Jun. 1, 2013) 19(12):3153-3164.
Hudecek et al., "The Nonsignaling Extracellular Spacer Domain of Chimeric Antigen Receptors Is Decisive for In Vivo Antitumor Activity", Cancer Immunologoy Research (Sep. 11, 2014) vol. 3, No. 2, pp. 125-135.
Hudecek et al., "The Non-Signaling Extracellular Spacer Domain of CD19-Specific Chimeric Antigen Receptors Is Decisive for in Vivo Anti-Tumor Activity," Blood (2012) vol. 120, No. 21, Abstract 951, 3 pages.
Huls et al., "First Clinical Trials Employing Sleeping Beauty Gene Transfer System and Artificial Antigen Presenting Cells to Generate and Infuse T Cells Expressing CD19-Specific Chimeric Antigen Receptor," Blood (2013) 122:166-166.
Jensen et al., "Design and implementation of adoptive therapy with chimeric antigen receptor-modified T cells," Immunological Reviews (2014) vol. 257, No. 1, pp. 127-144, with a 1 page Corrigendum.
Johansen et al., "Evaluation of Tet-on system to avoid transgene down-regulation in ex vivo gene transfer to the CNS," Gene Therapy (2002) 9:1291-1301.
Johnston et al., "Regulated expression of erythropoietin from an AAV vector safely improves the anemia of beta-thalassemia in a mouse model," Mol Ther. (Apr. 1, 2003) 7(4):493-497.
Jonnalagadda et al., "Efficient selection of genetically modified human T cells using methotrexate-resistant human dihydrofolate reductase", Gene Therapy (2013) 20:853-860.
Kacherovsky et al., "Combination of Sleeping Beauty transposition and chemically induced dimerization selection for robust production of engineered cells," Nucleic Acids Research (2012) 49(11):e85.
Kacherovsky et al., "Multiplexed 1-16 gene transfer to a human T-cell line by combining Sleeping Beauty transposon system with methotrexate selection," Biotechnology and Bioengineering (Jul. 23, 2015) vol. 112, No. 7, pp. 1429-1436.
Kay et al., "A robust system for production of minicircle DNA vectors," Nature Biotechnology (2010) 28:1287-1296.
Klebanoff et al., "IL-15 enhances the in vivo antitumor activity of tumor-reactive CD8+ T Cells," PNAS (Feb. 17, 2004) vol. 101, No. 7, pp. 1969-1974.
Kowolik et al., "CD28 costimulation provided through a CD19-specific chimeric antigen receptor enhances in vivo persistence and antitumor efficacy of adoptively transferred T cells," Cancer Res. (2006) 66(22):10995-11004.
Kunkele et al., "Functional Tuning of CARs Reveals Signaling Threshold above which CD8+ CTL Antitumor Potency is Attenuated Due to Cell Fas-FasL-Dependent AICD," Cancer Immunol Res. (Jan. 9, 2015) vol. 3, No. 4, pp. 368-379.
Lemaigre et al., "Transcriptional control of genes that regulate glycolysis and gluconeogenesis in adult liver," Biochem. J. (1994) 303:1-14.
Leung et al., "Luminescent detection of DNA-binding proteins," Nuc Acids Res (2012) 40(3): 941-955.
Likar et al., "Using a mutated variant human deoxycytidine-kinase as a reporter gene for assessing adoptive T-cell therapy," Questions hematology, oncology and immunopathology in pediatrics (2012) vol. 11, No. 2, pp. 23-31. (Russian Language).
Littlewood et al., "A modified oestrogen receptor ligand-binding domain as an improved switch for the regulation of heterologous proteins," Nucleic Acids Res (May 25, 1995) 23(10):686-1690.
Litvinova et al., "The influence of immunoregulatory cytokines IL-2, IL-7, and IL-15 upon activation, proliferation, and apoptosis of immune memory T-cells in vitro," Cell and Tissue Biology (Dec. 11, 2013) vol. 7, No. 6, pp. 539-544.
Liu et al., "IL-21 synergizes with IL-7 to augment expansion and anti-tumor function of cytotoxic T cells," International Immunology (2007) vol. 19, No. 10, pp. 1213-1221.
Loeken, Mary R., "Effects of mutation of the CREB binding site of the somatostatin promoter on cyclic AMP responsiveness in CV-1 cells", Gene Expression (1993) 3(3):253-264.
Lupton et al., "Dominant positive and negative selection using a hygromycin phosphotransferase-thymidine kinase fusion gene," Mol Cell Biol. (Jun. 1991) 11(6):3374-3378.
Maher, John, "Immunotherpay of Malignant Disease Using Chimeric Antigen Receptor Engrafted T Cells," ISRN Oncology, (2012) vol. 2012, Article ID 278093, pp. 1-23.
Mátés et al., "Molecular evolution of a novelhyperactive Sleeping Beauty transposase enables robust stable gene transfer in vertebrates," Nature Genetics (Jun. 2009) vol. 41, No. 6, pp. 753-761.

(56) References Cited

OTHER PUBLICATIONS

McGehee et al., "Differentiation-specific element: a cis-acting developmental switch required for the sustained transcriptional expression of the angiotensinogen gene during hormonal-induced differentiation of 3T3-L1 fibroblasts to adipocytes," Mol. Endocrinol. (Apr. 1993) 7(4):551-560.

McKinlay et al., "Blood monocytes, myeloid dendritic cells and the cytokines interleukin (IL)-7 and IL-15 maintain human CD4+ T memory celllls with mixed helper/regulatory function," Immunology (2006) vol. 120, pp. 392-403.

Morgan et al., "Case report of a serious adverse event following the administration of T cells transduced with a chimeric antigen receptor recognizing ERBB2," Mol Ther. (Apr. 2010) 18(4):843-51. doi: 10.1038/mt.2010.24. Epub Feb. 23, 2010.

Muftuoglu et al., "CD161 Expression Identifies a Distinct Subset of Drug-Effluxing Viral-Specific Memory CD4+ T Cells That Preferentially Survive Cytotoxic Chemotherapy," Blood (2012) 122(21):2024.

O'Reilly et al., "Identification of an activating transcription factor (ATF) binding site in the human transforming growth factor-beta 2 promoter," J. Biol. Chern. (Oct. 5, 1992) 267:19938-19943.

Pakula et al., "Genetic analysis of protein stability and function," Annual review of genetics (1989) vol. 23, No. 1, p. 289-310, c.305-306.

Papapetrou et al., "Harnessing endogenous miR-181a to segregate transgenic antigen receptor expression in developing versus postthymic T cells in murine hematopoietic chimeras," The Journal of Clinical Investigation Jan. 5, 2009; 119(1): pp. 157-168.

Park et al., "Adoptive Transfer of Chimeric Antigen Receptor Re-Directed Cytolytic T Lmphocyte Clones in Patients with Neuroblastoma," Mol. Ther. (Apr. 2007) vol. 15, No. 4; pp. 825-833.

Pelloquin et al., Dec. 1986, Human B lymphocytes immortalization by Epstein-Barr virus in the presence of cyclosporin A, In Vitro Cell Dev Biol, 22(12):689-694.

Pezzutto et al., "CD19 monoclonal antibody HD37 inhibits anti-immunoglobulin-induced B cell activation and proliferation," J Immunol. (May 1, 1987) 138(9):2793-2799.

Pollock et al., "Delivery of a stringent dimerizer-regulated gene expression system in a single retroviral vector," PNAS USA (Nov. 21, 2000) 97(24):13221-1326.

Promega, "pSP64 Poly(A) Vector Sequence and Map," Technical Bulletin No. 052, Revised May 2000, pp. 1-8.

Riddell et al., "Adoptive Therapy With Chimeric Antigen Receptor-Modified T Cells of Defined Subset Composition," The Cancer Journal (Mar./Apr. 2014) vol. 20, No. 2, pp. 141-144.

Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3(3):319-338.

Robinsons et al., Jan. 1991, Metabolites, pharmacodynamics, and pharmacokinetics of tamoxifen in rats and mice compared to the breast cancer patient, Drug Metab Dispos, 19(1):36-43.

Roscilli et al., "Long-term and tight control of gene expression in mouse skeletal muscle by a new hybrid human transcription factor," Molecular Therapy (Nov. 1, 2002) 6(5):653-63.

Sadelain et al., "The basic principles of chimeric antigen receptor (CAR) design," Cancer discovery (2013) 3 (4): 388-98. DOI: 10.1158/2159-8290.CD-12-0548.

Schmittgen et al., "Analyzing real-time PCR data by the comparative C(T) method," Nature Protocols (2008) 3(6):1101-8.

Sengupta et al., "Interleukin-13 Receptor Alpha 2-Targeted Glioblastoma Immunotherapy," BioMed Research International, (Aug. 27, 2014) vol. 2014, Article ID: 952128, pp. 1-8.

Sharma et al., "Efficient Sleeping Beauty DNA Transposition from DNA Minicircles," Mol Ther Nuc Acids (2013) 2:e74, 1-10.

Surh et al., "Homeostatsis of memory T cells," Immunological Reviews (2006) vol. 211, pp. 154-163.

Terakura et al., "Generation of CD19-chimeric antigen receptor modified CD8+ T cells derived from virus-specific central memory T cells," Gene Therapy (Oct. 26, 2011) 119(1), pp. 72-82.

Treisman, Richard, "The SRE: a growth factor responsive transcriptional regulator," Seminars in Cancer Biology (Feb. 1, 1990) 1(1):47-58.

Vigna et al., "Robust and Efficient Regulation of Transgene Expression in Vivo by Improved Tetracycline-Dependent Lentiviral Vectors," Mol. Therapy (2002) 5(3):252-261.

Vogt et al., "Doxycycline-regulated gene expression in the opportunistic fungal pathogen Aspergillus fumigatus," BMC Microbiol. (2005) 5(1):11 pages.

Wang et al., "Phenotypic and Functional Attributes of Lentivirus Modified CD19-specific Human CD8+ Central Memory Tcells Manufactured at Clinical Scale," J Immunotherapy (2012) vol. 35, pp. 689-701.

Wang et al., "A transgene-encoded cell surface polypeptide for selection, in vivo tracking, and ablation of engineered cells," Blood (Aug. 4, 2011) vol. 118, No. 5, pp. 1255-1263.

Weill et al., "Translational control by changes in poly(A) tail length: recycling mRNAs," Nature Structural & Molecular Biology (Jun. 2012) vol. 19, No. 6, pp. 577-585.

Wilke et al., Apr. 27, 2012, Dual targeting of ErbB2 and MUC1 in breast cancer using chimeric antigen receptors engineered to provide complementary signaling, Journal of Clinical Immunology, 32(5):1059-1070.

Xu et al., "Closely related T-memory stem cells correlate with in vivo expansion of CAR.CD19-T cells and are preserved by IL-7 and IL-15," Blood (Jun. 12, 2014) vol. 123, No. 24, pp. 3750-3759.

Yant et al., "Mutational Analysis of the N-Terminal DNA-Binding Domain of Sleeping Beauty Transposase: Critical Residues for DNA Binding and Hyperactivity in Mammalian Cells," Mol. Cell. Biol. (2004) 24(20):9239-9247.

Ye et al., "Characterization of a silencer regulatory element in the human interferon-gamma promoter," J. Biol. Chem. (Oct. 14, 1994) 269:25728-25734.

Zambon et al., "Increased Expression of the Pro-Apoptotic Protein BIM: A Mechanism for cAMP/PKA-Induced Apoptosis of Immature T Cells," J. Biol. Chem. (2011) 286(38):33260-33267.

Zeng et al., "Synergy of IL-21 and IL-15 in regulating CD8+ T cell expansion and function," JEM (Jan. 3, 2005) vol. 201, No. 1, pp. 139-148.

Zheng, Changyu et al., "All Human EF1 Promoters Are Not Equal: Markedly Affect Gene Expression in Constructs from Different Sources," International Journal of Medical Sciences (2014) 11(5):404-408.

Chen et al., Sep. 15, 2005, NF-κ-B RelA phosphorylation regulates RelA acetylation, Molecular and Cellular Biology, 25(18):7966-7975.

Courtney et al., 2018, TCR signaling: mechanisms of initiation and propagation, Trends in Biochemical Sciences, 43(2):108-123.

Dolezal et al., 2000, ScFv multimers of the anti-neuraminidase antibody NC10: shortening of the linker in single-chain Fv fragment assembled in VL to VH orientation drives the formation of dimers, trimers, tetramers and higher molecular mass multimers, Protein Engineering, 13(8):565-574.

Fang ed., Modern Tumor Immunological Targeted Therapy, Southeast University Press, 118-119, Nov. 2010.

Guedan et al., 2018, Enhancing CAR T cell persistence through ICOS and 4-1BB costimulation, JCI Insight, 3(1):11-13.

Guha et al., 2017, Frontline science: functionally impaired geriatric CAR-T cells rescued by increased 51 integrin expression, Journal of Leukocyte Biology, 102(2):201-208.

Hege et al., 2017, Safety, tumor trafficking and immunogenicity of chimeric antigen receptor (CAR)-T cells specific for TAG-72 in colorectal cancer, Journal for Immunotherapy of Cancer, 5(1):1-14.

Jensen et al., "Designing chimeric antigen receptors to effectively and safely target tumors," Curr Opin Immunol. (Apr. 2015) 33:9-15.

Kanamori et al., A human-tissue type whose host is a human cell expression of plasminogen activator, Tissue Culture Research, 8(2):31-39, 1990.

Kochenderfer et al., Accession No. ADM64594.1, FMC63-28Z receptor protein, Jun. 11, 2012, Genbank.

(56) References Cited

OTHER PUBLICATIONS

Lin et al., 2009, Optimization and validation of a robust human T-cell culture method for monitoring phenotypic and polyfunctional antigen-specific CD4 and CD8 T-cell responses, Cytotherapy, 11(7):912-922.

Long et al., 2015, 4-1BB costimulation ameliorates T cell exhaustion induced by tonic signaling of chimeric antigen receptors, Nature Medicine, 21(6):581-590.

Maeda et al., 1997, Engineering of functional chimeric protein G—Vargula Luciferase, Analytical Biochemistry, 249(2):147-152.

Maus et al., 2013, T cells expressing chimeric antigen receptors can cause anaphylaxis in humans, Cancer Immunology Research, 1(1):26-31.

Richman et al., 2018, High-affinity GD2-specific CART cells induce fatal encephalitis in a preclinical neuroblastoma model, Cancer Immunology Research, 6(1):36-46.

Schamel et al., 2019, The TCR is an allosterically regulated macromolecular machinery changing its conformation while working, Immunological Reviews, 291(1):8-25.

Teplyakov et al., 2014, Antibody modeling assessment II. Structures and models, Proteins: Structure, Function, and Bioinformatics, 82(8):1563-1582.

Turtle et al., 2016, CD19 Car-T cells of defined CD4+: CD8+ composition in adult B cell ALL patients, The Journal of Clinical Investigation, 126(6):2123-2138.

Yang et al., Feb. 16, 2010, Functional interplay between acetylation and methylation of the RelA subunit of NF-κ-B, Molecular and Cellular Biology, 30(9):2170-2180.

\* cited by examiner

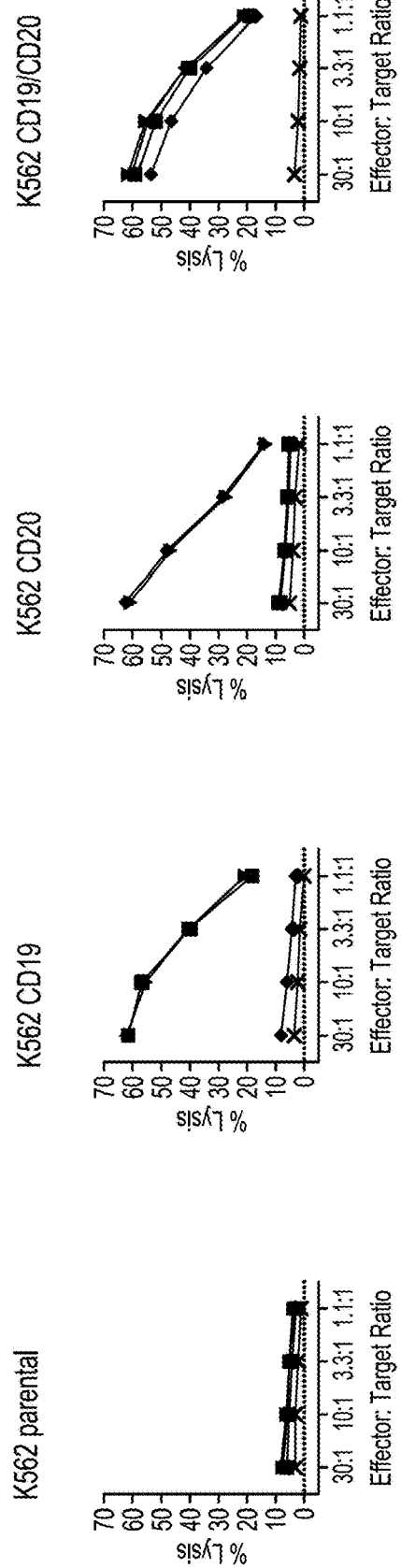
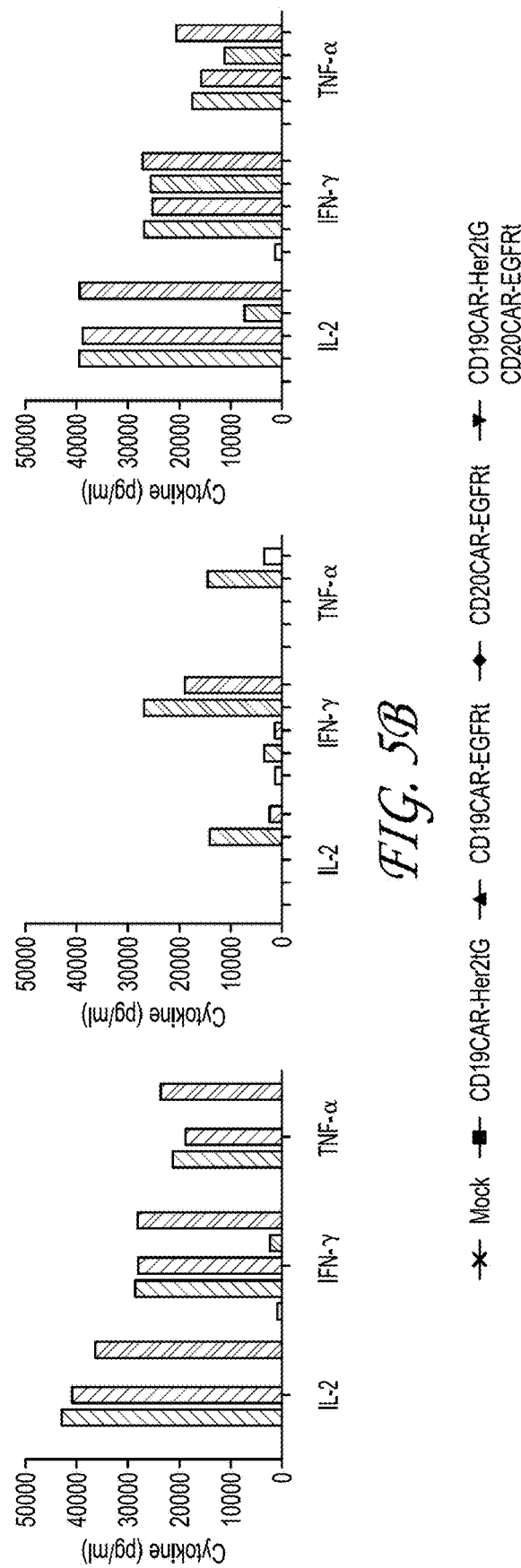
FIG. 5A
FIG. 5B

SEQUENCE LISTING

<160> NUMBER OF SEQ ID NOS: 40

<210> SEQ ID NO 1
<211> LENGTH: 12
<212> TYPE: PRT
<213> ORGANISM: Artificial Sequence
<220> FEATURE:
<223> OTHER INFORMATION: IgG4 hinge spacer

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Artificial Sequence
<220> FEATURE:
<223> OTHER INFORMATION: IgG4 hinge spacer

<400> SEQUENCE: 2
gagagcaagt acggaccgcc ctgccccct tgccct                          36

<210> SEQ ID NO 3
<211> LENGTH: 119
<212> TYPE: PRT
<213> ORGANISM: Artificial Sequence
<220> FEATURE:
<223> OTHER INFORMATION: IgG4-CH3 hinge spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 4
<211> LENGTH: 357
<212> TYPE: DNA
<213> ORGANISM: Artificial Sequence
<220> FEATURE:
<223> OTHER INFORMATION: IgG4-CH3 hinge spacer

<400> SEQUENCE: 4
gagagcaagt acggaccgcc ctgccccct tgcctggcc agcctcgcga gcccaggtg       60 tacaccctgc ctccctccca ggaagagatg accaagaacc aggtgtccct gacctgcctg    120
gtgaagggct tctaccccag cgacatcgcc gtggagtggg agagcaacgg ccagcctgag    180
aacaactaca agaccacccc ctccgtgctg gacagcgacg gcagcttctt cctgtacagc    240

```
cggctgaccg tggacaagag ccggtggcag gaaggcaacg tctttagctg cagcgtgatg      300
cacgaggccc tgcacaacca ctacacccag aagagcctga gcctgtccct gggcaag         357
```

```
<210> SEQ ID NO 5
<211> LENGTH: 28
<212> TYPE: PRT
<213> ORGANISM: Artificial Sequence
<220> FEATURE:
<223> OTHER INFORMATION: Transmembrane CD28 domain

<400> SEQUENCE: 5
```

Met Phe Trp Val Leu Val Val Gly Gly Val Leu Ala Cys Tyr Ser
1               5                   10                  15

Leu Leu Val Thr Val Ala Phe Ile Ile Phe Trp Val
            20                  25

```
<210> SEQ ID NO 6
<211> LENGTH: 84
<212> TYPE: DNA
<213> ORGANISM: Artificial Sequence
<220> FEATURE:
<223> OTHER INFORMATION: Transmembrane CD28 domain

<400> SEQUENCE: 6
atgttctggg tgctggtggt ggtcggaggc gtgctggcct gctacagcct gctggtcacc      60
gtggccttca tcatcttttg ggtg                                             84
```

```
<210> SEQ ID NO 7
<211> LENGTH: 45
<212> TYPE: PRT
<213> ORGANISM: Artificial Sequence
<220> FEATURE:
<223> OTHER INFORMATION: 4-1BB domain

<400> SEQUENCE: 7
```

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys
            35                  40                  45

```
<210> SEQ ID NO 8
<211> LENGTH: 135
<212> TYPE: DNA
<213> ORGANISM: Artificial Sequence
<220> FEATURE:
<223> OTHER INFORMATION: 4-1BB domain

<400> SEQUENCE: 8
aaacggggca gaagaaaact cctgtatata ttcaaacaac catttatgag accagtacaa      60
actactcaag aggaagatgg ctgtagctgc cgatttccag aagaagaaga aggaggatgt     120
gaactgcggg tgaag                                                     135
```

```
<210> SEQ ID NO 9
<211> LENGTH: 109
<212> TYPE: PRT
<213> ORGANISM: Artificial Sequence
<220> FEATURE:
<223> OTHER INFORMATION: CD3-zeta domain
```

<400> SEQUENCE: 9

Phe Ser Arg Ser Ala Asp Ala Pro Ala Tyr Gln Gln Gly Gln Asn Gln
1               5                   10                  15

Leu Tyr Asn Glu Leu Asn Leu Gly Arg Arg Glu Glu Tyr Asp Val Leu
            20                  25                  30

Asp Lys Arg Arg Gly Arg Asp Pro Glu Met Gly Gly Lys Pro Arg Arg
        35                  40                  45

Lys Asn Pro Gln Glu Gly Leu Tyr Asn Glu Leu Gln Lys Asp Lys Met
    50                  55                  60

Ala Glu Ala Tyr Ser Glu Ile Gly Met Lys Gly Glu Arg Arg Arg Gly
65                  70                  75                  80

Lys Gly His Asp Gly Leu Tyr Gln Gly Leu Ser Thr Ala Thr Lys Asp
                85                  90                  95

Thr Tyr Asp Ala Leu His Met Gln Ala Leu Pro Pro Arg
            100                 105

<210> SEQ ID NO 10
<211> LENGTH: 327
<212> TYPE: DNA
<213> ORGANISM: Artificial Sequence
<220> FEATURE:
<223> OTHER INFORMATION: CD3-zeta domain

<400> SEQUENCE: 10
ttcagcagaa gcgccgacgc ccctgcctac cagcagggcc agaatcagct gtacaacgag      60
ctgaacctgg gcagaaggga agagtacgac gtcctggata gcggagagg ccgggaccct     120 gagatgggcg gcaagcctcg gcggaagaac ccccaggaag gcctgtataa cgaactgcag     180
aaagacaaga tggccgaggc ctacagcgag atcggcatga agggcgagcg gaggcggggc     240
aagggccacg acggcctgta tcagggcctg tccaccgcca caaggatac ctacgacgcc     300 ctgcacatgc aggccctgcc cccaagg                                         327

<210> SEQ ID NO 11
<211> LENGTH: 244
<212> TYPE: PRT
<213> ORGANISM: Artificial Sequence
<220> FEATURE:
<223> OTHER INFORMATION: FMC63 CD19scFv

<400> SEQUENCE: 11

Asp Ile Gln Met Thr Gln Thr Thr Ser Ser Leu Ser Ala Leu Gly Asp
1               5                   10                  15

Arg Val Thr Ile Ser Cys Arg Ala Ser Gln Asp Ile Ser Lys Tyr Leu
            20                  25                  30

Asn Trp Tyr Gln Gln Lys Pro Asp Gly Thr Val Lys Leu Leu Ile Tyr
        35                  40                  45

His Thr Ser Arg Leu His Ser Gly Val Pro Ser Arg Phe Ser Gly Ser
    50                  55                  60

Gly Ser Gly Thr Asp Tyr Ser Leu Thr Ile Ser Asn Leu Glu Gln Glu
65                  70                  75                  80

Asp Ile Ala Thr Tyr Phe Cys Gln Gln Gly Asn Thr Leu Pro Tyr Thr
                85                  90                  95

Phe Gly Gly Gly Thr Lys Leu Glu Ile Thr Gly Ser Thr Ser Gly Ser
            100                 105                 110

Gly Lys Pro Gly Ser Gly Glu Gly Ser Thr Lys Gly Glu Val Lys Leu
        115                 120                 125

```
Gln Glu Ser Gly Pro Gly Leu Val Ala Pro Ser Gln Ser Leu Ser Val
        130                 135                 140

Thr Cys Thr Val Ser Gly Val Ser Leu Pro Asp Tyr Gly Val Ser Trp
145                 150                 155                 160

Ile Arg Gln Pro Pro Arg Lys Gly Leu Glu Trp Leu Gly Val Ile Trp
                165                 170                 175

Gly Ser Glu Thr Thr Tyr Tyr Asn Ser Ala Leu Lys Ser Arg Leu Thr
            180                 185                 190

Ile Ile Lys Asp Asn Ser Lys Ser Gln Val Phe Leu Lys Met Asn Ser
        195                 200                 205

Leu Gln Thr Asp Asp Thr Ala Ile Tyr Tyr Cys Ala Lys His Tyr Tyr
210                 215                 220

Tyr Gly Gly Ser Tyr Ala Met Asp Tyr Trp Gly Gln Gly Thr Ser Val
225                 230                 235                 240

Thr Val Ser Ser

<210> SEQ ID NO 12
<211> LENGTH: 735
<212> TYPE: DNA
<213> ORGANISM: Artificial Sequence
<220> FEATURE:
<223> OTHER INFORMATION: FMC63 CD19scFv

<400> SEQUENCE: 12
gacatccaga tgacccagac cacctccagc ctgagcgcca gcctgggcga ccgggtgacc    60
atcagctgcc gggccagcca ggacatcagc aagtacctga actggtatca gcagaagccc   120
gacggcaccg tcaagctgct gatctaccac accagccggc tgcacagcgg cgtgcccagc   180
cggtttagcg gcagcggctc cggcaccgac tacagcctga ccatctccaa cctggaacag   240
gaagatatcg ccacctactt tgccagcag ggcaacacac tgccctacac ctttggcggc   300
ggaacaaagc tggaaatcac cggcagcacc tccggcagcg gcaagcctgg cagcggcgag   360
ggcagcacca agggcgaggt gaagctgcag gaaagcggcc ctggcctggt ggcccccagc   420
cagagcctga gcgtgacctg caccgtgagc ggcgtgagcc tgcccgacta cggcgtgagc   480
tggatccggc agcccccag aagggcctg gaatggctgg gcgtgatctg gggcagcgag   540
accacctact acaacagcgc cctgaagagc cggctgacca tcatcaagga caacagcaag   600
agccaggtgt tcctgaagat gaacagcctg cagaccgacg acaccgccat ctactactgc   660
gccaagcact actactacgg cggcagctac gccatggact actggggcca gggcaccagc   720
gtgaccgtga gcagc                                                    735

<210> SEQ ID NO 13
<211> LENGTH: 266
<212> TYPE: PRT
<213> ORGANISM: Artificial Sequence
<220> FEATURE:
<223> OTHER INFORMATION: CD20scFv

<400> SEQUENCE: 13

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ile Leu Ser
            20                  25                  30

Ala Ser Pro Gly Glu Lys Val Thr Met Thr Cys Arg Ala Ser Ser Ser
        35                  40                  45
```

Val Asn Tyr Met Asp Trp Tyr Gln Lys Lys Pro Gly Ser Ser Pro Lys
 50                  55                  60

Pro Trp Ile Tyr Ala Thr Ser Asn Leu Ala Ser Gly Val Pro Ala Arg
 65                  70                  75                  80

Phe Ser Gly Ser Gly Ser Gly Thr Ser Tyr Ser Leu Thr Ile Ser Arg
                 85                  90                  95

Val Glu Ala Glu Asp Ala Ala Thr Tyr Tyr Cys Gln Gln Trp Ser Phe
            100                 105                 110

Asn Pro Pro Thr Phe Gly Gly Gly Thr Lys Leu Glu Ile Lys Gly Ser
            115                 120                 125

Thr Ser Gly Gly Gly Ser Gly Gly Gly Ser Gly Gly Gly Gly Ser Ser
130                 135                 140

Glu Val Gln Leu Gln Gln Ser Gly Ala Glu Leu Val Lys Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Gly Gln Gly Leu Glu Trp Ile
            180                 185                 190

Gly Ala Ile Tyr Pro Gly Asn Gly Asp Thr Ser Tyr Asn Gln Lys Phe
            195                 200                 205

Lys Gly Lys Ala Thr Leu Thr Ala Asp Lys Ser Ser Ser Thr Ala Tyr
210                 215                 220

Met Gln Leu Ser Ser Leu Thr Ser Glu Asp Ser Ala Asp Tyr Tyr Cys
225                 230                 235                 240

Ala Arg Ser Asn Tyr Tyr Gly Ser Ser Tyr Trp Phe Phe Asp Val Trp
                245                 250                 255

Gly Ala Gly Thr Thr Val Thr Val Ser Ser
            260                 265

<210> SEQ ID NO 14
<211> LENGTH: 798
<212> TYPE: DNA
<213> ORGANISM: Artificial Sequence
<220> FEATURE:
<223> OTHER INFORMATION: CD20scFv

<400> SEQUENCE: 14

```
atggagacag acacactcct gctatgggtg ctgctgctct gggttccagg ttccacaggt      60
gacattgtgc tgacccaatc tccagctatc ctgtctgcat ctccagggga aaggtcaca     120 atgacttgca gggccagctc aagtgtaaat tacatggact ggtaccagaa gaagccagga     180
tcctccccca aaccctggat ttatgccaca tccaacctgg cttctggagt ccctgctcgc     240
ttcagtggca gtgggtctgg gacctcttac tctctcacaa tcagcagagt ggaggctgaa     300
gatgctgcca cttattactg ccagcagtgg agttttaatc cacccacgtt cggagggggg     360
accaagctgg aaataaaagg cagtactagc ggtggtggct ccgggggcgg ttccggtggg     420
ggcggcagca gcgaggtgca gctgcagcag tctgggctg agctggtgaa gcctggggcc     480
tcagtgaaga tgtcctgcaa ggcttctggc tacacattta ccagttacaa tatgcactgg     540
gtaaagcaga cacctggaca gggcctggaa tggattggag ctatttatcc aggaaatggt     600
gatacttcct acaatcagaa gttcaaaggc aaggccacat tgactgcaga caaatcctcc     660
agcacagcct acatgcagct cagcagcctg acatctgagg actctgcgga ctattactgt     720
gcaagatcta attattacgg tagtagctac tggttcttcg atgtctgggg cgcagggacc     780
acggtcaccg tctcctca                                                  798
```

-continued

```
<210> SEQ ID NO 15
<211> LENGTH: 242
<212> TYPE: PRT
<213> ORGANISM: Artificial Sequence
<220> FEATURE:
<223> OTHER INFORMATION: CE7scFv

<400> SEQUENCE: 15
```

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Gly Tyr
            20                  25                  30

Trp Met His Trp Val Lys Gln Arg Pro Gly His Gly Leu Glu Trp Ile
        35                  40                  45

Gly Glu Ile Asn Pro Ser Asn Gly Arg Thr Asn Tyr Asn Glu Arg Phe
    50                  55                  60

Lys Ser Lys Ala Thr Leu Thr Val Asp Lys Ser Ser Thr Thr Ala Phe
65                  70                  75                  80

Met Gln Leu Ser Gly Leu Thr Ser Glu Asp Ser Ala Val Tyr Phe Cys
                85                  90                  95

Ala Arg Asp Tyr Tyr Gly Thr Ser Tyr Asn Phe Asp Tyr Trp Gly Gln
            100                 105                 110

Gly Thr Thr Leu Thr Val Ser Ser Gly Gly Gly Gly Ser Gly Gly Gly
        115                 120                 125

Gly Ser Gly Gly Gly Gly Ser Asp Ile Gln Met Thr Gln Ser Ser Ser
    130                 135                 140

Ser Phe Ser Val Ser Leu Gly Asp Arg Val Thr Ile Thr Cys Lys Ala
145                 150                 155                 160

Asn Glu Asp Ile Asn Asn Arg Leu Ala Trp Tyr Gln Gln Thr Pro Gly
                165                 170                 175

Asn Ser Pro Arg Leu Leu Ile Ser Gly Ala Thr Asn Leu Val Thr Gly
            180                 185                 190

Val Pro Ser Arg Phe Ser Gly Ser Gly Lys Asp Tyr Thr Leu
        195                 200                 205

Thr Ile Thr Ser Leu Gln Ala Glu Asp Phe Ala Thr Tyr Tyr Cys Gln
    210                 215                 220

Gln Tyr Trp Ser Thr Pro Phe Thr Phe Gly Ser Gly Thr Glu Leu Glu
225                 230                 235                 240

Ile Lys

```
<210> SEQ ID NO 16
<211> LENGTH: 726
<212> TYPE: DNA
<213> ORGANISM: Artificial Sequence
<220> FEATURE:
<223> OTHER INFORMATION: CE7scFv

<400> SEQUENCE: 16
caggtgcagc tgcagcagcc tggcgccgag ctggtgaagc caggcgccag cgtgaagctg      60
tcctgcaagg ccagcggcta caccttcacc ggctactgga tgcactgggt gaagcagaga     120
cccggccacg gcctggaatg gatcggcgag atcaacccca gcaacggccg gaccaactac     180
aacgagcggt tcaagagcaa ggccaccctg accgtggaca agagcagcac caccgccttc     240
atgcagctgt ccggcctgac cagcgaggac agcgccgtgt acttctgcgc cagggactac     300
tacggcacca gctacaactt cgactactgg ggccagggca ccacactgac cgtgagcagc     360
ggcggagggg gctctggcgg cggaggatct gggggagggg gcagcgacat ccagatgacc     420
```

```
cagagcagca gcagcttcag cgtgagcctg ggcgaccggg tgaccatcac ctgtaaggcc    480
aacgaggaca tcaacaaccg gctggcctgg tatcagcaga ccccccggcaa cagccccagg    540 ctgctgatca gcggcgccac caacctggtg accggcgtgc ccagccggtt tagcggcagc    600
ggctccggca aggactacac cctgaccatc acaagcctgc aggccgagga cttcgccacc    660
tactactgcc agcagtactg gtccaccccc ttcaccttcg gcagcggcac cgagctggaa    720
atcaaa                                                              726
```

```
<210> SEQ ID NO 17
<211> LENGTH: 250
<212> TYPE: PRT
<213> ORGANISM: Artificial Sequence
<220> FEATURE:
<223> OTHER INFORMATION: ROR1scFv

<400> SEQUENCE: 17
```

```
Pro Gln Glu Gln Leu Val Glu Ser Gly Gly Arg Leu Val Thr Pro Gly
 1               5                  10                  15

Gly Ser Leu Thr Leu Ser Cys Lys Ala Ser Gly Phe Asp Phe Ser Ala
             20                  25                  30

Tyr Tyr Met Ser Trp Val Arg Gln Ala Pro Gly Lys Gly Leu Glu Trp
         35                  40                  45

Ile Ala Thr Ile Tyr Pro Ser Ser Gly Lys Thr Tyr Tyr Ala Thr Trp
     50                  55                  60

Val Asn Gly Arg Phe Thr Ile Ser Ser Asp Asn Ala Gln Asn Thr Val
 65                  70                  75                  80

Asp Leu Gln Met Asn Ser Leu Thr Ala Ala Asp Arg Ala Thr Tyr Phe
                 85                  90                  95

Cys Ala Arg Asp Ser Tyr Ala Asp Asp Gly Ala Leu Phe Asn Ile Trp
            100                 105                 110

Gly Pro Gly Thr Leu Val Thr Ile Ser Ser Gly Gly Gly Gly Ser Gly
        115                 120                 125

Gly Gly Gly Ser Gly Gly Gly Ser Glu Leu Val Leu Thr Gln Ser
    130                 135                 140

Pro Ser Val Ser Ala Ala Leu Gly Ser Pro Ala Lys Ile Thr Cys Thr
145                 150                 155                 160

Leu Ser Ser Ala His Lys Thr Asp Thr Ile Asp Trp Tyr Gln Gln Leu
                165                 170                 175

Gln Gly Glu Ala Pro Arg Tyr Leu Met Gln Val Gln Ser Asp Gly Ser
            180                 185                 190

Tyr Thr Lys Arg Pro Gly Val Pro Asp Arg Phe Ser Gly Ser Ser
        195                 200                 205

Gly Ala Asp Arg Tyr Leu Ile Ile Pro Ser Val Gln Ala Asp Asp Glu
    210                 215                 220

Ala Asp Tyr Tyr Cys Gly Ala Asp Tyr Ile Gly Gly Tyr Val Phe Gly
225                 230                 235                 240

Gly Gly Thr Gln Leu Thr Val Thr Gly Gly
                245                 250
```

```
<210> SEQ ID NO 18
<211> LENGTH: 745
<212> TYPE: DNA
<213> ORGANISM: Artificial Sequence
<220> FEATURE:
<223> OTHER INFORMATION: ROR1scFv
```

<400> SEQUENCE: 18

```
ccaggaacag ctcgtcgaaa gcggcggcag actggtgaca cctggcggca gcctgaccct    60
gagctgcaag gccagcggct tcgacttcag cgcctactac atgagctggg tccgccaggc   120
ccctggcaag gactggaatg gatcgccac catctacccc agcagcggca agacctacta   180
cgccacctgg gtgaacggac ggttcaccat ctccagcgac aacgcccaga acaccgtgga   240
cctgcagatg aacagcctga cagccgccga ccgggccacc tacttttgcg ccagagacag   300
ctacgccgac gacggcgccc tgttcaacat ctggggccct ggcaccctgg tgacaatctc   360
tagcggcgga ggcggatctg gtggcggagg aagtggcggc ggaggatctg agctggtgct   420
gacccagagc ccctctgtgt ctgctgccct gggaagccct gccaagatca cctgtaccct   480
gagcagcgcc cacaagaccg acaccatcga ctggtatcag cagctgcagg gcgaggcccc   540
cagatacctg atgcaggtgc agagcgacgg cagctacacc aagaggccag gcgtgcccga   600
ccggttcagc ggatctagct ctggcgccga ccgctacctg atcatcccca gcgtgcaggc   660
cgatgacgag gccgattact actgtggcgc cgactacatc ggcggctacg tgttcggcgg   720
aggcacccag ctgaccgtga ccggc                                          745
```

<210> SEQ ID NO 19
<211> LENGTH: 242
<212> TYPE: PRT
<213> ORGANISM: Artificial Sequence
<220> FEATURE:
<223> OTHER INFORMATION: EGFR 806 scFv

<400> SEQUENCE: 19

```
Asp Val Gln Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ala Gly Ser Thr Ser Gly Ser Gly Lys Pro Gly Ser Gly
        115                 120                 125

Glu Gly Ser Thr Lys Gly Asp Ile Leu Met Thr Gln Ser Pro Ser Ser
    130                 135                 140

Met Ser Val Ser Leu Gly Asp Thr Val Ser Ile Thr Cys His Ser Ser
145                 150                 155                 160

Gln Asp Ile Asn Ser Asn Ile Gly Trp Leu Gln Gln Arg Pro Gly Lys
                165                 170                 175

Ser Phe Lys Gly Leu Ile Tyr His Gly Thr Asn Leu Asp Asp Glu Val
            180                 185                 190

Pro Ser Arg Phe Ser Gly Ser Gly Ser Gly Ala Asp Tyr Ser Leu Thr
        195                 200                 205
```

```
Ile Ser Ser Leu Glu Ser Glu Asp Phe Ala Asp Tyr Tyr Cys Val Gln
    210                 215                 220

Tyr Ala Gln Phe Pro Trp Thr Phe Gly Gly Gly Thr Lys Leu Glu Ile
225                 230                 235                 240

Lys Arg

<210> SEQ ID NO 20
<211> LENGTH: 725
<212> TYPE: DNA
<213> ORGANISM: Artificial Sequence
<220> FEATURE:
<223> OTHER INFORMATION: EGFR 806 scFv

<400> SEQUENCE: 20
atgtgcagct gcaggaatca ggcccaagcc tggtcaaacc ctcccagtct ctgagtctga     60
cctgtacagt gactgggtac tccatcacat ctgatttcgc atggaactgg attaggcagt    120
ttccaggcaa taagctggag tggatgggct acatctcata tagcgggaac actcgctata    180
atcccagtct gaaatcacgg atcagcatta ctagagacac cagcaagaac cagttctttc    240
tgcagctgaa ttccgtgacc attgaggata ccgccacata ctattgcgtc acagctggca    300 gaggcttttcc atactgggga cagggcacac tggtgactgt cagcgccggc tccacctctg    360
ggagtggaaa acctggctcc ggggaaggat ctacaaaggg agacatcctg atgactcagt    420
ccccaagctc catgtcagtg agcctgggcg acaccgtctc tattacatgt cactctagtc    480
aggatatcaa cagtaatatt ggctggctgc agcagcgacc cggcaagtct ttcaaagggc    540
tgatctatca tggaactaac ctggacgatg aagtgcctag cagattttcc ggctctggga    600
gtggagctga ttacagtctg accatttcaa gcctggagtc agaagacttc gcagattact    660
attgcgtcca gtatgcccag ttcccctgga cttttggcgg gggaaccaag ctggagatca    720
aacgg                                                                725

<210> SEQ ID NO 21
<211> LENGTH: 245
<212> TYPE: PRT
<213> ORGANISM: Artificial Sequence
<220> FEATURE:
<223> OTHER INFORMATION: Her2scFv

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
            100                 105                 110

Gly Gly Ser Gly Gly Gly Ser Gly Gly Gly Ser Ser Glu Val Gln
        115                 120                 125
```

```
Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
                180                 185                 190

Phe Thr Ile Ser Ala Asp Thr Ser Lys Asn Thr Ala Tyr Leu Gln Met
            195                 200                 205

Asn Ser Leu Arg Ala Glu Asp Thr Ala Val Tyr Tyr Cys Ser Arg Trp
210                 215                 220

Gly Gly Asp Gly Phe Tyr Ala Met Asp Tyr Trp Gly Gln Gly Thr Leu
225                 230                 235                 240

Val Thr Val Ser Ser
                245
```

<210> SEQ ID NO 22
<211> LENGTH: 735
<212> TYPE: DNA
<213> ORGANISM: Artificial Sequence
<220> FEATURE:
<223> OTHER INFORMATION: Her2scFv

<400> SEQUENCE: 22

```
gatatccaga tgacccagtc cccgagctcc ctgtccgcct ctgtgggcga tagggtcacc    60
atcacctgcc gtgccagtca ggatgtgaat actgctgtag cctggtatca acagaaacca   120
ggaaaagctc cgaaactact gatttactcg gcatccttcc tctactctgg agtcccttct   180
cgcttctctg gttccagatc tgggacggat ttcactctga ccatcagcag tctgcagccg   240
gaagacttcg caacttatta ctgtcagcaa cattatacta ctcctcccac gttcggacag   300
ggtaccaagg tggagatcaa aggcagtact agcggcggtg ctccggggg cggatccggt   360
gggggcggca gcagcgaggt tcagctggtg agtctggcg gtggcctggt gcagccaggg   420
ggctcactcc gtttgtcctg tgcagcttct ggcttcaaca ttaaagacac ctatatacac   480
tgggtgcgtc aggccccggg taagggcctg gaatggttg caaggattta cctacgaat   540
ggttatacta gatatgccga tagcgtcaag ggccgtttca ctataagcgc agacacatcc   600
aaaaacacag cctacctgca gatgaacagc ctgcgtgctg aggacactgc cgtctattat   660
tgttctagat ggggagggga cggcttctat gctatggact actggggtca aggaaccctg   720
gtcaccgtct cgagt                                                    735
```

<210> SEQ ID NO 23
<211> LENGTH: 239
<212> TYPE: PRT
<213> ORGANISM: Artificial Sequence
<220> FEATURE:
<223> OTHER INFORMATION: huGD2scFv

<400> SEQUENCE: 23

```
Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
                20                  25                  30

Val Thr Trp Tyr Gln Gln Lys Pro Gly Gln Ala Pro Arg Leu Leu Ile
            35                  40                  45
```

Tyr Ser Ala Ser Asn Arg Tyr Ser Gly Val Pro Ala Arg Phe Ser Gly
            50                  55                  60
Ser Gly Tyr Gly Thr Glu Phe Thr Phe Thr Ile Ser Ser Val Gln Ser
 65                  70                  75                  80
Glu Asp Phe Ala Val Tyr Phe Cys Gln Gln Asp Tyr Ser Ser Phe Gly
                 85                  90                  95
Gln Gly Thr Lys Leu Glu Ile Lys Arg Gly Gly Gly Ser Gly Gly
            100                 105                 110
Gly Gly Ser Gly Gly Gly Gly Ser Gln Val Gln Leu Val Glu Ser Gly
            115                 120                 125
Pro Gly Val Val Gln Pro Gly Arg Ser Leu Arg Ile Ser Cys Ala Val
        130                 135                 140
Ser Gly Phe Ser Val Thr Asn Tyr Gly Val His Trp Val Arg Gln Pro
145                 150                 155                 160
Pro Gly Lys Gly Leu Glu Trp Leu Gly Val Ile Trp Ala Gly Gly Ile
                165                 170                 175
Thr Asn Tyr Asn Ser Ala Phe Met Ser Arg Leu Thr Ile Ser Lys Asp
            180                 185                 190
Asn Ser Lys Asn Thr Val Tyr Leu Gln Met Asn Ser Leu Arg Ala Glu
        195                 200                 205
Asp Thr Ala Met Tyr Tyr Cys Ala Ser Arg Gly Gly His Tyr Gly Tyr
210                 215                 220
Ala Leu Asp Tyr Trp Gly Gln Gly Thr Leu Val Thr Val Ser Ser
225                 230                 235

<210> SEQ ID NO 24
<211> LENGTH: 717
<212> TYPE: DNA
<213> ORGANISM: Artificial Sequence
<220> FEATURE:
<223> OTHER INFORMATION: huGD2scFv

<400> SEQUENCE: 24

```
gagatcgtga tgacccagac ccccgccacc ctgagcgtga gcgccggcga gagggtgacc        60
atcacctgca aggccagcca gagcgtgagc aacgacgtga cctggtacca gcagaagccc       120
ggccaggccc ccaggctgct gatctacagc gccagcaaca ggtacagcgg cgtgcccgcc       180
aggttcagcg gcagcggcta cggcaccgag ttcaccttca ccatcagcag cgtgcagagc       240
gaggacttcg ccgtgtactt ctgccagcag gactacagca gcttcggcca gggcaccaag       300
ctggagatca agaggggtgg cggtggcagc ggcggtggtg gttccggagg cggcggttct       360
caggtgcagc tggtggagag cggccccggc gtggtgcagc ccggcaggag cctgaggatc       420
agctgcgccg tgagcggctt cagcgtgacc aactacggcg tgcactgggt gaggcagccc       480
cccggcaagg gcctggagtg gctgggcgtg atctgggccg gcggcatcac caactacaac       540
agcgccttca tgagcaggct gaccatcagc aaggacaaca gcaagaacac cgtgtacctg       600
cagatgaaca gcctgagggc cgaggacacc gccatgtact actgcgccag caggggcggc       660
cactacggct acgccctgga ctactggggc cagggcaccc tggtgaccgt gagcagc         717
```

<210> SEQ ID NO 25
<211> LENGTH: 237
<212> TYPE: PRT
<213> ORGANISM: Artificial Sequence
<220> FEATURE:
<223> OTHER INFORMATION: EphA2 (2H4) scFv

<400> SEQUENCE: 25

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Gln Ala Leu Glu Trp Met
        35                  40                  45

Gly Thr Ile Ser Ser Arg Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Ile Phe Thr His Trp Gly Arg Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Gln Leu Thr Gln Ser Pro Ser Ser Leu Ser Ala Ser
    130                 135                 140

Val Gly Asp Arg Val Thr Ile Thr Cys Lys Ala Ser Gln Asp Ile Asn
145                 150                 155                 160

Asn Tyr His Ser Trp Tyr Gln Gln Lys Pro Gly Gln Ala Pro Arg Leu
                165                 170                 175

Leu Ile Tyr Arg Ala Asn Arg Leu Val Asp Gly Val Pro Asp Arg Phe
            180                 185                 190

Ser Gly Ser Gly Tyr Gly Thr Asp Phe Thr Leu Thr Ile Asn Asn Ile
        195                 200                 205

Glu Ser Glu Asp Ala Ala Tyr Tyr Phe Cys Leu Lys Tyr Asn Val Phe
    210                 215                 220

Pro Tyr Thr Phe Gly Gln Gly Thr Lys Val Glu Ile Lys
225                 230                 235

<210> SEQ ID NO 26
<211> LENGTH: 711
<212> TYPE: DNA
<213> ORGANISM: Artificial Sequence
<220> FEATURE:
<223> OTHER INFORMATION: EphA2 (2H4) scFv

<400> SEQUENCE: 26
caggtgcagc tgttggagtc tgggggaggc ttggtacagc ctggggggtc cctgagactc      60
tcctgtgcag cctctggatt cacctttagc agctatacca tgtcttgggt gcgacaggcc     120
cctggacaag cgcttgagtg gatgggaacc attagtagtc gtggtactta cacctactat     180
ccagacagtg tgaagggccg attcaccatc tccagagaca cgccaagaa ctcactgtat      240 ctgcaaatga acagcctgag agccgaggac acggctgtgt attactgtgc gagagaagct     300
atctttactc actggggccg tggcacccta gtcaccgtct cctcaggtgg tggtggttct     360
ggcggcggcg gctccggtgg tggtggttct gacatccagt tgacccagtc tccatcctcc     420
ctgtctgcat ctgtaggaga cagagtcacc atcacttgca aggcgagtca ggacattaat     480
aactatcaca gctggtacca gcagaaacct ggccaggctc ccaggctcct catctatcgt     540
gcaaacagat tggtcgatgg ggtcccagac aggttcagtg gcagcgggta tggaacagat     600

```
tttaccctca caattaataa catagaatct gaggatgctg catattactt ctgtctgaaa    660
tataatgtgt ttccgtacac gttcggccaa gggaccaagg tggagatcaa a             711
```

<210> SEQ ID NO 27
<211> LENGTH: 237
<212> TYPE: PRT
<213> ORGANISM: Artificial Sequence
<220> FEATURE:
<223> OTHER INFORMATION: EphA2 (4H5) scFv

<400> SEQUENCE: 27

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Gln Ala Leu Glu Trp Met
        35                  40                  45

Gly Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Ile Phe Thr Tyr Trp Gly Arg Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Gln Leu Thr Gln Ser Pro Ser Ser Leu Ser Ala Ser
    130                 135                 140

Val Gly Asp Arg Val Thr Ile Thr Cys Lys Ala Ser Gln Asp Ile Asn
145                 150                 155                 160

Asn Tyr Leu Ser Trp Tyr Gln Gln Lys Pro Gly Gln Ala Pro Arg Leu
                165                 170                 175

Leu Ile Tyr Arg Ala Asn Arg Leu Val Asp Gly Val Pro Asp Arg Phe
            180                 185                 190

Ser Gly Ser Gly Tyr Gly Thr Asp Phe Thr Leu Thr Ile Asn Asn Ile
        195                 200                 205

Glu Ser Glu Asp Ala Ala Tyr Tyr Phe Cys Leu Lys Tyr Asp Val Phe
    210                 215                 220

Pro Tyr Thr Phe Gly Gln Gly Thr Lys Val Glu Ile Lys
225                 230                 235
```

<210> SEQ ID NO 28
<211> LENGTH: 711
<212> TYPE: DNA
<213> ORGANISM: Artificial Sequence
<220> FEATURE:
<223> OTHER INFORMATION: EphA2 (4H5) scFv

<400> SEQUENCE: 28

```
caggtgcagc tgttggagtc tgggggaggc ttggtacagc ctgggggttc cctgagactc    60
tcctgtgcag cctctggatt cacctttagc agctatacca tgtcttgggt gcgacaggcc   120
cctggacaag cgcttgagtg gatgggaacc attagtagtg gtggtactta cacctactat   180
ccagacagtg tgaagggccg attcaccatc tccagagaca cgccaagaa ctcactgtat   240 ctgcaaatga acagcctgag agccgaggac acggctgtgt attactgtgc gagagaagct   300
```

```
atctttactt actggggccg tggcaccctg gtcaccgtct cctcaggtgg tggtggttct    360
ggcggcggcg gctccggtgg tggtggttct gacatccagt tgacccagtc tccatcctcc    420
ctgtctgcat ctgtaggaga cagagtcacc aagtgaacgt tccgctcagt cctgtaatta    480
ttgataaatt cgaccatggt cgtctttgga ccggtccgag ggtccgagga gtagatagca    540
cgtttgtcta aggtagatgg ggtcccagac aggttcagtg gcagcgggta tggaacagat    600
tttaccctca caattaataa catagaatct gaggatgctg catattactt ctgtctgaaa    660
tatgatgtgt tccgtacac gttcggccaa gggaccaagg tggagatcaa a              711
```

<210> SEQ ID NO 29
<211> LENGTH: 22
<212> TYPE: PRT
<213> ORGANISM: Artificial Sequence
<220> FEATURE:
<223> OTHER INFORMATION: GMCSF signal sequence

<400> SEQUENCE: 29

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 30
<211> LENGTH: 66
<212> TYPE: DNA
<213> ORGANISM: Artificial Sequence
<220> FEATURE:
<223> OTHER INFORMATION: GMCSF signal sequence

<400> SEQUENCE: 30

```
atgcttctcc tggtgacaag ccttctgctc tgtgagttac cacacccagc attcctcctg    60
atccca                                                                66
```

<210> SEQ ID NO 31
<211> LENGTH: 20
<212> TYPE: PRT
<213> ORGANISM: Artificial Sequence
<220> FEATURE:
<223> OTHER INFORMATION: CD20scFv signal sequence

<400> SEQUENCE: 31

Met Glu Thr Asp Thr Leu Leu Leu Trp Val Leu Leu Leu Trp Val Pro
1               5                   10                  15

Gly Ser Thr Gly
            20

<210> SEQ ID NO 32
<211> LENGTH: 60
<212> TYPE: DNA
<213> ORGANISM: Artificial Sequence
<220> FEATURE:
<223> OTHER INFORMATION: CD20scFv signal sequence

<400> SEQUENCE: 32

```
atggagacag acacactcct gctatgggtg ctgctgctct gggttccagg ttccacaggt    60
```

<210> SEQ ID NO 33
<211> LENGTH: 24
<212> TYPE: PRT
<213> ORGANISM: Artificial Sequence
<220> FEATURE:
<223> OTHER INFORMATION: T2A sequence

<400> SEQUENCE: 33

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 34
<211> LENGTH: 72
<212> TYPE: DNA
<213> ORGANISM: Artificial Sequence
<220> FEATURE:
<223> OTHER INFORMATION: T2A sequence

<400> SEQUENCE: 34
ctcgagggcg gcggagaggg cagaggaagt cttctaacat gcggtgacgt ggaggagaat    60
cccggcccta gg                                                       72

<210> SEQ ID NO 35
<211> LENGTH: 142
<212> TYPE: PRT
<213> ORGANISM: Artificial Sequence
<220> FEATURE:
<223> OTHER INFORMATION: Her2tG sequence

<400> SEQUENCE: 35

Met Leu Leu Leu Val Thr Ser Leu Leu Leu Cys Glu Leu Pro His Pro
1               5                   10                  15

Ala Phe Leu Leu Ile Pro Cys His Pro Glu Cys Gln Pro Gln Asn Gly
            20                  25                  30

Ser Val Thr Cys Phe Gly Pro Glu Ala Asp Gln Cys Val Ala Cys Ala
        35                  40                  45

His Tyr Lys Asp Pro Pro Phe Cys Val Ala Arg Cys Pro Ser Gly Val
    50                  55                  60

Lys Pro Asp Leu Ser Tyr Met Pro Ile Trp Lys Phe Pro Asp Glu Glu
65                  70                  75                  80

Gly Ala Cys Gln Pro Cys Pro Ile Asn Cys Thr His Ser Cys Val Asp
                85                  90                  95

Leu Asp Asp Lys Gly Cys Pro Ala Glu Gln Arg Ala Ser Pro Leu Thr
            100                 105                 110

Gly Gly Gly Ser Gly Gly Gly Ser Ile Ile Ser Ala Val Val Gly Ile
        115                 120                 125

Leu Leu Val Val Val Leu Gly Val Val Phe Gly Ile Leu Ile
    130                 135                 140

<210> SEQ ID NO 36
<211> LENGTH: 426
<212> TYPE: DNA
<213> ORGANISM: Artificial Sequence
<220> FEATURE:
<223> OTHER INFORMATION: Her2tG sequence

<400> SEQUENCE: 36
atgcttctcc tggtgacaag ccttctgctc tgtgagttac cacacccagc attcctcctg    60
atcccatgcc accctgagtg tcagccccag aatggctcag tgacctgttt tggaccggag   120
gctgaccagt gtgtggcctg tgcccactat aaggaccctc ccttctgcgt ggcccgctgc   180
cccagcggtg tgaaacctga cctctcctac atgcccatct ggaagtttcc agatgaggag   240
ggcgcatgcc agccttgccc catcaactgc acccactcct gtgtggacct ggatgacaag   300

```
ggctgccccg ccgagcagag agccagcccg ttaacgggtg gaggcagcgg aggtggctcg    360
tagtagagac gccaccaacc gtaagacgac cagcaccaga accccaccaga gaaaccctag    420 gagtag                                                                426
```

<210> SEQ ID NO 37
<211> LENGTH: 357
<212> TYPE: PRT
<213> ORGANISM: Artificial Sequence
<220> FEATURE:
<223> OTHER INFORMATION: EGFRt sequence

<400> SEQUENCE: 37

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335
```

Thr Gly Met Val Gly Ala Leu Leu Leu Leu Val Val Ala Leu Gly
            340                 345                 350

Ile Gly Leu Phe Met
        355

<210> SEQ ID NO 38
<211> LENGTH: 1071
<212> TYPE: DNA
<213> ORGANISM: Artificial Sequence
<220> FEATURE:
<223> OTHER INFORMATION: EGFRt sequence

<400> SEQUENCE: 38

| | | | | |
|---|---|---|---|---|
| atgcttctcc | tggtgacaag | ccttctgctc | tgtgagttac | cacacccagc attcctcctg | 60 |
| atcccacgca | aagtgtgtaa | cggaataggt | attggtgaat | taaagactc actctccata | 120 |
| aatgctacga | atattaaaca | cttcaaaaac | tgcacctcca | tcagtggcga tctccacatc | 180 |
| ctgccggtgg | catttagggg | tgactccttc | acacatactc | ctcctctgga tccacaggaa | 240 |
| ctggatattc | tgaaaaccgt | aaaggaaatc | acagggtttt | gctgattca ggcttggcct | 300 |
| gaaaacagga | cggacctcca | tgcctttgag | aacctagaaa | tcatacgcgg caggaccaag | 360 |
| caacatggtc | agttttctct | tgcagtcgtc | agcctgaaca | taacatcctt gggattacgc | 420 |
| tccctcaagg | agtaagtga | tggagatgtg | ataatttcag | gaaacaaaaa tttgtgctat | 480 |
| gcaaatacaa | taaactggaa | aaaactgttt | gggacctccg | gtcagaaaac caaaattata | 540 |
| agcaacagag | gtgaaaacag | ctgcaaggcc | acaggccagg | tctgccatgc cttgtgctcc | 600 |
| cccgagggct | gctggggccc | ggagcccagg | gactgcgtct | cttgccggaa tgtcagccga | 660 |
| ggcagggaat | gcgtggacaa | gtgcaaccttt | ctggagggtg | agccaaggga gtttgtggag | 720 |
| aactctgagt | gcatacagtg | ccacccagag | tgcctgcctc | aggccatgaa catcacctgc | 780 |
| acaggacggg | gaccagacaa | ctgtatccag | tgtgcccact | acattgacgg ccccactgc | 840 |
| gtcaagacct | gcccggcagg | agtcatggga | gaaaacaaca | ccctggtctg aagtacgca | 900 |
| gacgccggcc | atgtgtgcca | cctgtgccat | ccaaactgca | cctacggatg cactgggcca | 960 |
| ggtcttgaag | gctgtccaac | gaatgggcct | aagatcccgt | ccatcgccac tgggatggtg | 1020 |
| ggggccctcc | tcttgctgct | ggtggtggcc | ctggggatcg | gcctcttcat g | 1071 |

<210> SEQ ID NO 39
<211> LENGTH: 110
<212> TYPE: PRT
<213> ORGANISM: Artificial Sequence
<220> FEATURE:
<223> OTHER INFORMATION: IgG4-CH2(L235D, N297Q) mutant

<400> SEQUENCE: 39

Ala Pro Glu Phe Asp Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Gln Ser Thr Tyr Arg Val Val Ser Val Leu Thr Val Leu His
65                  70                  75                  80

```
Gln Asp Trp Leu Asn Gly Lys Glu Tyr Lys Cys Lys Val Ser Asn Lys
             85                  90                  95

Gly Leu Pro Ser Ser Ile Glu Lys Thr Ile Ser Lys Ala Lys
            100                 105                 110

<210> SEQ ID NO 40
<211> LENGTH: 330
<212> TYPE: DNA
<213> ORGANISM: Artificial Sequence
<220> FEATURE:
<223> OTHER INFORMATION: IgG4-CH2(L235D, N297Q) mutant

<400> SEQUENCE: 40
gcccccgagt tcgacggcgg acccagcgtg ttcctgttcc ccccaagcc  caaggacacc      60 ctgatgatca gccggacccc cgaggtgacc tgcgtggtgg tggacgtgag ccaggaagat     120
cccgaggtcc agttcaattg gtacgtggac ggcgtggaag tgcacaacgc caagaccaag     180
cccagagagg aacagttcca gagcacctac cgggtggtgt ctgtgctgac cgtgctgcac     240
caggactggc tgaacggcaa agaatacaag tgcaaggtgt ccaacaaggg cctgcccagc     300
agcatcgaaa agaccatcag caaggccaag                                     330
```

BISPECIFIC CAR T-CELLS FOR SOLID TUMOR TARGETING

INCORPORATION BY REFERENCE TO ANY PRIORITY APPLICATIONS

This application is a division of U.S. application Ser. No. 15/750,708 filed Feb. 6, 2018, which is the U.S. National Phase of Int. App. No. PCT/US2016/045360 filed Aug. 3, 2016, which designated the United States and was published in English and, which claims the benefit of priority to U.S. Prov. No. 62/202,698, filed Aug. 7, 2015, which are each incorporated herein by reference in its entirety.

REFERENCE TO SEQUENCE LISTING

The present application is being filed along with a Sequence Listing in electronic format. The Sequence Listing is provided as a file entitled SCRI.95D1.TXT, created Oct. 13, 2020, which is 45 kb in size. The information is the electronic format of the Sequence Listing is incorporated herein by reference in its entirety.

FIELD OF THE INVENTION

Aspects of the present invention described herein, include methods, cells and compositions for augmenting the therapeutic potency of adoptively transferred chimeric antigen receptor (CAR) bearing T-cells against solid tumors. In particular, methods, cells and compositions for CAR T-cell products that co-express two CARs in individual T-cells, such as a B cell targeting "driver" CAR for promoting in vivo expansion and activation of an effector cell, and a CAR or T-cell receptor (TcR) of a desired specificity for targeting a solid tumor (passenger CAR/TcR), are provided herein.

BACKGROUND OF THE INVENTION

A variety of cellular therapies have been integrated into the standard methods used in the treatment of cancer. The cellular therapy for patients suffering from cancer or disease is the injection of cellular material, such as living cells into a patient in need. This can include the infusion of polyclonal or antigen specific T-cells, lymphokine activated killer cells, natural killer cells, dendritic cells as well as macrophages. Advancements have been made in the development of chimeric antigen receptor (CAR) bearing T-cells for adoptive T-cell therapies for cancer therapy, which are a promising therapeutic route for cancer immunotherapy and viral therapy.

CAR T-cell therapy is an immunotherapy in which the patient's own T-cells are isolated in a laboratory, genetically manipulated to express a synthetic receptor to recognize a particular antigen or protein, and reinfused into the patient. A CAR can be comprised of several domains. Without being limiting, the CAR can have 1) an antigen-binding region, typically derived from an antibody, (2) a transmembrane domain to anchor the CAR into the T-cells, and/or (3) 1 or more intracellular T-cell signaling domains. First-generation CARs commonly incorporated a single chain variable fragment (scFv) that is derived from a monoclonal antibody (mAb) plus a signaling motif from a TCR chain. The second- and third-generation CARs are an improvement over the first-generation CARs with co-stimulatory activating motifs, which can lead to the enhanced proliferation, cytotoxicity and persistence of the CAR bearing cells in vivo. Clinical trials have shown some evidence of anti-tumor activity, with insufficient activation, persistence and homing to cancer tissue. Some anti-tumor responses have been reported in patients with B cell lymphoma, for example, and some neuroblastoma patients have reported partial response, stable disease and remission. Second- and third-generation CAR-modified T-cells have been shown to be able to provide enhanced activation signals, proliferation, production of cytokines and effector function of CAR-modified T-cells in pre-clinical trials. Initial clinical trials have been shown to exhibit some promising results.

Unfortunately, the field of immunotherapy is unable to adequately address the problems associated with CAR bearing T-cells. Problems can include the suboptimal expansion and activation cells as well as toxic effects that occur upon infusion of cells. There are several types of toxicities that can occur with the administration of CAR T-cells. Adverse reactions can include B cell aplasia, cytokine release syndrome (CRS) and tumor lysis syndrome upon infusion of CAR bearing T-cells. B cell aplasia can occur due to effective targeting of antigens on a B-cell. However, B cells are not a life sustaining type of tissue and can be an initial target for CAR T-cells.

Expanding the CAR T-Cells in the body can be associated with CRS. The symptoms of CRS can include fever, hypotension, hypoxia, and neurologic changes. Neurologic changes can include seizures, aphasia, and mental status changes. Additional clinical and biochemical changes may occur, such as disseminated intravascular coagulation and/or transaminitis associated with marked elevations in ferritin and C-reactive protein, which are found to be similar to macrophage activation syndrome or hemophagocytic lymphohistiocytosis (HLH).

Adverse effects can also include failure to exhibit engraftment, which may be due to the limited migration of infused T-cells to the sites of tumor metastasis, and the limited immunostimulatory activity of solid tumors and their immunosuppressive environment. As the development for CARs is still in its infancy, advancements in the field of CAR T-cell therapy are much needed to circumvent the adverse effects that arise during therapy.

SUMMARY

In a first aspect, a nucleic acid encoding a chimeric antigen receptor is provided. The nucleic acid comprises a first nucleic acid comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule, and wherein the first nucleic acid is covalently attached to a 5' end of the second nucleic acid, a third nucleic acid comprising a sequence encoding a de-immunized extracellular spacer, wherein the third nucleic acid is covalently attached to a 3' end of the second nucleic acid, a fourth nucleic acid comprising a sequence encoding a transmembrane domain, wherein the fourth nucleic acid is covalently attached to a 3' end of the third nucleic acid, a fifth nucleic acid comprising a sequence encoding a signaling domain, wherein the signaling domain comprises a 4-1BB domain and/or CD3-zeta domain, and wherein the fifth nucleic acid is covalently attached to a 3' end of the fourth nucleic acid, a sixth nucleic acid comprising a sequence encoding a linker, wherein the sixth nucleic acid is covalently attached to a 3' end of the fifth nucleic acid and a seventh nucleic acid comprising a sequence encoding a marker domain, wherein the seventh nucleic acid is covalently attached to a 3' end of the sixth nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

In a second aspect, a nucleic acid encoding a chimeric antigen receptor is provided. The nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule, and wherein the third nucleic acid is covalently attached to a 3' end of the second nucleic acid, a fourth nucleic acid comprising a sequence encoding a de-immunized extracellular spacer, wherein the fourth nucleic acid is covalently attached to a 3' end of the third nucleic acid, a fifth nucleic acid comprising a sequence encoding a transmembrane domain, wherein the fifth nucleic acid is covalently attached to a 3' end of the fourth nucleic acid, a sixth nucleic acid comprising a sequence encoding a signaling domain, wherein the signaling domain comprises a 4-1BB domain and/or CD3-zeta domain, and wherein the sixth nucleic acid is covalently attached to a 3' end of the fifth nucleic acid, a seventh nucleic acid comprising a sequence encoding a linker, wherein the seventh nucleic acid is covalently attached to a 3' end of the sixth nucleic acid; and an eighth nucleic acid comprising a sequence encoding a marker domain, wherein the eighth nucleic acid is covalently attached to a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/

CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

In a third aspect, a nucleic acid encoding a chimeric antigen receptor is provided. The nucleic acid comprises a first nucleic acid comprising a sequence encoding a leader sequence, a second nucleic acid comprising a sequence encoding an antibody or binding fragment thereof or scFv, wherein the antibody or binding fragment thereof or scFv is specific for a cell surface tumor specific molecule, and wherein the first nucleic acid is covalently attached at a 5' end of the second nucleic acid, a third nucleic acid comprising a sequence encoding a de-immunized extracellular spacer, wherein the third nucleic acid sequence is covalently attached at a 3' end of the second nucleic acid, a fourth nucleic acid comprising a sequence encoding a transmembrane domain, wherein the fourth nucleic acid is covalently attached at a 3' end of the third nucleic acid, a fifth nucleic acid comprising a sequence encoding a signaling domain sequence, wherein the signaling domain comprises a 4-1BB domain, CD3-zeta domain and/or CD28-zeta domain, and wherein the fifth nucleic acid is covalently attached at a 3' end of the fourth nucleic acid, a sixth nucleic acid comprising a sequence encoding a linker, wherein the sixth nucleic acid is covalently attached at a 3' end of the fifth nucleic acid and a seventh nucleic acid comprising a sequence encoding a marker domain, wherein the seventh nucleic acid is covalently attached at a 3' end of the sixth nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the sequence encoding the transmembrane domain further comprises an IRES sequence at the 3' end of the sequence encoding the transmembrane domain. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

In a fourth aspect, a nucleic acid encoding a chimeric antigen receptor is provided. The nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid sequence is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a 4-1BB domain, CD3-zeta domain and/or CD28-zeta domain, and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid and an eighth nucleic acid comprising a sequence encoding a marker domain, wherein the eighth nucleic acid is covalently attached at a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

In a fifth aspect, a nucleic acid encoding a bi-specific chimeric antigen receptor is provided. The nucleic acid encoding the bi-specific chimeric antigen receptor comprises a first nucleic acid sequence comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the first nucleic acid is covalently attached at a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid and an eighth nucleic acid comprising a sequence encoding a marker domain, wherein the eighth nucleic acid is covalently attached at a 3' end of the seventh nucleic acid, thereby having said nucleic acid encoding a bi-specific chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

In a sixth aspect, a nucleic acid encoding a bi-specific chimeric antigen receptor is provided. The nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the fourth nucleic acid is covalently attached at a 3' end of the third nucleic acid, a fifth nucleic acid comprising a sequence encoding a de-immunized extracellular spacer, wherein the fifth nucleic acid is covalently attached at a 3' end of the fourth nucleic acid, a sixth nucleic acid comprising a sequence encoding a transmembrane domain, wherein the sixth nucleic acid is covalently attached at a 3' end of the fifth nucleic acid, a seventh nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the seventh nucleic acid is covalently attached at a 3' end of the sixth nucleic acid, an eighth nucleic acid comprising a sequence encoding a linker, wherein the eighth nucleic acid is covalently attached at a 3' end of the seventh nucleic acid, and a ninth nucleic acid comprising a sequence encoding a marker domain, wherein the ninth nucleic acid is covalently attached at a 3' end of the eighth nucleic acid, thereby having said nucleic acid encoding a bi-specific chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

In a seventh aspect, a vector for expression of a chimeric antigen receptor specific for promoting in vivo expansion and activation of B cells is provided. The vector can comprise the nucleic acid of any one of the alternatives described herein. In some alternatives, the nucleic acid comprises a first nucleic acid comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule, and wherein the first nucleic acid is covalently attached to a 5' end of the second nucleic acid, a third nucleic acid comprising a sequence encoding a de-immunized extracellular spacer, wherein the third nucleic acid is covalently attached to a 3' end of the second nucleic acid, a fourth nucleic acid comprising a sequence encoding a transmembrane domain, wherein the fourth nucleic acid is covalently attached to a 3' end of the third nucleic acid, a fifth nucleic acid comprising a sequence encoding a signaling domain, wherein the signaling domain comprises a 4-1BB domain and/or CD3-zeta domain, and wherein the fifth nucleic acid is covalently attached to a 3' end of the fourth nucleic acid, a sixth nucleic acid comprising a sequence encoding a linker, wherein the sixth nucleic acid is covalently attached to a 3' end of the fifth nucleic acid and a seventh nucleic acid comprising a sequence encoding a marker domain, wherein the seventh nucleic acid is covalently attached to a 3' end of the sixth nucleic acid, thereby having said nucleic acid encoding a chimeric antigen receptor. In some alternatives, the nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule, and wherein the third nucleic acid is covalently attached to a 3' end of the second nucleic acid, a fourth nucleic acid comprising a sequence encoding a de-immunized extracellular spacer, wherein the fourth nucleic acid is covalently attached to a 3' end of the third nucleic acid, a fifth nucleic acid comprising a sequence encoding a transmembrane domain, wherein the fifth nucleic acid is covalently attached to a 3' end of the fourth nucleic acid, a sixth nucleic acid comprising a sequence encoding a signaling domain, wherein the signaling domain comprises a 4-1BB domain and/or CD3-zeta domain, and wherein the sixth nucleic acid is covalently attached to a 3' end of the fifth nucleic acid, a seventh nucleic acid comprising a sequence encoding a linker, wherein the seventh nucleic acid is covalently attached to a 3' end of the sixth nucleic acid; and an eighth nucleic acid comprising a sequence encoding a marker domain, wherein the eighth nucleic acid is covalently attached to a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. The leader sequence can comprise a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. The vector can be a viral vector in some alternatives. In some alternatives, the vector is a lentiviral vector, retroviral vector, gammaretroviral vectors or a foamy viral vector. In some alternatives, the vector is a transposon, integrase vector system, or an mRNA vector.

In an eighth aspect, a vector for expression of a chimeric antigen receptor or TcR specific for targeting a solid tumor is provided. The vector can comprise the nucleic acid of any one of the alternatives described herein. In some alternatives, the nucleic acid comprises a first nucleic acid comprising a sequence encoding a leader sequence, a second nucleic acid comprising a sequence encoding an antibody or binding fragment thereof or scFv, wherein the antibody or binding fragment thereof or scFv is specific for a cell surface tumor specific molecule, and wherein the first nucleic acid is covalently attached at a 5' end of the second nucleic acid, a third nucleic acid comprising a sequence encoding a de-immunized extracellular spacer, wherein the third nucleic acid sequence is covalently attached at a 3' end of the second nucleic acid, a fourth nucleic acid comprising a sequence encoding a transmembrane domain, wherein the fourth nucleic acid is covalently attached at a 3' end of the third nucleic acid, a fifth nucleic acid comprising a sequence encoding a signaling domain sequence, wherein the signaling domain comprises a 4-1BB domain, CD3-zeta domain and/or CD28-zeta domain, and wherein the fifth nucleic acid is covalently attached at a 3' end of the fourth nucleic acid, a sixth nucleic acid comprising a sequence encoding a linker, wherein the sixth nucleic acid is covalently attached at a 3' end of the fifth nucleic acid and a seventh nucleic acid comprising a sequence encoding a marker domain, wherein the seventh nucleic acid is covalently attached at a 3' end of the sixth nucleic acid, thereby having said nucleic acid encoding a chimeric antigen receptor. In some alternatives, the nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid sequence is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a 4-1BB domain, CD3-zeta domain and/or CD28-zeta domain, and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid and an eighth nucleic acid comprising a sequence encoding a marker domain, wherein the eighth nucleic acid is covalently attached at a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. The vector can be a viral vector in some alternatives. In some alternatives, the vector is a lentiviral vector, retroviral vector, gammaretroviral vectors or a foamy viral vector. In some alternatives, the vector is a transposon, integrase vector system, or an mRNA vector.

In a ninth aspect, a vector for expression of a bi-specific chimeric antigen receptor is provided. The bi-specific chimeric antigen receptor is specific for a B cell specific cell surface molecule and is specific for a cell surface tumor specific molecule. The vector can comprise the nucleic acid of any one of the alternatives described herein. In some alternatives, the nucleic acid encoding the bi-specific chimeric antigen receptor comprises a first nucleic acid sequence comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the first nucleic acid is covalently attached at a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid and an eighth nucleic acid comprising a sequence encoding a marker domain, wherein the eighth nucleic acid is covalently attached at a 3' end of the seventh nucleic acid, thereby having said nucleic acid encoding a bi-specific chimeric antigen receptor. In some alternatives, the nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the fourth nucleic acid is covalently attached at a 3' end of the third nucleic acid, a fifth nucleic acid comprising a sequence encoding a de-immunized extracellular spacer, wherein the fifth nucleic acid is covalently attached at a 3' end of the fourth nucleic acid, a sixth nucleic acid comprising a sequence encoding a transmembrane domain, wherein the sixth nucleic acid is covalently attached at a 3' end of the fifth nucleic acid, a seventh nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the seventh nucleic acid is covalently attached at a 3' end of the sixth nucleic acid, an eighth nucleic acid comprising a sequence encoding a linker, wherein the eighth nucleic acid is covalently attached at a 3' end of the seventh nucleic acid, and a ninth nucleic acid comprising a sequence encoding a marker domain, wherein the ninth nucleic acid is covalently attached at a 3' end of the eighth nucleic acid, thereby having said nucleic acid encoding a bi-specific chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. In some alternatives, the vector is a viral vector. In some alternatives, the vector is a lentiviral vector, retroviral vector, gammaretroviral vectors or a foamy viral vector. In some alternatives, the vector is a transposon, integrase vector system, or an mRNA vector.

In a tenth aspect, a chimeric antigen receptor or TcR specific for a B-cell specific cell surface molecule encoded by a nucleic acid or vector of any one of the alternatives described herein is provided. The vector can comprise the nucleic acid of any one of the alternatives described herein. In some alternatives, the nucleic acid comprises a first nucleic acid comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule, and wherein the first nucleic acid is covalently attached to a 5' end of the second nucleic acid, a third nucleic acid comprising a sequence encoding a de-immunized extracellular spacer, wherein the third nucleic acid is covalently attached to a 3' end of the second nucleic acid, a fourth nucleic acid comprising a sequence encoding a transmembrane domain, wherein the fourth nucleic acid is covalently attached to a 3' end of the third nucleic acid, a fifth nucleic acid comprising a sequence encoding a signaling domain, wherein the signaling domain comprises a 4-1BB domain and/or CD3-zeta domain, and wherein the fifth nucleic acid is covalently attached to a 3' end of the fourth nucleic acid, a sixth nucleic acid comprising a sequence encoding a linker, wherein the sixth nucleic acid is covalently attached to a 3' end of the fifth nucleic acid and a seventh nucleic acid comprising a sequence encoding a marker domain, wherein the seventh nucleic acid is covalently attached to a 3' end of the sixth nucleic acid, thereby having said nucleic acid encoding a chimeric antigen receptor. In some alternatives, the nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule, and wherein the third nucleic acid is covalently attached to a 3' end of the second nucleic acid, a fourth nucleic acid comprising a sequence encoding a de-immunized extracellular spacer, wherein the fourth nucleic acid is covalently attached to a 3' end of the third nucleic acid, a fifth nucleic acid comprising a sequence encoding a transmembrane domain, wherein the fifth nucleic acid is covalently attached to a 3' end of the fourth nucleic acid, a sixth nucleic acid comprising a sequence encoding a signaling domain, wherein the signaling domain comprises a 4-1BB domain and/or CD3-zeta domain, and wherein the sixth nucleic acid is covalently attached to a 3' end of the fifth nucleic acid, a seventh nucleic acid comprising a sequence encoding a linker, wherein the seventh nucleic acid is covalently attached to a 3' end of the sixth nucleic acid; and an eighth nucleic acid comprising a sequence encoding a marker domain, wherein the eighth nucleic acid is covalently attached to a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. The leader sequence comprises a Granulocyte-macrophage colony-stimulating factor signal sequence in some alternatives. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. In some alternatives, the vector is a viral vector. In some alternatives, the vector is a lentiviral vector, retroviral vector, gammaretroviral vectors or a foamy viral vector. In some alternatives, the vector is a transposon, integrase vector system, or an mRNA vector.

In an eleventh aspect, a chimeric antigen receptor or TcR specific for targeting a solid tumor, encoded by a nucleic acid or vector of any one of the alternatives described herein, is provided. The vector can comprise the nucleic acid of any one of the alternatives described herein. In some alternatives, the nucleic acid comprises a first nucleic acid comprising a sequence encoding a leader sequence, a second nucleic acid comprising a sequence encoding an antibody or binding fragment thereof or scFv, wherein the antibody or binding fragment thereof or scFv is specific for a cell surface tumor specific molecule, and wherein the first nucleic acid is covalently attached at a 5' end of the second nucleic acid, a third nucleic acid comprising a sequence encoding a de-immunized extracellular spacer, wherein the third nucleic acid sequence is covalently attached at a 3' end of the second nucleic acid, a fourth nucleic acid comprising a sequence encoding a transmembrane domain, wherein the fourth nucleic acid is covalently attached at a 3' end of the third nucleic acid, a fifth nucleic acid comprising a sequence encoding a signaling domain sequence, wherein the signaling domain comprises a 4-1BB domain, CD3-zeta domain and/or CD28-zeta domain, and wherein the fifth nucleic acid is covalently attached at a 3' end of the fourth nucleic acid, a sixth nucleic acid comprising a sequence encoding a linker, wherein the sixth nucleic acid is covalently attached at a 3' end of the fifth nucleic acid and a seventh nucleic acid comprising a sequence encoding a marker domain, wherein the seventh nucleic acid is covalently attached at a 3' end of the sixth nucleic acid, thereby having said nucleic acid encoding a chimeric antigen receptor. In some alternatives, the nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid sequence is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a 4-1BB domain, CD3-zeta domain and/or CD28-zeta domain, and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid and an eighth nucleic acid comprising a sequence encoding a marker domain, wherein the eighth nucleic acid is covalently attached at a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. The vector is a viral vector in some alternatives. In some alternatives, the vector is a lentiviral vector, retroviral vector, gammaretroviral vectors or a foamy viral vector. In some alternatives, the vector is a transposon, integrase vector system, or an mRNA vector.

In a twelfth aspect, a bi-specific chimeric antigen receptor specific for a B cell specific cell surface molecule and specific for a cell surface tumor specific molecule, encoded by a nucleic acid or vector of any one of the alternatives described herein is provided. The vector can comprise the nucleic acid of any one of the alternatives described herein. In some alternatives, the nucleic acid encoding the bi-specific chimeric antigen receptor comprises a first nucleic acid sequence comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the first nucleic acid is covalently attached at a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid and an eighth nucleic acid comprising a sequence encoding a marker domain, wherein the eighth nucleic acid is covalently attached at a 3' end of the seventh nucleic acid, thereby having said nucleic acid encoding a bi-specific chimeric antigen receptor. In some alternatives, the nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the fourth nucleic acid is covalently attached at a 3' end of the third nucleic acid, a fifth nucleic acid comprising a sequence encoding a de-immunized extracellular spacer, wherein the fifth nucleic acid is covalently attached at a 3' end of the fourth nucleic acid, a sixth nucleic acid comprising a sequence encoding a transmembrane domain, wherein the sixth nucleic acid is covalently attached at a 3' end of the fifth nucleic acid, a seventh nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the seventh nucleic acid is covalently attached at a 3' end of the sixth nucleic acid, an eighth nucleic acid comprising a sequence encoding a linker, wherein the eighth nucleic acid is covalently attached at a 3' end of the seventh nucleic acid, and a ninth nucleic acid comprising a sequence encoding a marker domain, wherein the ninth nucleic acid is covalently attached at a 3' end of the eighth nucleic acid, thereby having said nucleic acid encoding a bi-specific chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. In some alternatives, the vector is a viral vector. In some alternatives, the vector is a lentiviral vector, retroviral vector, gammaretroviral vectors or a foamy viral vector. In some alternatives, the vector is a transposon, integrase vector system, or an mRNA vector.

In a thirteenth aspect, a cell comprising a first and second chimeric antigen receptor or TcR is provided. In some alternatives, the first chimeric antigen receptor is specific for a ligand on a B cell, which promotes the in vivo expansion and activation of an effector cell and, wherein the second chimeric antigen receptor or TcR is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the first chimeric antigen receptor and/or the second chimeric antigen receptor or TcR are inducibly expressed in said cell. In some alternatives, expression of the first chimeric antigen receptor and/or the second chimeric antigen receptor or TcR is under the control of a regulatory element. In some alternatives, the first chimeric antigen receptor comprises an antibody or binding fragment thereof or scFv, a receptor ligand or mutant thereof, peptide, and/or polypeptide affinity molecule or binding partner. In some alternatives, the second chimeric antigen receptor or TcR comprises an antibody or binding fragment thereof or scFv, a receptor ligand or mutant thereof, peptide, and/or polypeptide affinity molecule or binding partner. In some alternatives, a first marker protein is co-expressed with the first chimeric antigen receptor and a second marker protein is co-expressed with the second chimeric antigen receptor or TcR. In some alternatives, the first marker protein co-expressed with the first chimeric antigen receptor is EGFRt and the second marker protein co-expressed with the second chimeric antigen receptor or TcR is Her2tg or first marker protein co-expressed with the first chimeric antigen receptor is Her2tg and the second marker protein co-expressed with the second chimeric antigen receptor or TcR is EGFRt. In some alternatives, the cell further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the cell expresses a soluble protein for therapy. In some alternatives, the soluble protein is a homeostatic cytokine, wherein the homeostatic cytokine is IL2, IL7, IL12 or IL15. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+ T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the first chimeric antigen receptor is specific for a ligand on a B cell, wherein the ligand on the B cell is CD19, and wherein the second chimeric antigen receptor is specific for L1CAM, and wherein the chimeric antigen receptors further comprises a 4-1 BB and CD3-zeta signaling domain. In some alternatives, the first chimeric antigen receptor is specific for a ligand on a B cell, wherein the ligand on the B cell is CD19, and wherein the second chimeric antigen receptor is specific for ROR1, and wherein the chimeric antigen receptors further comprises a 4-1 BB and CD3-zeta signaling domain.

In a fourteenth aspect, a cell comprising a bi-specific chimeric antigen receptor is provided, wherein the bi-specific chimeric antigen receptor comprises two binding domains, wherein a first binding domain is specific for a ligand on a B cell, which promotes the in vivo expansion and activation of the B cell and a second binding domain, wherein the second binding domain is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the first and second binding domain comprises an antibody or portion thereof, a receptor ligand or mutant thereof, peptide, and/or polypeptide affinity molecule or binding partner. In some alternatives, the cell further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the cell expresses a soluble protein for therapy. In some alternatives, the soluble protein is a homeostatic cytokine, wherein the homeostatic cytokine is IL2, IL7, IL12 or IL15. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the first chimeric antigen receptor is specific for a ligand on a B cell, wherein the ligand on the B cell is CD19, and wherein the second chimeric antigen receptor is specific for L1 CAM, and wherein the chimeric antigen receptors further comprises a 4-1 BB and CD3-zeta signaling domain. In some alternatives, the first chimeric antigen receptor is specific for a ligand on a B cell, wherein the ligand on the B cell is CD19, and wherein the second chimeric antigen receptor is specific for ROR1, and wherein the chimeric antigen receptors further comprises a 4-1 BB and CD3-zeta signaling domain. In some alternatives, the first binding domain is specific for a ligand on a B cell, wherein the ligand on the B cell is CD19, and wherein the second binding domain is specific for L1CAM. In some alternatives, the first binding domain is specific for a ligand on a B cell, wherein the ligand on the B cell is CD19, and wherein the second binding domain is specific for ROR1.

In a fifteenth aspect, a method of making a cell having a chimeric antigen receptor is provided. The method can comprise the following steps: introducing into a cell a first nucleic acid or a first vector comprising a polynucleotide sequence encoding a first chimeric antigen receptor that comprises a binding domain specific for a ligand on a B cell, which promotes the in vivo expansion and activation of the B cell, introducing into the cell a second nucleic acid or a second vector comprising a polynucleotide sequence encoding a second chimeric antigen receptor or TcR that comprises a binding domain specific for a ligand on a solid tumor, expanding the cell and isolating the cell. In some alternatives, the first nucleic acid and the second nucleic acid reside on separate viral vectors. In some alternatives, the viral vectors are retroviral vectors, gammaretroviral vectors, foamy viral vector and/or lentiviral vectors. In some alternatives, the viral vectors are co-introduced into the cell as a composition comprising the viral vectors. In some alternatives, the vectors are a transposon, integrase vector system, and/or an mRNA vector. In some alternatives, expression of the first chimeric antigen receptor is linked to co-expression of EGFRt and expression of the second chimeric antigen receptor is linked to co-expression of Her2tg, or wherein expression of the first chimeric antigen receptor is linked to co-expression of Her2tg, and expression of the second chimeric antigen receptor is linked to co-expression of EGFRt. In some alternatives, the method further comprises introducing a vector comprising a sequence encoding a soluble protein into said cell. In some alternatives, the soluble protein is a homeostatic cytokine. In some alternatives, the homeostatic cytokine is IL2, IL7, IL12 or IL15. In some alternatives, the viral vectors further comprise a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the method further comprises introducing a vector comprising a sequence encoding a suicide gene system. In some alternatives, the suicide gene system is a Herpes Simplex Virus Thymidine Kinase (HSVTK)/Ganciclovir (GCV) suicide gene system or an inducible Caspase suicide gene system.

In a sixteenth aspect, a method of making a cell having a chimeric antigen receptor is provided, wherein the method comprises co-delivering into a cell two vectors, wherein the first vector comprises a first nucleic acid sequence encoding a first chimeric antigen receptor that comprises a binding domain specific for a ligand on a B cell, which promotes the in vivo expansion and activation of the B cell, and a second vector wherein the second vector comprises a second polynucleotide sequence encoding a second chimeric antigen receptor or TcR that comprises a binding domain specific for a ligand on a solid tumor, expanding the cell and isolating the cell. In some alternatives, the vectors are plasmids and/or minicircle transposons. In some alternatives, the first nucleic acid and the second nucleic acid reside between a first inverted terminal repeat gene sequence and a second inverted terminal repeat gene sequence. In some alternatives, the inverted terminal repeat gene sequences are inverted repeats of a Sleeping Beauty transposon or PiggyBac transposons. In some alternatives, the method further comprises introducing a vector encoding the Sleeping Beauty transposase or PiggyBac transposase into the cell.

In a seventeenth aspect, a method of making a cell having a bi-specific chimeric antigen receptor is provided, wherein the method comprises introducing into a cell a nucleic acid comprising a polynucleotide sequence encoding a bi-specific chimeric antigen receptor that comprises a first binding domain specific for a ligand on a B cell, which promotes the in vivo expansion and activation of the B cell, and a second binding domain specific for a ligand on a solid tumor, expanding the cells and isolating the cells. In some alternatives, the polynucleotide resides on a viral vector. In some alternatives, the viral vector is a lentiviral, retroviral vector, foamy viral vector or a gammaretroviral vector. In some alternatives, the bi-specific chimeric antigen receptor is co-expressed with a marker protein. In some alternatives, the marker protein is EGFRt or Her2tg. In some alternatives, the method further comprises introducing a vector comprising a sequence encoding a soluble protein into said cell. In some alternatives, the soluble protein is a homeostatic cytokine. In some alternatives, the homeostatic cytokine is IL2, IL7, IL12 or IL15. In some alternatives, the viral vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the method further comprises introducing a vector comprising a sequence encoding a suicide gene system. In some alternatives, the suicide gene system is a Herpes Simplex Virus Thymidine Kinase (HSVTK)/Ganciclovir (GCV) suicide gene system or an inducible Caspase suicide gene system.

In an eighteenth aspect, a method of making a cell having a bi-specific chimeric antigen receptor is provided, wherein the method comprises introducing into a cell a vector, wherein the vector comprises a first nucleic acid encoding a bi-specific chimeric antigen receptor that comprises a first binding domain specific for a ligand on a B cell, which promotes the in vivo expansion and activation of the B cell, and a second binding domain wherein the second binding domain comprises a binding domain specific for a ligand on a solid tumor, expanding the cell and isolating the cell. In some alternatives, the vector is a plasmid or minicircle transposon. In some alternatives, the first nucleic acid resides between a first inverted terminal repeat gene sequence and a second inverted terminal repeat gene sequence. In some alternatives, the inverted terminal repeat gene sequences are inverted repeats of a Sleeping Beauty transposon or PiggyBac transposons. In some alternatives, the method further comprises introducing a vector encoding a Sleeping Beauty transposase or PiggyBac transposase into the cell.

In a nineteenth aspect, a composition is provided, wherein the composition comprises any one or more of the cells of any of the alternatives described herein. In some alternatives, the cell comprises a first and second chimeric antigen receptor or TcR. In some alternatives, the cell comprises a bi-specific chimeric antigen receptor, wherein the bi-specific chimeric antigen receptor comprises two binding domains, wherein a first binding domain is specific for a ligand on a B cell, which promotes the in vivo expansion and activation of the B cell and a second binding domain, wherein the second binding domain is specific for a ligand on a tumor. In some alternatives, the first chimeric antigen receptor is specific for a ligand on a B cell, which promotes the in vivo expansion and activation of an effector cell and, wherein the second chimeric antigen receptor or TcR is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the first chimeric antigen receptor and/or the second chimeric antigen receptor or TcR are inducibly expressed in said cell. In some alternatives, expression of the first chimeric antigen receptor and/or the second chimeric antigen receptor or TcR is under the control of a regulatory element. In some alternatives, the first chimeric antigen receptor comprises an antibody or binding fragment thereof or scFv, a receptor ligand or mutant thereof, peptide, and/or polypeptide affinity molecule or binding partner. In some alternatives, the second chimeric antigen receptor or TcR comprises an antibody or binding fragment thereof or scFv, a receptor ligand or mutant thereof, peptide, and/or polypeptide affinity molecule or binding partner. In some alternatives, a first marker protein is co-expressed with the first chimeric antigen receptor and a second marker protein is co-expressed with the second chimeric antigen receptor or TcR. In some alternatives, the first marker protein co-expressed with the first chimeric antigen receptor is EGFRt and the second marker protein co-expressed with the second chimeric antigen receptor or TcR is Her2tg or first marker protein co-expressed with the first chimeric antigen receptor is Her2tg and the second marker protein co-expressed with the second chimeric antigen receptor or TcR is EGFRt. In some alternatives, the cell further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the cell expresses a soluble protein for therapy. In some alternatives, the soluble protein is a homeostatic cytokine, wherein the homeostatic cytokine is IL2, IL7, IL12 or IL15. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+ T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the first chimeric antigen receptor is specific for a ligand on a B cell, wherein the ligand on the B cell is CD19, and wherein the second chimeric antigen receptor is specific for L1CAM, and wherein the chimeric antigen receptors further comprises a 4-1 BB and CD3-zeta signaling domain. In some alternatives, the first chimeric antigen receptor is specific for a ligand on a B cell, wherein the ligand on the B cell is CD19, and wherein the second chimeric antigen receptor is specific for ROR1, and wherein the chimeric antigen receptors further comprises a 4-1 BB and CD3-zeta signaling domain. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the first and second binding domain comprises an antibody or portion thereof, a receptor ligand or mutant thereof, peptide, and/or polypeptide affinity molecule or binding partner. In some alternatives, the cell further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the cell expresses a soluble protein for therapy. In some alternatives, the soluble protein is a homeostatic cytokine, wherein the homeostatic cytokine is IL2, IL7, IL12 or IL15. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+ T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the first chimeric antigen receptor is specific for a ligand on a B cell, wherein the ligand on the B cell is CD19, and wherein the second chimeric antigen receptor is specific for L1CAM, and wherein the chimeric antigen receptors further comprises a 4-1 BB and CD3-zeta signaling domain. In some alternatives, the first chimeric antigen receptor is specific for a ligand on a B cell, wherein the ligand on the B cell is CD19, and wherein the second chimeric antigen receptor is specific for ROR1, and wherein the chimeric antigen receptors further comprises a 4-1 BB and CD3-zeta signaling domain. In some alternatives, the first binding domain is specific for a ligand on a B cell, wherein the ligand on the B cell is CD19, and wherein the second binding domain is specific for L1CAM. In some alternatives, the first binding domain is specific for a ligand on a B cell, wherein the ligand on the B cell is CD19, and wherein the second binding domain is specific for ROR1.

In a twentieth aspect, a method of treating, ameliorating, or inhibiting a non-B cell related disease in a subject is provided. The method can comprise identifying a subject that does not have a B-cell related disease for therapy, introducing, providing, or administering any one or more of the cells of any of the alternatives provided herein or the cells made by any one or more of any of the alternatives provided herein or a composition of any of the alternatives described herein into a subject for therapy. In some alternatives, the method comprises introducing into a cell a vector, wherein the vector comprises a first nucleic acid encoding a bi-specific chimeric antigen receptor that comprises a first binding domain specific for a ligand on a B cell, which promotes the in vivo expansion and activation of the B cell, and a second binding domain wherein the second binding domain comprises a binding domain specific for a ligand on a solid tumor, expanding the cell and isolating the cell. In some alternatives, the vector is a plasmid or minicircle transposon. In some alternatives, the first nucleic acid resides between a first inverted terminal repeat gene sequence and a second inverted terminal repeat gene sequence. In some alternatives, the inverted terminal repeat gene sequences are inverted repeats of a Sleeping Beauty transposon or PiggyBac transposons. In some alternatives, the method further comprises introducing a vector encoding a Sleeping Beauty transposase or PiggyBac transposase into the cell. In some alternatives, the composition comprises any one or more of the cells of any of the alternatives described herein. In some alternatives, the cell comprises a first and second chimeric antigen receptor or TcR. In some alternatives, the cell comprises a bi-specific chimeric antigen receptor, wherein the bi-specific chimeric antigen receptor comprises two binding domains, wherein a first binding domain is specific for a ligand on a B cell, which promotes the in vivo expansion and activation of the B cell and a second binding domain, wherein the second binding domain is specific for a ligand on a tumor. In some alternatives, the first chimeric antigen receptor is specific for a ligand on a B cell, which promotes the in vivo expansion and activation of an effector cell and, wherein the second chimeric antigen receptor or TcR is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the first chimeric antigen receptor and/or the second chimeric antigen receptor or TcR are inducibly expressed in said cell. In some alternatives, expression of the first chimeric antigen receptor and/or the second chimeric antigen receptor or TcR is under the control of a regulatory element. In some alternatives, the first chimeric antigen receptor comprises an antibody or binding fragment thereof or scFv, a receptor ligand or mutant thereof, peptide, and/or polypeptide affinity molecule or binding partner. In some alternatives, the second chimeric antigen receptor or TcR comprises an antibody or binding fragment thereof or scFv, a receptor ligand or mutant thereof, peptide, and/or polypeptide affinity molecule or binding partner. In some alternatives, a first marker protein is co-expressed with the first chimeric antigen receptor and a second marker protein is co-expressed with the second chimeric antigen receptor or TcR. In some alternatives, the first marker protein co-expressed with the first chimeric antigen receptor is EGFRt and the second marker protein co-expressed with the second chimeric antigen receptor or TcR is Her2tg or first marker protein co-expressed with the first chimeric antigen receptor is Her2tg and the second marker protein co-expressed with the second chimeric antigen receptor or TcR is EGFRt. In some alternatives, the cell further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the cell expresses a soluble protein for therapy. In some alternatives, the soluble protein is a homeostatic cytokine, wherein the homeostatic cytokine is IL2, IL7, IL12 or IL15. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+ T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the first chimeric antigen receptor is specific for a ligand on a B cell, wherein the ligand on the B cell is CD19, and wherein the second chimeric antigen receptor is specific for L1CAM, and wherein the chimeric antigen receptors further comprises a 4-1 BB and CD3-zeta signaling domain. In some alternatives, the first chimeric antigen receptor is specific for a ligand on a B cell, wherein the ligand on the B cell is CD19, and wherein the second chimeric antigen receptor is specific for ROR1, and wherein the chimeric antigen receptors further comprises a 4-1 BB and CD3-zeta signaling domain. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1 CAM. In some alternatives, the cancer antigen is ROR1. In some alternatives, the first and second binding domain comprises an antibody or portion thereof, a receptor ligand or mutant thereof, peptide, and/or polypeptide affinity molecule or binding partner. In some alternatives, the cell further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the cell expresses a soluble protein for therapy. In some alternatives, the soluble protein is a homeostatic cytokine, wherein the homeostatic cytokine is IL2, IL7, IL12 or IL15. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the first chimeric antigen receptor is specific for a ligand on a B cell, wherein the ligand on the B cell is CD19, and wherein the second chimeric antigen receptor is specific for L1 CAM, and wherein the chimeric antigen receptors further comprises a 4-1 BB and CD3-zeta signaling domain. In some alternatives, the first chimeric antigen receptor is specific for a ligand on a B cell, wherein the ligand on the B cell is CD19, and wherein the second chimeric antigen receptor is specific for ROR1, and wherein the chimeric antigen receptors further comprises a 4-1 BB and CD3-zeta signaling domain. In some alternatives, the first binding domain is specific for a ligand on a B cell, wherein the ligand on the B cell is CD19, and wherein the second binding domain is specific for L1CAM. In some alternatives, the first binding domain is specific for a ligand on a B cell, wherein the ligand on the B cell is CD19, and wherein the second binding domain is specific for ROR1. In some alternatives, the composition comprises any one or more of the cells of any of the alternatives described herein or the cells made by any one or more of the alternative methods described herein. In some alternatives, the composition comprises CD8+ T cytotoxic lymphocyte cells and/or CD4+ T helper lymphocyte cells, wherein the CD8+ T cytotoxic lymphocyte cells are selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells and, wherein the CD4+ T helper lymphocyte cells are selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the composition has a ratio of CD4+ T helper lymphocyte cells to CD8+ T lymphocytes of 1:10 to 10:1. In some alternatives, the ratio of CD4+ T helper lymphocyte cells to CD8+ T lymphocytes is 1:1. In some alternatives, the subject does not have a B-cell related disease. In some alternatives, the subject does not have B-cell lymphoma, Hodgkin's lymphomas, non-Hodgkins lymphomas, Diffuse large B cell lymphoma, Follicular lymphoma, marginal zone lymphoma, Mucosa-Associated Lymphatic Tissue lymphoma, small lymphocytic lymphoma, chronic lymphocytic leukemia, mantle cell lymphoma, Burkitt lymphoma, primary mediastinal (thymic) large B cell lymphoma, Lymphoplasmacytic lymphoma, Waldenstrom macroglobulinermia, Nodal marginal zone B cell lymphoa, splenic marginal zone lymphoma, intravascular large B cell lymphoma, Intravascular large B-cell lymphoma, Primary effusion lymphoma, Lymphomatoid granulomatosis, T cell/histiocyte-rich large B-cell lymphoma, Primary central nervous system lymphoma, Primary cutaneous diffuse large B-cell lymphoma (leg type), EBV positive diffuse large B-cell lymphoma of the elderly, Diffuse large B-cell lymphoma associated with inflammation, Intravascular large B-cell lymphoma, ALK-positive large B-cell lymphoma, ALK-positive large B-cell lymphoma, Plasmablastic lymphoma, Large B-cell lymphoma arising in HHV8-associated multicentric Castleman's disease, B-cell lymphoma, unclassifiable with features intermediate between diffuse large B-cell lymphoma and Burkitt lymphoma, B-cell lymphoma, unclassifiable with features intermediate between diffuse large B-cell lymphoma and classical Hodgkin lymphoma, or nodular lymphocyte predominant Hodgkin's lymphoma. In some alternatives, the disease is a cancer. In some alternatives, the disease is an infection, wherein the infection is a bacterial or viral infection. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the subject has refractory and relapsed neuroblastoma. In some alternatives, the subject is identified or selected to receive a non-B cell related disease therapy, anti-cancer therapy, anti-infection therapy, antibacterial therapy, anti-viral therapy, or anti-tumoral therapy. In some alternatives, the method further comprises measuring or evaluating an inhibition of said non-B cell related disease, cancer, infection, bacterial infection, viral infection, or tumor. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, during, or after introducing, providing, or administering any one or more of the cells of the alternatives described herein or the cells made by any one or more of the alternative methods described herein or the composition of any one of the alternatives described herein into the subject for therapy. In some alternatives, the composition comprises any one or more of the cells of any of the alternatives described herein or the cells made by any one or more of the methods of the alternatives described herein. In some alternatives, the composition comprises CD8+ T cytotoxic lymphocyte cells and/or CD4+ T helper lymphocyte cells, wherein the CD8+ T cytotoxic lymphocyte cells are selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells and, wherein the CD4+T helper lymphocyte cells are selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the composition has a ratio of CD4+ T helper lymphocyte cells to CD8+ T lymphocytes of 1:10 to 10:1. In some alternatives, the ratio of CD4+ T helper lymphocyte cells to CD8+ T lymphocytes is 1:1. In some alternatives, the cells or compositions are introduced, provided, or administered to said subject by adoptive cell transfer. In some alternatives, the method further comprises introducing, providing, or administering a drug that induces expression of a chimeric antigen receptor or TcR. In some alternatives, the drug is a steroid. In some alternatives, the drug is tamoxifen and/or its metabolites. In some alternatives, the subject is a mammalian species. In some alternatives, the subject is a cow, sheep, pig, horse, dog, cat, primate or a human. In some alternatives, the subject is human. In some alternatives, the subject is of pediatric age. In some alternatives, the method further comprises evaluating the subject for symptoms of cytokine storm or B-cell aplasia. In some alternatives, the method further comprises administering to the subject a prodrug. In some alternatives, the prodrug is Erbitux, Herceptin, Ganciclovir, FK506 or a chemical inducer of dimerization. In some alternatives, the subject is suffering from refractory and relapsed neuroblastoma and wherein the method comprises administering the cell of any one of the alternatives described herein.

BRIEF DESCRIPTION OF THE DRAWINGS

In addition to the features described above, additional features and variations will be readily apparent from the following descriptions of the drawings and exemplary alternatives. It is to be understood that these drawings depict typical alternatives, and are not intended to be limiting in scope.

FIG. 3A depicts H9 T cells were transduced with 3 ul of lentivirus containing the Her2t variant Her2t (CD28hinge), Her2t(IgG4hinge) or Her2tG (gly-ser linker). The transduced H9 cells were then cultured for 5 days and stained with biotinylated Herceptin (Herceptin-bio) and a streptavidin conjugated secondary fluorophore (SA-PE). Results demonstrate that the Her2t variant Her2tG displays the greatest ability to bind Herceptin, Her2t(IgG4hinge) with modest Herceptin binding and Her2t(CD28hinge) with the weakest Herceptin binding. FIG. 3B depicts A timeline for the isolation (D0), growth (D0-21), selection (D14 and D21) and expansion (REP—D21) of CD4+ and CD8+ primary T cells isolated from PBMCs as per FIG. 4. FIG. 3C depicts CD8+ T cells were transduced with two separate lentiviruses containing CD19CAR-T2A-Her2tG or CD20CAR-T2A-EGFRt at an MOI=1 for each lentivirus. Pre-selection CD8+ T cells were stained with Erbitux-APC, biotinylated-Herceptin and a streptavidin conjugated secondary fluorophore (SA-PE) seven days post transduction (D10 of culture), while Post-selection cells were stained on S1Sp1D12 (See FIG. 4) FIG. 3D depicts a western blot that indicates the proteins in the cells. Cell lysis for western blot analysis was carried out in RIPA buffer containing protease inhibitor cocktail. Cell lysates were analyzed by BCA assay (Pierce), equally loaded onto gels and western blots were probed with the primary antibody anti CD247 (CD3ζ) and the secondary IRDye 800CW conjugated goat anti-mouse antibody (LI-COR). Blots were imaged on the Odyssey Infrared Imaging System (LI-COR).

FIG. 5A depicts 4-hour chromium release assay showing CD19- and CD20-CAR T cell specificity against K562 target panel cells. CD8 Tcm were co-cultured with K562 target cells at a 30:1, 10:1, 3.3:1 or 1.1:1 ratio. Only the dual transduced T cells were able to target all antigen expressing K562 cells. The CD19CAR-T2A-Her2t and CD19CAR-T2A-EGFRt CD8 Tcm demonstrate similar lytic capacity. As shown representations are Mock (X), CD19CAR-Her2tG (square), CD19CAR-EGFTt (triangle), CD20CAR-EGFRt (diamond) and CD19CAR-Her2tG/CD20CAR-EGFRt (upside-down triangle) FIG. 5B depicts 24-hour cytokine release assay. CD8 Tcm were co-cultured with K562 target cells at a 2:1 T cell-to-target ratio for 24 hours and then the supernatant was analyzed for the presence of effector cytokines. CD19CAR-T2A-Her2t transduced CD8 Tcm produced a more diverse repertoire and higher levels of effector cytokines relative to CD19CAR-T2A-EGFRt transduced CD8 Tcm. The panels are the same as FIG. 5A and FIG. 5B (Left to right in the bar graphs: K562 CD19, K562 CD20 and K562 CD19/CD20).

FIG. 6A depicts even days post electroporation the Raji cells were subjected to negative selection using CD19 microbeads. Post-depletion of CD19+ cells the CD19− cells were clonally selected and expanded for downstream experiments. FIG. 6B and FIG. 6C depict 4 hour chromium release assays and bioplex assay using the same cells from FIG. 5. As shown representations are Mock (X), CD19CAR-Her2tG (square), CD19CAR-EGFTt (triangle), CD20CAR-EGFRt (diamond) and CD19CAR-Her2tG/CD20CAR-EGFRt (upside-down triangle). Against Raji parental and three Raji CRISPR clones. Shown in 6C clockwise, the top left graph are the Raji parental, Raji CRISPR (3), Raji CRISPR (15) and Raji CRISPR (27). The results on the bottom graph are results from left to right, mock, CD19CAR-Her2tG, CD19CAR-EGFRt, CD20CAR-EGFRt and CD19CAR-Her2tG/CD20CAR-EGFRt (For IL-2, IFN-γ and TNF-α). FIG. 6D depicts CD4+ chromium release assay.

FIG. 7 shows experimental results of NSG mice injected with $5e^6$ NSO-IL15 cells and then $10e^6$ Mock or CAR expressing T cells i.v. As shown in the top row, on Day 14 post T cell injection, mouse bone marrow was harvested and subjected to flow analysis. The top row gates live, singlets. The middle row gates CD8+×CD45+ cells. The bottom row looks at the CD45+ cell population and stains for the markers Her2tG and EGFRt. Results demonstrate that EGFRt and Her2tG can be used to efficiently track T cells in vivo. The panels in the middle row show cells gated for viable (93.6% lymphocytes), single (98.8%), and alive cells (99.9%). As shown are CD8 and CD45 staining from left to right: Mock, CD19CAR-T2A-Her2t, CD19CAR-T2A-EGFRt Tcm and CD19CAR-Her2tg/CD20CAR-EGFRt). At least $1\times10^7$ cells were recorded inside of the viable, single cell and alive gates. So although the CD45+ cells represent around 1% of the population, it is equivalent to $1\times10^5$ cells. The remaining cells are mouse bone marrow cells. Third row: Multisort purification of Her2t and EGFRt positive T cells. H9 cells ($5\times10^6$ parental, Her2t$^+$, EGFRt$^+$, or Her2t$^+$/EGFRt$^+$) were mixed together and then subjected to purification. The cells were initially purified based on biotinylated Herceptin and anti-biotin multisort beads. The multisort beads were then removed and the positive fraction subsequently subjected to purification based on Erbitux-APC and anti-APC microbeads. The final positive fraction was dual positive for Her2t and EGFRt. D) Chromium Release Assays

DEFINITIONS

Figure 1:
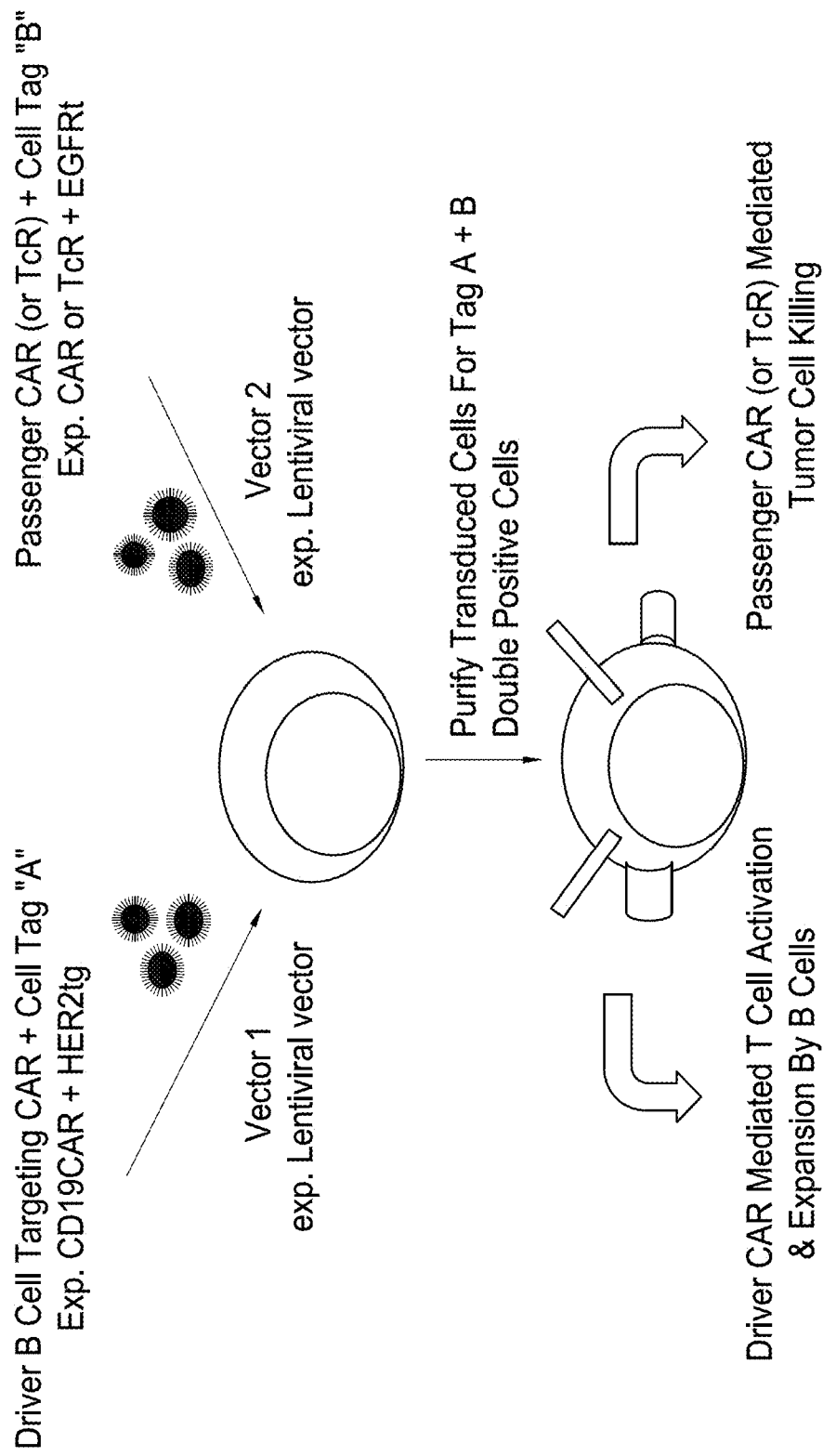
FIG. 1 shows a T-cell expressing a "driver" B cell targeting chimeric antigen receptor (CAR) that is co-expressed with a "passenger" CAR that is directed to a tumor cell.

The following definitions are provided to facilitate understanding of the alternatives or alternatives of the invention.

As used herein, "a" or "an" can mean one or more than one.

As used herein, the term "about" indicates that a value includes the inherent variation of error for the method being employed to determine a value, or the variation that exists among experiments.

"Chimeric antigen receptors" (CARs), as described herein, refers to genetically engineered protein receptors, which can confer specificity onto an immune effector cell, such as for example, a T-cell. Without being limiting, the use of CAR bearing T-cells can promote in vivo expansion and activation. The CARs can also be designed to redirect T-cells to target cells that express specific cell-surface antigens, where they can activate lymphocytes, such as T-cells, upon target recognition. The CARs graft the specificity of a monoclonal antibody or binding fragment thereof or scFv onto a T-cell, with the transfer of their coding sequence facilitated by vectors. In order to use CARs as a therapy for a subject in need, a technique called adoptive cell transfer is used in which T-cells are removed from a subject and modified so that they can express the CARs that are specific for an antigen. The T-cells, which can then recognize and target an antigen, are reintroduced into the patient. In some alternatives, CAR expressing lymphocytes are described, wherein the CAR expressing lymphocyte can be delivered to a subject to target specific cells. In some alternatives, the lymphocyte can express two CARs for bi-specificity. In some alternatives, the lymphocyte can express a CAR and a specific T-cell receptor (TcR) for bi-specificity. A TcR is a molecule on the surface of T lymphocytes or T-cells that can recognize antigens. In some alternatives, the lymphocyte can express a bi-specific CAR for bi-specificity, wherein the bi-specific CAR comprises a first domain for binding a B-cell specific ligand, and a second domain for binding a tumor specific ligand on a tumor that is a non-B cell specific cancer. In some alternatives, the cancer is not a B-cell malignancy. As described herein, the B-cell specific CAR promotes in vivo expansion and activation of effector cells.

The structure of the CAR can comprise fusions of single-chain variable fragments (scFv) that are derived from monoclonal antibodies that are attached to transmembrane and cytoplasmic signaling domains. Most CARs can include an extracellular scFv that is linked to an intracellular CD3ζ domain (first generation CAR). Additionally, the scFv can be linked to a co-stimulatory domain, which can increase their efficacy in the therapy of a subject in need (second generation CAR). When T-cells express this molecule they can recognize and kill target cells that express a specific antigen targeted by the CAR.

In some alternatives, a CAR directed against CD19 comprises an amino acid sequence set forth in SEQ ID NO: 11 and is encoded by a nucleic acid sequence set forth in SEQ ID NO: 12

In some alternatives, a CAR directed against CD20 comprises an amino acid sequence set forth in SEQ ID NO: 13 and is encoded by a nucleic acid sequence set forth in SEQ ID NO: 14.

In some alternatives, a CAR directed against CE7 comprises an amino acid sequence set forth in SEQ ID NO: 15 and is encoded by a nucleic acid sequence set forth in SEQ ID NO: 16.

In some alternatives, a CAR directed against ROR1 comprises an amino acid sequence set forth in SEQ ID NO: 17 and is encoded by a nucleic acid sequence set forth in SEQ ID NO: 18.

In some alternatives, a CAR directed against EGFR 806 comprises an amino acid sequence set forth in SEQ ID NO: 19 and is encoded by a nucleic acid sequence set forth in SEQ ID NO: 20.

In some alternatives, a CAR directed against Her2 comprises an amino acid sequence set forth in SEQ ID NO: 21 and is encoded by a nucleic acid sequence set forth in SEQ ID NO: 22.

In some alternatives, a CAR directed against GD2 comprises an amino acid sequence set forth in SEQ ID NO: 23 and is encoded by a nucleic acid sequence set forth in SEQ ID NO: 24.

In some alternatives, a CAR directed against EphA2 comprises an amino acid sequence set forth in SEQ ID NO: 25 and is encoded by a nucleic acid sequence set forth in SEQ ID NO: 26.

In some alternatives, a CAR directed against EphA2 comprises an amino acid sequence set forth in SEQ ID NO: 27 and is encoded by a nucleic acid sequence set forth in SEQ ID NO: 28.

In some alternatives, the polynucleotide encoding the chimeric antigen receptor comprises a sequence encoding a GMCSF signal sequence. In some alternatives, the GMCSF signal sequence signal sequence comprises an amino acid sequence set forth in SEQ ID NO: 29 and is encoded by a nucleic acid sequence set forth in SEQ ID NO: 30.

In some alternatives, the polynucleotide encoding the chimeric antigen receptor comprises a sequence encoding a signal sequence. In some alternatives, the signal sequence signal sequence comprises an amino acid sequence set forth in SEQ ID NO: 31 and is encoded by a nucleic acid sequence set forth in SEQ ID NO: 32. In some alternatives, the polynucleotide encodes a scFv specific for CD20.

"EGFR 806," as described herein, is a conformational epitope of wild type EGFR.

The chimeric antigen receptor can comprise a binding portion that is specific for a ligand. Without being limiting, the binding portion can comprise an antibody or binding fragment thereof or scFv, a receptor ligand or mutants thereof, peptide, and/or polypeptide affinity molecule or binding partner. In some alternatives of the first chimeric antigen receptor, the first chimeric antigen receptor comprises a binding portion, wherein the binding portion comprises an antibody or binding fragment thereof or scFv, a receptor ligand or mutants thereof, peptide, and/or polypeptide affinity molecule or binding partner. In some alternatives, the binding portion is specific for a ligand on a B-cell. In some alternatives of the second chimeric antigen receptor, the second chimeric antigen receptor comprises a binding portion, wherein the binding portion comprises an antibody or binding fragment thereof or scFv, a receptor ligand or mutants thereof, peptide, and/or polypeptide affinity molecule or binding partner. In some alternatives, the binding portion is specific for a ligand on a tumor cell. In some alternatives, the tumor is not a tumor of a B-cell related cancer. As shown in FIG. 1, vectors for the B-cell targeting CAR (Driver) and the tumor targeting CAR (Passenger) are delivered by two separate lentiviral vectors. Cells that contain the specific markers co-expressed with the two CARs are then purified and used for therapy.

Figure 2:
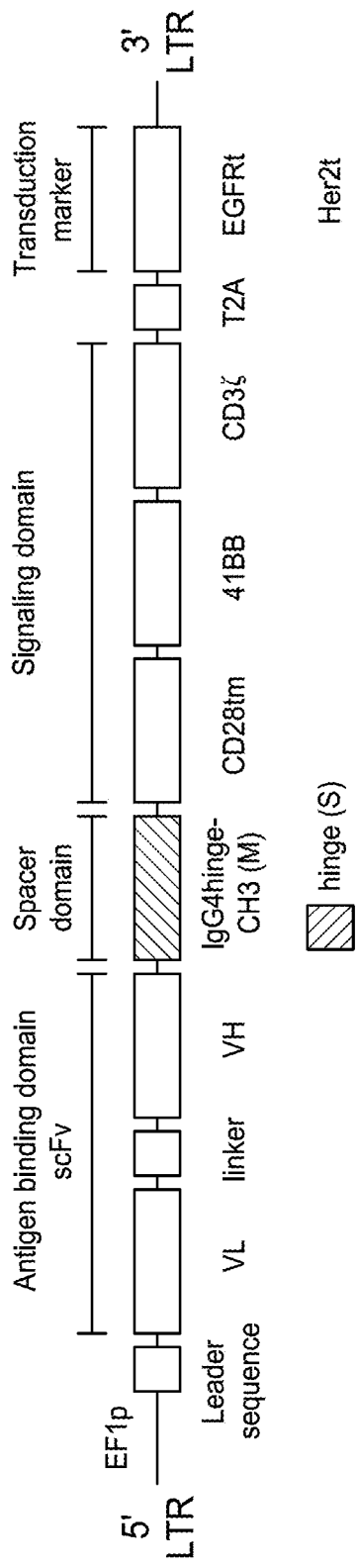
FIG. 2 shows a schematic of the primary sequence of a CAR described in the alternatives herein. As shown, the sequence encoding the CAR comprises a leader sequence (such as a sequence for targeting the protein to the cell surface), an antigen binding domain (variable light chain and variable heavy chain sequence of an immunoglobulin and a linker, a spacer domain (IgG4 hinge CH3 region, a signaling domain (CD28 transmembrane region, 4-1BB domain, CD3 zeta), a T2A ribosome skip sequence, and a transduction marker (EGFRt or Her2tg marker).
Figure 3A:
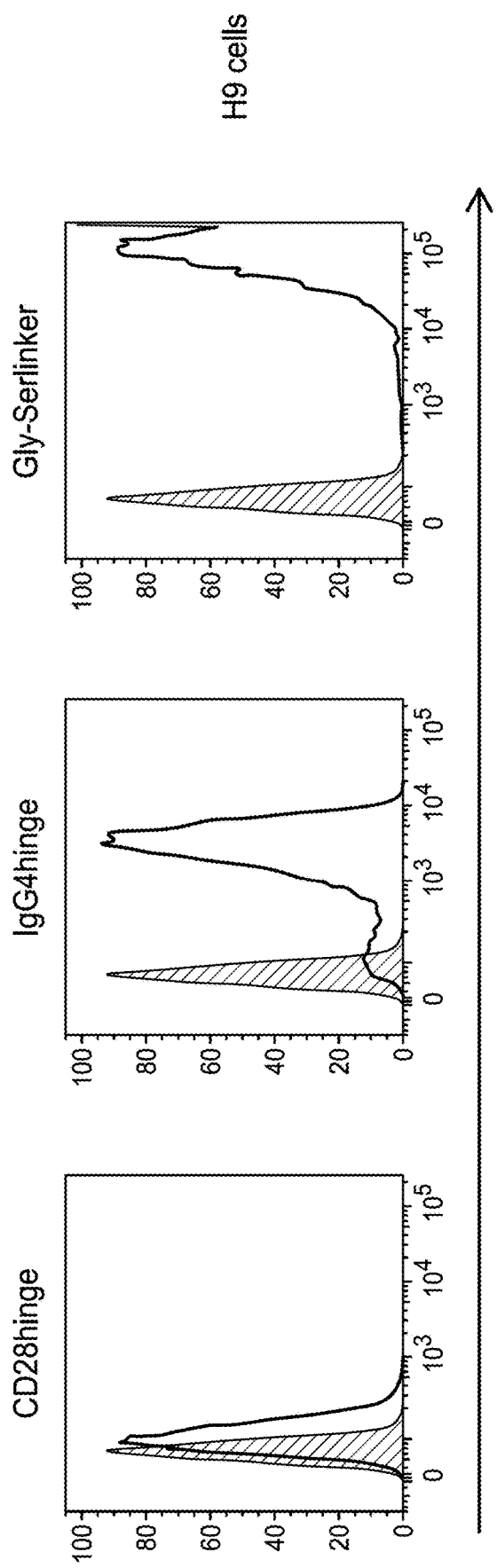
FIGS. 3A-3D show the marker Her2t and its variants that demonstrate variable binding affinity to Herceptin based on their respective linker. The CARs used were dual CD19CAR-T2A-Her2tG/CD20CAR-T2A-EGFRt in the T-lymphocytes.
Figure 3B:
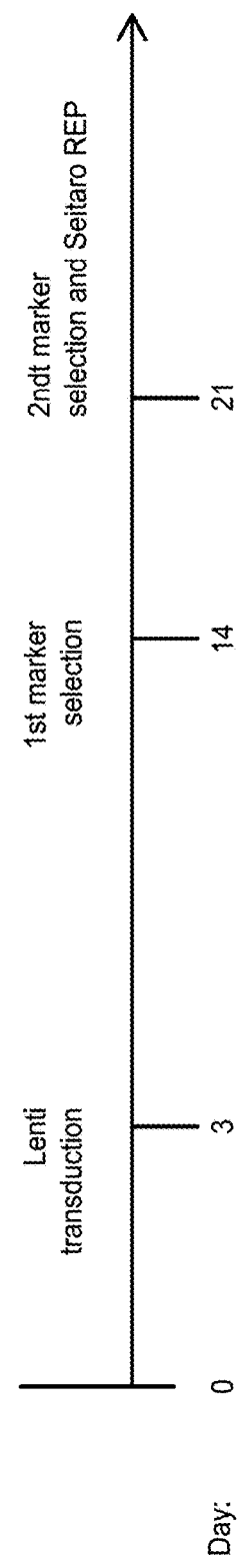
Figure 3C:
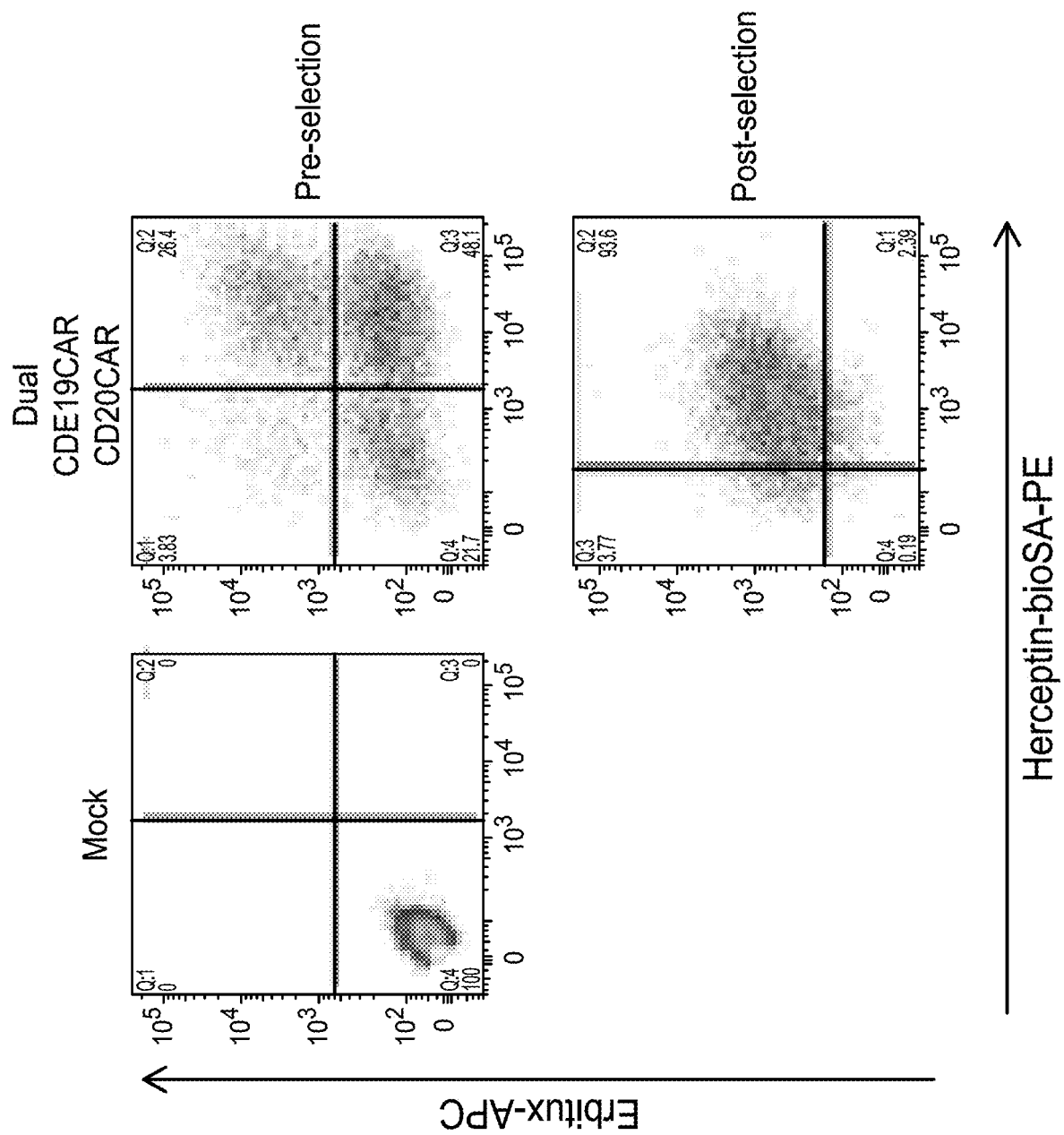
Figure 3D:
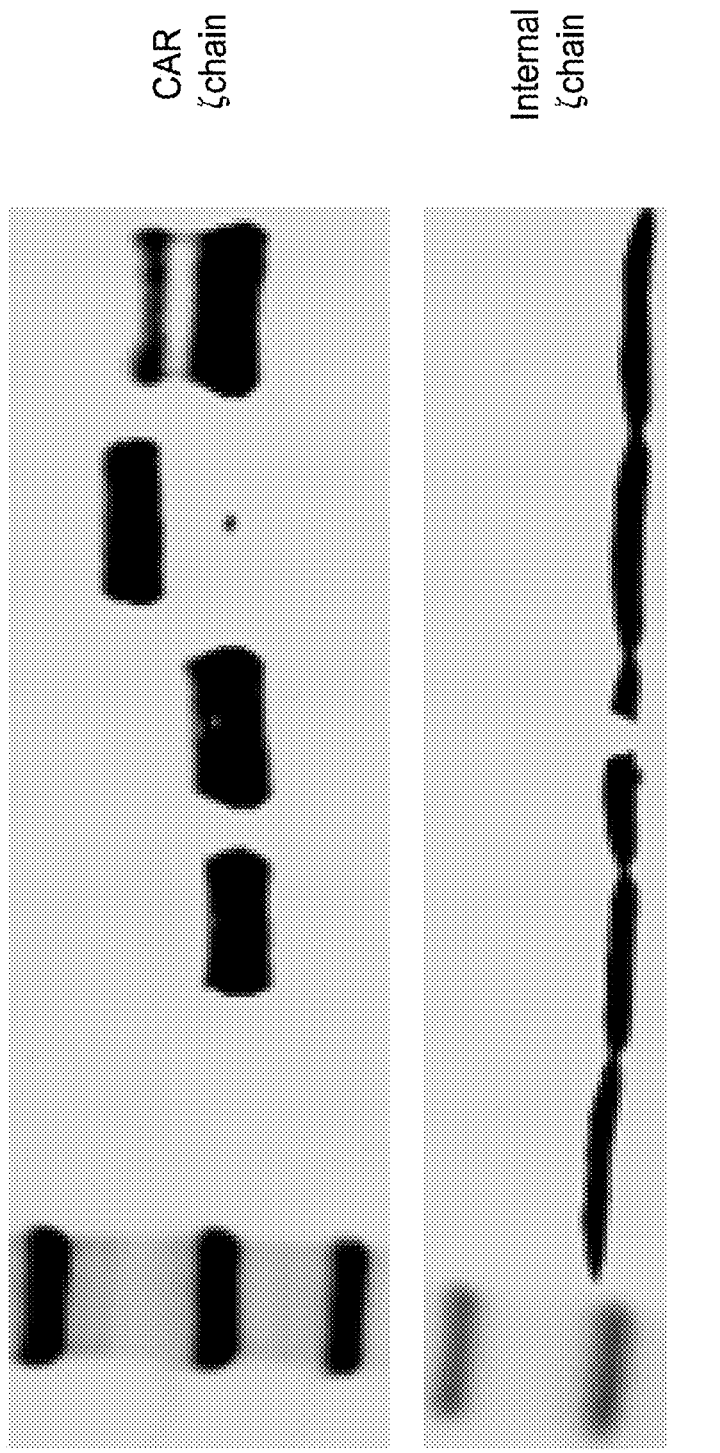

As shown in FIG. 2 is the schematic of the primary sequence of a CAR described in the alternatives herein. The CAR comprises a leader sequence, an antigen binding domain (variable light chain and variable heavy chain sequence of an immunoglobulin and a linker, a spacer domain (IgG4 hinge CH3 region, a signaling domain (CD28 transmembrane region, 4-1BB domain, CD3 zeta), a T2A ribosome skip sequence, and a transduction marker (EGFRt or Her2tg marker). CAR bearing T-cells described herein, in several alternatives are CD19CAR-T2A-Her2tG, CD19CAR-T2A-EGFRt, CD20CAR-T2A-EGFRt, or CD19CAR-T2A-Her2tG/CD20CAR-T2A-EGFRt.

"Co-stimulation" as described herein, refers to the activation of lymphocytes. In some alternatives of the chimeric antigen receptor, the chimeric antigen receptor comprises an endodomain, wherein the endodomain comprises co-stimulatory domains for co-stimulatory signaling. In some alternatives, the co-stimulatory domains comprise a transmembrane CD28 domain, 4-1BB domain and/or a CD3zeta domain. In some alternatives, the transmembrane CD28 domain comprises the amino acid sequence set forth in SEQ ID NO: 5; M F W V L V V V G G V L A C Y S L L V T V A F I I F W V). In some alternatives, the transmembrane CD28 domain is encoded by the acid sequence set forth in SEQ ID NO: 6 (SEQ ID NO: 6; ATGTTCTG-GGTGCTGGTGGTCGGAGGCGTGCTGGCCTGC-TACAGCCTGCTGGTCACCGTGGCCTTCATCATCTT- TTGGGTG). In some alternatives, the 4-1BB domain comprises the amino acid sequence set forth in SEQ ID NO: 7 (SEQ ID NO: 7; K R G R K K L L Y I F K Q P F M R P V Q T T Q E E D G C S C R F P E E E E G G C E L R V K). In some alternatives, the 4-1BB domain is encoded by the nucleic acid sequence set forth in SEQ ID NO: 8 (SEQ ID NO: 8; AAACGGGGCAGAAAGAAACTCCTGTATATATT-CAAACAACCATTTATGAGACCA GTACAAACTACT-CAAGAGGAAGATGGCTGTAGCTGCCGAT-TTCCAGAAGAAGAA GAAGGAGGATGTGAACTGCGGGTGAAG). In some alternatives, the CD3-zeta domain comprises the amino acid sequence set forth in SEQ ID NO: 9 (SEQ ID NO: 9; F S R S A D A P A Y Q Q G Q N Q L Y N E L N L G R R E E Y D V L D K R R G R D P E M G G K P R R K N P Q E G L Y N E L Q K D K M A E A Y S E I G M K G E R R R G K G H D G L Y Q G L S T A T K D T Y D A L H M Q A L P P R). In some alternatives, the CD3-zeta domain is encoded by the nucleic acid sequence set forth in SEQ ID NO: 10 (SEQ ID NO: 10; TTCAGCAGAAGCGCCGACGCCCCTGCC-TACCAGCAGGGCCAGAATCAGCTGT ACAACGAGCTGAACCTGGGCAGAAGG-GAAGAGTACGACGTCCTGGATAAGCGG AGAGGCCGGGACCCT-GAGATGGGCGGCAAGCCTCGGCG-GAAGAACCCCCAGGA AGGCCTGTATAACGAACTGCAGAAAGACAA-GATGGCCGAGGCCTACAGCGAGA TCGGCAT-GAAGGGCGAGCGGAGGCGGGGCAAGGGC-CACGACGGCCTGTATCAG GGCCTGTCCACCGCCACCAAGGATACC-TACGACGCCCTGCACATGCAGGCCCTG CCCC-CAAGG).

"Ligand" as described herein, refers to a substance that can form a complex with a biomolecule. By way of example and not of limitation, ligands can include substrates, proteins, small molecules, inhibitors, activators, nucleic acids and neurotransmitters. Binding can occur through intermolecular forces, for example ionic bonds, hydrogen bonds, and van der walls interactions. Ligand binding to a receptor protein can alter the three dimensional structure and determine its functional state. The strength of binding of a ligand is referred to as the binding affinity and can be determined by direct interactions and solvent effects. A ligand can be bound by a "ligand binding domain." A ligand binding domain, for example, can refer to a conserved sequence in a structure that can bind a specific ligand or a specific epitope on a protein. The ligand binding domain or ligand binding portion can comprise an antibody or binding fragment thereof or scFv, a receptor ligand or mutants thereof, peptide, and/or polypeptide affinity molecule or binding partner. Without being limiting, a ligand binding domain can be a specific protein domain or an epitope on a protein that is specific for a ligand or ligands.

A "B-cell ligand" or a "B-cell antigen" as described herein, refers to a target antigen that is expressed in a B-cell or B-cell surface of a subject, in which the subject or patient does not have a B-cell related disease. In some alternatives, the subject does not have a B cell related disease. In some alternatives, the subject does not have a B-cell related disease and/or is being treated for a solid tumor. Without being limiting, examples of B-cell related diseases can include B-cell lymphoma, Hodgkin's lymphomas, non-Hodgkins lymphomas, Diffuse large B cell lymphoma, Follicular lymphoma, marginal zone lymphoma, Mucosa-Associated Lymphatic Tissue lymphoma, small lymphocytic lymphoma, chronic lymphocytic leukemia, mantle cell lymphoma, Burkitt lymphoma, primary mediastinal (thymic) large B cell lymphoma, Lymphoplasmacytic lymphoma, Waldenstrom macroglobulinermia, Nodal marginal zone B cell lymphoa, splenic marginal zone lymphoma, intravascular large B cell lymphoma, Intravascular large B-cell lymphoma, Primary effusion lymphoma, Lymphomatoid granulomatosis, T cell/histiocyte-rich large B-cell lymphoma, Primary central nervous system lymphoma, Primary cutaneous diffuse large B-cell lymphoma (leg type), EBV positive diffuse large B-cell lymphoma of the elderly, Diffuse large B-cell lymphoma associated with inflammation, Intravascular large B-cell lymphoma, ALK-positive large B-cell lymphoma, ALK-positive large B-cell lymphoma, Plasmablastic lymphoma, Large B-cell lymphoma arising in HHV8-associated multicentric Castleman's disease, B-cell lymphoma, unclassifiable with features intermediate between diffuse large B-cell lymphoma and Burkitt lymphoma, B-cell lymphoma, unclassifiable with features intermediate between diffuse large B-cell lymphoma and classical Hodgkin lymphoma, and nodular lymphocyte predominant Hodgkin's lymphoma. In some alternatives, the patient does not have a B-cell related disease. In some alternatives, the patient does not have B-cell lymphoma, Hodgkin's lymphomas, non-Hodgkins lymphomas, Diffuse large B cell lymphoma, Follicular lymphoma, marginal zone lymphoma, Mucosa-Associated Lymphatic Tissue lymphoma, small lymphocytic lymphoma, chronic lymphocytic leukemia, mantle cell lymphoma, Burkitt lymphoma, primary mediastinal (thymic) large B cell lymphoma, Lymphoplasmacytic lymphoma, Waldenstrom macroglobulinermia, Nodal marginal zone B cell lymphoa, splenic marginal zone lymphoma, intravascular large B cell lymphoma, Intravascular large B-cell lymphoma, Primary effusion lymphoma, Lymphomatoid granulomatosis, T cell/histiocyte-rich large B-cell lymphoma, Primary central nervous system lymphoma, Primary cutaneous diffuse large B-cell lymphoma (leg type), EBV positive diffuse large B-cell lymphoma of the elderly, Diffuse large B-cell lymphoma associated with inflammation, Intravascular large B-cell lymphoma, ALK-positive large B-cell lymphoma, ALK-positive large B-cell lymphoma, Plasmablastic lymphoma, Large B-cell lymphoma arising in HHV8-associated multicentric Castleman's disease, B-cell lymphoma, unclassifiable with features intermediate between diffuse large B-cell lymphoma and Burkitt lymphoma, B-cell lymphoma, unclassifiable with features intermediate between diffuse large B-cell lymphoma and classical Hodgkin lymphoma, or nodular lymphocyte predominant Hodgkin's lymphoma.

Although rare, lymphomas can also transform into a malignant tumor or mass and metastasize or spread to other organs that are not in the lymphatic system. In this case, a patient has B-cell lymphoma and a solid tumor. Furthermore, patients with B-cell diseases, such as systemic lupus erythematosus and rheumatoid arthritis, are also susceptible to cancers such as solid tumors, for example. In some alternatives, the subject does not have a B-cell disease and/or is being treated for a cancer. In some alternatives, the cancer is a solid tumor.

In some alternatives, the ligand binding domain is an antibody, or a portion thereof. In some alternatives, the ligand binding domain is an antibody or binding fragment thereof or scFv, a receptor ligand or mutants thereof, peptide, and/or polypeptide affinity molecule or binding partner. In some alternatives, the ligand binding domain is an scFv. In some alternatives described herein, a ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148 or EMMPRIN/CD147. In some alternatives described herein, a ligand on a B-cell is B-cell specific.

"B-cells" as described herein refers to a type of lymphocyte in the humoral immunity of the adaptive immune system. B cells can be distinguished from other lymphocytes, such as T-cells and natural killer cells (NK cells), by the presence of a protein on the B cell's outer surface known as a B cell receptor (BCR). This specialized receptor protein allows a B cell to bind to a specific antigen. In mammals, immature B cells are formed in the bone marrow. The principal functions of B cells are to make antibodies in response to antigens, to perform the role of antigen-presenting cells (APCs), and to develop into memory B cells after activation by antigen interaction. B cells also release cytokines used for signaling immune regulatory functions. B cells have a short-life span and undergo apoptosis when the inciting agent that induced immune response is eliminated. This occurs because of cessation of continuous exposure to various colony-stimulating factors, which is required for survival. In some alternatives described herein, a chimeric antigen receptor is provided, wherein the chimeric antigen receptor is specific for a ligand on a B cell, which promotes the in vivo expansion and activation of an effector cell. In some alternatives, binding of the B-cell ligand leads to the release of cytokines. In some alternatives described herein, a bi-specific chimeric antigen receptor is provided, wherein the bi-specific chimeric antigen receptor comprises two binding domains, wherein a first binding domain is specific for a ligand on a B cell, which promotes the in vivo expansion and activation of the B cell and a second binding domain is specific for a ligand on a tumor. In some alternatives, the chimeric antigen receptor is specific for a B-cell ligand, wherein the chimeric antigen receptor is specific for CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148 or EMMPRIN/CD147. In some alternatives, the first binding domain on the bi-specific chimeric antigen receptor is specific for CD1 d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, EMMPRIN/CD147 and/or tumor targets that are non-B cell tumors. In some alternatives, the first and second binding domain comprises an antibody or portion thereof, a receptor ligand or mutant version thereof, peptide, and/or polypeptide affinity molecule or binding partner.

In some alternatives, binding of a chimeric antigen receptor to a B-cell ligand elicits a cytokine response and supports T-cell expansion.

In some alternatives, a chimeric antigen receptor is provided, wherein the ligand or target molecule is a cell surface molecule that is found on tumor cells and is not substantially found on normal tissues, or restricted in its expression to non-vital normal tissues. In some alternatives, the tumor does not originate from a B-cell related cancer. In some alternatives, the ligand or target molecule is found on a tumor cell as well as on normal tissues. In some alternatives the cells expressing a CAR that is specific for a ligand on tumor cells and normal tissue further comprises a suicide gene to limit the time of therapy and increase their safety profile. Conditional suicide genes may also be applied to the donor T-cells to limit the attack on normal tissue that may express a tumor associated antigen or ligand.

"Effector cells" as described herein, refers to a lymphocyte that has been induced to differentiate into another cell type that can be capable of mounting a specific immune response, such as a terminally differentiated leukocyte that performs one or more specific functions. The main effector cells of the immune system, for example, are activated lymphocytes and phagocytes that are involved in destroying pathogens and removing them from the body. The effector cells can include large granular lymphocytes, such as, for example, natural killer cells and cytotoxic T lymphocytes. In some alternatives of the cells provided herein, the cell comprises a first and second chimeric antigen receptor, wherein the first chimeric antigen receptor is specific for a ligand on a B cell, which promotes the in vivo expansion and activation of an effector cell and, wherein the second chimeric antigen receptor is specific for a ligand on a tumor. In some alternatives, the cells that undergo expansion and activation are lymphocytes, phagocytes, large granular lymphocytes, natural killer cells and/or cytotoxic T lymphocytes.

"Cancer antigen," "tumor antigen" or "tumor marker" refers to an antigenic substance that is produced in a tumor cell, which can therefore trigger an immune response in the host. These cancer antigens can be useful as markers for identifying a tumor cell, which will be a potential candidate during treatment or therapy. There are several types of cancer or tumor antigens. There are tumor specific antigens (TSA) which are present only on tumor cells and not on healthy cells, as well as tumor associated antigens (TAA) which are present in tumor cells and also on some normal cells. In some alternatives of the methods and chimeric antigens provided herein, the chimeric antigen receptors are specific for tumor specific antigens. In some alternatives, the chimeric antigen receptors are specific for tumor associated antigens. In some alternatives described herein, the tumor does not originate from a B-cell related cancer. In some alternatives, cells expressing a CAR that is specific for a TAA is further modified by the introduction of a suicide gene to limit the time of the CAR T-cell therapy and to reduce the attack of normal tissues expressing the TAA.

In some alternatives of the methods provided herein, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cell surface tumor specific molecule is ROR1. In some alternatives, the cancer antigen is expressed by a tumor, wherein the tumor is not a B-cell related cancer.

"Specific" or "Specificity" can refer to the characteristic of a ligand for the binding partner or alternatively, the binding partner for the ligand, and can include complementary shape, charge and hydrophobic specificity for binding. Specificity for binding can include stereospecificity, regioselectivity and chemoselectivity. In some alternatives, a chimeric antigen receptor is provided, wherein the chimeric antigen receptor is specific for a B-cell ligand. In some alternatives, a chimeric antigen receptor is provided, wherein the chimeric antigen receptor is specific for a tumor cell ligand.

"CE7" as described herein is an epitope on L1CAM.

In some alternatives, the lymphocyte can express a CAR and a specific T-cell receptor (TcR) for bi-specificity. In some alternatives, the specific T-cell receptor is specific for EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, ROR1 or NY-ESO-1.

"Inducibly expressed" or "inducible expression" refers to the initiation or increase in the production of a protein at the level of genetic transcription. Induction of a protein can occur if a gene encoding a protein of interest is under the control of a promoter. As used herein, a promoter can be constitutively active, repressible or inducible. If a promoter is an inducible promoter, then the rate of transcription increases in response to an inducing agent. In contrast, the rate of transcription is not regulated by an inducing agent if the promoter is a constitutive promoter. Repressible promoters are also known. In some alternatives described herein, the first chimeric antigen receptor and/or the second chimeric antigen receptor or TcR are inducibly expressed in said cell. In some alternatives, expression of the first chimeric antigen receptor and/or the second chimeric antigen receptor or TcR is under the control of a regulatory element. In some alternatives the repressible systems are controlled by a Tet-On/Off system using doxycycline. In some alternatives, the repressible systems are controlled by tamoxifen. In some alternatives, the expressible systems are controlled by riboswitch/small molecule mRNA regulation. In some alternatives, the expressible system is controlled by a riboswitch, shRNA or microRNA.

A "regulatory element" as described herein, can refer to a regulatory sequence, which is any DNA sequence that is responsible for the regulation of gene expression, such as promoters and operators. The regulatory element can be a segment of a nucleic acid molecule which is capable of increasing or decreasing the expression of specific genes within an organism. In some alternatives described herein, a cell is provided, wherein the cell comprises a first and second chimeric antigen receptor or TcR, wherein the first chimeric antigen receptor is specific for a ligand on a B cell, which promotes the in vivo expansion and activation of an effector cell and, wherein the second chimeric antigen receptor or TcR is specific for a ligand on a tumor. In some alternatives, the first chimeric antigen receptor and/or the second chimeric antigen receptor or TcR are inducibly expressed in said cell. In some alternatives, expression of the first chimeric antigen receptor and/or the second chimeric antigen receptor or TcR is under the control of a regulatory element.

"Transmembrane domain" as described herein is an integral protein that can span a cellular membrane.

A "promoter" is a nucleotide sequence that directs the transcription of a structural gene. In some alternatives, a promoter is located in the 5' non-coding region of a gene, proximal to the transcriptional start site of a structural gene. Sequence elements within promoters that function in the initiation of transcription are often characterized by consensus nucleotide sequences. Without being limiting, these promoter elements can include RNA polymerase binding sites, TATA sequences, CAAT sequences, differentiation-specific elements (DSEs; McGehee et al., Mol. Endocrinol. 7:551 (1993); incorporated by reference in its entirety), cyclic AMP response elements (CREs), serum response elements (SREs; Treisman, Seminars in Cancer Biol. 1:47 (1990); incorporated by reference in its entirety), glucocorticoid response elements (GREs), and binding sites for other transcription factors, such as CRE/ATF (O'Reilly et al., J. Biol. Chem. 267:19938 (1992); incorporated by reference in its entirety), AP2 (Ye et al., J. Biol. Chem. 269:25728 (1994); incorporated by reference in its entirety), SP1, cAMP response element binding protein (CREB; Loeken, Gene Expr. 3:253 (1993); incorporated by reference in its entirety) and octamer factors (see, in general, Watson et al., eds., Molecular Biology of the Gene, 4th ed. (The Benjamin/Cummings Publishing Company, Inc. 1987; incorporated by reference in its entirety)), and Lemaigre and Rousseau, Biochem. J. 303:1 (1994); incorporated by reference in its entirety). As used herein, a promoter can be constitutively active, repressible or inducible. If a promoter is an inducible promoter, then the rate of transcription increases in response to an inducing agent. In contrast, the rate of transcription is not regulated by an inducing agent if the promoter is a constitutive promoter. Repressible promoters are also known. In some alternatives of the nucleic acid is provided, the nucleic acid comprises a promoter sequence. In some alternatives of the chimeric antigen, the chimeric antigen is inducibly expressed in response to an inducing agent. In some alternatives, the TcR is inducibly expressed in response to an inducing agent.

In some alternatives, promoters used herein can be inducible or constitutive promoters. Without being limiting, inducible promoters can include, for example, a tamoxifen inducible promoter, tetracycline inducible promoter, and doxocycline inducible promoter (e.g. tre) promoter. Constitutive promoters can include, for example, SV40, CMV, UBC, EFlalpha, PGK, and CAGG. In some alternatives, the regulatory is a promoter. In some alternatives, the promoter is a tamoxifen inducible promoter, a tetracycline inducible promoter, or a doxocycline inducible promoter (e.g. tre) promoter. In some alternatives provided herein, expression of a chimeric antigen receptor or a TcR on a cell is induced by tamoxifen and/or its metabolites. Metabolites for tamoxifen are active metabolites such as 4-hyroxytamoxifen (afimoxifene) and N-desmethyl-4-hydroxytamoxifen (endoxifen), which can have 30-100 times more affinity with an estrogen receptor than tamoxifen itself. In some alternatives, the tamoxifen metabolites are 4-hyroxytamoxifen (afimoxifene) and/or N-desmethyl-4-hydroxytamoxifen (endoxifen). In some alternatives, vectors are provided wherein the vector has a first promoter for the CAR/TcR and a second promoter for the marker protein.

An "antibody" as described herein, refers to a large Y-shape protein produced by plasma cells that is used by the immune system to identify and neutralize foreign objects such as bacteria and viruses. The antibody protein can comprise four polypeptide chains; two identical heavy chains and two identical light chains connected by disulfide bonds. Each chain is composed of structural domains called immunoglobulin domains. These domains can contain about 70, 80, 90, 100, 110, 120, 130, 140, 150 amino acids or any number of amino acids in between in a range defined by any two of these values, and are classified into different categories according to their size and function. In some alternatives, the ligand binding domain comprises an antibody or binding fragment thereof or scFv, a receptor ligand or mutants thereof, peptide, and/or polypeptide affinity molecule or binding partner. In some alternatives, the ligand binding domain is an antibody fragment, desirably, a binding portion thereof. In some alternatives, the antibody fragment or binding portion thereof present on a CAR is specific for a ligand on a B-cell. In some alternatives, the antibody fragment or binding portion thereof present on a CAR or TcR is specific for a ligand on a tumor cell. In some alternatives, the tumor is not derived from a B-cell related cancer. In some alternatives, the antibody fragment or binding portion thereof present on a CAR is specific for a ligand present on a tumor cell. In some alternatives, the ligand binding domain is an antibody fragment or a binding portion thereof, such as a single chain variable fragment (scFv). In some alternatives, the ligand comprises a tumor specific mutation. In some alternatives, the antibody fragment or binding portion thereof present on a CAR comprises one or more domains from a humanized antibody, or binding portion thereof.

"ScFv" as described herein, is a fusion protein of the variable regions of the heavy (VH) and light chains (VL) of immunoglobulins, connected with a short linker peptide of ten to about 25 amino acids. In some alternatives, a CAR is provided, wherein the CAR comprises a ScFv specific for a cell surface tumor molecule. In some alternatives, the chimeric antigen receptor comprises a scFV specific for CD19. In some alternatives, the scFV specific for CD19 comprises an amino acid sequence set forth in SEQ ID NO: 11 and is encoded by a nucleic acid sequence set forth in SEQ ID NO: 12. In some alternatives, the chimeric antigen receptor comprises a scFV specific for CD20. In some alternatives, the scFV specific for CD20 comprises an amino acid sequence set forth in SEQ ID NO: 13 and is encoded by a nucleic acid sequence set forth in SEQ ID NO: 14. In some alternatives, the chimeric antigen receptor comprises a scFV specific for CE7. In some alternatives, the scFV specific for CE7 comprises an amino acid sequence set forth in SEQ ID NO: 15 and is encoded by a nucleic acid sequence set forth in SEQ ID NO: 16. In some alternatives, the chimeric antigen receptor comprises a scFV specific for ROR1. In some alternatives, the scFV specific for ROR1 comprises an amino acid sequence set forth in SEQ ID NO: 17 and is encoded by a nucleic acid sequence set forth in SEQ ID NO: 18. In some alternatives, the chimeric antigen receptor comprises a scFV specific for EGFR 806. In some alternatives, the scFV specific for EGFR 806 comprises an amino acid sequence set forth in SEQ ID NO: 19 and is encoded by a nucleic acid sequence set forth in SEQ ID NO: 20. In some alternatives, the chimeric antigen receptor comprises a scFV specific for Her2. In some alternatives, the scFV specific for Her2 comprises an amino acid sequence set forth in SEQ ID NO: 21 and is encoded by a nucleic acid sequence set forth in SEQ ID NO: 22. In some alternatives, the chimeric antigen receptor comprises a scFV specific for GD2. In some alternatives, the scFV specific for GD2 comprises an amino acid sequence set forth in SEQ ID NO: 23 and is encoded by a nucleic acid sequence set forth in SEQ ID NO: 24. In some alternatives, the chimeric antigen receptor comprises a scFV specific for EphA2 (2H4). In some alternatives, the scFV specific for EphA2 (2H4) comprises an amino acid sequence set forth in SEQ ID NO: 25 and is encoded by a nucleic acid sequence set forth in SEQ ID NO: 26. In some alternatives, the chimeric antigen receptor comprises a scFV specific for EphA2 (4H5). In some alternatives, the scFV specific for EphA2 (4H5) comprises an amino acid sequence set forth in SEQ ID NO: 27 and is encoded by a nucleic acid sequence set forth in SEQ ID NO: 28.

"Marker domains" as described herein, refers to a protein that serves as a label for a cell. In some alternatives of the cells described herein, the cells co-express a marker protein for a specific chimeric antigen protein that is expressed. In some alternatives of the cells provided herein, the chimeric antigen receptor is co-expressed with a specific marker protein. In some alternatives of the cells provided herein, the cells comprise a nucleic acid encoding a chimeric antigen receptor. In some alternatives, the nucleic acid comprises a first nucleic acid comprising a sequence encoding a leader sequence, a second nucleic acid comprising a sequence encoding an antibody or binding fragment thereof or scFv, wherein the antibody or binding fragment thereof or scFv is specific for a B-cell specific cell surface molecule, and wherein the first nucleic acid is covalently attached to a 5' end of the second nucleic acid, a third nucleic acid comprising a sequence encoding a de-immunized extracellular spacer, wherein the third nucleic acid is covalently attached to a 3' end of the second nucleic acid, a fourth nucleic acid comprising a sequence encoding a transmembrane domain, wherein the fourth nucleic acid is covalently attached to a 3' end of the third nucleic acid, a fifth nucleic acid comprising a sequence encoding a signaling domain, wherein the signaling domain comprises a 4-1BB domain and/or CD3-zeta domain, and wherein the fifth nucleic acid is covalently attached to a 3' end of the fourth nucleic acid, a sixth nucleic acid comprising a sequence encoding a linker, wherein the sixth nucleic acid is covalently attached to a 3' end of the fifth nucleic acid and a seventh nucleic acid comprising a sequence encoding a marker domain, wherein the seventh nucleic acid is covalently attached to a 3' end of the sixth nucleic acid, thereby having said nucleic acid encoding a chimeric antigen receptor. In some alternatives, the linker is a ribosome skip sequence or an IRES sequence.

A "ribosome skip sequence" as described herein refers to a sequence that during translation, forces the ribosome to "skip" the ribosome skip sequence and translate the region after the ribosome skip sequence without formation of a peptide bond. Several viruses, for example, have ribosome skip sequences that allow sequential translation of several proteins on a single nucleic acid without having the proteins linked via a peptide bond. As described herein, this is the "linker" sequence. In some alternatives of the nucleic acids provided herein, the nucleic acids comprise a ribosome skip sequence between the sequence for the chimeric antigen receptor and the sequence of the marker protein, such that the proteins are co-expressed and not linked by a peptide bond. In some alternatives, the ribosome skip sequence is a P2A, T2A, E2A or F2A sequence. In some alternatives, the ribosome skip sequence is a T2A sequence. In some alternatives, the T2A sequence comprises the amino acid sequence set forth in SEQ ID NO: 33 and is encoded by a nucleic acid sequence set forth in SEQ ID NO: 34. In some alternatives the marker protein is a EGFRt protein. In some alternatives, the marker protein is a Her2tg protein. By placing the marker gene after the ribosome skip motif, the expressed marker protein will not be bound to the CAR but can be used in determining or purifying cells that express the CAR of interest. In some alternatives, the T-cell is identified for being a bi-specific T-cell by the determination of two marker proteins wherein the first marker protein is indicative of the presence of the B-cell specific CAR, and the second marker is indicative of the presence of the tumor specific CAR. Determination of the marker proteins can be performed by immunoselection, antibody binding to the marker protein and other methods of selection known to those skilled in the art.

In some alternatives the T2A sequence comprises an amino acid sequence set forth in SEQ ID NO: 33 and is encoded by a nucleic acid sequence set forth in SEQ ID NO: 34.

"Internal ribosome entry site (IRES)," as described herein, is a nucleotide sequence that allows for translation initiation in the middle of a messenger RNA (mRNA) sequence as part of the greater process of protein synthesis.

"Bi-specific chimeric antigen receptor" refers to a CAR that comprises two domains, wherein the first domain is specific for a first ligand, and wherein the second domain is specific for a second ligand. In some alternatives, the first ligand is a B-cell specific protein. In some alternatives, the second ligand is a tumor-specific ligand.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives, a nucleic acid encoding a chimeric antigen receptor is provided. In some alternatives, a method of making a nucleic acid encoding a chimeric antigen receptor is provided. In some alternatives, a nucleic acid encoding a chimeric antigen receptor specific for a ligand on a B cell is provided. In some alternatives, a nucleic acid encoding a chimeric antigen receptor specific for a ligand on a tumor cell is provided. In some alternatives the nucleic acid is a DNA encoding a chimeric antigen receptor. In some alternatives, the nucleic acid is an mRNA encoding a chimeric antigen receptor. In some alternatives, the chimeric antigen receptor is bi-specific.

"Vector" as described herein, is a nucleic acid vehicle that carries a generic material encoding a protein or mRNA of interest into another cell, such that it is replicated and/or expressed in the cell. There are several types of vectors. Without being limiting, a vector can be a plasmid, viral vector, cosmid, artificial chromosome, or an mRNA. The vector can be linear or circular. In some alternatives provided herein, a viral vector is used to carry the nucleic acid encoding a chimeric antigen receptor. In some alternatives, the viral vector is a lentiviral vector. In some alternatives, the viral vector is a retroviral vector. In some embodiments, the viral vector is a gammaretroviral vector. In some alternatives, the vector is a foamy viral vector. In some alternatives, the vector is a plasmid. In some alternatives, the vector is an mRNA. In some alternatives, the vector is linear and comprises telomeres.

"Plasmid" as described herein, is a genetic structure in a cell that can replicate independently of the chromosomes. Without being limiting, the plasmid can be a small circular DNA strand in the cytoplasm of a bacterium or protozoan, or a linear nucleic acid.

"Minicircles," as described herein, are small circular plasmid derivatives that have been freed from all prokaryotic vector parts. Minicircles can serve as an expression vector, where they have been applied as transgene carriers for the genetic modification of mammalian cells, with the advantage that, since they contain no bacterial DNA sequences, they are less likely to be perceived as foreign and destroyed. As such, typical transgene delivery methods involve plasmids, which contain foreign DNA. The smaller size of minicircles also extends their cloning capacity and facilitates their delivery into cells. Without being limiting, the preparation of minicircles can follow a two-step procedure, which can involve production of a parental plasmid (bacterial plasmid with eukaryotic inserts) in E. coli and induction of a site-specific recombinase at the end of this process but still in bacteria. These steps can be followed by the excision of prokaryotic vector parts via two recombinase-target sequences at both ends of the insert and recovery of the resulting minicircle (vehicle for the highly efficient modification of the recipient cell) and the miniplasmid by capillary gel electrophoresis (CGE).

An "inverted terminal repeat," as described herein, is a sequence of nucleotides followed downstream by its reverse complement and occur at opposite ends of a transposon.

As described herein, "transposable element" (TE), transposon or retrotransposon, can be referred to as a DNA sequence that can change its position within the genome. The transposon can create or reverse mutations and alter the cell's genome size. Transposition often results in duplication of the TE. TEs can make up a large fraction of the C-value of eukaryotic cells. "C-values," as described herein, refers to amount, in picograms, of DNA contained within a haploid nucleus of one half the amount in a diploid somatic cells of a eukaryotic organism. In some alternatives, the nucleic acid encoding a chimeric antigen receptor resides within a vector, wherein the vector is a minicircle transposon. In some alternatives, the vector comprises a transposon.

The "Sleeping Beauty transposon system" as described herein, is composed of a Sleeping Beauty (SB) transposase and a transposon that was designed in 1997 to insert specific sequences of DNA into genomes of vertebrate animals. DNA transposons can translocate from one DNA site to another in a simple, cut-and-paste manner. Transposition is a precise process in which a defined DNA segment is excised from one DNA molecule and moved to another site in the same or different DNA molecule or genome. In some alternatives of the vectors provided herein, the vector comprises a Sleeping Beauty transposon.

An SB transposase can insert a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, in which case the transposon becomes a non-autonomous element.

"PiggyBac (PB) transposon," as described herein refers to a mobile genetic element that efficiently transposes between vectors and chromosomes via a "cut and paste" mechanism. During transposition, the PB transposase recognizes transposon-specific inverted terminal repeat sequences (ITRs) located on both ends of the transposon vector and efficiently moves the contents from the original sites and efficiently integrates them into TTAA chromosomal sites. The powerful activity of the PiggyBac transposon system enables genes of interest between the two ITRs in the PB vector to be easily mobilized into target genomes.

In some alternatives, the vector is a PiggyBac transposon. The PiggyBac (PB) transposon is a mobile genetic element that efficiently transposes between vectors and chromosomes via a "cut and paste" mechanism. During transposition, the PB transposase recognizes transposon-specific inverted terminal repeat sequences (ITRs) located on both ends of the transposon vector and efficiently moves the contents from the original sites and efficiently integrates them into TTAA chromosomal sites. The powerful activity of the PiggyBac transposon system enables genes of interest between the two ITRs in the PB vector to be easily mobilized into target genomes.

In some alternatives, a PB contains a promoter linked to a polynucleotide coding for a chimeric antigen receptor operably linked to a genetic tag. One or more PB transposons can be employed. In some alternatives, a PB comprises a promoter linked to a polynucleotide coding for a chimeric antigen receptor and a first genetic tag, another PB comprises a promoter linked to a polynucleotide coding for a chimeric antigen receptor, and a second and different genetic tag. Each element of the constructs is separated by a nucleic acid, such as that coding for a self-cleaving T2A sequence. In some alternatives, each PB differs from one another in the chimeric antigen receptor including but not limited to the spacer length and sequence, the intracellular signaling domain, and/or the genetic tag sequence.

"Adoptive cell transfer" as described herein, refers to the transfer of cells into a patient. In some alternatives, a method of treating, ameliorating, or inhibiting a non-B cell related disease in a subject is provided, wherein the method comprises introducing, providing, or administering any one or more of the cells or compositions of any of the alternatives described herein into a subject for therapy. In some alternatives, the cells are administered by adoptive cell transfer.

A "leader sequence" as described herein is also known as a signal sequence that can direct a protein to the cell surface. The leader sequence under the context of a CAR, refers to the first sequence of amino acids in a CAR that directs surface expression. This leader sequence, or signal sequence can be required for surface expression of a protein. In some alternatives, the leader sequence comprises a Granulocyte-macrophage colony-stimulating factor signal sequence. In some alternatives, the signal sequence comprises an amino acid sequence set forth in SEQ ID NO: 29 and is encoded by a nucleic acid sequence set forth in SEQ ID NO: 30. In some alternatives, the signal sequence comprises an amino acid sequence set forth in SEQ ID NO: 31 and is encoded by a nucleic acid sequence set forth in SEQ ID NO: 32.

A "de-immunized spacer" as described herein, refers to a spacer that induces little to no immune response from a patient. In some alternatives, the chimeric antigen receptor comprises a spacer, wherein the spacer does not induce an immune response in a subject in need.

The de-immunized spacer can comprise a polypeptide chain that can range in length from a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239 or 240 amino acids or a length within a range defined by any two of the aforementioned lengths. A de-immunized spacer can comprise any of the 20 amino acids in any order to create a desirable length of polypeptide chain in a chimeric antigen receptor, which includes the amino acids arginine, histidine, lysine, aspartic acid, glutamic acid, serine, threonine, asparagine, glutamine, cysteine, glycine, proline, alanine, valine, isoleucine, methionine, phenylalanine, tyrosine and/or tryptophan. A de-immunized spacer sequence can be a linker between the scFv and the transmembrane domain of the chimeric antigen receptor. In some alternatives, a method of making a nucleic acid encoding a chimeric antigen receptor is provided. In some alternatives, a nucleic acid encoding a chimeric antigen receptor is provided. In some alternatives, the nucleic acid comprises a sequence for a de-immunized spacer. In some alternatives, the de-immunized spacer comprises a sequence with a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239 or 240 amino acids or a length within a range defined by any two of the aforementioned lengths. In some alternatives, the de-immunized spacer resides between the scFv and the transmembrane region of the chimeric antigen receptor.

In some alternatives, a spacer region has at least 10 to 229 amino acids, 10 to 200 amino acids, 10 to 175 amino acids, 10 to 150 amino acids, 10 to 125 amino acids, 10 to 100 amino acids, 10 to 75 amino acids, 10 to 50 amino acids, 10 to 40 amino acids, 10 to 30 amino acids, 10 to 20 amino acids, or 10 to 15 amino acids, or a length that is within a range defined by any two of the aforementioned amino acid lengths. In some alternatives, a spacer region has 12 amino acids or less but greater than 1 amino acid, 119 amino acids or less but greater than 1 amino acid, or 229 amino acids or less but greater than 1 amino acid.

In some alternatives, the spacer comprises an IgG4 hinge spacer. In some alternatives, the spacer comprises an amino acid sequence set forth in SEQ ID NO: 1 (SEQ ID NO: 1; E S K Y G P P C P P C P). In some alternatives, the spacer is encoded by a sequence set forth in SEQ ID NO: 2 (SEQ ID NO: 2; GAGAGCAAGTACGGACCGCCCTGCCCCCCTTGCCCT).

In some alternatives, the spacer comprises an IgG4-CH3 hinge spacer. In some alternatives, the spacer comprises an amino acid sequence set forth in SEQ ID NO: 3 (SEQ ID NO:3; E S K Y G P P C P P C P G Q P R E P Q V Y T L P P S Q E E M T K N Q V S L T C L V K G F Y P S D I A V E W E S N G Q P E N N Y K T T P P V L D S D G S F F L Y S R L T V D K S R W Q E G N V F S C S V M H E A L H N H Y T Q K S L S L S L G K). In some alternatives, the spacer is encoded by a sequence set forth in SEQ ID NO: 4 (SEQ ID NO: 4; GAGAGCAAGTACGGACCGCCCTGCCCCCCTTGCCCTGGCCAGCCTCGCGAGCCCCAGGTGTACACCCTGCCTCCCTCCCAGGAAGAGATGACCAAGAACCAGGTGTCCCTGACCTGCCTGGTGAAGGGCTTCTACCCCAGCGACATCGCCGTGGAGTGGGAGAGCAACGGCCAGCCTGAGAACAACTACAAGACCACCCCTCCCGTGCTGGACAGCGACGGCAGCTTCTTCCTGTACAGCCGGCTGACCGTGGACAAGAGCCGGTGGCAGGAAGGCAACGTCTTTAGCTGCAGCGTGATGCACGAGGCCCTGCACAACCACTACACCCAGAAGAGCCTGAGCCTGTCCCTGGGCAAG).

In some alternatives, the de-immunized spacer comprises a IgG4-CH2 spacer (L235D, N297Q mutant). In some alternatives, the IgG4-CH2 spacer (L235D, N297Q mutant) comprises an amino acid sequence set forth in SEQ ID NO: 39 and is encoded by a nucleic acid sequence set forth in SEQ ID NO: 40.

In some alternatives, the de-immunized spacer comprises a IgG4 hinge. In some alternatives, the de-immunized spacer comprises a CD8αhinge. In some alternatives, the de-immunized spacer comprises a CD28hinge and their fusion to the CH2 and/or CH3 domains of IgG molecules.

"Signaling domain" as described herein is a domain on a chimeric antigen receptor that can promote cytokine release, in vivo T cell survival and tumor elimination. In some alternatives herein, a signaling domain comprises CD28, 4-1BB and/or CD3-zeta cytoplasmic domains.

"Steroid" as described herein refers to a small cyclic organic compound with a common characteristic comprising an arrangement of seventeen carbon atoms within a four ring structure. In some alternatives provided herein, the expression of a CAR is induced by a steroid, such as estrogen, testosterone, or a glucocorticoid or retinoic acid. In some alternatives described here, the steroid tamoxifen is used to induce expression of a CAR or TcR. In some alternatives, estrogen or glucocorticoid are used to induce expression of a CAR or TcR.

"Non-B cell related disease" refers to any cancer or disease that is not related to B-cell cancers or diseases. Therefore expression of specific proteins on the cell surface that are markers for a cancer are markers for diseases that are not caused by any B-cell related abnormalities in the alternatives described herein. Without being limiting, non-B cell related diseases can include B-cell lymphoma, Hodgkin's lymphomas, non-Hodgkins lymphomas, Diffuse large B cell lymphoma, Follicular lymphoma, marginal zone lymphoma, Mucosa-Associated Lymphatic Tissue lymphoma, small lymphocytic lymphoma, chronic lymphocytic leukemia, mantle cell lymphoma, Burkitt lymphoma, primary mediastinal (thymic) large B cell lymphoma, Lymphoplasmacytic lymphoma, Waldenstrom macroglobulinermia, Nodal marginal zone B cell lymphoa, splenic marginal zone lymphoma, intravascular large B cell lymphoma, Intravascular large B-cell lymphoma, Primary effusion lymphoma, Lymphomatoid granulomatosis, T cell/histiocyte-rich large B-cell lymphoma, Primary central nervous system lymphoma, Primary cutaneous diffuse large B-cell lymphoma (leg type), EBV positive diffuse large B-cell lymphoma of the elderly, Diffuse large B-cell lymphoma associated with inflammation, Intravascular large B-cell lymphoma, ALK-positive large B-cell lymphoma, ALK-positive large B-cell lymphoma, Plasmablastic lymphoma, Large B-cell lymphoma arising in HHV8-associated multicentric Castleman's disease, B-cell lymphoma, unclassifiable with features intermediate between diffuse large B-cell lymphoma and Burkitt lymphoma, B-cell lymphoma, unclassifiable with features intermediate between diffuse large B-cell lymphoma and classical Hodgkin lymphoma, or nodular lymphocyte predominant Hodgkin's lymphoma.

"Solid Tumors" as described herein, refers to a malignant cancerous mass of tissue. In some alternatives of the methods of treating, ameliorating, or inhibiting a non-B cell related disease in a subject provided herein, the method comprises introducing, providing, or administering any one or more of the cells or compositions of any of the alternatives herein or the cells made by any one or more of the methods of the alternatives herein into a subject for therapy. In some alternatives, the subject has a cancer. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer.

"Neuroblastoma" as described herein, refers to an extracranial solid cancer in childhood and infancy that is a neuroendocrine tumor that can arise from a neural crest element of the sympathetic nervous system. Without being limiting, a tumor can originate, for example, in the adrenal glands, and nerve tissues of the neck, check, abdomen, and/or pelvis. In some alternatives of the methods described herein, T-cells comprising a bi-specific chimeric antigen receptor or two chimeric antigen receptors for bi-specificity are administered to a subject in need by adoptive cell transfer. In some alternatives, the subject in need suffers from neuroblastoma. In some alternatives, the subject in need is a person of pediatric age. Pediatric age as described herein refers to a person of age 24 or under. A person of pediatric age is at age 0, 1, 2, 3, 4, 5, 6, 7, 8, 9, 10, 11, 12, 13, 14, 15, 16, 17, 18, 19, 20, 21, 22, 23, 24 years old or any other age within a range in between any two of the aforementioned values described.

"Refractory and relapsed neuroblastoma" as described herein, refers to the children who are considered "high risk" that do not respond completely to treatment and are labeled refractory. The children that are considered high-risk are removed from frontline therapy and are considered to be eligible for clinical trials that can use new therapies. Children who have had a good response to frontline therapy and achieved a disease reoccurrence (relapse) are considered high-risk and are also eligible for new therapies tested in clinical trials. In some alternatives of the methods described herein, the patients suffer from refractory and/or relapsed neuroblastoma. In some alternatives, the subject in need is a person of pediatric age. Pediatric age as described herein refers to a person of age 24 or under. A person of pediatric age is at age 0, 1, 2, 3, 4, 5, 6, 7, 8, 9, 10, 11, 12, 13, 14, 15, 16, 17, 18, 19, 20, 21, 22, 23, 24 years old or any other age within a range in between any two of the aforementioned values described. In some alternatives, the patient is receiving cancer therapy. In some alternatives, the cancer therapy comprises administration of 131I-MIBG to the patient.

"Suicide gene therapy," "suicide genes" and "suicide gene systems" as described herein, can refer to methods to destroy a cell through apoptosis, which requires a suicide gene that will cause a cell to kill itself by apoptosis. Due to safety concerns for the patients in need of CAR therapy, strategies are being developed in order to prevent or abate adverse events. Adverse effects of CAR T-cell therapy can include "cytokine storms" which is a cytokine release syndrome in which the infused T-cells release cytokines into the bloodstream, which can lead to dangerously high fevers as well as a precipitous drop in blood pressure. To date, cytokine-release syndrome is a common problem in patients treated with CAR T-cells and patients with the most extensive disease, prior to receiving the CAR T-cells were shown to be more likely to experience severe cases of cytokine-release syndrome. Off target adverse effects can also occur, if a tumor specific antigen is also expressed in healthy tissue.

Suicide gene therapy can be used to increase the safety of chimeric antigen receptor redirected T-cells and manage the adverse events that can occur following infusion of CAR bearing T-cells. Pharmacologic therapies, suicide genes or novel strategies are needed to limit the cytotoxic effect only to malignant cells. There are several methods for suicide gene therapy. Without being limiting, methods can include gene-directed enzyme producing therapy or virus directed enzyme prodrug therapy. For gene-directed enzyme producing therapy (GDEPT), a gene is taken from the cancer cell and then modified with other genes to form enzymes that are harmless to healthy cells. This foreign enzyme is inserted into the tumor cells where it releases a prodrug, which is a small molecule harmless to healthy cells, but destructive to cancerous cells. The modified suicide gene converts the non-toxic prodrug into a cytotoxic substance. For virus directed enzyme prodrug therapy, a virus, such as herpes simplex or cold virus, as the carrier, or vector, is used to deliver the modified genes to the cancer cells. Suicide gene therapy is not necessarily expected to completely eliminate the need for chemotherapy and radiation treatment for all cancerous tumors. The damage inflicted upon the tumor cells, however, makes them more susceptible to the chemo or radiation. This approach has already proven effective against prostate and bladder cancers. The application of suicide gene therapy is being expanded to several other forms of cancer as well. Cancer patients often experience depressed immune systems, so they can suffer some side effects of the use of a virus as a delivery agent. Management of adverse effects of CAR T-cell therapy can be performed by expressing the CARs under the control of a promoter. As previously described in several reviews, T-lymphocytes that express a CAR can further be genetically modified ex vivo with a suicide gene. Without being limiting, the suicide gene can be a gene encoding for a factor that is able to convert at a cellular level a non-toxic prodrug into a toxic compound. During adverse effect that may follow infusion of CAR T-cells by adoptive cell transfer, the prodrug can be administrated to the subject suffering from adverse effects, and the prodrug can selectively eliminate suicide gene modified T-cells without interfering with the process of immune reconstitution operated by the non-modified T-cells. Suicide systems using the herpes simplex thymidine kinase (Hsv-tk)/ganciclovir (GCV) suicide system have been described. (Casucci et al. 2011, Journal of Cancer 2011, 2; incorporated in its entirety herein). In some alternatives, a cell comprising a first and second chimeric antigen receptor is provided, wherein the first chimeric antigen receptor is specific for a ligand on a B cell, which promotes the in vivo expansion and activation of an effector cell and, wherein the second chimeric antigen receptor is specific for a ligand on a tumor. In some alternative, a cell comprising a bi-specific chimeric antigen receptor is provided, wherein the bi-specific chimeric antigen receptor comprises two binding domains, wherein a first binding domain is specific for a ligand on a B cell, which promotes the in vivo expansion and activation of the B cell and a second binding domain is specific for a ligand on a tumor. In some alternatives, the cell further comprises a suicide gene system.

In some alternatives, the suicide gene system is an EGFRt suicide gene system, wherein the patient is administered Erbitux as the prodrug. In some alternatives, the subject is administered 0.04 mg/cm$^2$ Erbitux a day. In some alternatives, wherein Erbitux is the prodrug, 0.04 mg/cm$^2$ can be considered the initial dose and in some alternatives includes a weekly 0.025 mg/cm$^2$ dose of Erbitux after the initial dose. In some alternatives, wherein a rash develops on the patient, the weekly dose can go down to 0.03 mg/cm$^2$, 0.02 mg/cm$^2$ or 0.01 mg/cm$^2$, or any other dosage between any two of the aforementioned values described. In some alternatives, the suicide gene system is a Her2tG suicide gene system, wherein the patient is administered Herceptin as the prodrug. In some alternatives, the subject is administered 2 mg/kg, 3 mg/kg or 4 mg/kg Herceptin or any dosage between any two of the aforementioned values described. In some alternatives of the methods of making a cell comprising a first and second chimeric antigen receptor or TcR, the method further comprises introducing into a cell a nucleic acid encoding a suicide gene. In some alternatives, the nucleic acid encoding a suicide gene is resides on a vector. In some alternatives, the vector is a viral vector. In some alternatives, the viral vector is a lentiviral vector or a retroviral vector. In some alternatives, the Her2tG comprises an amino acid sequence set forth in SEQ ID NO: 35 and is encoded by a nucleic acid sequence set forth in SEQ ID NO: 36.

"Herpes Simplex Virus Thymidine Kinase (HSVTK)/ Ganciclovir (GCV) suicide gene system," as described herein, is a suicide gene system using the thymidine kinase gene from the herpes simplex virus in combination with the prodrug ganciclovir.

In some alternatives of the methods of making a cell comprising a first and second chimeric antigen receptor or TcR, the method further comprises introducing into a cell a nucleic acid encoding a suicide gene system. In some alternatives, the suicide gene system is a Herpes Simplex Virus Thymidine Kinase (HSVTK)/Ganciclovir (GCV) suicide gene system. In some alternatives, the nucleic acid encoding the suicide gene is resides on a vector. In some alternatives, the vector is a viral vector. In some alternatives, the viral vector is a lentiviral vector or a retroviral vector. In some alternatives, the suicide gene resides on the vector carrying the nucleic acid encoding the chimeric antigen receptor, wherein the suicide gene system is located upstream or downstream from the nucleic acid encoding the chimeric antigen receptor, and wherein the suicide gene system is separated from the nucleic acid encoding the chimeric antigen receptor by a gene encoding a cleavable linker. In some alternatives, 1000 mg of Ganciclovir is administered to a subject in need three times a day with food.

In some alternatives, wherein Ganciclovir is the prodrug, the patient can be administered Ganciclovir as induction therapy at a 5 mg/kg intravenously (IV) at a constant rate for 1, 2, or 3 hours or any amount of time in between any two of the aforementioned values, every 12 hours for 14 days, 15 days, 16 days, 17 days, 18 days, 19 days, 20 days or 21 days or any number of days within a range in between any two aforementioned values. In some alternatives, wherein Ganciclovir is the prodrug, the amount of Ganciclovir in the patient is maintained, wherein the patient is administered Ganciclovir intravenously (IV) at 5 mg/kg at a constant rate over 1, 2 or 3 hours or any amount of time within a range in between any two of the aforementioned values. In some alternatives, the Ganciclovir is administered once a day, for seven days a week. In some alternatives, wherein Ganciclovir is the prodrug, the amount of Ganciclovir in the patient is maintained, wherein the patient is administered Ganciclovir intravenously (IV) at 6 mg/kg at a constant rate over 1, 2 or 3 hours or any amount of time in between any two of the aforementioned values, once a day, for five days a week.

In some alternatives of the methods of making a cell comprising a first and second chimeric antigen receptor or TcR, the method further comprises introducing into a cell a nucleic acid encoding a suicide gene system. In some alternatives, the suicide gene system is a Caspase based suicide gene system. Without being limiting, examples of inducible caspase suicide gene systems can include the inducible caspase-9 suicide gene system and the casepace-8 suicide gene system. The use of inducible caspase 9 (iCasp9) mediated suicide is based on the conditional dimerization of pro-apoptotic molecules that are constructed from human proteins and are less likely to be immunogenic. In some alternatives, wherein the iCasp9 suicide system is used, the iCasp9 protein comprises a human FK506 binding protein.

In some alternatives of the suicide gene system is a Caspase system, such as the Caspase 9 suicide gene system. In some alternatives, the prodrug is FK506 or another chemical inducer of dimerization. In some alternatives of the methods of making a cell comprising a first and second chimeric antigen receptor or TcR, the cell comprises introducing into a cell a nucleic acid encoding a suicide gene. In some alternatives, the nucleic acid encoding a suicide gene is resides on a vector. In some alternatives, the vector is a viral vector. In some alternatives, the viral vector is a lentiviral vector or a retroviral vector. In some alternatives, the subject is administered a prodrug to induce apoptosis. In some alternatives, the prodrug is FK506. In some alternatives, the subject is administered a dosage of 0.075 mg/kg/day, 0.1 mg/kg/day, 0.125 mg/kg/day, 0.150 mg/kg/day, 0.175 mg/kg/day or 0.2 mg/kg/day or any dosage within a range in between any two of the aforementioned values described.

In some alternatives, the suicide gene system comprises a suicide vector for tamoxifen inducible apoptosis. In particular, an inducible apoptosis system with a Fas-estrogen receptor fusion protein can be used in order to rapidly eliminate transduced cells. In some alternatives, the system can induce apoptosis independently from endogenously expressed estrogen.

"Prodrug" as described herein, is a medication that is administered in a pharmacologically inactive form which is then converted to an active form through a normal metabolic process. In some alternatives, a method of treating, ameliorating, or inhibiting a non-B cell related disease in a subject is provided wherein the method comprise introducing, providing, or administering any one or more of the cells or compositions of any of the alternatives described herein or the cells made by any one or more of the methods of any of the alternatives described herein into a subject for therapy. In some alternatives, the method further comprises evaluating the subject for symptoms of cytokine storm or B-cell aplasia. In some alternatives, the subject is suffering from high fevers, increase or decrease of blood pressure, hypotension, hypoxia, seizures, or aphasia. In some alternatives, the subject has an elevation in ferritin and/or C-reactive protein. In some alternatives of the methods provided herein, wherein the cells comprise a suicide gene system, the methods further comprise administering to the subject a prodrug.

In some alternatives, wherein the transduced T-cell comprises a suicide gene system, wherein the suicide gene system is a Herpes Simplex Virus Thymidine Kinase (HSVTK)/Ganciclovir (GCV) suicide gene system or inducible Caspase 9 suicide gene system, the prodrug is FK506. In some alternatives, the subject is administered 0.075-0.2 mg/kg/day of FK506. In some alternatives, the subject is administered a dosage of 0.075 mg/kg/day, 0.1 mg/kg/day, 0.125 mg/kg/day, 0.150 mg/kg/day, 0.175 mg/kg/day or 0.2 mg/kg/day or any dosage within a range in between any two of the aforementioned values described.

In some alternatives, wherein the transduced T-cell comprises a suicide gene system, wherein the suicide gene system is the suicide gene system comprises a suicide vector for tamoxifen inducible apoptosis, the prodrug is tamoxifen. In some alternatives, the subject is administered 20 mg/day tamoxifen.

In some alternatives, wherein the transduced T-cell comprises a suicide gene system, wherein the suicide gene system is the Herpes Simplex Virus Thymidine Kinase (HSVTK) suicide gene system comprises a suicide vector for tamoxifen inducible apoptosis, the prodrug is GCV. In some alternatives, the subject is administered 1000 mg orally 3x/day GCV with food.

"Engraftment" as described herein, refers to the incorporation of grafted tissue into the body of the host. Several characteristics of effective CAR T-cells include showing signs of adequate engraftment, which is required for responses. For example, detection of the CAR transgene by polymerase chain reaction is not informative about the surface expression of the CAR, which is the only form that matters for efficacy. Thus, the availability of reagents to specifically detect CARs at the cell surface by flow cytometry or other methods known to those skilled in the art is crucial to understand the activity and engraftment of CAR T-cells. In the alternatives described herein, the therapeutic potency of the adoptively transferred CARs are improved by allowing a B-cell targeting CAR to drive the activation, proliferation and dispersion of infused CAR T-cells that have a second CAR that provides for redirected killing of the solid tumor. In some alternatives described herein, the methods and cells comprising a CAR with B-cell specificity led to the surprising effect of having an improved level of engraftment compared to T-cells that only comprised CARs specific for a tumor ligand. As described in the alternatives herein, the obstacle of failure to exhibit engraftment is overcome by allowing a B cell targeting CAR to drive the activation, proliferation and dispersion of infused CAR T-cells that have a CAR that provides for redirected killing of the solid tumor.

"Subject" or "patient," as described herein, refers to any organism upon which the alternatives described herein may be used or administered, e.g., for experimental, diagnostic, prophylactic, and/or therapeutic purposes. Subjects or patients include, for example, animals. In some alternatives, the subject is mice, rats, rabbits, non-human primates, and humans. In some alternatives, the subject is a cow, sheep, pig, horse, dog, cat, primate or a human.

DETAILED DESCRIPTION

Although the invention is described in various exemplary alternatives and implementations as provided herein, it should be understood that the various features, aspects, and functionality described in one or more of the individual alternatives are not limited in their applicability to the particular alternative with which they are described. Instead, they can be applied alone or in various combinations to one or more of the other alternatives of the invention, whether the alternatives are described or whether the features are presented as being a part of the described alternative. The breadth and scope of the present invention should not be limited by any exemplary alternatives described or shown herein.

Aspects of the present invention relate to methods, cells and compositions for augmenting the therapeutic potency of adoptively transferred chimeric antigen receptor (CAR) bearing T-cells against solid tumors. In particular, methods, cells and compositions for CAR T-cell products that co-express two CARs in individual T-cells, a B cell targeting "driver" CAR for promoting in vivo expansion and activation of an effector cell, and a CAR or T-cell receptor (TcR) of a desired specificity for targeting a solid tumor (passenger CAR/TcR), are provided herein.

Cells Expressing a First and Second Chimeric Antigen Receptor

In accordance with some preferred alternatives, there are cells provided wherein the cells comprise a first and second chimeric antigen receptor or TcR, wherein the first chimeric antigen receptor is specific for a ligand on a B cell, which promotes the in vivo expansion and activation of an effector cell and, wherein the second chimeric antigen receptor or TcR is specific for a ligand on a tumor. In some alternatives of the cells, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, EMMPRIN/CD147 and/or tumor targets on tumors that are non-B cell tumors. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the first chimeric antigen receptor and/or the second chimeric antigen receptor or TcR are inducibly expressed in said cell. In some alternatives, expression of the first chimeric antigen receptor and/or the second chimeric antigen receptor or TcR is under the control of a regulatory element. In some alternatives, the first chimeric antigen receptor comprises an antibody or binding fragment thereof or scFv, a receptor ligand or mutant thereof, peptide, and/or polypeptide affinity molecule or binding partner. In some alternatives, the second chimeric antigen receptor or TcR comprises an antibody or binding fragment thereof or scFv, a receptor ligand or mutant thereof, peptide, and/or polypeptide affinity molecule or binding partner. In some alternatives, a first marker protein is co-expressed with the first chimeric antigen receptor and a second marker protein is co-expressed with the second chimeric antigen receptor or TcR. In some alternatives, the first marker protein co-expressed with the first chimeric antigen receptor is EGFRt and the second marker protein co-expressed with the second chimeric antigen receptor or TcR is Her2tg or first marker protein co-expressed with the first chimeric antigen receptor is Her2tg and the second marker protein co-expressed with the second chimeric antigen receptor or TcR is EGFRt.

In some alternatives, the lymphocyte can express a CAR and a specific T-cell receptor (TcR) for bi-specificity. In some alternatives, the specific T-cell receptor is specific for EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1.

In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cell surface tumor specific molecule is ROR1. In some alternatives, the first chimeric antigen receptor and/or the second chimeric antigen receptor are inducibly expressed in said cell. In some alternatives, expression of the first chimeric antigen receptor and/or the second chimeric antigen receptor is under the control of a regulatory element. In some alternatives, the first chimeric receptor comprises a first ligand binding domain and the second chimeric receptor comprises a second ligand binding domain. In some alternatives, the ligand binding domain comprises an antibody or binding fragment thereof or scFv, a receptor ligand or mutants thereof, peptide, and/or polypeptide affinity molecule or binding partner. In some alternatives, the first chimeric antigen receptor comprises an antibody or binding fragment thereof or scFv, a receptor ligand, peptide, and/or polypeptide affinity molecule. In some alternatives, the second chimeric antigen receptor comprises an antibody or binding fragment thereof or scFv, a receptor ligand, peptide, and/or polypeptide affinity molecule. In some alternatives, a first marker protein is co-expressed with the first chimeric antigen receptor and a second marker protein is co-expressed with the second chimeric antigen receptor. In some alternatives, the first marker protein co-expressed with the first chimeric antigen receptor is EGFRt and the second marker protein co-expressed with the second chimeric antigen receptor is Her2tg or first marker protein co-expressed with the first chimeric antigen receptor is Her2tg and the second marker protein co-expressed with the second chimeric antigen receptor is EGFRt. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+ T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the EGFRt comprises an amino acid sequence set forth in SEQ ID NO: 37 and is encoded by a nucleic acid sequence set forth in SEQ ID NO: 38.

Some alternatives described herein, incorporate a novel strategy to augment the therapeutic potency of adoptively transferred CAR redirected T cells against solid tumors. The alternatives also include CAR T cell products that co-express two CARs in individual T-cells (CD4+ and CD8+ T-cells subsets) incorporating a B cell targeting "driver" CAR (specific for CD19, CD22, CD20, CD10, CD79c, ROR1 or another cell surface molecule expressed by B cells) for promoting in vivo expansion and activation and a CAR or TcR of a desired specificity for targeting a solid tumor (passenger CAR/TcR). Dual CAR (or CAR/TcR) T-cells can be identified and selected by using two cell surface tags developed in the alternatives described herein, that consist of modified human EGFR and HER2 polypeptides, EGFRt and HER2tg, respectively. Additionally, single CARs that house a B cell targeting domain and solid tumor targeting domain are also envisioned to achieve bi-specificity for B cells and solid tumors. A variety of gene transfer methods are envisioned to generate bispecific CAR T-cells inclusive of viral vectors, non-viral transposon vectors, and mRNA. Additionally, a genetic system is envisioned in which the B cell targeting CAR is housed in a drug regulated expression format such as TamR. A preferred alternative of this system is the co-expression of a CD19 specific CAR, ideally housing a human scFv binding domain, deimmunized extracellular spacer and 4-1 BB:zeta second generation cytoplasmic tail, in conjunction with either EGFRt or HER2tg (or another appropriate cell surface tag) coexpressed via a genetic element that links the cDNA's, such as a ribosome skip sequence or IRES, along with a CAR or TcR developed for solid tumor therapy co-expressed with the second cell surface tag. One iteration of this system allows for separate lentiviral vectors to house each CAR/tag (or TcR/tag) and the use of a mixture of the two lentiviruses to co-transduce human T cells. These alternatives anticipates cell selections (immunomagnetic, cell sorting, other) that allows for purification of transduced T cells that express both cell surface tags and their corresponding CARs.

The dual CAR (or CAR/TcR) T-cells can be identified and selected by using two cell surface tags developed and described herein, and can consist of marker proteins (e.g., modified human EGFR and HER2 polypeptides, EGFRt and HER2tg, respectively). Additionally, single CARs that house a B cell targeting domain and solid tumor targeting domain are also envisioned to achieve bi-specificity for B cells and solid tumors, and are provided herein. A variety of gene transfer methods are envisioned to generate bispecific CAR T-cells inclusive of viral vectors, non-viral transposon vectors, and mRNA. Additionally, a genetic system is envisioned in which the B cell targeting CAR is housed in a drug regulated expression format such as TamR. A preferred alternative of this system is the co-expression of a CD19 specific CAR, which can also house a human scFv binding domain, deimmunized extracellular spacer and 4-1 BB:zeta second generation cytoplasmic tail, in conjunction with an cell surface tag (e.g. EGFRt or HER2tg) or the CAR can be co-expressed via a genetic element that links the cDNA's, such as a ribosome skip sequence or IRES, along with a CAR or TcR developed for solid tumor therapy co-expressed with the second cell surface tag. One alternative of this system allows for separate lentiviral vectors to house each CAR/tag (or TcR/tag) and the use of a mixture of the two lentiviruses to co-transduce human T-cells. The alternatives described herein, anticipates cell selections (immunomagnetic, cell sorting, other) that allows for purification of transduced T-cells that express both cell surface tags and their corresponding CARs.

The novel feature of bispecific CAR T-cells housing a driver CAR that targets normal B cells and a second solid tumor targeting passenger CAR, arises from the observations made from the several alternatives described herein, that CD19 CAR T-cells infused into leukemia patients undergo multi-log expansion and are activated to mediate the regression of systemic leukemia inclusive of the central nervous system (CNS). This phenomenon has been observed in patients in remission who have CD19 CAR T-cell expansion in response to activation by non-malignant B cells. The expansion mediated by B cells reflects their unique immune-stimulatory properties for CD19 CAR T-cells and their distribution in the blood, lymph nodes, and bone marrow where infused CAR T-cells migrate following intravenous infusion.

In contrast, CAR T-cells targeting solid tumors such as CE7 CAR T-cells used in clinical trials involving patients with metastatic neuroblastoma fail to exhibit engraftment, presumably due to limited migration of infused T-cells to sites of tumor metastasis, and the limited immune-stimulatory activity of solid tumors and their immunosuppressive environment. The cells described herein overcomes this obstacle by allowing a B cell targeting CAR to drive the activation, proliferation and dispersion of infused CAR T-cells that have a second passenger CAR that provides for redirected killing of the solid tumor.

In several of the alternatives described herein, data has been generated that can demonstrate the following: 1) Human T-cells can be co-transduced with two lentiviruses that house a CD19CAR-T2AEGFRt and a second CAR (antiCD20)-T2A-HER2t; 2) Co-transduced human T-cells have a portion of cells that co-express both EGFRt and HER2t. 3) Double positive T-cells can be purified to homogeneity using immunomagnetic selection reagents specific for EGFRt (Erbitux) and HER2 (Herceptin); 4) Dual CAR T-cells retain CD19 redirected specificity and an acquired second specificity (example CD20); 5) The TamR regulated transgene expression genetic system allows for tamoxifen dependent expression of the CD19CAR; 6) Ongoing experiments are testing CD19 driver×L1CAM passenger dual CAR expressing T-cells to be activated by B cells and subsequently exhibit enhanced anti-solid tumor activity.

The anticipated use of the alternatives described herein, is to augment the curative potential of CAR T-cell therapy for human cancer, specifically solid tumors. This driver/passenger CAR product could be used in the treatment any patient harboring a solid tumor for which there is a passenger CAR and overcome suboptimal activation and expansion following administration to patient by the driver CAR that recognizes a B cell lineage cell surface antigen, such as CD19. In one alternative, the driver CAR is placed into a drug regulated expression system, such as TamR-tf, allowing for cycles of driver CAR expansion followed by periods of "rest" and B cell reconstitution. Further, boosting of this effect to achieve augmented tumor targeting is anticipated by the infusion of patient derived B cells, T-APCs that express the cell surface B cell antigen. This strategy could be employed in the setting by which the tumor specificity is achieved by isolating tumor reactive T-cells through their endogenous TcR or an introduced TcR and the driver is the B cell antigen specific CAR.

In some alternatives, it is demonstrated that the dual CAR constructs can be introduced using co-transduction with lentivirus. It is contemplated to condense the vectorization into a single vector, e.g., using a nonviral transposon systems such as Sleeping Beauty Transposon Transposase.

CAR bearing T-cells exhibit the potential for prolonged B cell aplasia in treated patients. Accordingly, the TamR regulated expression system is contemplated for use to turn ON and OFF CD19 driver CAR reactivity, allowing for episodic B cell reconstitution. Alternately, CAR T-cells are equipped with a suicide gene to allow for periods of B cell recovery, and or the re-infusion of patient B cells after CAR T-cell ablation. In some alternatives, the B-cell targeting CAR is under the control of a drug.

However, other adverse effects of the CAR bearing T-cells of the present invention can also include cytokine storms. Therefore management of the adverse effects of CAR T-cell therapy can be performed by expressing the CARs under the control of a promoter or by the incorporation of a suicide gene system by ex vivo methods known to those skilled in the art. In some alternatives of the cells provided herein, the cells further comprise a suicide gene system.

Cells Expressing a Bi-Specific Chimeric Antigen Receptor

As described herein, cells comprising a bi-specific CAR are also provided. In some alternatives, a cell is provided wherein the cell comprises a bi-specific chimeric antigen receptor, wherein the bi-specific chimeric antigen receptor comprises two binding domains, wherein a first binding domain is specific for a ligand on a B cell, which promotes the in vivo expansion and activation of the B cell and a second binding domain is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, EMMPRIN/CD147 and/or tumor targets that are non-B cell tumors. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cell surface tumor specific molecule is ROR1. In some alternatives, the epitope for binding L1CAM is a CE7 epitope. In some alternatives, the target for binding L1CAM is the CE7 epitope. In some alternatives, the first and second binding domain comprises an antibody or portion thereof, a receptor ligand or mutant version thereof, peptide, and/or polypeptide affinity molecule or binding partner.

T-cells expressing a bi-specific CAR, wherein the bi-specific CAR comprises two binding domains is provided, wherein a first binding domain is specific for a ligand on a B cell, which promotes the in vivo expansion and activation of the B cell and a second binding domain is specific for a ligand on a tumor, are also anticipated to augment the therapeutic potency of adoptively transferred CAR redirected T cells against solid tumors, as the B-cell binding domain promotes in vivo expansion and activation of effector cells. In some alternatives, the first and second binding domain comprises an antibody or portion thereof, a receptor ligand or mutant version thereof, peptide, and/or polypeptide affinity molecule or binding partner.

Bi-specific CAR bearing T-cells have the potential for prolonged B cell aplasia in treated patients. This is mitigated by use of the TamR regulated expression system to turn ON and OFF the bi-specific CAR reactivity, allowing for episodic B cell reconstitution. Alternately, bi-specific CAR T-cells could be equipped with a suicide gene to allow for periods of B cell recovery, and or the re-infusion of patient B cells after bi-specific CAR T-cell ablation. In some alternatives, the bi-specific CAR is under the control of a drug.

In some instances, bi-specific CAR bearing T-cells can cause cytokine storms. Management of these adverse effects of bi-specific CAR T-cell therapy can be performed by expressing the bi-specific CARs under the control of a promoter or by the incorporation of a suicide gene system by ex vivo methods known to those skilled in the art. In some alternatives of the cells provided herein, the cells further comprise a suicide gene system.

Compositions

In some alternatives of the methods and compositions, the methods and composition are used to treat, ameliorate or eliminate cancer in a human suffering from cancer. In some alternatives of the methods and compositions provided herein, the patients in need are people of pediatric age with relapsed refractory neuroblastoma. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer.

The cell product will be a defined composition CD4+ and CD8+ subset product. The product will be co-transduced with the SCR lentivirus that directs the expression of the CD19CAR(4-1BB:zeta) and EGFRt along with the CE7R CAR(4-1 BB:zeta) and EGFRt. In some alternatives described herein trials have used a CAR/lentivirus pair that used EGFRt and HER2tg.

As described herein, are developed CD19 specific CARs and solid tumor targeting CARs. The alternatives described herein are dual specific CAR products through expressing multiple CARs in T-cells or engineering of bispecific CARs. The concept of using a driver CAR specific for B cells co-expressed with a passenger CAR or TcR having solid tumor specificity as a strategy for driving high levels of engraftment for augmented tumor responses is original.

In some alternatives, a composition is provided, wherein the composition comprises any one or more of the cells described herein. In some alternatives, the cell comprises a bi-specific chimeric antigen receptor, wherein the bi-specific chimeric antigen receptor comprises two binding domains, wherein a first binding domain is specific for a ligand on a B cell, which promotes the in vivo expansion and activation of the B cell and a second binding domain is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, EMMPRIN/CD147 and/or tumor targets that are non-B cell tumors. In some alternatives, the ligand on the tumor is a cancer antigen. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cell surface tumor specific molecule is ROR1. In some alternatives, the first and second binding domain comprises an antibody or portion thereof, a receptor ligand or mutant version thereof, peptide, and/or polypeptide affinity molecule or binding partner.

In some alternatives, the cell comprises a bi-specific chimeric antigen receptor. In some alternatives, the bi-specific chimeric antigen receptor comprises two binding domains, wherein a first binding domain is specific for a ligand on a B cell, which promotes the in vivo expansion and activation of the B cell and a second binding domain is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, EMMPRIN/CD147 and/or tumor targets that are non-B cell tumors. In some alternatives, the ligand on the tumor is a cancer antigen. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cell surface tumor specific molecule is ROR1. In some alternatives, the first and second binding domain comprises an antibody or portion thereof, a receptor ligand or mutant version thereof, peptide, and/or polypeptide affinity molecule or binding partner.

Pharmaceutical excipient," or pharmaceutical vehicle as described herein can refer to a carrier or inert medium used as a solvent in which the medicinally active agent or T-cells for treatment is formulated and or administered. Vehicles can include polymeric micelles, liposomes, lipoprotein-based carriers, nano-particle carriers, dendrimers, and/or other vehicles for T-cells that are known to one skilled in the art. An ideal vehicle or excipient can be non-toxic, biocompatible, non-immunogenic, biodegradable, and can avoid recognition by the host's defense mechanisms.

In some alternatives, a composition or product combination for human therapy is provided, wherein the composition or product combination comprises a pharmaceutical excipient and at least one population of genetically modified T-cells of any of the alternatives described herein. In some alternatives, the excipients are pharmaceutical vehicles. In some alternatives, the pharmaceutical vehicles include pharmaceutical compositions.

The composition can further comprise a vehicle, or pharmaceutical vehicle. Vehicles as described herein can refer to a substance of no therapeutic value that is used to convey an active medicine or cells for administration. Pharmaceutical vehicle as described herein can refer to a carrier or inert medium used as a solvent in which the medicinally active agent is formulated and or administered. An ideal vehicle can be non-toxic, biocompatible, non-immunogenic, biodegradable, and can avoid recognition by the host's defense mechanisms. In several alternatives described herein, compositions are described which comprise vehicles or excipients that help maintain the integrity of the T-cells. In some alternatives, the vehicles are pharmaceutical vehicles. In some alternatives, the pharmaceutical vehicles include pharmaceutical compositions.

In some alternatives, the composition comprises CD8+ T cytotoxic lymphocyte cells and/or CD4+ T helper lymphocyte cells, wherein the CD8+ T cytotoxic lymphocyte cells are selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells, and wherein the CD4+ T helper lymphocyte cells are selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the composition has a ratio of CD4+ T helper lymphocyte cells to CD8+ T lymphocytes of 1:10 to 10:1. In some alternatives, the ratio of CD4+ T helper lymphocyte cells to CD8+ T lymphocytes is 1:1.

Methods of Making a Cell Comprising Two Chimeric Antigen Receptors for Bi-Specificity In some alternatives, a method of making a cell comprising a chimeric antigen receptor is provided. In some alternatives, the method comprises introducing into a cell a first nucleic acid comprising a polynucleotide sequence encoding a first chimeric antigen receptor that comprises a binding domain specific for a ligand on a B cell, which promotes the in vivo expansion and activation of the B cell, introducing into the cell a second nucleic acid comprising a polynucleotide sequence encoding a second chimeric antigen receptor or TcR that comprises a binding domain specific for a ligand on a solid tumor, expanding the cell and isolating the cell. In some alternatives, the first nucleic acid and the second nucleic acid reside on two separate vectors. In some alternatives, the first nucleic acid and the second nucleic acid reside on the same vector. In some alternatives, the first nucleic acid and the second nucleic acid reside on two separate viral vectors. In some alternatives, the first nucleic acid and the second nucleic acid reside on the same vectors. In some alternatives, the viral vectors are retroviral vectors, gammaretroviral vectors, foamy viral vectors and/or lentiviral vectors. In some alternatives of the method, the vectors are introduced to the cell in a composition comprising a mixture of the two vectors. In some alternatives, the first and/or the second nucleic acid are introduced by a plasmid or a minicircle transposon. In some alternatives, the introducing the first and second nucleic acid is performed concurrently, wherein the first and second nucleic acid are prepared as a composition for delivery to the cell. In some alternatives, expression of the first chimeric antigen receptor is linked to co-expression of EGFRt and expression of the second chimeric antigen receptor is linked to co-expression of Her2tg, or wherein expression of the first chimeric antigen receptor is linked to co-expression of Her2tg, and expression of the second chimeric antigen receptor is linked to co-expression of EGFRt. In some alternatives, the method further comprises further comprising introducing a vector comprising a sequence encoding a soluble protein into said cell. In some alternatives, the soluble proteins are dominant negative versions of inhibitory proteins or constitutively active versions of pro-proliferative, T cell signal regulating or tumor microenvironment responsive proteins. In some alternatives, the soluble protein is a bi-specific T-cell engager (BiTE). BiTEs, as described herein are artificial bispecific monoclonal antibodies that can be used as anti-cancer drugs. In some alternatives, the BiTE is a Blinatomomab or Solitomab. BiTEs are fusion proteins comprising single chain variable fragments of different antibodies or amino acid sequences from four different genes. In some alternatives, the soluble proteins are homeostatic cytokines, fusion proteins or peptides. In some alternatives, the homeostatic cytokines are IL2, IL7, IL12 and/or IL15. In some alternatives of the method, the method further comprises stimulating the cells. In some alternatives, cells are stimulated (S1) with 50 U/ml interleukin-2 (IL-2) for CD8 cells. In some alternatives, cells are stimulated with interleukin-7 (IL-7) for CD4 cells. In some alternatives cells are stimulated with anti-CD3/CD28 beads.

In some aspects, utilization of Her2tg or EGFRt tag as a genetic tag/marker allows for the ex vivo selection and purification of homogenous populations of cellular therapeutics that express the transgene of interest. In addition, Her2tg can be used to track cellular therapeutics in vivo; for instance, Her2tg can be used as a target for Herceptin staining of blood, bone marrow and cerebrospinal fluid aspirates to check for the persistence of transgene-expressing cellular therapeutics to follow cancer remission to therapeutic persistence in a patient. Her2tg extends the therapeutic reach of CAR therapy by allowing for the concerted purification of cells expressing multiple transgenes when used with another genetic tag such as EGFRt. In some alternatives, the method further comprises selecting the cells by immunomagnetic selection or cell sorting. In some alternatives, the method further comprises selecting the cells by immunobinding the marker protein on the cell surface. In some alternatives, the marker protein is Her2tg and/or EGFRt.

Method of Making a Cell Comprising Two Chimeric Antigen Receptors with a Transposase System In some alternatives, a method of making a cell comprising a chimeric antigen receptor is provided. In some alternatives, the method comprises co-delivering into a cell two vectors, wherein a first vector comprises a first nucleic acid encoding a first chimeric antigen receptor, wherein the chimeric antigen receptor comprises a binding domain specific for a ligand on a B cell, which promotes the in vivo expansion and activation of the B cell, and a second vector comprising a second nucleic acid sequence encoding a second chimeric antigen receptor or TcR that comprises a binding domain specific for a ligand on a solid tumor, expanding the cell and isolating the cell. In some alternatives, the first nucleic acid and the second nucleic acid reside between a two inverted terminal repeat gene sequences. In some alternatives, the inverted terminal repeat gene sequences are Sleeping Beauty inverted terminal repeat gene sequences or PiggyBaC inverted terminal repeat gene sequences. In some alternatives, the vector is a plasmid or a minicircle transposon. In some alternatives, the method further comprises introducing into the cell a polynucleotide, wherein the polynucleotide sequence encodes an mRNA, wherein the mRNA encodes a transposase. In some alternatives, the transposase is a Sleeping Beauty transposase or a Piggyback transposase. In some alternatives, expression of the first chimeric antigen receptor is linked to co-expression of EGFRt and expression of the second chimeric antigen receptor is linked to co-expression of Her2tg, or wherein expression of the first chimeric antigen receptor is linked to co-expression of Her2tg, and expression of the second chimeric antigen receptor is linked to co-expression of EGFRt. In some alternatives, the method further comprises further comprising introducing a vector comprising a sequence encoding a soluble protein into said cell.

In some alternatives, the vector contains a promoter linked to a polynucleotide coding for a chimeric antigen receptor operably linked to a genetic tag. One or more PiggyBac transposons can be employed. In some alternatives, a PB comprises a promoter linked to a polynucleotide coding for a chimeric antigen receptor and a first genetic tag, another PiggyBac comprises a promoter linked to a polynucleotide coding for a chimeric antigen receptor, and a second and different genetic tag. Each element of the constructs is separated by a nucleic acid, such as that coding for a self-cleaving T2A sequence. In some alternatives, each PiggyBac differs from one another in the chimeric antigen receptor including but not limited to the spacer length and sequence, the intracellular signaling domain, and/or the genetic tag sequence.

In some aspects, utilization of Her2tg or EGFRt tag as a genetic tag/marker allows for the ex vivo selection and purification of homogenous populations of cellular therapeutics that express the transgene of interest. In addition, Her2tg can be used to track cellular therapeutics in vivo; for instance, Her2tg can be used as a target for Herceptin staining of blood, bone marrow and cerebrospinal fluid aspirates to check for the persistence of transgene-expressing cellular therapeutics to follow cancer remission to therapeutic persistence in a patient. Her2tg extends the therapeutic reach of CAR therapy by allowing for the concerted purification of cells expressing multiple transgenes when used with another genetic tag such as EGFRt. In some alternatives, the method further comprises selecting the cells by immunomagnetic selection or cell sorting. In some alternatives, the method further comprises selecting the cells by immunobinding the marker protein on the cell surface. In some alternatives, the marker protein is Her2tg and/or EGFRt.

Methods of Making a Cell Comprising a Bi-Specific Chimeric Antigen Receptor for Bi-Specificity In some alternatives, a method of making a cell having a bi-specific chimeric antigen receptor is provided, wherein the method comprises introducing into a cell a nucleic acid comprising a polynucleotide sequence encoding a bi-specific chimeric antigen receptor that comprises a first binding domain specific for a ligand on a B cell, which promotes the in vivo expansion and activation of the B cell, and a second binding domain specific for a ligand on a solid tumor, expanding the cells and isolating the cells. In some alternatives, the polynucleotide resides on a viral vector. In some alternatives, the viral vector is a lentiviral vector or a retroviral vector. In some embodiments, the viral vector is a gammaretroviral vector. In some alternatives, the bi-specific chimeric antigen receptor is co-expressed with a marker protein. In some alternatives, the marker protein is EGFRt or Her2tg. In some alternatives, the method further comprises introducing a vector encoding a soluble protein into said cell.

In some alternatives, the method further comprises selecting the cells by immunomagnetic selection or cell sorting. In some alternatives, the method further comprises selecting the cells by immunobinding the marker protein on the cell surface.

In some aspects, utilization of Her2tg or EGFRt tag as a genetic tag/marker allows for the ex vivo selection and purification of homogenous populations of cellular therapeutics that express the transgene of interest. In addition, Her2t can be used to track cellular therapeutics in vivo; for instance, Her2t can be used as a target for Herceptin staining of blood, bone marrow and cerebrospinal fluid aspirates to check for the persistence of transgene-expressing cellular therapeutics to follow cancer remission to therapeutic persistence in a patient. Her2t extends the therapeutic reach of CAR therapy by allowing for the concerted purification of cells expressing multiple transgenes when used with another genetic tag such as EGFRt. In some alternatives, the method further comprises selecting the cells that express the bi-specific CAR by immunomagnetic selection or cell sorting. In some alternatives, the method further comprises selecting the cells expressing the bi-specific marker by immunobinding the marker protein on the cell surface. In some alternatives, the marker protein is Her2tg and/or EGFRt.

Methods of Making a Cell Comprising a Bi-Specific Chimeric Antigen Receptor for Bi-Specificity Using a Transposase System In some alternatives, a method of making a cell comprising a bi-specific chimeric antigen receptor is provided. In some alternatives, the method comprises introducing into a cell a vector, wherein the vector comprises a first nucleic acid encoding a bi-specific chimeric antigen receptor comprising a first binding domain and a second binding domain, wherein the first binding domain is specific for a ligand on a B cell, which promotes the in vivo expansion and activation of the B cell, and the second binding domain is specific for a ligand on a solid tumor, expanding the cell and isolating the cell. In some alternatives, the first nucleic acid and the second nucleic acid reside between a first inverted terminal repeat gene sequence and a second inverted terminal repeat gene sequence. In some alternatives, the first inverted terminal repeat gene sequence and the second inverted terminal repeat gene sequence are Sleeping Beauty inverted terminal repeat gene sequences or PiggyBaC inverted terminal repeat gene sequences. In some alternatives, the vector is a plasmid or a minicircle transposon. In some alternatives, the method further comprises introducing into the cell a polynucleotide, wherein the polynucleotide sequence encodes an mRNA, wherein the mRNA encodes a transposase. In some alternatives, the transposase is a Sleeping Beauty transposase or a Piggyback transposase. In some alternatives, expression of the bi-specific chimeric antigen receptor is linked to co-expression of EGFRt or Her2tg. In some alternatives, the method further comprises further comprising introducing a vector comprising a sequence encoding a soluble protein into said cell.

In some alternatives, the vector contains a promoter linked to a polynucleotide coding for a chimeric antigen receptor operably linked to a genetic tag. One or more PiggyBac transposons can be employed. In some alternatives, a PB comprises a promoter linked to a polynucleotide coding for a chimeric antigen receptor and a first genetic tag, another PiggyBac comprises a promoter linked to a polynucleotide coding for a chimeric antigen receptor, and a second and different genetic tag. Each element of the constructs is separated by a nucleic acid, such as that coding for a self-cleaving T2A sequence. In some alternatives, each PiggyBac differs from one another in the chimeric antigen receptor including but not limited to the spacer length and sequence, the intracellular signaling domain, and/or the genetic tag sequence.

In some aspects, utilization of Her2tg or EGFRt tag as a genetic tag/marker allows for the ex vivo selection and purification of homogenous populations of cellular therapeutics that express the transgene of interest. In addition, Her2tg can be used to track cellular therapeutics in vivo; for instance, Her2tg can be used as a target for Herceptin staining of blood, bone marrow and cerebrospinal fluid aspirates to check for the persistence of transgene-expressing cellular therapeutics to follow cancer remission to therapeutic persistence in a patient. Her2tg extends the therapeutic reach of CAR therapy by allowing for the concerted purification of cells expressing multiple transgenes when used with another genetic tag such as EGFRt. In some alternatives, the method further comprises selecting the cells by immunomagnetic selection or cell sorting. In some alternatives, the method further comprises selecting the cells by immunobinding the marker protein on the cell surface. In some alternatives, the marker protein is Her2tg and/or EGFRt.

Methods of Treating, Ameliorating, or Inhibiting a Non-B Cell Related Disease in a Subject In some alternatives, a method of treating, ameliorating, or inhibiting a non-B cell related disease in a subject is provided, wherein the method comprises introducing, providing, or administering any one or more of the cells or compositions of any of the alternatives described herein or the cells made by any one or more of the methods of any of the alternatives described herein into a subject for therapy. In some alternatives, the cells that are administered are provided by an allogeneic transfer. In some alternatives, the cells that are administered are provided by an autologous transfer. In some alternatives the cells comprise a first and second chimeric antigen receptor, wherein the first chimeric antigen receptor is specific for a ligand on a B cell, which promotes the in vivo expansion and activation of an effector cell and, wherein the second chimeric antigen receptor is specific for a ligand on a tumor. In some alternatives of the cells, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, EMMPRIN/CD147 and/or tumor targets on tumors that are non-B cell tumors.

In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cell surface tumor specific molecule is ROR1. In some alternatives, the first chimeric antigen receptor and/or the second chimeric antigen receptor are inducibly expressed in said cell. In some alternatives, expression of the first chimeric antigen receptor and/or the second chimeric antigen receptor is under the control of a regulatory element. In some alternatives, the first chimeric antigen receptor comprises an antibody or binding fragment thereof or scFv, a receptor ligand, peptide, and/or polypeptide affinity molecule. In some alternatives, the second chimeric antigen receptor comprises an antibody or binding fragment thereof or scFv, a receptor ligand, peptide, and/or polypeptide affinity molecule. In some alternatives, a first marker protein is co-expressed with the first chimeric antigen receptor and a second marker protein is co-expressed with the second chimeric antigen receptor. In some alternatives, the first marker protein co-expressed with the first chimeric antigen receptor is EGFRt and the second marker protein co-expressed with the second chimeric antigen receptor is Her2tg or first marker protein co-expressed with the first chimeric antigen receptor is Her2tg and the second marker protein co-expressed with the second chimeric antigen receptor is EGFRt. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+ T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells.

In some alternatives, the cell comprises a bi-specific chimeric antigen receptor, wherein the bi-specific chimeric antigen receptor comprises two binding domains, wherein a first binding domain is specific for a ligand on a B cell, which promotes the in vivo expansion and activation of the B cell and a second binding domain is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, EMMPRIN/CD147 and/or tumor targets that are non-B cell tumors. In some alternatives, the ligand on the tumor is a cancer antigen. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAMS, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cell surface tumor specific molecule is ROR1. In some alternatives, the first and second binding domain comprises an antibody or portion thereof, a receptor ligand or mutant thereof, peptide, and/or polypeptide affinity molecule or binding partner.

In some alternatives, the subject is monitored for B-cell aplasia. In some alternatives, the subject is administered a drug to induce the B-Cell specific CAR expression.

In some alternatives, expression of a CAR is under the control of a first promoter inducible by a drug. The drug is selected based on safety record, favorable pharmacokinetic profile, tissue distribution, a low partition coefficient between the extracellular space and cytosol, low immunogenicity, low toxicities, and/or high expression in lymphocytes. In a specific alternative, a drug is selected that is FDA approved, provides for transgene expression in lymphocytes, does not activate other undesirable gene expression, and induces a promoter that does not contain any xenogeneic components. In some alternatives, the inducible promoter is activated by a transcriptional activator that interacts with a drug. The transcriptional activator is activated or able to bind to and activate the inducible promoter in the presence of the drug.

A specific alternative of a drug is a drug that binds to an estrogen receptor ligand binding domain of a transcriptional activator. In some alternatives, the drug includes tamoxifen, its metabolites, analogs, and pharmaceutically acceptable salts and/or hydrates or solvates thereof. In some alternatives, a specific alternative of a drug is a drug that binds to an estrogen receptor ligand binding domain of a transcriptional activator. In some alternatives, the drug is estrogen or glucocorticoid.

Tamoxifen, CAS RN: 10540-29-1, is also known as 2-(4-((1Z)-1,2-diphenyl-1-butenyl)phenoxy)-N,N-dimethyl-ethanamine, or (Z)-2-(para-(1,2-Diphenyl-1-butenyl)phenoxy)-N,N-dimethylamine (IUPAC), and has a molecular formula of $C_{26}H_{29}NO$, M.W. 371.52. Tamoxifen is a Selective Estrogen Receptor Modulator with tissue-specific activities. Tamoxifen acts as an anti-estrogen (inhibiting agent) agent in the mammary tissue, but as an estrogen (stimulating agent) in cholesterol metabolism, bone density, and cell proliferation in the endometrium. Tamoxifen is frequently administered orally as a pharmaceutically acceptable salt. For example, Tamoxifen citrate (RN 54965-24-1, M.W. 563.643) is indicated for treatment of metastatic breast cancer, and as an adjuvant for the treatment of breast cancer in women following mastectomy axillary dissection, and breast irradiation. Tamoxifen citrate is also indicated to reduce incidence of breast cancer in women at high risk for breast cancer.

Metabolites of tamoxifen in rat, mouse and human breast cancer patients, including major metabolites N-desmethyl-tamoxifen (RN 31750-48-8, M.W. 357.494) and 4-hydroxytamoxifen (4-OHT) (RN 68392-35-8, M.W. 387.52, Afimoxifene), are disclosed in Robinson et al., Metabolites, pharmacodynamics, and pharmacokinetics of tamoxifen in rats and mice compared to the breast cancer patient. Drug Metab Dispos January 1991 19:36-43, which is incorporated by reference herein in its entirety. Additional cytochrome P-450 metabolites are disclosed in Crewe et al., 2002, including cis-4-hydroxytamoxifen (RN 174592, M.W. 387.52; Afimoxifene, E-isomer), and 4'-hydroxytamoxifen ((Z)-4-(1-(4-(2-(dimethylamino)ethoxy)phenyl)-1-phenyl-but-1-en-2-yl)phenol). See Crewe et al., 2002, Metabolism of Tamoxifen by recombinant human cytochrome P-450 enzymes: Formation of the 4-hydroxy, 4'-hydroxy and N-desmethyl metabolites and isomerization of trans-4-hydroxytamoxifen, Drug Metab Dispos, 30(8): 869-874, FIG. 1, which is incorporated herein in its entirety by reference.

Compounds with structural similarity to tamoxifen include, but are not limited to, cis-tamoxifen (RN 13002-65-8, M.W. 371.521), 4-methyltamoxifen (RN 73717-95-5, M.W. 385.548), N-desmethyltamoxifen (RN 31750-48-8, M.W. 357.494), (Z)-desethyl methyl tamoxifen (RN 15917-50-7, M.W. 357.494), (E)-desethyl methyl tamoxifen (RN 31750-45-5, M.W. 357.494), trans-4-hydoxytamoxifen (RN 68047-06-3, M.W. 387.52), Afimoxifene (RN 68392-35-8, M.W. 387.52, 4-hydroxytamoxifen), Afimoxifene, E-isomer (RN 174592-47-3, M.W. 387.52), 4-chlorotamoxifen (RN 77588-46-6, M.W. 405.966), 4-fluorotamoxifen (RN 73617-96-6, M.W. 389.511), Toremifene (RN 89778-26-7, M.W. 405.966), desethyl tamoxifen (RN 19957-51-8, M.W. 343.47), (E)-desethyl tamoxifen (RN 97151-10-5, M.W. 343.47), (Z)-desethyl tamoxifen (RN 97151-11-6, M.W. 343.47), Miproxifene (RN 129612-87-9, M.W. 429.6), 2-(p-(beta-ethyl-alpha-phenylstyryl)phenoxy)triethylamine (RN 749-86-0, M.W. 399.575), Droloxifene (RN 82413-20-5, M.W. 387.52), 4-iodo-tamoxifen (RN 116057-68-2, M.W. 497.413), dihydrotamoxifen (RN 109640-20-2, M.W. 373.537), (E)-N,N-dimethyl-2-(4-(1-(2-methylphenyl)-2-phenyl-1-butenyl)phenoxy)ethanamine (RN 97150-96-4, M.W. 385.548), or 4-hydroxytoremifene (RN 110503-62-3, M.W. 421.965); and/or pharmaceutically acceptable salts and/or hydrates or solvates thereof.

For example, citrate salts of tamoxifen, or citrate salts of compounds with structural similarity to tamoxifen, include, but are not limited to tamoxifen citrate (RN 54965-24-1, M.W. 563.64), 2-(p-(1,2-diphenyl-1-butenyl)phenoxy)-N,N-dimethylethylamine citrate (RN 7244-97-5, 563.64), (E)-tamoxifen citrate (RN 76487-65-5, M.W. 563.64), Toremifene citrate (RN 89778-27-8, M.W. 598.088), Droloxifene citrate (RN 97752-20-0, M.W. 579.64), 2-(p-(1,2-bis(p-methoxyphenyl)-1-butenyl)phenoxy)triethylamine citrate (RN 42920-39-8, M.W. 651.748), 2-(4-(1,2-diphenylethenyl)phenoxy)-N,N-diethyl-ethanamine 2-hydroxy-1,2,3-propanetricarboxylate (RN 40297-42-5, M.W. 563.643), 2-(p-(alpha-phenylstyryl)phenoxy)triethylamine citrate (RN 102433-95-4, M.W. 563.64), 2-(p-(2-(p-methoxyphenyl)-1-phenyl-1-butenyl)phenoxy)triethylamine citrate (1:1) (RN 42824-34-0, M.W. 637.72), 2-(p-(1-(p-methoxyphenyl)-2-phenylpropenyl)phenoxy)triethylamine citrate (RN 13554-24-0, M.W. 607.696), 2-(p-(alpha-(p-methoxyphenyl)styryl)phenoxy)triethylamine citrate monohydrate (RN 13542-71-7, M.W. 593.669), 2-(p-(p-methoxy-alpha-phenylphenethyl) phenoxy)triethylamine citrate (RN 16421-72-0, M.W. 595.685), alpha-(p-(2-(diethylamino)ethoxy)phenyl)-beta-ethyl-p-methoxy-alpha-phenylphenethyl alcohol citrate (1:1) (RN 35263-93-5, M.W. 639.737), 1-(p-(2-(diethylamino)ethoxy)phenyl)-2-(p-methoxyphenyl)-1-phenylethanol citrate (M.W. 611.68), alpha-p-(2-(diethylamino)ethoxy)phenyl)-beta-ethyl-alpha-(p-hydroxyphenyl)-p-methoxyphenethyl alcohol citrate (RN 35263-96-8, M.W. 655.737), and/or 2-(p-(p-methoxy-alpha-methylphenethyl)phenoxy)-triethylamine citrate (RN 15624-34-7, M.W. 533.614).

In some alternatives, an affective amount of the drug for inducing expression of a chimeric antigen receptor is an amount that provides for an increase in transgene expression over uninduced and/or basal level of expression. In some alternatives, this amount can be readily determined using known dosages and pharmacokinetic profile of the drug.

In some alternatives, the inducible promoter has a low level of basal activity. When a lentiviral vector is used, the level of basal activity in uninduced cells is 20%, 15%, 10%, 5%, 4%, 3%, 2%, 1% or less, as compared to when cells are induced to express the gene. The level of basal activity can be determined by measuring the amount of the expression of the transgene (e.g. marker gene) in the absence of the inducer (e.g. drug) using flow cytometry.

In some alternatives, the inducible promoter provides for a high level of induced activity, as compared to uninduced or basal activity. In some alternatives, the level of activity in the induced state is 2, 4, 6, 8, or 10 fold or greater than the activity level in the uninduced state. In some alternatives, transgene expression under control of the inducible promoter is turned off in the absence of a transactivator in less than 10, 8, 6, 4, 2, or 1 days excluding 0 days.

In some alternatives, an inducible promoter can be designed and/or modified to provide for a low level of basal activity, a high level of inducibility, and/or a short time for reversibility. In some alternatives, the inducible promoter is the 7xHBD/mE1b promoter.

In some alternatives, the subject is administered a drug to induce a CAR that is specific for tumor targeting. In some alternatives, the subject is administered tamoxifen, or its active metabolite, wherein the tamoxifen, or its active metabolite induce expression of the B-Cell specific CAR. In some alternatives, wherein the subject is diagnosed with B-cell aplasia, the administration of tamoxifen or its metabolite is stopped. In some alternatives, the method further comprises cycles of administering tamoxifen or its metabolite and periods of rest. In some alternatives, the method further comprises administering to the subject in need, subject derived B-cells. In some alternatives, the method further comprises administering T-APCs that express the cell surface B cell ligand or antigen. In some alternatives, the subject does not have a B-cell related disease. In some alternatives, the disease is a cancer. In some alternatives, the disease is an infection. In some alternatives, the infection is a bacterial or viral infection. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the subject is identified or selected to receive a non-B cell related disease therapy, anti-cancer therapy, anti-infection therapy, antibacterial therapy, anti-viral therapy, or anti-tumoral therapy. In some alternatives, the method further comprises further comprising measuring or evaluating an inhibition of said non-B cell related disease, cancer, infection, bacterial infection, viral infection, or tumor. In some alternatives, the method further comprises measuring or evaluating an inhibition of said non-B cell related disease, cancer, infection, bacterial infection, viral infection, or tumor. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, during, or after introducing, providing, or administering any one or more of the cells or compositions provided herein or the cells made by any one or more of the methods provided herein into the subject. In some alternatives, the cells or compositions are introduced, provided, or administered to said subject by adoptive cell transfer. In some alternatives, the method further comprises introducing, providing, or administering a drug that induces expression of a chimeric antigen receptor. In some alternatives, the drug is tamoxifen and/or its metabolites. In some alternatives, the drug is a steroid. In some alternatives, the subject is a mammalian species. In some alternatives, the subject is a cow, sheep, pig, horse, dog, cat, primate or a human. In some alternatives, the subject is human.

In some alternatives, the method further comprises evaluating the subject for symptoms of cytokine storm or B-cell aplasia. In some alternatives, the subject is suffering from high fevers, increase or decrease of blood pressure, hypotension, hypoxia, seizures, or aphasia. In some alternatives, the subject has an elevation in ferritin and/or C-reactive protein. In some alternatives of the methods provided herein, wherein the cells comprise a suicide gene system, the methods further comprise administering to the subject a prodrug.

In some alternatives, the subject does not have B-cell lymphoma, Hodgkin's lymphomas, non-Hodgkins lymphomas, Diffuse large B cell lymphoma, Follicular lymphoma, marginal zone lymphoma, Mucosa-Associated Lymphatic Tissue lymphoma, small lymphocytic lymphoma, chronic lymphocytic leukemia, mantle cell lymphoma, Burkitt lymphoma, primary mediastinal (thymic) large B cell lymphoma, Lymphoplasmacytic lymphoma, Waldenstrom macroglobulinermia, Nodal marginal zone B cell lymphoa, splenic marginal zone lymphoma, intravascular large B cell lymphoma, Intravascular large B-cell lymphoma, Primary effusion lymphoma, Lymphomatoid granulomatosis, T cell/histiocyte-rich large B-cell lymphoma, Primary central nervous system lymphoma, Primary cutaneous diffuse large B-cell lymphoma (leg type), EBV positive diffuse large B-cell lymphoma of the elderly, Diffuse large B-cell lymphoma associated with inflammation, Intravascular large B-cell lymphoma, ALK-positive large B-cell lymphoma, ALK-positive large B-cell lymphoma, Plasmablastic lymphoma, Large B-cell lymphoma arising in HHV8-associated multicentric Castleman's disease, B-cell lymphoma, unclassifiable with features intermediate between diffuse large B-cell lymphoma and Burkitt lymphoma, B-cell lymphoma, unclassifiable with features intermediate between diffuse large B-cell lymphoma and classical Hodgkin lymphoma, or nodular lymphocyte predominant Hodgkin's lymphoma. In some alternatives, the subject has breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas or ovarian cancer. In some alternatives, the subject has refractory and relapsed neuroblastoma.

Nucleic Acids Encoding a Chimeric Antigen Receptor or a Bi-Specific Chimeric Antigen Receptor and Method of Making the Nucleic Acids Encoding a Chimeric Antigen Receptor or a Bi-Specific Chimeric Antigen Receptor In some alternatives, a nucleic acid encoding a chimeric antigen receptor is provided wherein the nucleic acid comprises a first nucleic acid comprising a sequence encoding a leader sequence, a second nucleic acid comprising a sequence encoding an antibody or binding fragment thereof or scFv, wherein the antibody or binding fragment thereof or scFv is specific for a B-cell specific cell surface molecule, and wherein the first nucleic acid is covalently attached to a 5' end of the second nucleic acid, a third nucleic acid comprising a sequence encoding a de-immunized extracellular spacer, wherein the third nucleic acid is covalently attached to a 3' end of the second nucleic acid, a fourth nucleic acid comprising a sequence encoding a transmembrane domain, wherein the fourth nucleic acid is covalently attached to a 3' end of the third nucleic acid, a fifth nucleic acid comprising a sequence encoding a signaling domain, wherein the signaling domain comprises a 4-1BB domain and/or CD3-zeta domain, and wherein the fifth nucleic acid is covalently attached to a 3' end of the fourth nucleic acid, a sixth nucleic acid comprising a sequence encoding a linker, wherein the sixth nucleic acid is covalently attached to a 3' end of the fifth nucleic acid and a seventh nucleic acid comprising a sequence encoding a marker domain, wherein the seventh nucleic acid is covalently attached to a 3' end of the sixth nucleic acid, thereby having said nucleic acid encoding a chimeric antigen receptor. In some alternatives, the linker sequence is a ribosome skip sequence or an IRES sequence. In some alternatives, the first promoter is inducible by tamoxifen and/or its metabolites. In some alternatives, the first promoter is inducible by a steroid e.g., a compound capable of binding to the estrogen receptor, or an estrogen receptor ligand. In some alternatives, the steroid is flustravant.

In some alternatives, a nucleic acid encoding a chimeric antigen receptor is provided wherein the nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a cell surface molecule expressed by B cells, and wherein the third nucleic acid is covalently attached to a 3' end of the second nucleic acid, a fourth nucleic acid comprising a sequence encoding a de-immunized extracellular spacer, wherein the fourth nucleic acid is covalently attached to a 3' end of the third nucleic acid, a fifth nucleic acid comprising a sequence encoding a transmembrane domain, wherein the fifth nucleic acid is covalently attached to a 3' end of the fourth nucleic acid, a sixth nucleic acid comprising a sequence encoding a signaling domain, wherein the signaling domain comprises a 4-1BB domain and/or CD3-zeta domain, and wherein the sixth nucleic acid is covalently attached to a 3' end of the fifth nucleic acid, a seventh nucleic acid comprising a sequence encoding a linker, wherein the seventh nucleic acid is covalently attached to a 3' end of the sixth nucleic acid and an eighth nucleic acid comprising a sequence encoding a marker domain, wherein the eighth nucleic acid is covalently attached to a 3' end of the seventh nucleic acid, thereby having said nucleic acid encoding a chimeric antigen receptor. In some alternatives, the linker sequence is a ribosome skip sequence or an IRES sequence. In some alternatives, the first promoter is inducible by tamoxifen and/or its metabolites. In some alternatives, the first promoter is inducible by flustravant. In some alternatives, the first promoter is inducible by a steroid (e.g. estrogen, glucocorticoid).

In some alternatives, a nucleic acid encoding a bi-specific chimeric antigen receptor is provided, wherein the nucleic acid comprises a first nucleic acid sequence comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the first nucleic acid is covalently attached at a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid and an eighth nucleic acid comprising a sequence encoding a marker domain, wherein the eighth nucleic acid is covalently attached at a 3' end of the seventh nucleic acid, thereby having said nucleic acid encoding a bi-specific chimeric antigen receptor. In some alternatives, the linker sequence is a ribosome skip sequence or an IRES sequence. In some alternatives, the fifth nucleic acid sequence further comprises an IRES sequence at the 3' end of the fifth nucleic acid sequence. In some alternatives, the second nucleic acid encodes an antibody or binding fragment thereof or scFv, and wherein the antibody or binding fragment thereof or scFv is specific for a B cell specific cell surface molecule and the third nucleic acid comprises a sequence encoding an antibody or binding fragment thereof or scFv, wherein the antibody or binding fragment thereof or scFv is specific for a cell surface tumor specific molecule or wherein the second nucleic acid encodes an antibody or binding fragment thereof or scFv, wherein the antibody or binding fragment thereof or scFv is specific for a cell surface tumor specific molecule and the third nucleic acid comprises a sequence encoding an antibody or binding fragment thereof or scFv, wherein the antibody or binding fragment thereof or scFv is specific B cell specific cell surface molecule.

In some alternatives, a nucleic acid encoding a suicide gene system is provided.

Vectors

In some alternatives, a vector for expression of a chimeric antigen receptor specific for promoting in vivo expansion and activation of B cells is provided, wherein the vector comprises the nucleic acid of any of the alternatives described herein. In some alternatives, the nucleic acid comprises a first nucleic acid comprising a sequence encoding a leader sequence, a second nucleic acid comprising a sequence encoding an antibody or binding fragment thereof or scFv, wherein the antibody or binding fragment thereof or scFv is specific for a B-cell specific cell surface molecule, and wherein the first nucleic acid is covalently attached to a 5' end of the second nucleic acid, a third nucleic acid comprising a sequence encoding a de-immunized extracellular spacer, wherein the third nucleic acid is covalently attached to a 3' end of the second nucleic acid, a fourth nucleic acid comprising a sequence encoding a transmembrane domain, wherein the fourth nucleic acid is covalently attached to a 3' end of the third nucleic acid, a fifth nucleic acid comprising a sequence encoding a signaling domain, wherein the signaling domain comprises a 4-1BB domain and/or CD3-zeta domain, and wherein the fifth nucleic acid is covalently attached to a 3' end of the fourth nucleic acid, a sixth nucleic acid comprising a sequence encoding a linker, wherein the sixth nucleic acid is covalently attached to a 3' end of the fifth nucleic acid and a seventh nucleic acid comprising a sequence encoding a marker domain, wherein the seventh nucleic acid is covalently attached to a 3' end of the sixth nucleic acid, thereby having said nucleic acid encoding a chimeric antigen receptor. In some alternatives, the linker sequence is a ribosome skip sequence or an IRES sequence. In some alternatives, the first promoter is inducible by tamoxifen and/or its metabolites. In some alternatives, the first promoter is inducible by a steroid.

In some alternatives, the nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a cell surface molecule expressed by B cells, and wherein the third nucleic acid is covalently attached to a 3' end of the second nucleic acid, a fourth nucleic acid comprising a sequence encoding a de-immunized extracellular spacer, wherein the fourth nucleic acid is covalently attached to a 3' end of the third nucleic acid, a fifth nucleic acid comprising a sequence encoding a transmembrane domain, wherein the fifth nucleic acid is covalently attached to a 3' end of the fourth nucleic acid, a sixth nucleic acid comprising a sequence encoding a signaling domain, wherein the signaling domain comprises a 4-1BB domain and/or CD3-zeta domain, and wherein the sixth nucleic acid is covalently attached to a 3' end of the fifth nucleic acid, a seventh nucleic acid comprising a sequence encoding a linker, wherein the seventh nucleic acid is covalently attached to a 3' end of the sixth nucleic acid and an eighth nucleic acid comprising a sequence encoding a marker domain, wherein the eighth nucleic acid is covalently attached to a 3' end of the seventh nucleic acid, thereby having said nucleic acid encoding a chimeric antigen receptor. In some alternatives, the linker sequence is a ribosome skip sequence or an IRES sequence. In some alternatives, the first promoter is inducible by tamoxifen and/or its metabolites. In some alternatives, the first promoter is inducible by flustravant. In some alternatives, the first promoter is inducible by a steroid.

In some alternatives, the nucleic acid comprises a first nucleic acid sequence comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the first nucleic acid is covalently attached at a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid and an eighth nucleic acid comprising a sequence encoding a marker domain, wherein the eighth nucleic acid is covalently attached at a 3' end of the seventh nucleic acid, thereby having said nucleic acid encoding a bi-specific chimeric antigen receptor. In some alternatives, the linker sequence is a ribosome skip sequence or an IRES sequence. In some alternatives, the fifth nucleic acid sequence further comprises an IRES sequence at the 3' end of the fifth nucleic acid sequence. In some alternatives, the second nucleic acid encodes an antibody or binding fragment thereof or scFv, and wherein the antibody or binding fragment thereof or scFv is specific for a B cell specific cell surface molecule and the third nucleic acid comprises a sequence encoding an antibody or binding fragment thereof or scFv, wherein the antibody or binding fragment thereof or scFv is specific for a cell surface tumor specific molecule or wherein the second nucleic acid encodes an antibody or binding fragment thereof or scFv, wherein the antibody or binding fragment thereof or scFv is specific for a cell surface tumor specific molecule and the third nucleic acid comprises a sequence encoding an antibody or binding fragment thereof or scFv, wherein the antibody or binding fragment thereof or scFv is specific B cell specific cell surface molecule.

In some alternatives, the vector expresses a chimeric antigen receptor specific for promoting in vivo expansion and activation of B cells. In some alternatives, the vector expresses a chimeric antigen receptor specific for targeting a solid tumor. In some alternatives, the vector comprises a first sequence encoding a first promoter sequence, wherein the first promoter sequence promotes expression of the chimeric antigen receptor, and wherein the vector comprises a second sequence encoding a second promoter sequence, wherein the second promoter sequence promotes expression of a marker protein.

In some alternatives, the vector further comprises a nucleic acid encoding a suicide gene system. In some alternatives, the vector comprises two inverted repeats, wherein the nucleic acid resides between the two inverted repeats. In some alternatives, the vector is a minicircle. In some alternatives, the inverted repeats are Sleeping Beauty or PiggyBac inverted repeats.

Additional Alternatives

Figure 4:
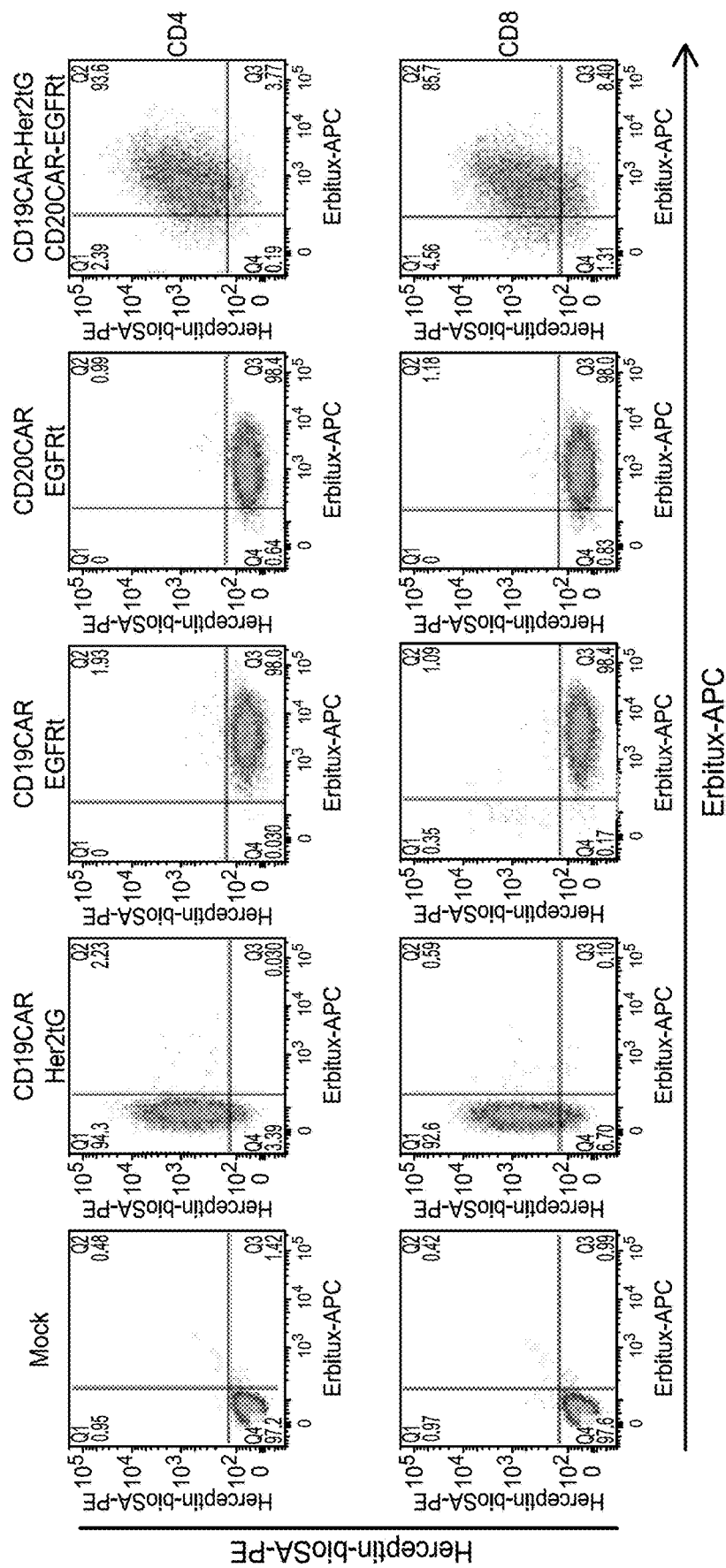
FIG. 4 shows a Western Blot of the cells of interest S1Sp1D12. The cells were purified for their respective marker/s. Dual CAR bearing CD8+ T cells carry CD19CAR-T2A-Her2tG and CD20CAR-T2A-EGFRt. This western blot is specific to the zeta portion of the CAR. The western demonstrates CAR expression in the CD8+ T cells. Most importantly, expression of both CARs (CD19CAR and CD20CAR) is demonstrated in the dual transduced CD8+ T cells.

Significant Expression of the Markers EGFRt and HertG Along with their Appended CARs As shown in FIG. 3, the marker Her2t and its variants demonstrate variable binding affinity to Herceptin based on their respective linker. The CARs used were dual CD19CAR-T2A-Her2tG/CD20CAR-T2A-EGFRt in the T-lymphocytes. As shown in FIG. 3A, H9 T cells were transduced with 3 ul of lentivirus containing the Her2t variant Her2t(CD28hinge), Her2t(IgG4hinge) or Her2tG (gly-ser linker). The transduced H9 cells were then cultured for 5 days and stained with biotinylated Herceptin (Herceptin-bio) and a streptavidin conjugated secondary fluorophore (SA-PE). Results demonstrate that the Her2t variant Her2tG displays the greatest ability to bind Herceptin, Her2t (IgG4hinge) with modest Herceptin binding and Her2t (CD28hinge) with the weakest Herceptin binding. These cells were never stimulated with CD3/CD28 beads (FIG. 3C). Shown in FIG. 3B, is a timeline for the isolation (D0), growth (D0-21), selection (D14 and D21) and expansion (REP—D21) of CD4+ and CD8+ primary T cells isolated from PBMCs as per FIG. 4 below. These are CD8+ T cells transduced with two separate lentiviruses containing CD19CAR-T2A-Her2tG or CD20CAR-T2A-EGFRt at an MOI=1 for each lentivirus. Pre-selection CD8+ T cells were stained with Erbitux-APC, biotinylated-Herceptin and a streptavidin conjugated secondary fluorophore (SA-PE) seven days post transduction (D10 of culture), while Post-selection cells were stained on S1Sp1D12 (See FIG. 4). As shown in FIG. 3D, cell lysis for western blot analysis was carried out in RIPA buffer containing protease inhibitor cocktail. Cell lysates were analyzed by BCA assay (Pierce), equally loaded onto gels and western blots were probed with the primary antibody anti CD247 (CD3ζ) and the secondary IRDye 800CW conjugated goat anti-mouse antibody (LI-COR). Blots were imaged on the Odyssey Infrared Imaging System (LI-COR).

Selection of CD4 and CD8 T-Cells

CD4 and CD8 bulk T cells were isolated from human peripheral blood mononuclear cells (PBMCs) derived from blood discard kits of healthy donors (Puget Sound Blood Center). PBMCs from each donor were split into two groups (CD4 or CD8 bulk isolation) and Automacs depleted using CD4 or CD8 isolation kits (Miltenyi Biotec) as per the manufacturer's protocol. Isolated cells were then stimulated (S1) with 50 U/ml interleukin-2 (IL-2) for CD8, 5 ng/ml interleukin-7 (IL-7) for CD4, 1 ng/ml interleukin-15 (IL-15) and anti-CD3/CD28 beads (Life Technologies). CD4 and CD8 T cells were transduced on day 3 after activation using protamine sulfate (1:100 dilution) and a virus MOI of 1 followed by centrifugation at 800×g for 30 minutes at 32° C. The Her2t+ or EGFRt subset of each cell line was enriched by immunomagnetic selection with biotin-conjugated Herceptin or Erbitux and anti-biotin microbeads (Miltenyi). Selected CD19CAR+ and/or CD20CAR+ T cells were expanded 12-18 days post transduction by stimulation with irradiated (8000 rad) TM-LCL (Sp1) at a T cell:TM-LCL ratio of 1:7 in the presence of 50 U/ml IL-2 (CD8), 5 ng/ml IL-7 (CD4) and 1 ng/ml IL-15. Cells were harvested on Day 12 (D12) post stimulation and subjected to flow analysis.

The cells of interest in the western blot are S1Sp1D12 (see FIG. 3) and have already been purified for their respective marker/s. The dual transduced cells are the CD19CAR-T2A-Her2tG and CD20CAR-T2A-EGFRt containing CD8+ T cells. This western blot is specific to the zeta portion of the CAR. It does not speak to the expression of the two marker proteins Her2tG or EGFRt (see FIG. 3C and FIG. 4). The western blot demonstrates CAR expression in the CD8+ T cells. Most importantly, expression of both CARs (CD19CAR and CD20CAR) in the dual transduced CD8+ T cells is seen.

Specificity of CD19 and CD20 CAR T-Cells Against K562 Target Panel Cells

CD8 Tcm were co-cultured with K562 target cells at a 30:1, 10:1, 3.3:1 or 1.1:1 ratio. Only the dual transduced T cells were able to target all antigen expressing K562 cells.

Figure 5C:
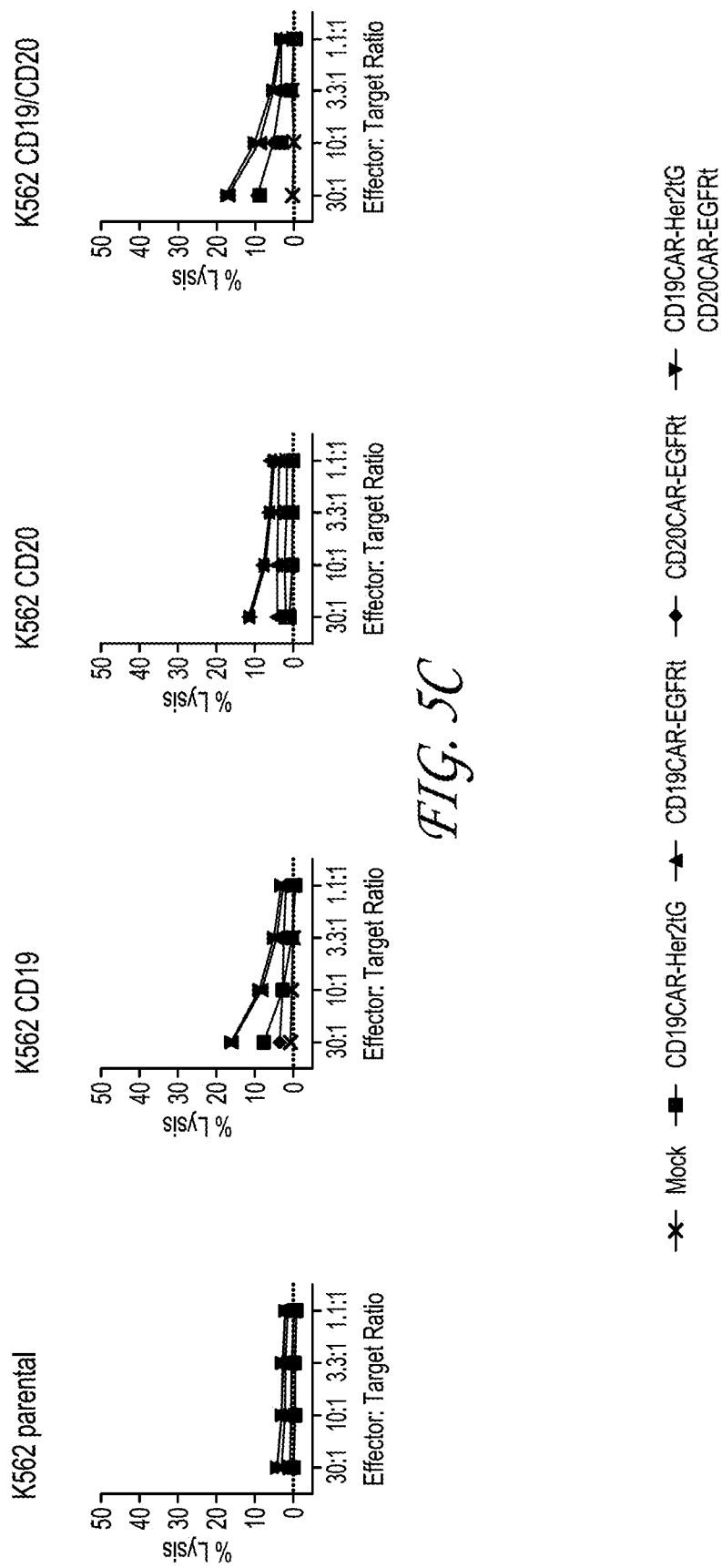
FIG. 5C depicts similar results were seen for CD4 Tcm. As shown representations are Mock (X), CD19CAR-Her2tG (square), CD19CAR-EGFTt (triangle), CD20CAR-EGFRt (diamond) and CD19CAR-Her2tG/CD20CAR-EGFRt (upside-down triangle).
Figure 6A:
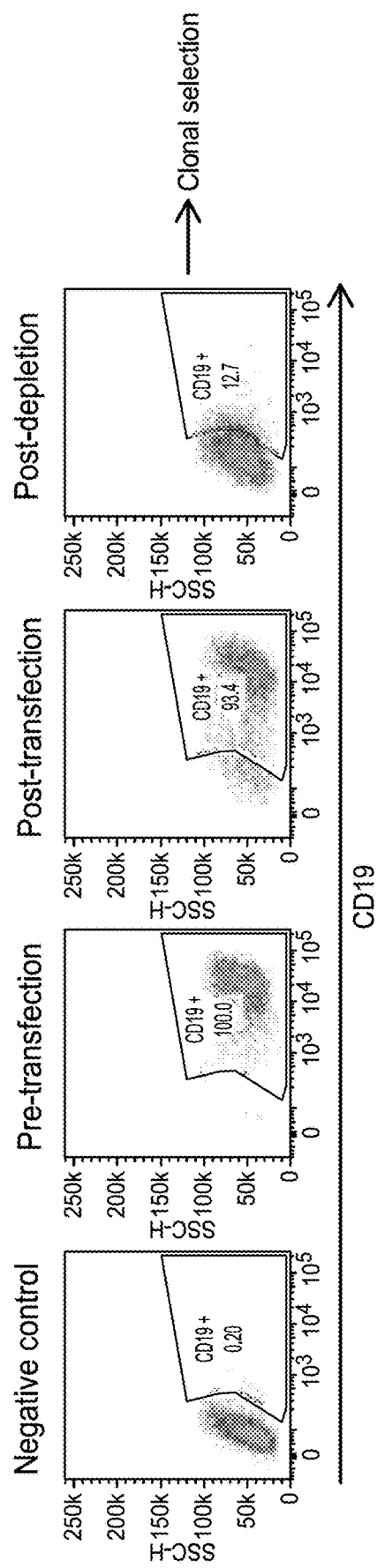
FIGS. 6A-6D show experimental results of Raji cells electroporated with plasmids containing CD19-targeted CRISPR guide sequences.
Figure 6B:
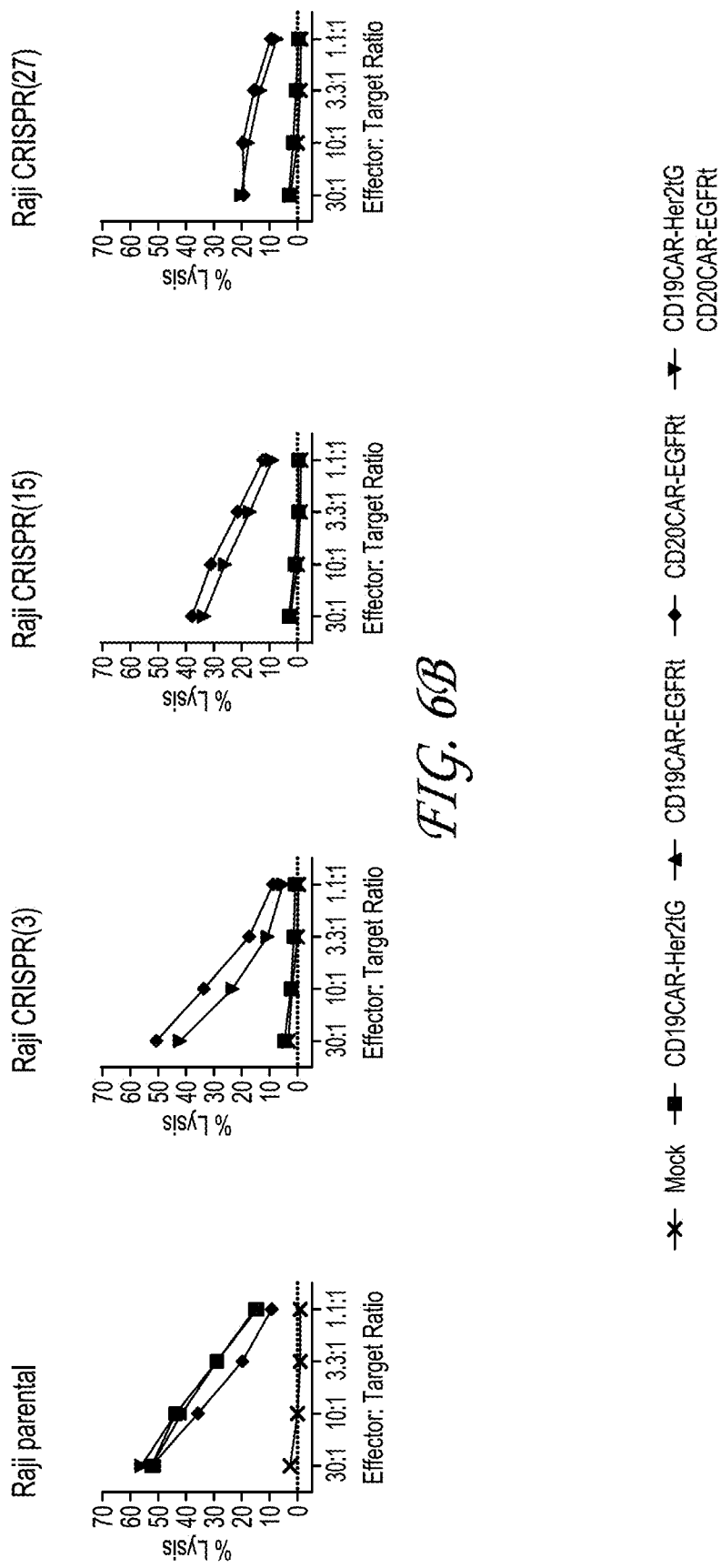
Figure 6C:
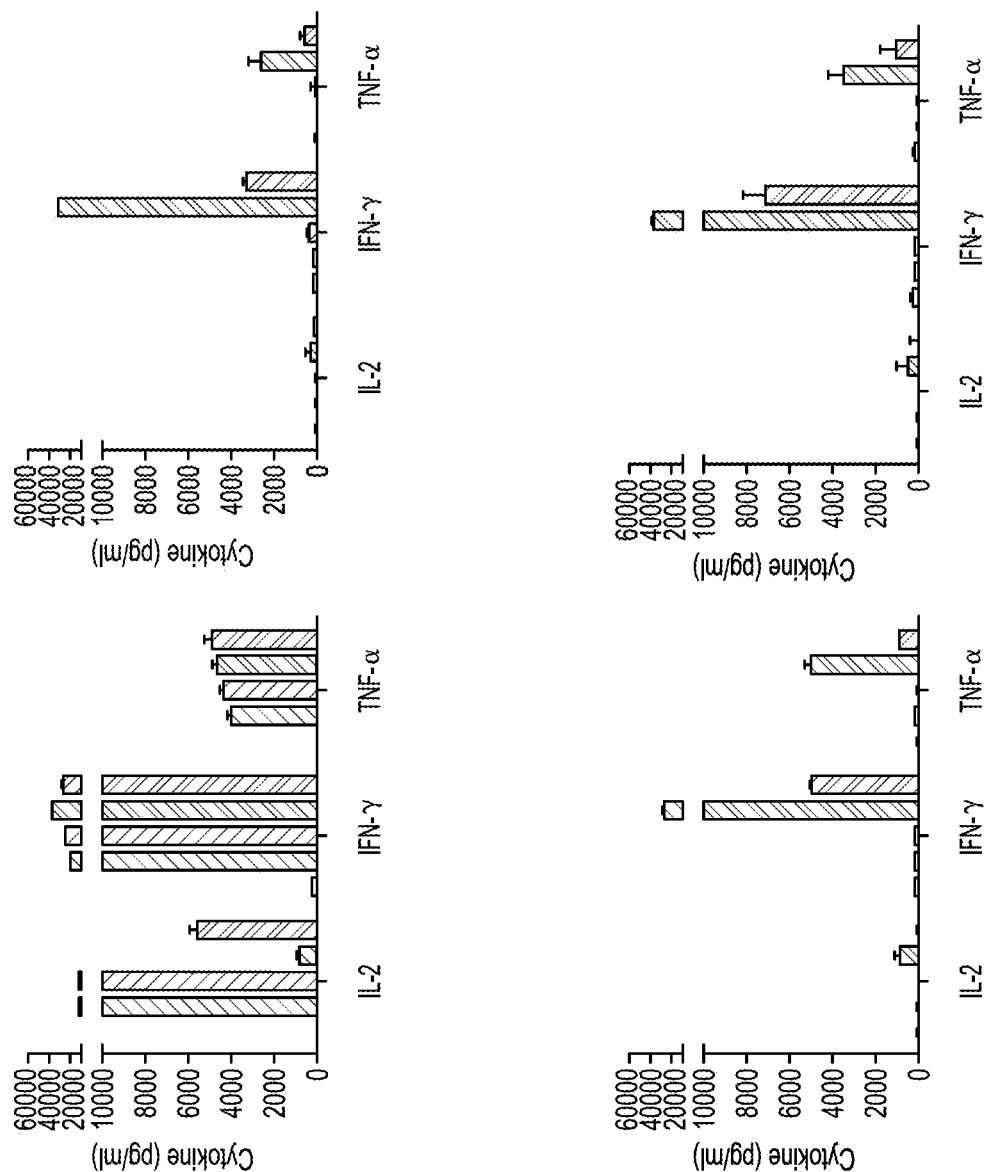
Figure 6D:
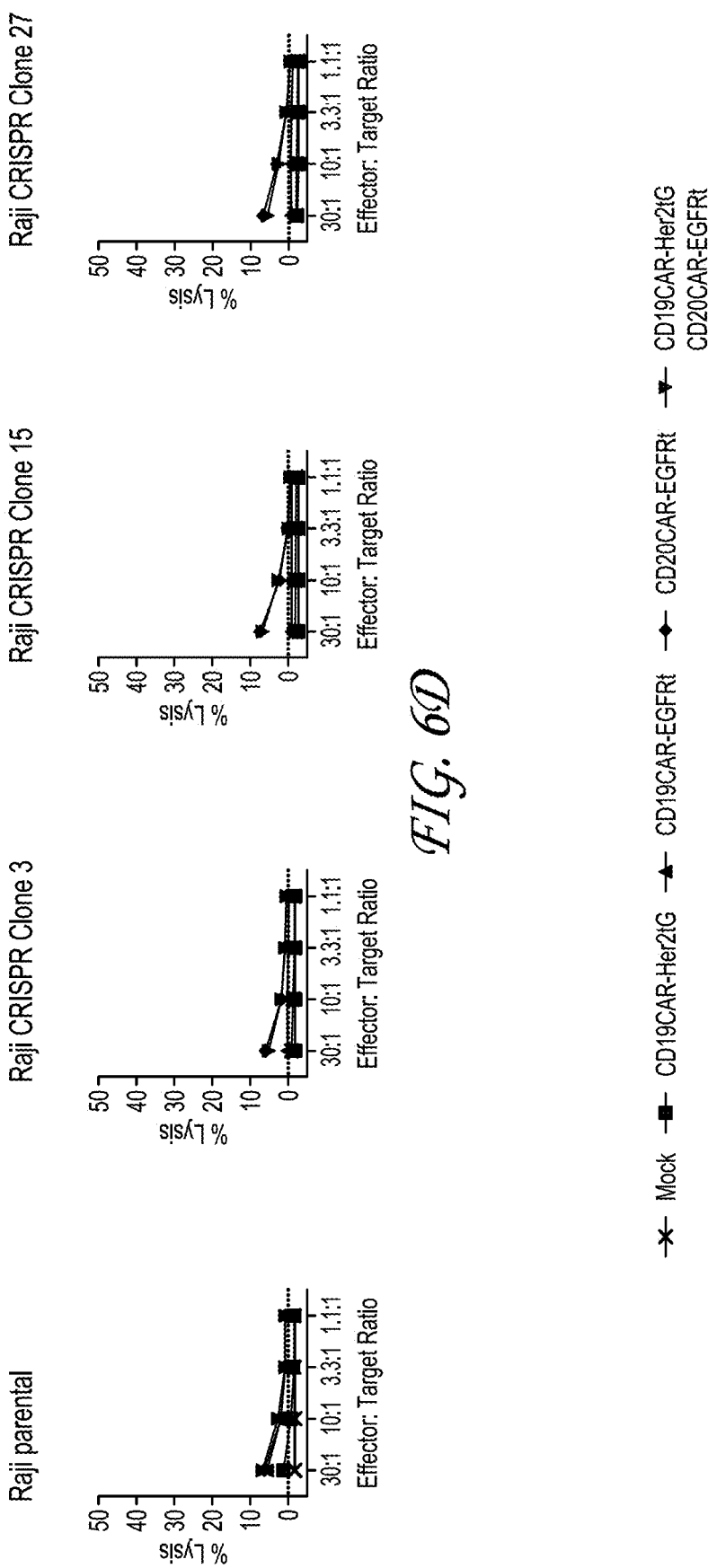

As shown in FIG. 5A, a 4-hour chromium release assay was performed showing CD19- and CD20-CAR T cell specificity against K562 target panel cells. CD8 Tcm were co-cultured with K562 target cells at a 30:1, 10:1, 3.3:1 or 1.1:1 ratio. Only the dual transduced T cells were able to target all antigen expressing K562 cells. The CD19CAR-T2A-Her2t and CD19CAR-T2A-EGFRt CD8 Tcm demonstrate similar lytic capacity. A 24-hour cytokine release assay was also performed using CD19, CD20 and CD19/CD20 bearing cells against K562 targets. CD8 Tcm were co-cultured with K562 target cells at a 2:1 T cell-to-target ratio for 24 hours and then supernatant was analyzed for the presence of effector cytokines. CD19CAR-T2A-Her2t transduced CD8 Tcm produced a more diverse repertoire and higher levels of effector cytokines relative to CD19CAR-T2A-EGFRt transduced CD8 Tcm. The panels are the same as in FIGS. 5A and 5B (Left to right: K562 CD19, K562 CD20 and K562 CD19/CD20). Similar results were seen for CD4 Tcm. The CD19CAR-T2A-Her2t and CD19CAR-T2A-EGFRt CD8 Tcm demonstrate similar lytic capacity, showing the efficacy of the CAR bearing T-cells. As shown in FIG. 5C, similar results were seen for CD4 Tcm.

Raji Cells Electroporated with Plasmids Containing CD19 Targeted CRISPR Guide Sequences Shown in FIGS. 6A-D are the experimental results of Raji cells electroporated with plasmids containing CD19-targeted CRISPR guide sequences. Raji cells were subjected to negative selection using CD19 microbeads. Post-depletion of CD19+ cells the CD19-cells were clonally selected and expanded for downstream experiments. Seven days post electroporation the Raji cells were subjected to negative selection using CD19 microbeads. (FIG. 6A). 4 hour chromium release assays and bioplex assays were then performed using the same cells from FIGS. 5B and C. A chromium release assay was also performed using CD4+ cells.

NSG Mice Injected with CAR Expressing T-Cells

Figure 7:
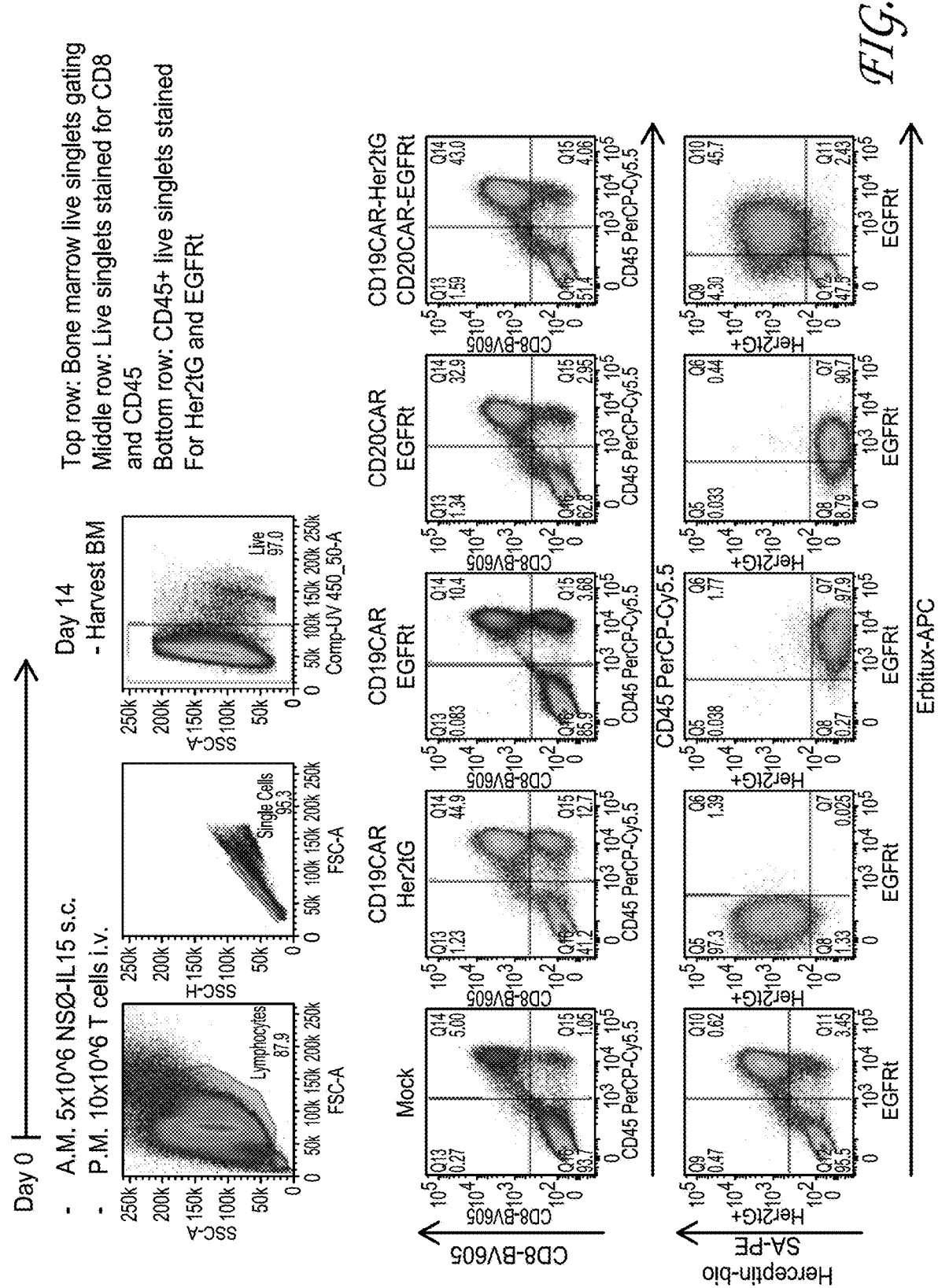

Shown in FIG. 7 are the experimental results of NSG mice injected with $5e^6$ NSO-IL15 cells and then $10e^6$ Mock or CAR expressing T cells i.v. On Day 14 post T cell injection, mouse bone marrow was harvested and subjected to flow analysis. Shown in the top row are gates live and singlets. The middle row gates show CD8+×CD45+ cells. The bottom row looks at the CD45+ cell population and stains for the markers Her2tG and EGFRt. Results demonstrate that EGFRt and Her2tG can be used to efficiently track T cells in vivo. (FIG. 7, top row). Shown in the middle row of FIG. 7, are cells gated for viable (93.6% lymphocytes), single (98.8%), and alive cells (99.9%). CD8 and CD45 staining of the cells are shown from left to right as Mock, CD19CAR-T2A-Her2t, CD19CAR-T2A-EGFRt Tcm, and CD19CAR-Her2tg/CD20CAR-EGFRt. At least $1\times10^7$ cells were recorded inside of the viable, single cell and alive gates. So although the CD45+ cells represent around 1% of the population, it is equivalent to $1\times10^5$ cells. The remaining cells are mouse bone marrow cells. Shown in the last row of FIG. 7, are the Multisort purification of Her2t and EGFRt positive T cells. For the experiment, H9 cells ($5\times10^6$ parental, Her2t+, EGFRt+, or Her2t+/EGFRt+ were mixed together and then subjected to purification. The cells were initially purified based on biotinylated Herceptin and anti-biotin multisort beads. The multisort beads were then removed and the positive fraction subsequently subjected to purification based on Erbitux-APC and anti-APC microbeads. The final positive fraction was dual positive for Her2t and EGFRt.

Mice Expressing CAR T-Cells to Inhibit Tumor Growth eGFP:ffluc expressing Raji target cells ($10^6$) were i.v. injected into 6-10 week old mice. Seven days later a total of $10^7$ CAR-Her2t+, CAR-EGFRt+ or dual CAR expressing T cells (1:1 ratio CD4:CD8) were injected intravenously (IV).

Figure 8:
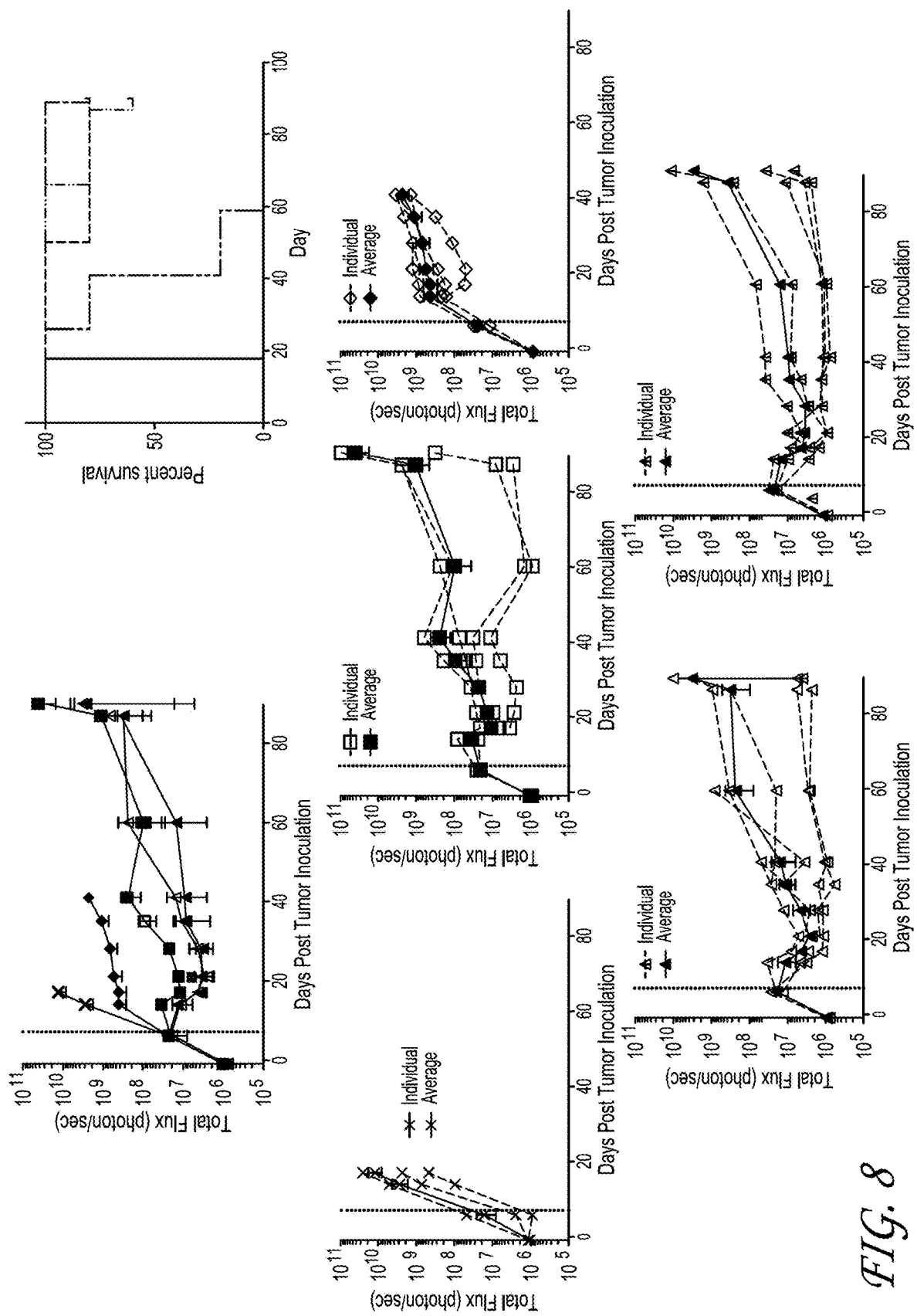
FIG. 8 shows the experimental results of NSG mice injected with $0.5e^6$ Raji eGFP:ffluc cells i.v. and then $10e^6$ Mock or CAR expressing T cells at a 1:1 ratio of CD4:CD8. Serial tumor imaging was performed and total flux graphed to demonstrate tumor growth or the inhibition of tumor growth. Results demonstrate that the single CAR or dual CAR expressing T cells were able to inhibit tumor growth relative to Mock T cells. As shown representations are Mock (✖), CD19CAR-Her2tG (square), CD19CAR-EGFTt (triangle), CD20CAR-EGFRt (diamond) and CD19CAR-Her2tG/CD20CAR-EGFRt (upside-down triangle).

Bioluminescent imaging was performed weekly by intraperitoneal (i.p.) injection of 4.29 mg/mouse D-luciferin (Xenogen), anesthetization by isoflurane and imaging 10 minutes post D-luciferin injection using the IVIS Spectrum Imaging System (Perkin Elmer). Luciferase activity was analyzed using Living Image Software Version 4.3 (Perkin Elmer) and photon flux was analyzed within regions of interest. Shown in FIG. 8, the single CAR or dual CAR expressing T cells were able to inhibit tumor growth relative to Mock T cells.

Figure 9A:
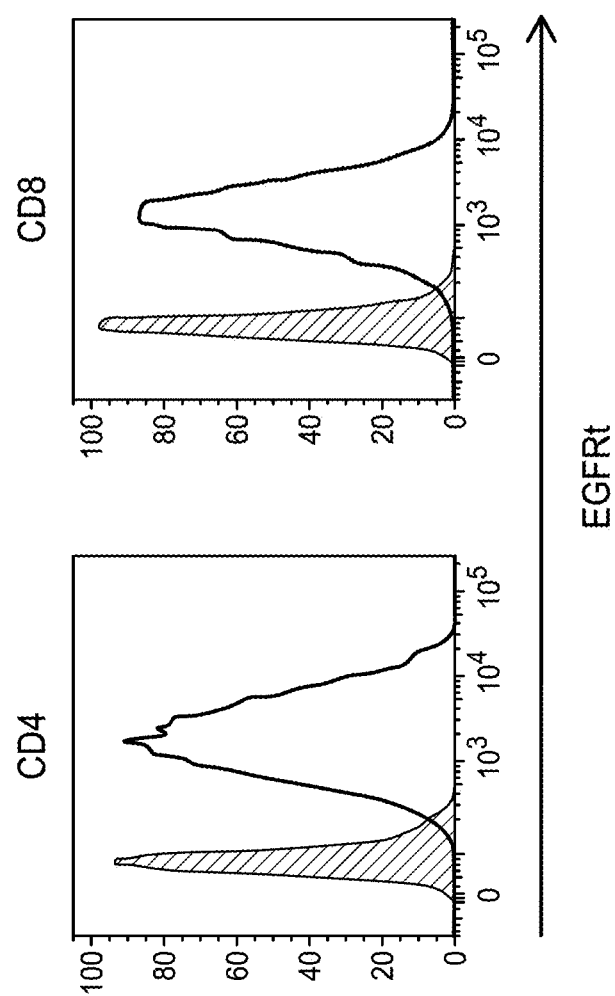
FIG. 9A shows that CD4 and CD8 T-cells can be transduced with two separate CAR-encoding lentiviral vectors. CD4 and CD8 purified T-cells were stimulated with CD3/CD28 beads and then co-transduced with clinical grade virus encoding the $2^{nd}$ generation 41BB-ζ short spacer FMC63CD19CAR or the $2^{nd}$ generation 41BB-ζ short spacer CE7CAR. Each CAR was followed by an in-frame T2A-EGFRt. Transduced T-cells were purified by EGFRt and frozen on S1D14 (CD4) or S1D15 (CD8). The process development project was PD0170. Flow analysis demonstrated that transduced cells were purified to homogeneity based on EGFRt expression. Results do not demonstrate what percentage of the CD19- or CE7CAR is represented in the EGFRt$^+$ population or whether the T-cells are indeed dual transduced with virus.

CD4 and CD8 T-Cells can be Transduced with Two Separate CAR-Encoding Lentiviral Vectors CD4 and CD8 purified T-cells were stimulated with CD3/CD28 beads and then co-transduced with clinical grade virus encoding the $2^{nd}$ generation 41BB-t short spacer FMC63CD19CAR or the 2nd generation 41BB-ζ short spacer CE7CAR. Each CAR was followed by an in-frame T2A-EGFRt. Transduced T-cells were purified by EGFRt and frozen on S1D14 (CD4) or S1D15 (CD8). The process development project was PD0170. Shown in FIG. 9A, the flow analysis demonstrates that transduced cells were purified to homogeneity based on EGFRt expression. Results do not demonstrate what percentage of the CD19- or CE7CAR is represented in the EGFRt$^+$ population or whether the T-cells are indeed dual transduced with virus. FMC63 CD19CAR comprises the amino acid sequence set forth in SEQ ID NO: 11 and is encoded by the sequence set forth in SEQ ID NO: 12. In some alternatives, FMC63 CD19CAR comprises the amino acid sequence set forth in SEQ ID NO: 11 and is encoded by the sequence set forth in SEQ ID NO: 12.

Figure 9B:
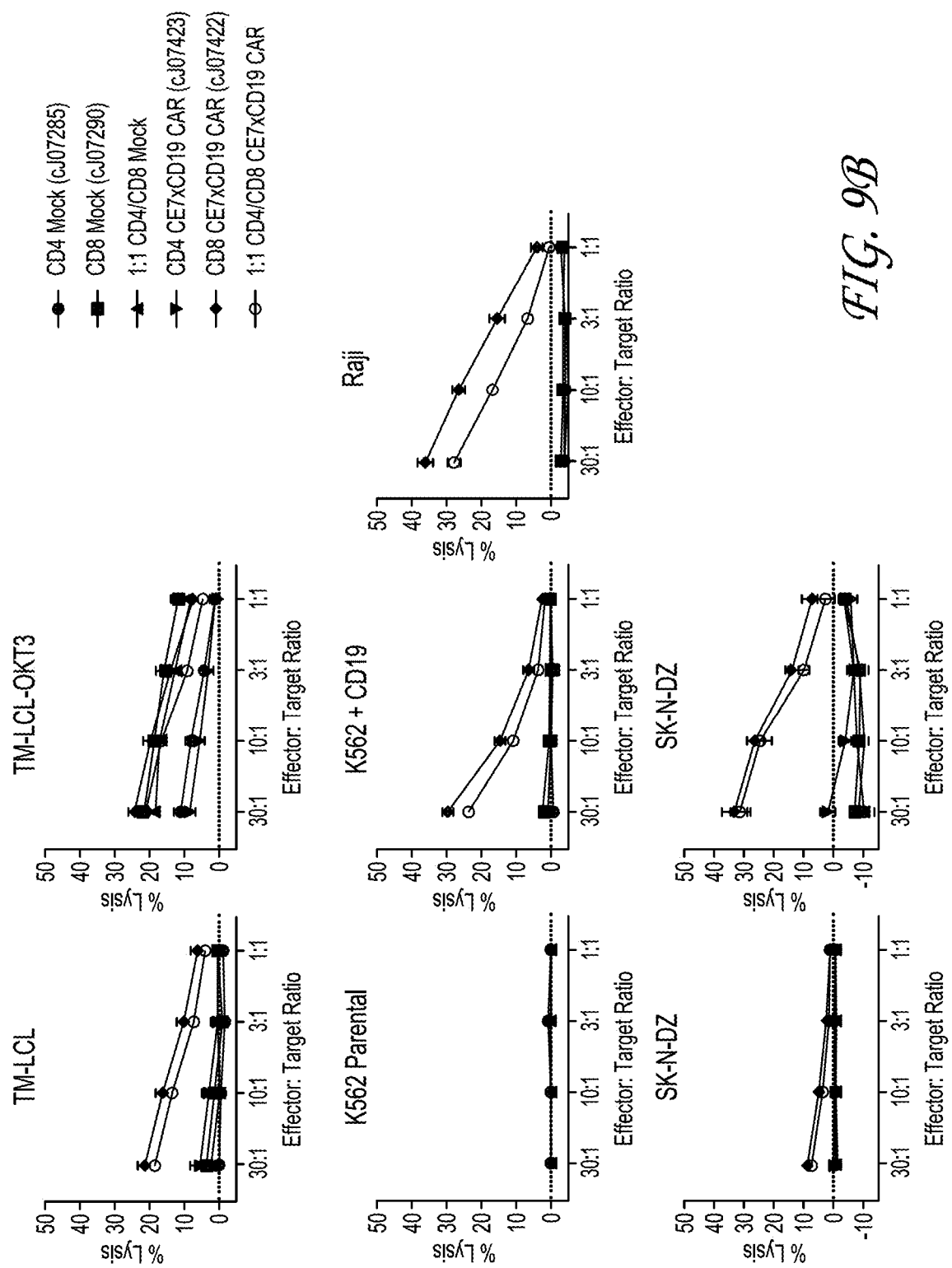
FIG. 9B shows that CD19 and CE7CAR dual transduced T-cells demonstrate specific lysis against CD19 or L1CAM positive target cell lines. Mock (CAR$^-$) T-cells and dual transduced T-cells were co-cultured with target cell lines at different effector to target ratios for 4-hours. K562 are negative for both targets CD19 and L1CAM. TM-LCL, TM-LCL-OKT3, K562+CD19, and Raji are CD19-positive alone. SK-N-DZ is L1 CAM-positive alone. SK-N-DZ+CD19 are positive for both targets. Results demonstrate that the transduced CD8 or mixed CD4:CD8 T-cells elicit high levels of CD19CAR activity. There was a lower level of CE7CAR activity as demonstrated against the SK-N-DZ cell line. These results indicate that T-cells can be successfully transduced with two separate CAR-encoding viruses and the resultant T-cell population is able to recognize multiple antigens.

CD19 and CE7CAR Dual Transduced T-Cells Demonstrate Specific Lysis Against CD19 or L1CAM Positive Target Cell Lines Mock (CAW) T-cells and dual transduced T-cells were co-cultured with target cell lines at different effector to target ratios for 4-hours. K562 are negative for both targets CD19 and L1CAM. TM-LCL, TM-LCL-OKT3, K562+CD19, and Raji are CD19-positive alone. SK-N-DZ are L1CAM-positive alone. SK-N-DZ+CD19 are positive for both targets. Shown in FIG. 9B, the transduced CD8 or mixed CD4:CD8 T-cells elicit high levels of CD19CAR activity. There was a lower level of CE7CAR activity as demonstrated against the SK-N-DZ cell line. These results indicate that T-cells can be successfully transduced with two separate CAR-encoding viruses and the resultant T-cell population is able to recognize multiple antigens.

Figure 9C:
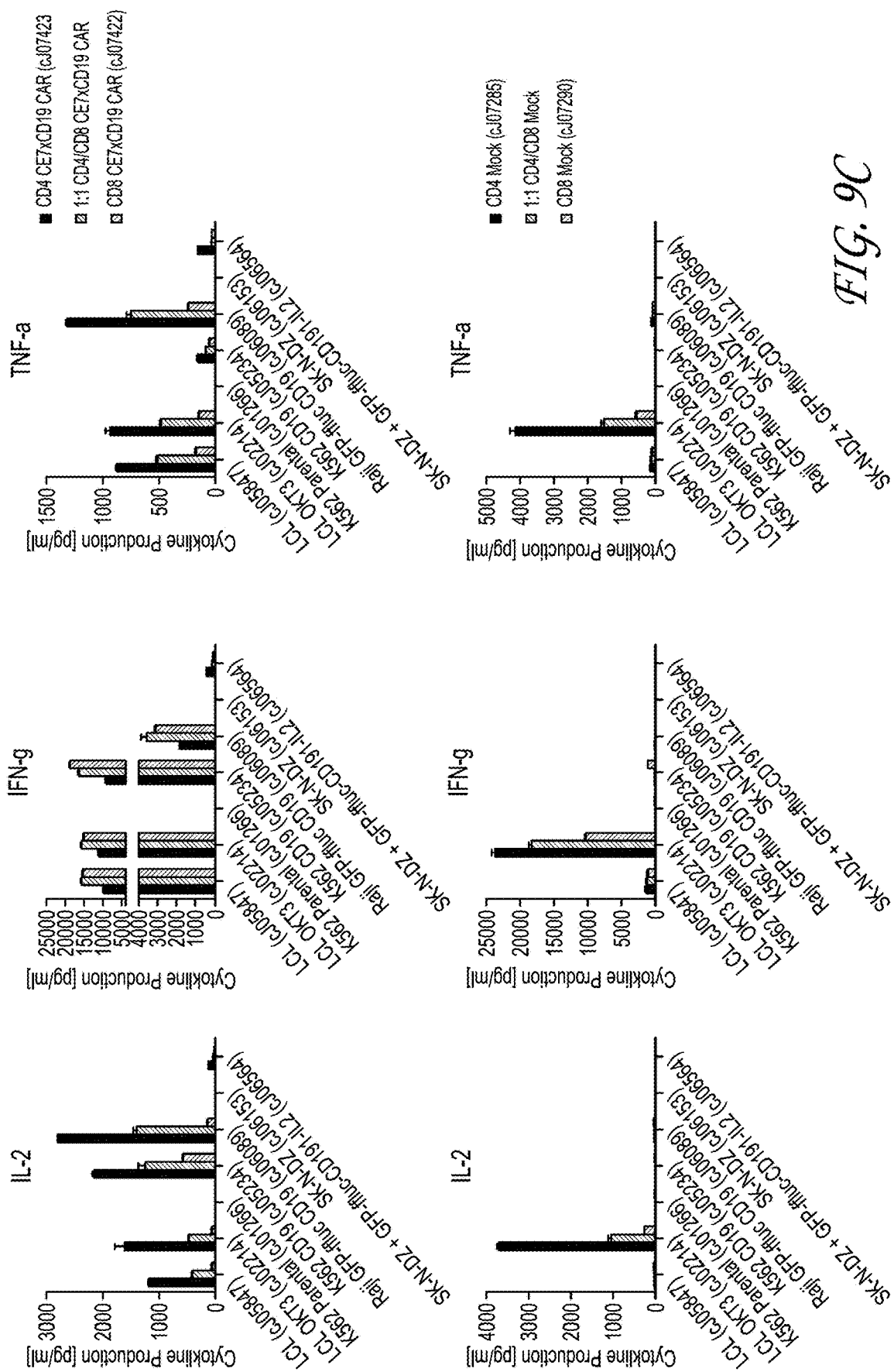
FIG. 9C shows that CD19- and CE7CAR dual transduced T-cell populations produce cytokines against CD19 or L1CAM positive target cell lines. Dual transduced CD4 and CD8 T-cell populations were co-cultured for 24 hours with target cell lines at a 2:1 effector-to-target ratio. Following the 24 hour incubation period, supernatant from the co-cultures was analyzed for the presence of IL-2, IFN-g, or TNF-a by Bioplex assay. The dual transduced T-cells produced cytokine in response to all suspension cell (LCL and K562) targets expressing CD19. There was little to no cytokine produced in response to SK-N-DZ which is not uncommon with the $2^{nd}$ Gen S-spacer CE7CAR even when expressed in 100% of the T-cell population. Since it was not known what percentage of the T-cell populations contain the CE7CAR this was not surprising when combined with the chromium data in FIG. 9B.

CD19- and CE7CAR Dual Transduced T-Cell Populations Produce Cytokines Against CD19 or L1CAM Positive Target Cell Lines Dual transduced CD4 and CD8 T-cell populations were co-cultured for 24 hours with target cell lines at a 2:1 effector-to-target ratio. Following the 24 hour incubation period, supernatant from the co-cultures was analyzed for the presence of IL-2, IFN-g, or TNF-a by Bioplex assay as shown in FIG. 9C. The dual transduced T-cells produced cytokine in response to all suspension cell (LCL and K562) targets expressing CD19. There was little to no cytokine produced in response to SK-N-DZ which is not uncommon with the $2^{nd}$ Gen S-spacer CE7CAR even when expressed in 100% of the T-cell population. Since it is not known what percentage of the T-cell populations contain the CE7CAR this is not surprising when combined with the chromium data in FIG. 9B.

Figure 9D:
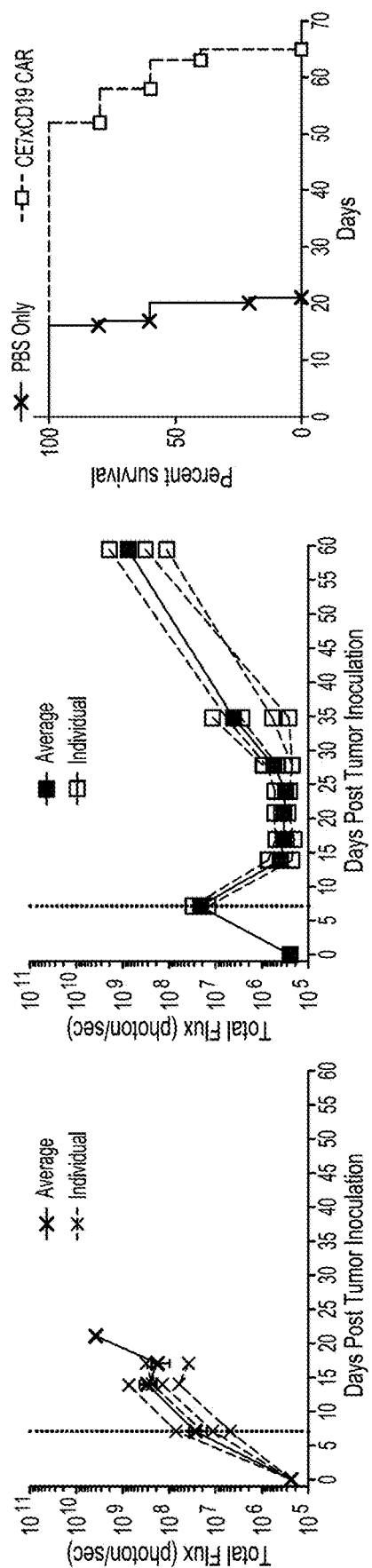
FIG. 9D shows that dual-transduced T-cells elicit antitumor activity in an intracranial xenograft tumor model. Cohorts of mice were inoculated with 0.2e6 SK-N-DZ that express GFP:ffluc, CD19t, and IL-2 (Day 0) and 2e6 dual transduced CD4:CD8 T-cells (1:1 ratio) (Day 7) intracranially (i.c.). Serial bioluminescence imaging of tumor in cohorts of mice treated with Mock (PBS only—left) or dual transduced CD4:CD8 CE7CAR T-cells (middle). Kaplan-Meier analysis (right) of survival in treatment and control groups. The dual-transduced cells were able to regress and control tumor growth as evidenced by a prolonged decrease in bioluminescence imaging.

Dual-Transduced T-Cells Elicit Antitumor Activity in an Intracranial Xenograft Tumor Model Cohorts of mice were inoculated with 0.2e6 SK-N-DZ that express GFP:ffluc, CD19t, and IL-2 (Day 0) and 2e6 dual transduced CD4:CD8 T-cells (1:1 ratio) (Day 7) intracranially (i.c.). Shown in FIG. 9D are the results from serial bioluminescence imaging of tumors in cohorts of mice treated with Mock (PBS only—left) or dual transduced CD4:CD8 CE7CAR T-cells (middle). Kaplan-Meier analysis (right) of survival in treatment and control groups. The dual-transduced cells were able to regress and control tumor growth as evidenced by a prolonged decrease in bioluminescence imaging. However, the tumor did grow out over time and the mice slowly succumbed to tumor growth and were euthanized.

Figure 10A:
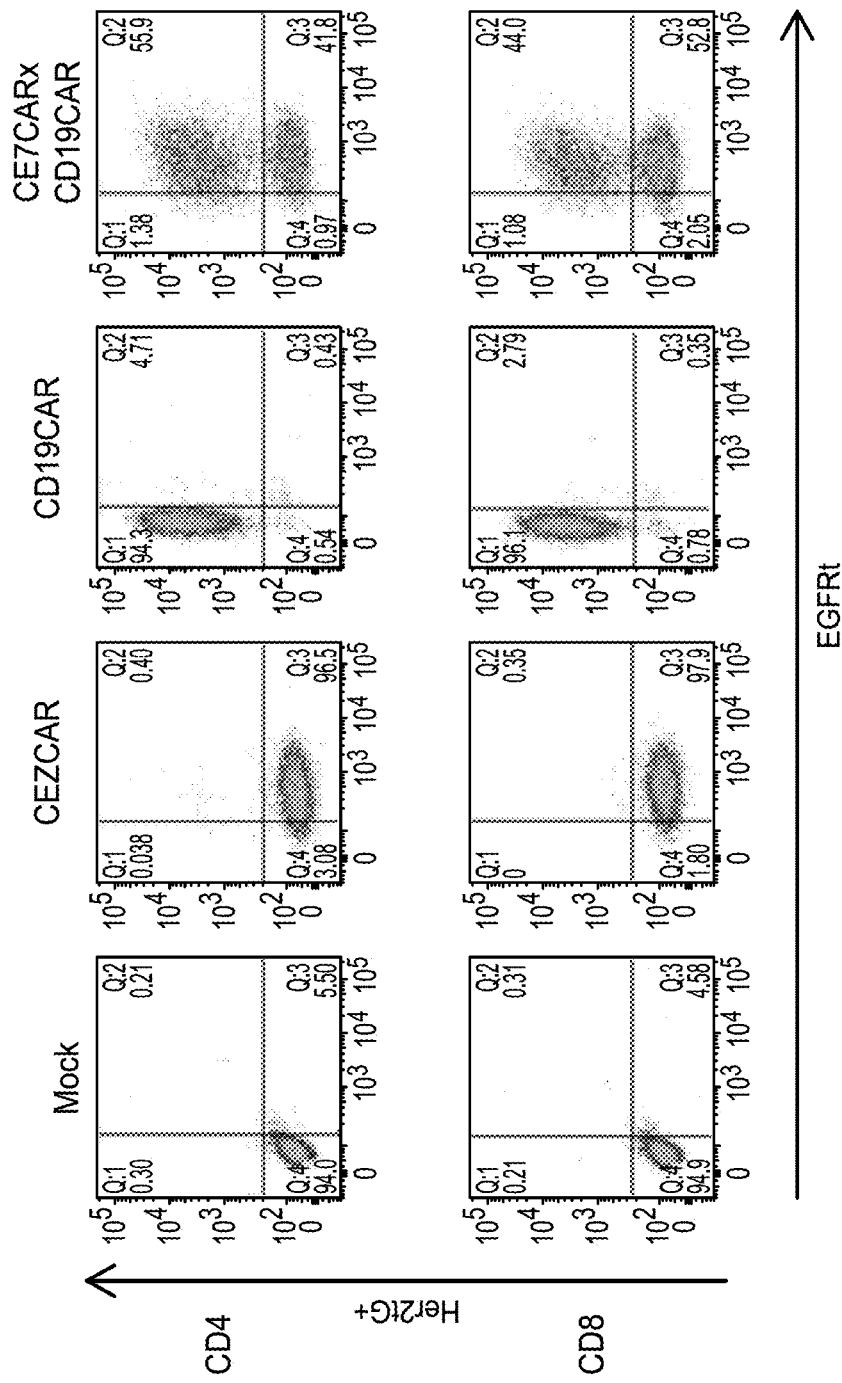
FIG. 10A shows that CD4 and CD8 T-cells can be transduced with two separate CAR-encoding lentiviral vectors and dual positive populations can be identified by associated markers. CD4 and CD8 purified T-cells were stimulated with CD3/CD28 beads and then individually or co-transduced with lentivirus encoding the $2^{nd}$ generation 41BB-t short spacer FMC63CD19CAR or/and the $2^{nd}$ generation 41BB-ζ long mutant (L235D, N297Q) spacer CE7CAR. The CD19CAR was followed by an in-frame T2A-Her2tG and the CE7CAR by a T2A-EGFRt. Transduced T-cells were purified by EGFRt (CE7CAR) and frozen. Flow analysis was performed on day 9 and demonstrates that transduced cells were purified to homogeneity based on EGFRt expression. For the CD4 T-cells there was ~56% Her2tG (CD19CAR) positivity and ~44% dual-positivity for the CD8 T-cells.

CD4 and CD8 T-Cells can be Transduced with Two Separate CAR-Encoding Lentiviral Vectors and Dual Positive Populations can be Identified by Associated Markers CD4 and CD8 purified T-cells were stimulated with CD3/CD28 beads and then individually or co-transduced with lentivirus encoding the $2^{nd}$ generation 41BB-t short spacer FMC63CD19CAR or/and the 2nd generation 41BB-ζ long mutant (L235D, N297Q) spacer CE7CAR. The CD19CAR was followed by an in-frame T2A-Her2tG and the CE7CAR by a T2A-EGFRt. Transduced T-cells were purified by EGFRt (CE7CAR) and frozen. Flow analysis was performed on day 9 and demonstrates that transduced cells were purified to homogeneity based on EGFRt expression (See FIG. 10A). For the CD4 T-cells there was ~56% Her2tG (CD19CAR) positivity and ~44% dual-positivity for the CD8 T-cells.

Figure 10B:
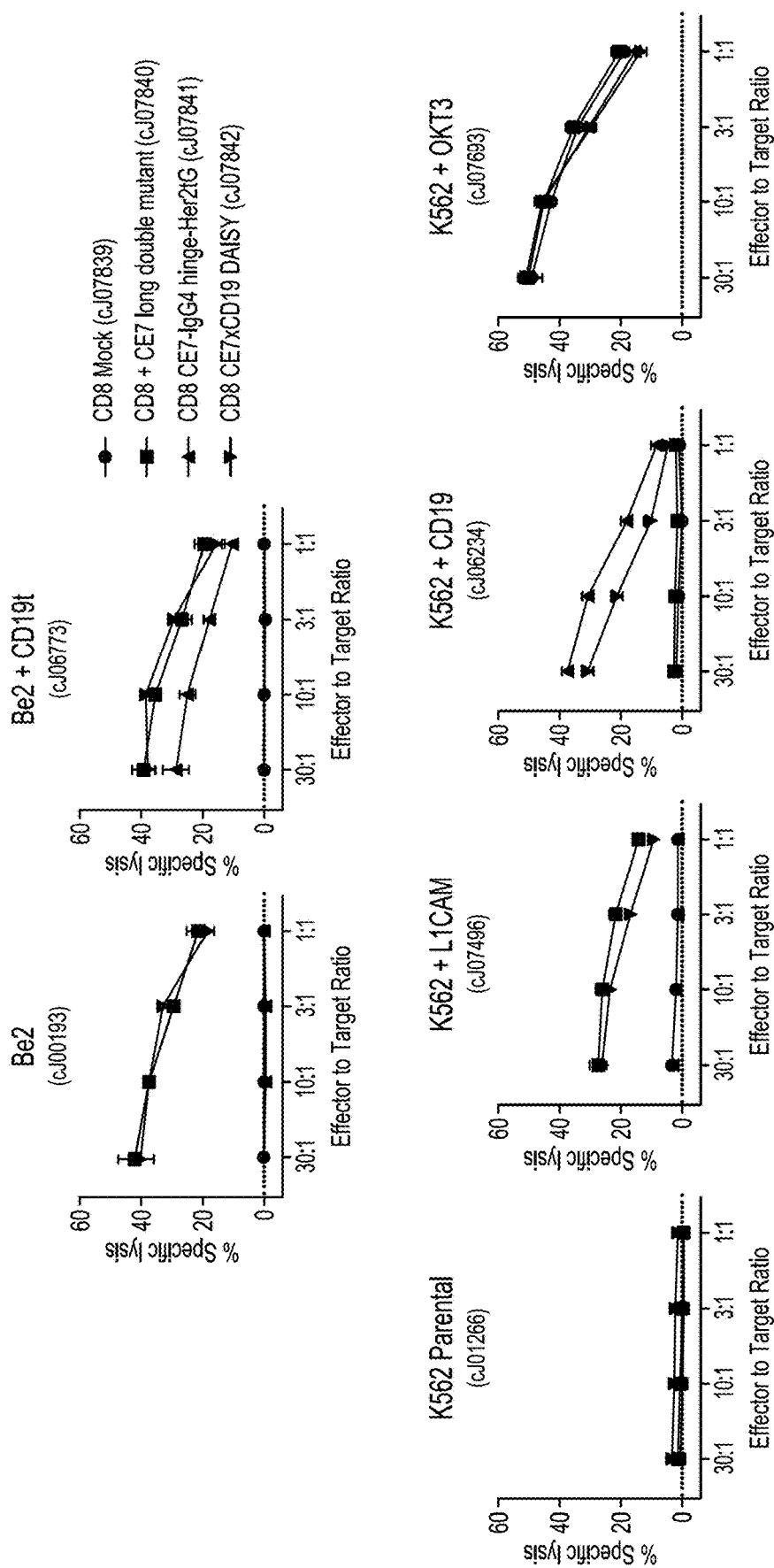
FIG. 10B shows that CD19 and CE7CAR dual transduced CD8$^+$ T-cells demonstrate specific lysis against CD19 or L1CAM positive target cell lines. Mock (CAR$^-$), single transduced (CD19CAR or CE7CAR) and dual transduced CD8$^+$ T-cells were co-cultured with target cell lines at different effector to target ratios for 4-hours. K562 are negative for both targets CD19 and L1CAM. K562-OKT3 was used as a positive control. Be2 are L1CAM-positive alone. Be2+CD19t are positive for both targets. Results demonstrate that the single transduced CD8$^+$ T-cells elicit specific lysis against their cognate antigen. However, the dual transduced T-cells efficiently recognized and lysed cells expressing CD19, L1CAM or both antigens. All CD8$^+$ T-cells were able to elicit similar levels of cell lysis against the K562-OKT3. These results indicate that T-cells can be successfully transduced with two separate CAR-encoding viruses, purified by a selectable marker, and the resultant T-cell population is able to recognize multiple antigens.

CD19 and CE7CAR Dual Transduced CD8$^+$ T-Cells Demonstrate Specific Lysis Against CD19 or L1CAM Positive Target Cell Lines Mock (CAR$^-$), single transduced (CD19CAR or CE7CAR) and dual transduced CD8$^+$ T-cells were co-cultured with target cell lines at different effector to target ratios for 4-hours. K562 are negative for both targets CD19 and L1CAM. K562-OKT3 was used as a positive control. Be2 are L1CAM-positive alone. Be2+CD19t are positive for both targets. Results demonstrate that the single transduced CD8$^+$ T-cells elicit specific lysis against their cognate antigen. However, the dual transduced T-cells efficiently recognized and lysed cells expressing CD19, L1CAM or both antigens. All CD8$^+$ T-cells were able to elicit similar levels of cell lysis against the K562-OKT3. These results indicate that T-cells can be successfully transduced with two separate CAR-encoding viruses, purified by a selection marker, and the resultant T-cell population is able to recognize multiple antigens (See FIG. 10B).

Figure 10C:
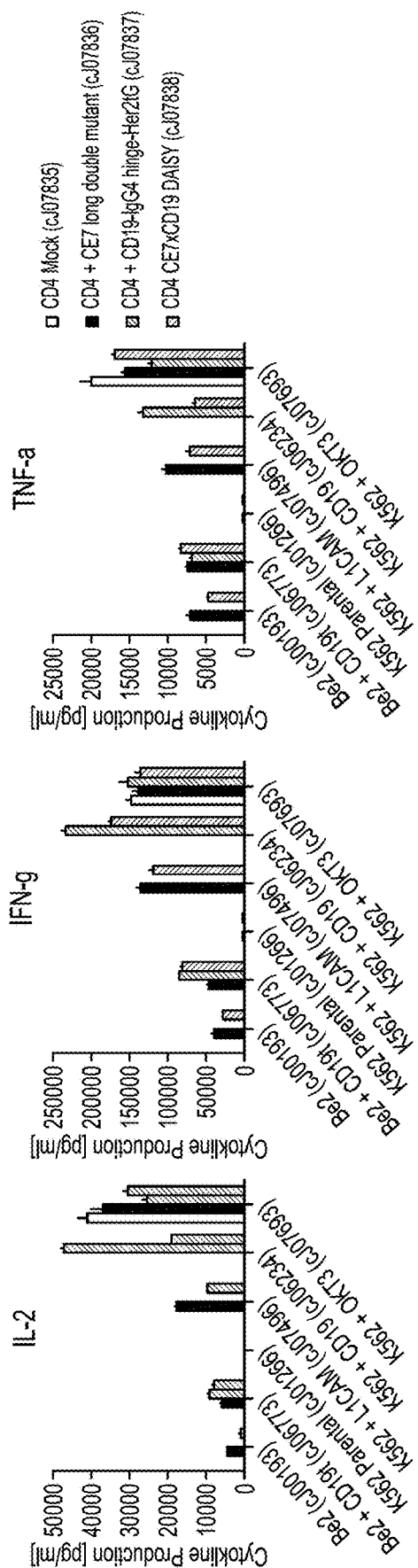
FIG. 10C shows that CD19- and CE7CAR dual transduced T-cell populations produce cytokines against CD19 or L1CAM positive target cell lines. Mock (CAR$^-$), single transduced (CD19CAR or CE7CAR) and dual transduced CD4$^+$ and CD8$^+$ T-cells were co-cultured for 24 hours with target cell lines at a 2:1 effector-to-target ratio. Following the 24 hour incubation period, supernatant from the co-cultures was analyzed for the presence of IL-2, IFN-g, or TNF-a by Bioplex assay. Dual-transduced cells were able to release cytokine against all target expressing cell lines. While there was no difference in cytokine production between individual CE7CAR-expressing and dual CAR expressing T-cells against Be2-CD19t, there was a difference in cytokine production between CD19CAR-expressing and dual transduced T-cells against K562-CD19t. This data coincides with the CD19CAR positivity of the dual transduced T-cell populations.
Figure 10C:
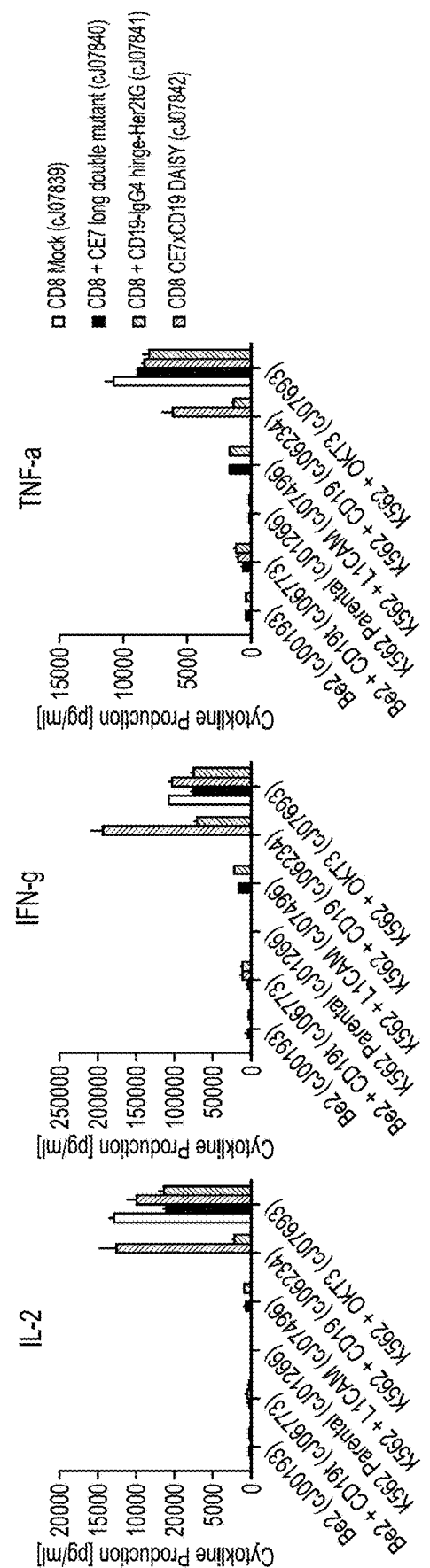

CD19- and CE7CAR Dual Transduced T-Cell Populations Produce Cytokines Against CD19 or L1CAM Positive Target Cell Lines Mock (CAR$^-$), single transduced (CD19CAR or CE7CAR) and dual transduced CD4$^+$ and CD8$^+$ T-cells were co-cultured for 24 hours with target cell lines at a 2:1 effector-to-target ratio. Following the 24 hour incubation period, supernatant from the co-cultures was analyzed for the presence of IL-2, IFN-g, or TNF-a by Bioplex assay, as shown in FIG. 10C. Dual-transduced cells were able to release cytokine against all target expressing cell lines. While there was no difference in cytokine production between individual CE7CAR-expressing and dual CAR expressing T-cells against Be2-CD19t, there was a difference in cytokine production between CD19CAR-expressing and dual transduced T-cells against K562-CD19t. This coincides with the CD19CAR positivity of the dual transduced T-cell populations.

Figure 10D:
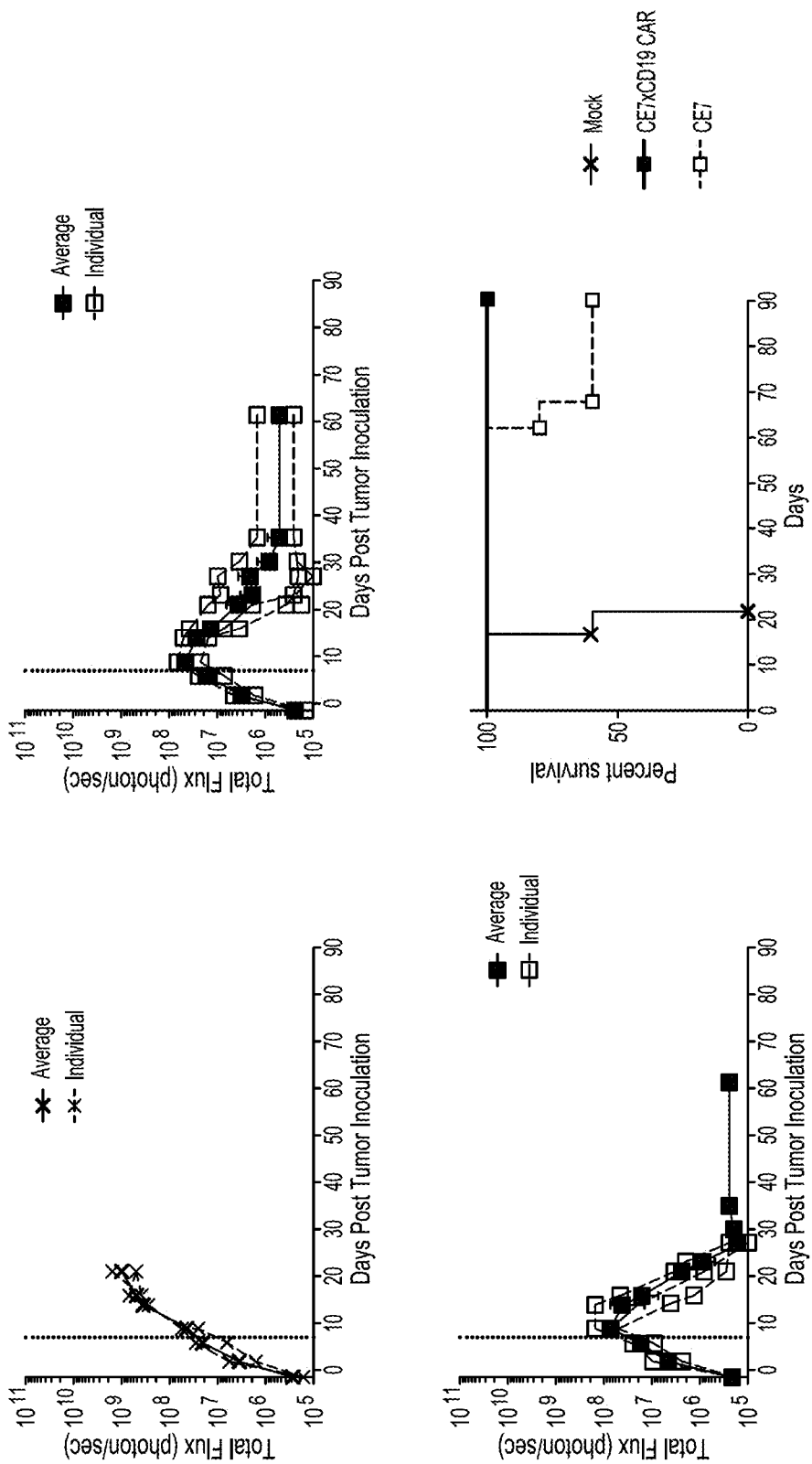
FIG. 10D shows that dual-transduced T-cells elicit anti-tumor activity in an intracranial xenograft tumor model. Cohorts of mice were inoculated with 0.2e6 SK-N-DZ that express GFP:ffluc and IL-2 (Day 0) and 2e6 dual transduced CD4:CD8 T-cells (1:1 ratio) (Day 7) intracranially (i.c.). Serial bioluminescence imaging of tumor in cohorts of mice treated with Mock (untransduced—left), CE7CAR-expressing (top row, middle) or dual-transduced CD4:CD8 CE7CAR T-cells (top row, right). Kaplan-Meier analysis (bottom) of survival in treatment and control groups. Both the single CE7CAR-expressing and dual-transduced cells were able to regress and control tumor growth as evidenced by a prolonged decrease in bioluminescence imaging. A subset of mice treated with single CE7CAR-expressing T-cells was euthanized prior to the arbitrary end point of the study due to outgrowth of tumor. These results show that dual-transduced T-cells are able to eradicate tumor in vivo at levels similar to single CE7CAR-expressing T-cells. There was therefore no inhibition in CE7CAR activity for the dual-transduced T-cell population.

Dual-Transduced T-Cells Elicit Antitumor Activity in an Intracranial Xenograft Tumor Model Cohorts of mice were inoculated with 0.2e6 SK-N-DZ that express GFP:ffluc and IL-2 (Day 0) and 2e6 dual transduced CD4:CD8 T-cells (1:1 ratio) (Day 7) intracranially (i.c.). Serial bioluminescence imaging of tumor in cohorts of mice treated with Mock (untransduced—left), CE7CAR-expressing (middle) or dual-transduced CD4:CD8 CE7CAR T-cells (right). Kaplan-Meier analysis (bottom) of survival in treatment and control groups. Both the single CE7CAR-expressing and dual-transduced cells were able to regress and control tumor growth as evidenced by a prolonged decrease in bioluminescence imaging. A subset of mice treated with single CE7CAR-expressing T-cells was euthanized prior to the arbitrary end point of the study due to outgrowth of tumor. These results show that dual-transduced T-cells are able to eradicate tumor in vivo at levels similar to single CE7CAR-expressing T-cells. There was therefore no inhibition in CE7CAR activity for the dual-transduced T-cell population (See FIG. 10D).

Figure 11A:
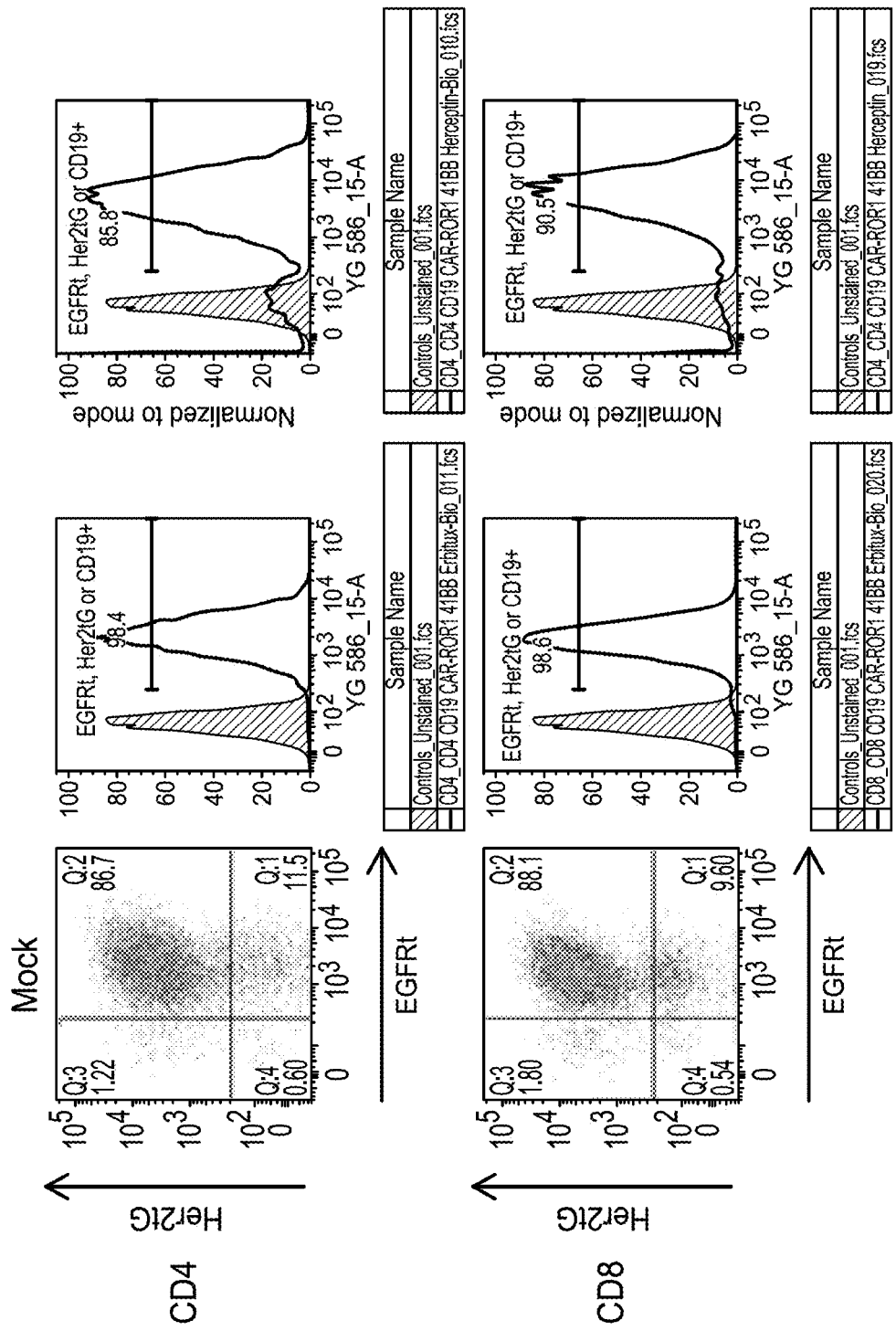
FIG. 11A shows that CD4 and CD8 T-cells can be transduced with two separate CAR-encoding lentiviral vectors and dual positive populations can be identified by associated markers. CD4 and CD8 purified T-cells were stimulated with CD3/CD28 beads and then individually or co-transduced with lentivirus encoding the $2^{nd}$ generation 41BB-t short spacer FMC63CD19CAR or/and the $2^{nd}$ generation 41BB-ζ short spacer ROR1CAR. The CD19CAR was followed by an in-frame T2A-Her2tG and the ROR1CAR by a T2A-EGFRt. Transduced T-cells were purified by EGFRt (ROR1CAR) and frozen. Flow analysis was performed on day 9 and demonstrates that transduced cells were purified to homogeneity based on EGFRt expression. For the CD4 T-cells there was ~86.7% Her2tG (CD19CAR) positivity and ~88.1% dual-positivity for the CD8 T-cells.

CD4 and CD8 T-Cells can be Transduced with Two Separate CAR-Encoding Lentiviral Vectors and Dual Positive Populations can be Identified by Associated Markers CD4 and CD8 purified T-cells were stimulated with CD3/CD28 beads and then individually or co-transduced with lentivirus encoding the $2^{nd}$ generation 41BB-t short spacer FMC63CD19CAR or/and the $2^{nd}$ generation 41BB-ζ short spacer ROR1CAR. The CD19CAR was followed by an in-frame T2A-Her2tG and the ROR1CAR by a T2A-EGFRt. Transduced T-cells were purified by EGFRt (ROR1CAR) and frozen. Flow analysis was performed on day 9 and demonstrates that transduced cells were purified to homogeneity based on EGFRt expression (See FIG. 11A). For the CD4 T-cells there was ~86.7% Her2tG (CD19CAR) positivity and ~88.1% dual-positivity for the CD8 T-cells.

Figure 11B:
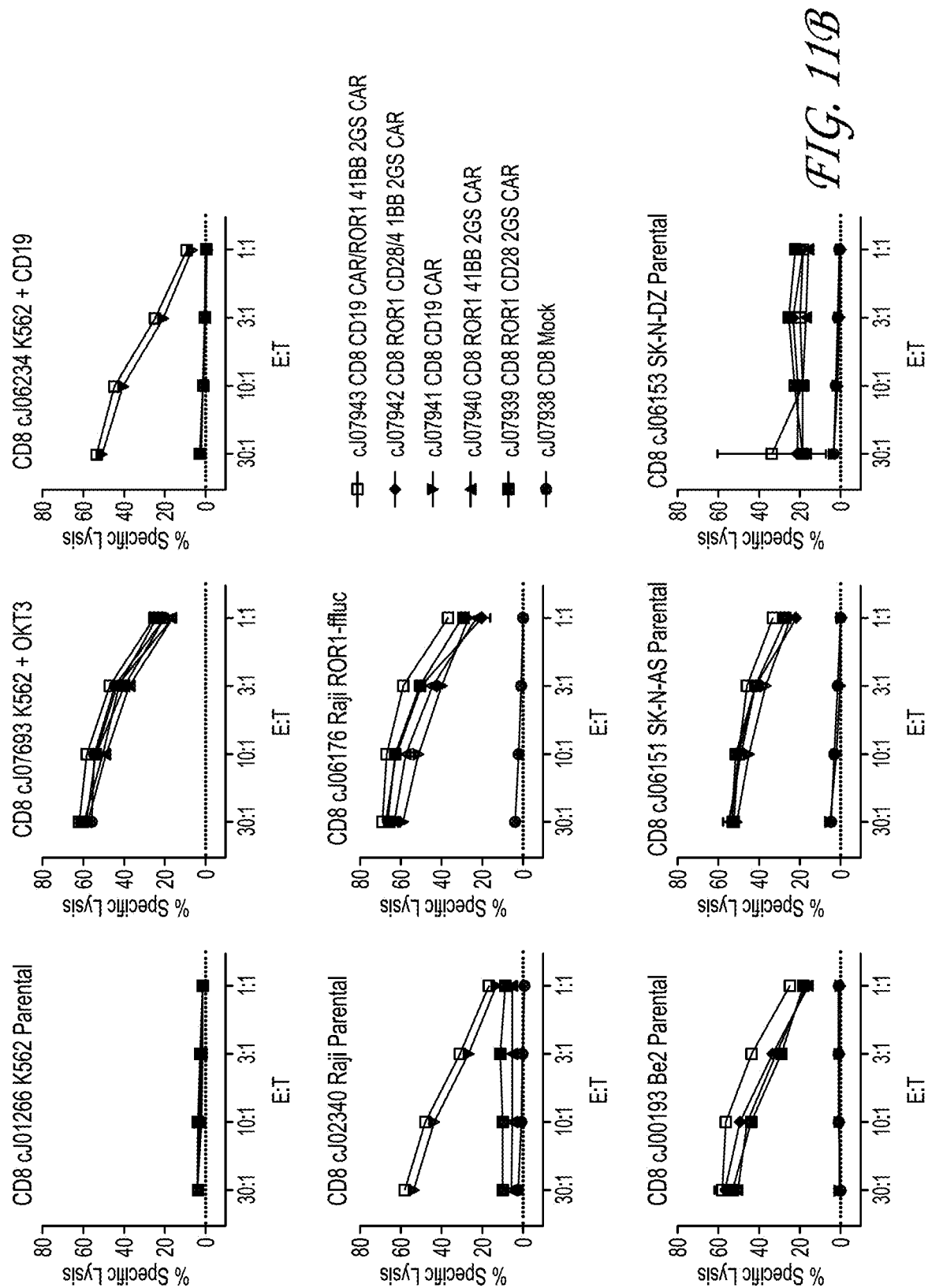
FIG. 11B shows that CD19 and ROR1CAR dual transduced CD8$^+$ T-cells demonstrate specific lysis against CD19 or ROR1 positive target cell lines. Mock (CAR), single transduced (CD19CAR or ROR1CAR) and dual transduced CD8$^+$ T-cells were co-cultured with target cell lines at different effector to target ratios for 4-hours. Single ROR1CAR T-cells contain either the $2^{nd}$ generation 41BB-ζ or CD28-ζ short spacer. K562 are negative for both targets CD19 and ROR1. K562-OKT3 was used as a positive control. Raji (CD19$^+$) were transduced to express ROR1. Be2, SK-N-AS and SK-N-DZ are ROR1 positive. Results demonstrate that the single transduced CD8$^+$ T-cells elicit specific lysis against their cognate antigen. However, the dual transduced T-cells efficiently recognized and lysed cells expressing CD19, ROR1 or both antigens (Raji ROR1). All CD8$^+$ T-cells were able to elicit similar levels of cell lysis against the K562-OKT3. These results indicate that T-cells can be successfully transduced with two separate CAR-encoding viruses, purified by a selection marker, and the resultant T-cell population is able to recognize multiple antigens.

CD19 and ROR1CAR Dual Transduced CD8+ T-Cells Demonstrate Specific Lysis Against CD19 or ROR1 Positive Target Cell Lines Mock (CAR−), single transduced (CD19CAR or ROR1CAR) and dual transduced CD8+ T-cells were co-cultured with target cell lines at different effector to target ratios for 4-hours. Single ROR1CAR T-cells contain either the $2^{nd}$ generation 41BB-ζ or CD28-t short spacer. K562 are negative for both targets CD19 and ROR1. K562-OKT3 was used as a positive control. Raji (CD19$^k$) were transduced to express ROR1. Be2, SK-N-AS and SK-N-DZ are ROR1 positive. Results demonstrate that the single transduced CD8+ T-cells elicit specific lysis against their cognate antigen. However, the dual transduced T-cells efficiently recognized and lysed cells expressing CD19, ROR1 or both antigens (Raji ROR1). All CD8+ T-cells were able to elicit similar levels of cell lysis against the K562-OKT3. These results indicate that T-cells can be successfully transduced with two separate CAR-encoding viruses, purified by a selection marker, and the resultant T-cell population is able to recognize multiple antigens (See FIG. 11B).

Figure 11C:
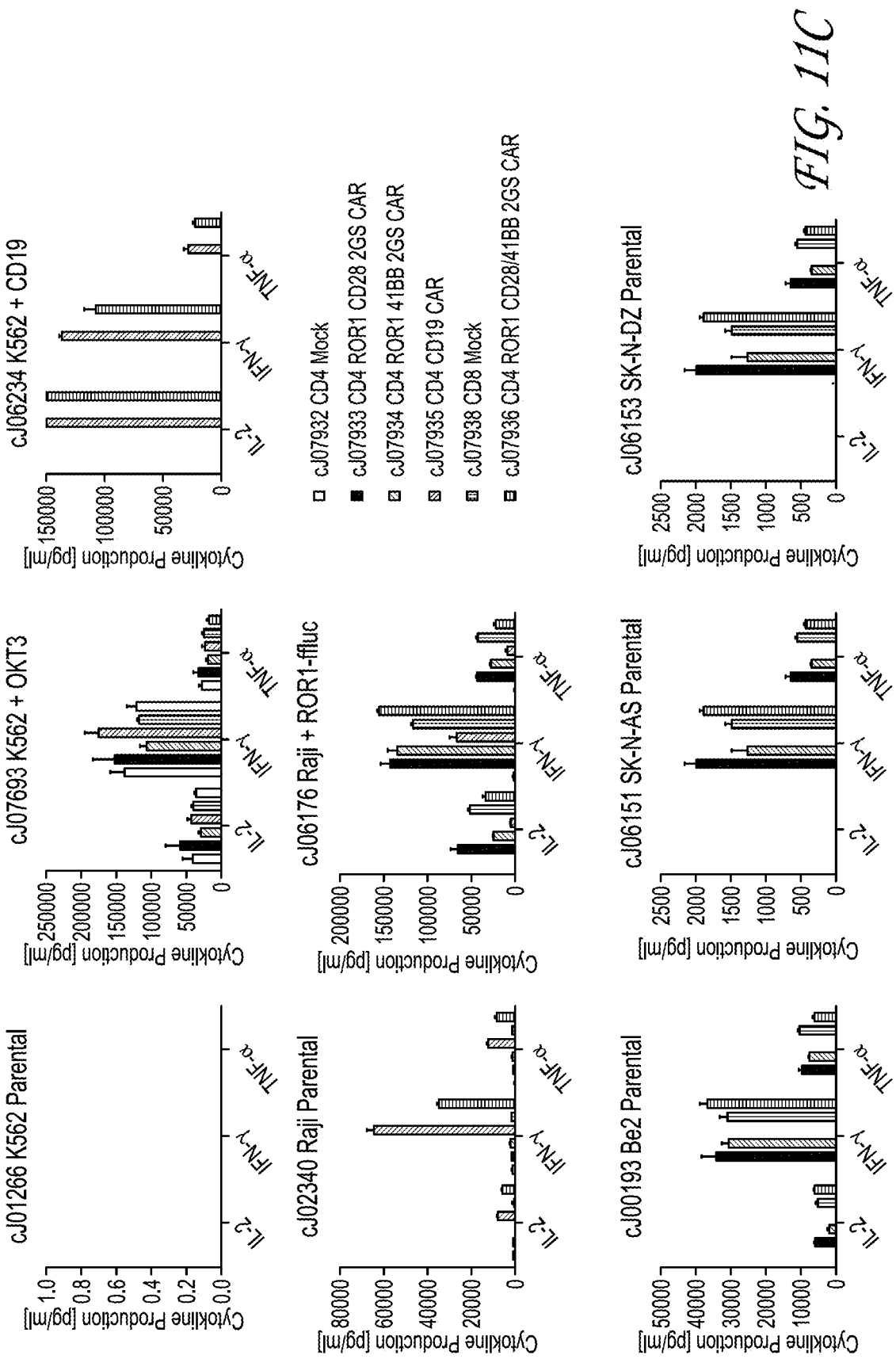
FIG. 11C shows that CD19- and ROR1CAR dual transduced T-cell populations produce cytokines against CD19 or ROR1 positive target cell lines. Mock (CAR), single transduced (CD19CAR or ROR1CAR) and dual transduced CD4$^+$ T-cells were co-cultured for 24 hours with target cell lines at a 2:1 effector-to-target ratio. Following the 24 hour incubation period, supernatant from the co-cultures was analyzed for the presence of IL-2, IFN-g, or TNF-a by Bioplex assay. Dual-transduced cells were able to release cytokine against all target expressing cell lines at similar levels to single CAR-expressing T-cells.

CD19- and ROR1CAR Dual Transduced T-Cell Populations Produce Cytokines Against CD19 or ROR1 Positive Target Cell Lines Mock (CAR−), single transduced (CD19CAR or ROR1CAR) and dual transduced CD4+ T-cells were cocultured for 24 hours with target cell lines at a 2:1 effector-to-target ratio. Following the 24 hour incubation period, supernatant from the co-cultures was analyzed for the presence of IL-2, IFN-gamma, or TNF-α by Bioplex assay. Dual-transduced cells were able to release cytokine against all target expressing cell lines at similar levels to single CAR-expressing T-cells (See FIG. 11C).

Figure 11D:
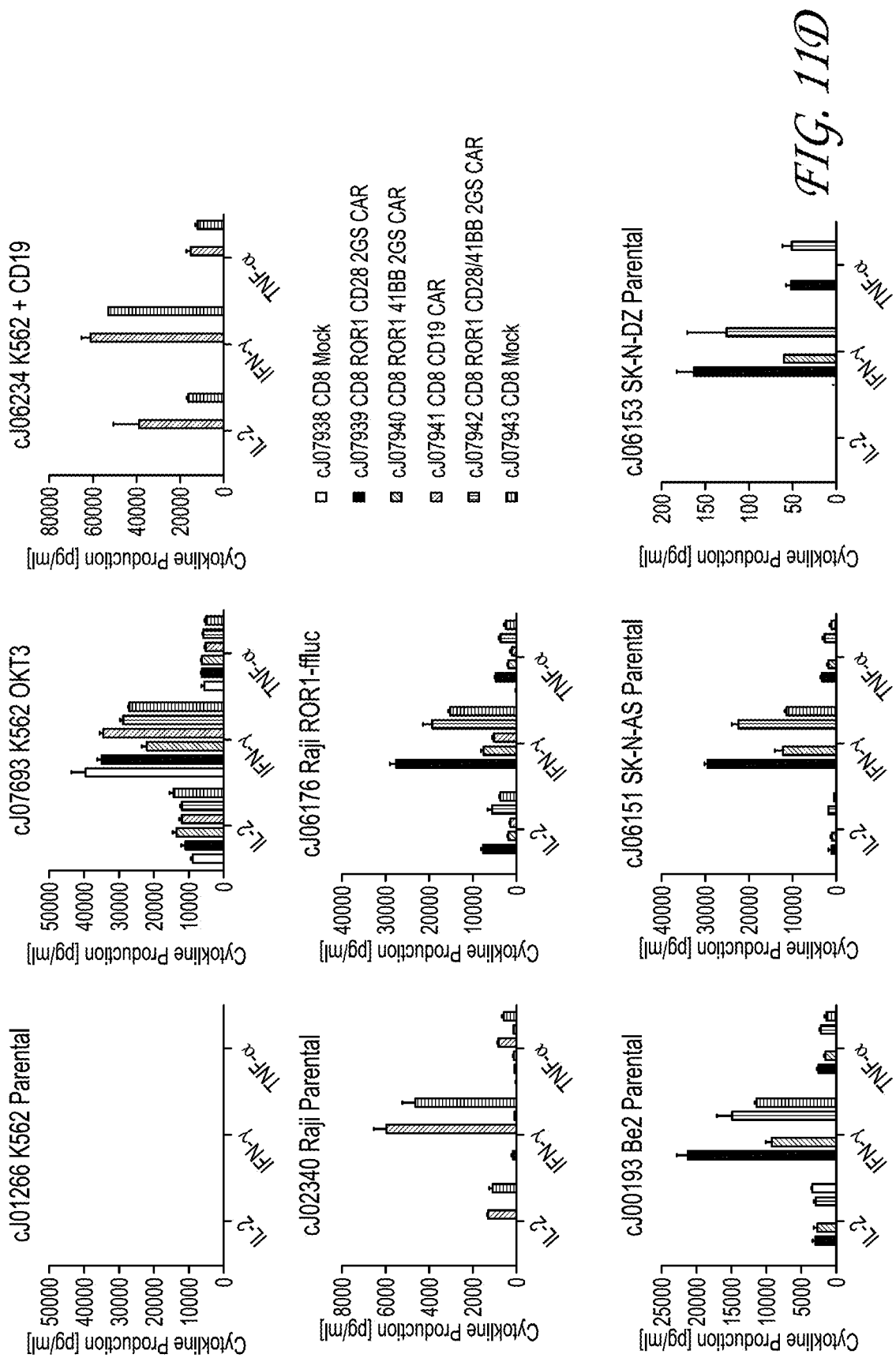
FIG. 11D shows that CD19- and ROR1CAR dual transduced T-cell populations produce cytokines against CD19 or ROR1 positive target cell lines. Mock (CAR), single transduced (CD19CAR or ROR1CAR) and dual transduced CD8$^+$ T-cells were co-cultured for 24 hours with target cell lines at a 2:1 effector-to-target ratio. Following the 24 hour incubation period, supernatant from the co-cultures was analyzed for the presence of IL-2, IFN-g, or TNF-a by Bioplex assay. Dual-transduced cells were able to release cytokine against all target expressing cell lines at similar levels to single CAR-expressing T-cells.
Figure 11E:
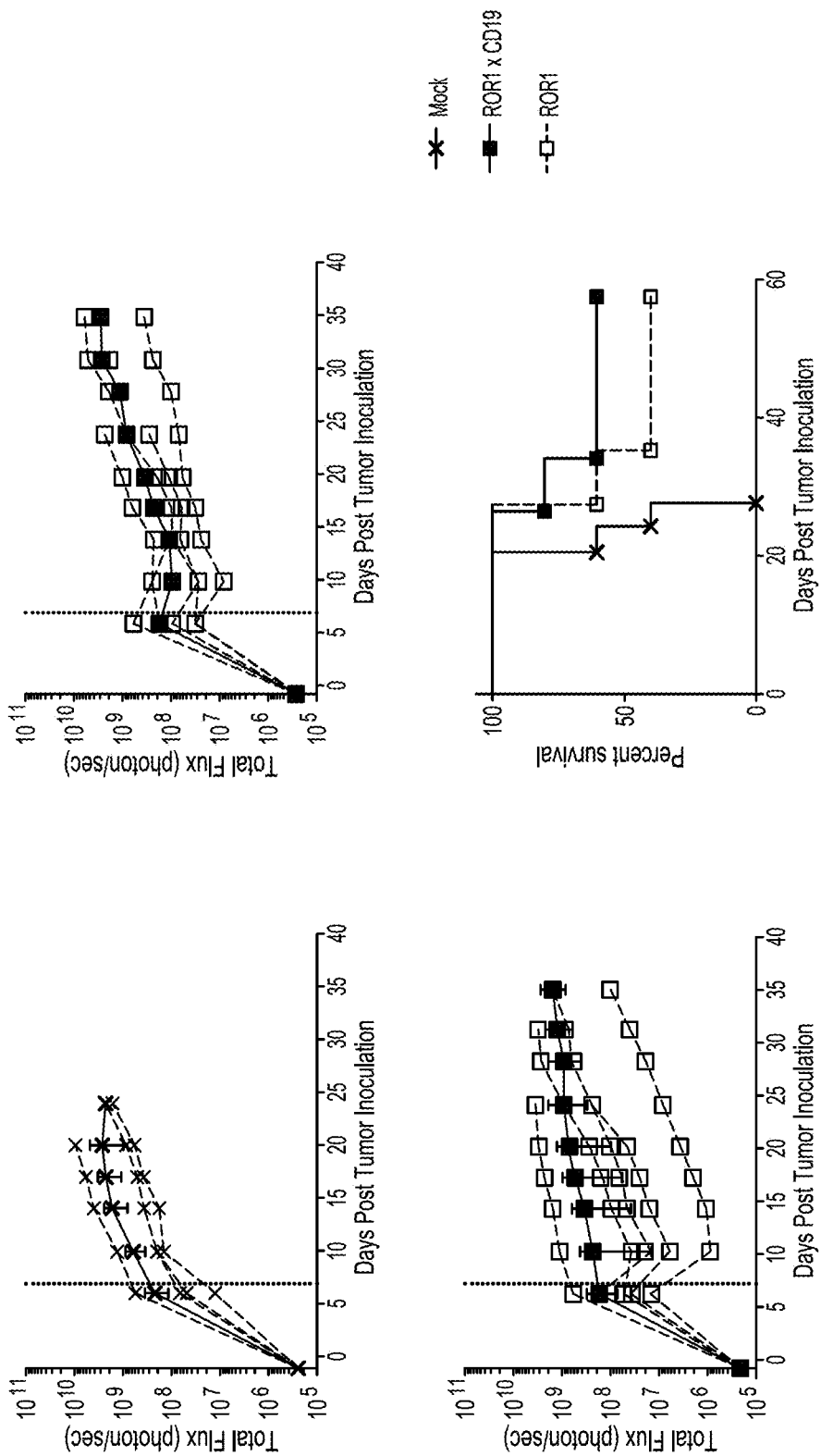
FIG. 11E shows that dual-transduced T-cells elicit anti-tumor activity in an intracranial xenograft tumor model. Cohorts of mice were inoculated with 0.2e6 Be2 that express GFP:ffluc (Day 0) and 2e6 dual transduced CD4:CD8 T-cells (1:1 ratio) (Day 7) intracranially (i.c.). Serial bioluminescence imaging of tumor in cohorts of mice treated with Mock (untransduced—left), ROR1CAR-expressing (middle-left) or dual-transduced CD4:CD8 CE7CAR T-cells (middle right). Kaplan-Meier analysis (right) of survival in treatment and control groups. Both the single ROR1CAR-expressing and dual-transduced cells were able to transiently regress tumor growth as evidenced by a short decrease in bioluminescence imaging. Both the single and dual transduced T-cells were able to significantly prolong survival. These results show that dual-transduced T-cells are able to treat tumor in vivo at levels similar to single ROR1CAR-expressing T-cells. There was therefore no inhibition in ROR1CAR activity for the dual-transduced T-cell population.

CD19- and ROR1CAR Dual Transduced T-Cell Populations Produce Cytokines Against CD19 or ROR1 Positive Target Cell Lines Mock (CAR−), single transduced (CD19CAR or ROR1CAR) and dual transduced CD4+ T-cells were cocultured for 24 hours with target cell lines at a 2:1 effector-to-target ratio. Following the 24 hour incubation period, supernatant from the co-cultures was analyzed for the presence of IL-2, IFN-gamma, or TNF-α by Bioplex assay. Dual-transduced cells were able to release cytokine against all target expressing cell lines at similar levels to single CAR-expressing T-cells (See FIG. 11D).

Dual-Transduced T-Cells Elicit Antitumor Activity in an Intracranial Xenograft Tumor Model Cohorts of mice were inoculated with 0.2e6 Be2 that express GFP:ffluc (Day 0) and 2e6 dual transduced CD4:CD8 T-cells (1:1 ratio) (Day 7) intracranially (i.c.). Serial bioluminescence imaging of tumor in cohorts of mice treated with Mock (untransduced—left), ROR1CAR-expressing (middle-left) or dual-transduced CD4:CD8 CE7CAR T-cells (middle right). Kaplan-Meier analysis (right) of survival in treatment and control groups. Both the single ROR1CAR-expressing and dual-transduced cells were able to transiently regress tumor growth as evidenced by a short decrease in bioluminescence imaging. However, mice succumbed to Be2 tumor outgrowth quickly thereafter. Both the single and dual transduced T-cells were able to significantly prolong survival. These results show that dual-transduced T-cells are able to treat tumor in vivo at levels similar to single ROR1CAR-expressing T-cells (See FIG. 11D). There was therefore no inhibition in ROR1CAR activity for the dual-transduced T-cell population.

More Alternatives

A Nucleic Acid Encoding a Chimeric Antigen Receptor Specific for a B Cell Specific Cell Surface Molecule In some alternatives, a nucleic acid encoding a chimeric antigen receptor is provided, wherein the nucleic acid comprises a first nucleic acid comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule, and wherein the first nucleic acid is covalently attached to a 5' end of the second nucleic acid, a third nucleic acid comprising a sequence encoding a de-immunized extracellular spacer, wherein the third nucleic acid is covalently attached to a 3' end of the second nucleic acid, a fourth nucleic acid comprising a sequence encoding a transmembrane domain, wherein the fourth nucleic acid is covalently attached to a 3' end of the third nucleic acid, a fifth nucleic acid comprising a sequence encoding a signaling domain, wherein the signaling domain comprises a 4-1BB domain and/or CD3-zeta domain, and wherein the fifth nucleic acid is covalently attached to a 3' end of the fourth nucleic acid, a sixth nucleic acid comprising a sequence encoding a linker, wherein the sixth nucleic acid is covalently attached to a 3' end of the fifth nucleic acid; and a seventh nucleic acid comprising a sequence encoding a marker domain, wherein the seventh nucleic acid is covalently attached to a 3' end of the sixth nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

A Nucleic Acid Encoding an Inducible Chimeric Antigen Receptor Specific for a B Cell Specific Cell Surface Molecule In some alternatives, a nucleic acid encoding a chimeric antigen receptor is provided wherein the nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule, and wherein the third nucleic acid is covalently attached to a 3' end of the second nucleic acid, a fourth nucleic acid comprising a sequence encoding a de-immunized extracellular spacer, wherein the fourth nucleic acid is covalently attached to a 3' end of the third nucleic acid, a fifth nucleic acid comprising a sequence encoding a transmembrane domain, wherein the fifth nucleic acid is covalently attached to a 3' end of the fourth nucleic acid, a sixth nucleic acid comprising a sequence encoding a signaling domain, wherein the signaling domain comprises a 4-1BB domain and/or CD3-zeta domain, and wherein the sixth nucleic acid is covalently attached to a 3' end of the fifth nucleic acid, a seventh nucleic acid comprising a sequence encoding a linker, wherein the seventh nucleic acid is covalently attached to a 3' end of the sixth nucleic acid and an eighth nucleic acid comprising a sequence encoding a marker domain, wherein the eighth nucleic acid is covalently attached to a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

A Nucleic Acid Encoding a Chimeric Antigen Receptor Specific for a Cell Surface Tumor Specific Molecule In some alternatives, a nucleic acid encoding a chimeric antigen receptor is provided wherein the nucleic acid comprises a first nucleic acid comprising a sequence encoding a leader sequence, a second nucleic acid comprising a sequence encoding an antibody or binding fragment thereof or scFv, wherein the antibody or binding fragment thereof or scFv is specific for a cell surface tumor specific molecule, and wherein the first nucleic acid is covalently attached at a 5' end of the second nucleic acid, a third nucleic acid comprising a sequence encoding a de-immunized extracellular spacer, wherein the third nucleic acid sequence is covalently attached at a 3' end of the second nucleic acid, a fourth nucleic acid comprising a sequence encoding a transmembrane domain, wherein the fourth nucleic acid is covalently attached at a 3' end of the third nucleic acid, a fifth nucleic acid comprising a sequence encoding a signaling domain sequence, wherein the signaling domain comprises a 4-1BB domain, CD3-zeta domain and/or CD28-zeta domain, and wherein the fifth nucleic acid is covalently attached at a 3' end of the fourth nucleic acid, a sixth nucleic acid comprising a sequence encoding a linker, wherein the sixth nucleic acid is covalently attached at a 3' end of the fifth nucleic acid and a seventh nucleic acid comprising a sequence encoding a marker domain, wherein the seventh nucleic acid is covalently attached at a 3' end of the sixth nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the sequence encoding the transmembrane domain further comprises an IRES sequence at the 3' end of the sequence encoding the transmembrane domain. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1 In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

A Nucleic Acid Encoding an Inducible Chimeric Antigen Receptor Specific for a Cell Surface Tumor Specific Molecule In some alternatives, a nucleic acid encoding a chimeric antigen receptor is provided, wherein the nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid sequence is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a 4-1BB domain, CD3-zeta domain and/or CD28-zeta domain, and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid, and an eighth nucleic acid comprising a sequence encoding a marker domain, wherein the eighth nucleic acid is covalently attached at a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1v the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

A Nucleic Acid Encoding a Bi-Specific Chimeric Antigen Receptor

In some alternatives, a nucleic acid encoding a bi-specific chimeric antigen receptor is provided, wherein the nucleic acid comprises a first nucleic acid sequence comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the first nucleic acid is covalently attached at a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid, and an eighth nucleic acid comprising a sequence encoding a marker domain, wherein the eighth nucleic acid is covalently attached at a 3' end of the seventh nucleic acid, thereby having said nucleic acid encoding a bi-specific chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

A Nucleic Acid Encoding an Inducible Bi-Specific Chimeric Antigen Receptor

In some alternatives, a nucleic acid encoding a bi-specific chimeric antigen receptor is provided, wherein the nucleic acid comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the fourth nucleic acid is covalently attached at a 3' end of the third nucleic acid, a fifth nucleic acid comprising a sequence encoding a de-immunized extracellular spacer, wherein the fifth nucleic acid is covalently attached at a 3' end of the fourth nucleic acid, a sixth nucleic acid comprising a sequence encoding a transmembrane domain, wherein the sixth nucleic acid is covalently attached at a 3' end of the fifth nucleic acid, a seventh nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the seventh nucleic acid is covalently attached at a 3' end of the sixth nucleic acid, an eighth nucleic acid comprising a sequence encoding a linker, wherein the eighth nucleic acid is covalently attached at a 3' end of the seventh nucleic acid, and a ninth nucleic acid comprising a sequence encoding a marker domain, wherein the ninth nucleic acid is covalently attached at a 3' end of the eighth nucleic acid, thereby having said nucleic acid encoding a bi-specific chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38.

A Vector for Expression of a Chimeric Antigen Receptor Specific for Promoting In Vivo Expansion and Activation of B Cells In some alternatives, a vector for expression of a chimeric antigen receptor specific for promoting in vivo expansion and activation of B cells is provided, wherein the vector comprises the nucleic acid of any one of the alternatives provided herein. In some alternatives, the nucleic acid encoding a chimeric antigen receptor comprises a first nucleic acid comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule, and wherein the first nucleic acid is covalently attached to a 5' end of the second nucleic acid, a third nucleic acid comprising a sequence encoding a de-immunized extracellular spacer, wherein the third nucleic acid is covalently attached to a 3' end of the second nucleic acid, a fourth nucleic acid comprising a sequence encoding a transmembrane domain, wherein the fourth nucleic acid is covalently attached to a 3' end of the third nucleic acid, a fifth nucleic acid comprising a sequence encoding a signaling domain, wherein the signaling domain comprises a 4-1BB domain and/or CD3-zeta domain, and wherein the fifth nucleic acid is covalently attached to a 3' end of the fourth nucleic acid, a sixth nucleic acid comprising a sequence encoding a linker, wherein the sixth nucleic acid is covalently attached to a 3' end of the fifth nucleic acid, and a seventh nucleic acid comprising a sequence encoding a marker domain, wherein the seventh nucleic acid is covalently attached to a 3' end of the sixth nucleic acid, thereby having said nucleic acid encoding a chimeric antigen receptor. In some alternatives, the nucleic acid encoding a chimeric antigen receptor comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule, and wherein the third nucleic acid is covalently attached to a 3' end of the second nucleic acid, a fourth nucleic acid comprising a sequence encoding a de-immunized extracellular spacer, wherein the fourth nucleic acid is covalently attached to a 3' end of the third nucleic acid, a fifth nucleic acid comprising a sequence encoding a transmembrane domain, wherein the fifth nucleic acid is covalently attached to a 3' end of the fourth nucleic acid, a sixth nucleic acid comprising a sequence encoding a signaling domain, wherein the signaling domain comprises a 4-1BB domain and/or CD3-zeta domain, and wherein the sixth nucleic acid is covalently attached to a 3' end of the fifth nucleic acid, a seventh nucleic acid comprising a sequence encoding a linker, wherein the seventh nucleic acid is covalently attached to a 3' end of the sixth nucleic acid and an eighth nucleic acid comprising a sequence encoding a marker domain, wherein the eighth nucleic acid is covalently attached to a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. In some alternatives, the vector is a viral vector. In some alternatives, the vector is a lentiviral vector, retroviral vector, gammaretroviral vectors or a foamy viral vector. In some alternatives, the vector is a transposon, integrase vector system, or an mRNA vector.

A Vector for the Expression of a Chimeric Antigen Receptor or TcR Specific for Targeting a Solid Tumor In some alternatives, a vector for expression of a chimeric antigen receptor or TcR specific for targeting a solid tumor is provided, wherein the vector comprises the nucleic acid of any one of alternatives provided herein. In some alternatives, the nucleic acid encoding a chimeric antigen receptor comprises a first nucleic acid comprising a sequence encoding a leader sequence, a second nucleic acid comprising a sequence encoding an antibody or binding fragment thereof or scFv, wherein the antibody or binding fragment thereof or scFv is specific for a cell surface tumor specific molecule, and wherein the first nucleic acid is covalently attached at a 5' end of the second nucleic acid, a third nucleic acid comprising a sequence encoding a de-immunized extracellular spacer, wherein the third nucleic acid sequence is covalently attached at a 3' end of the second nucleic acid, a fourth nucleic acid comprising a sequence encoding a transmembrane domain, wherein the fourth nucleic acid is covalently attached at a 3' end of the third nucleic acid, a fifth nucleic acid comprising a sequence encoding a signaling domain sequence, wherein the signaling domain comprises a 4-1BB domain, CD3-zeta domain and/or CD28-zeta domain, and wherein the fifth nucleic acid is covalently attached at a 3' end of the fourth nucleic acid, a sixth nucleic acid comprising a sequence encoding a linker, wherein the sixth nucleic acid is covalently attached at a 3' end of the fifth nucleic acid and a seventh nucleic acid comprising a sequence encoding a marker domain, wherein the seventh nucleic acid is covalently attached at a 3' end of the sixth nucleic acid, thereby having said nucleic acid encoding a chimeric antigen receptor. In some alternatives, the nucleic acid encoding a chimeric antigen receptor comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid sequence is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a 4-1BB domain, CD3-zeta domain and/or CD28-zeta domain, and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid and an eighth nucleic acid comprising a sequence encoding a marker domain, wherein the eighth nucleic acid is covalently attached at a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. In some alternatives, the vector is a viral vector. In some alternatives, the vector is a lentiviral vector, retroviral vector, gammaretroviral vectors or a foamy viral vector. In some alternatives, the vector is a transposon, integrase vector system, or an mRNA vector.

A Vector for the Expression of a Bi-Specific Chimeric Antigen Receptor

In some alternatives, a vector for expression of a bi-specific chimeric antigen receptor is provided, wherein the bi-specific chimeric antigen receptor is specific for a B cell specific cell surface molecule and is specific for a cell surface tumor specific molecule, the vector comprising the nucleic acid of any one of the alternatives provided herein. In some alternatives, the nucleic acid encoding a bi-specific chimeric antigen receptor comprises a first nucleic acid sequence comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the first nucleic acid is covalently attached at a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding a deimmunized extracellular spacer, wherein the fourth nucleic acid is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid, and an eighth nucleic acid comprising a sequence encoding a marker domain, wherein the eighth nucleic acid is covalently attached at a 3' end of the seventh nucleic acid, thereby having said nucleic acid encoding a bi-specific chimeric antigen receptor. In some alternatives, the nucleic acid encoding a bi-specific chimeric antigen receptor comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the fourth nucleic acid is covalently attached at a 3' end of the third nucleic acid, a fifth nucleic acid comprising a sequence encoding a de-immunized extracellular spacer, wherein the fifth nucleic acid is covalently attached at a 3' end of the fourth nucleic acid, a sixth nucleic acid comprising a sequence encoding a transmembrane domain, wherein the sixth nucleic acid is covalently attached at a 3' end of the fifth nucleic acid, a seventh nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the seventh nucleic acid is covalently attached at a 3' end of the sixth nucleic acid, an eighth nucleic acid comprising a sequence encoding a linker, wherein the eighth nucleic acid is covalently attached at a 3' end of the seventh nucleic acid, and a ninth nucleic acid comprising a sequence encoding a marker domain, wherein the ninth nucleic acid is covalently attached at a 3' end of the eighth nucleic acid, thereby having said nucleic acid encoding a bi-specific chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. In some alternatives, the vector is a viral vector. In some alternatives, the vector is a lentiviral vector, retroviral vector, gammaretroviral vectors or a foamy viral vector. In some alternatives, the vector is a transposon, integrase vector system, or an mRNA vector.

A Chimeric Antigen Receptor or TcR Specific for a B-Cell Specific Cell Surface Molecule In some alternatives, a chimeric antigen receptor or TcR specific for a B-cell specific cell surface molecule encoded by a nucleic acid or vector of any one of the alternatives is provided. In some alternatives, the vector is for expression of a chimeric antigen receptor specific for promoting in vivo expansion and activation of B cells, wherein the vector comprises the nucleic acid of any one of the alternatives provided herein. In some alternatives, the nucleic acid encoding a chimeric antigen receptor comprises a first nucleic acid comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule, and wherein the first nucleic acid is covalently attached to a 5' end of the second nucleic acid, a third nucleic acid comprising a sequence encoding a de-immunized extracellular spacer, wherein the third nucleic acid is covalently attached to a 3' end of the second nucleic acid, a fourth nucleic acid comprising a sequence encoding a transmembrane domain, wherein the fourth nucleic acid is covalently attached to a 3' end of the third nucleic acid, a fifth nucleic acid comprising a sequence encoding a signaling domain, wherein the signaling domain comprises a 4-1BB domain and/or CD3-zeta domain, and wherein the fifth nucleic acid is covalently attached to a 3' end of the fourth nucleic acid, a sixth nucleic acid comprising a sequence encoding a linker, wherein the sixth nucleic acid is covalently attached to a 3' end of the fifth nucleic acid, and a seventh nucleic acid comprising a sequence encoding a marker domain, wherein the seventh nucleic acid is covalently attached to a 3' end of the sixth nucleic acid, thereby having said nucleic acid encoding a chimeric antigen receptor. In some alternatives, the nucleic acid encoding a chimeric antigen receptor comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule, and wherein the third nucleic acid is covalently attached to a 3' end of the second nucleic acid, a fourth nucleic acid comprising a sequence encoding a de-immunized extracellular spacer, wherein the fourth nucleic acid is covalently attached to a 3' end of the third nucleic acid, a fifth nucleic acid comprising a sequence encoding a transmembrane domain, wherein the fifth nucleic acid is covalently attached to a 3' end of the fourth nucleic acid, a sixth nucleic acid comprising a sequence encoding a signaling domain, wherein the signaling domain comprises a 4-1BB domain and/or CD3-zeta domain, and wherein the sixth nucleic acid is covalently attached to a 3' end of the fifth nucleic acid, a seventh nucleic acid comprising a sequence encoding a linker, wherein the seventh nucleic acid is covalently attached to a 3' end of the sixth nucleic acid and an eighth nucleic acid comprising a sequence encoding a marker domain, wherein the eighth nucleic acid is covalently attached to a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. In some alternatives, the vector is a viral vector. In some alternatives, the vector is a lentiviral vector, retroviral vector, gammaretroviral vectors or a foamy viral vector. In some alternatives, the vector is a transposon, integrase vector system, or an mRNA vector.

A Chimeric Antigen Receptor or TcR Specific for a Cell Surface Tumor Specific Molecule In some alternatives, a chimeric antigen receptor or TcR specific for a cell surface tumor specific molecule encoded by a nucleic acid or vector of any one of the alternatives is provided. In some alternatives, the vector is for expression of a chimeric antigen receptor or TcR specific for targeting a solid tumor, wherein the vector comprises the nucleic acid of any one of alternatives provided herein. In some alternatives, the nucleic acid encoding a chimeric antigen receptor comprises a first nucleic acid comprising a sequence encoding a leader sequence, a second nucleic acid comprising a sequence encoding an antibody or binding fragment thereof or scFv, wherein the antibody or binding fragment thereof or scFv is specific for a cell surface tumor specific molecule, and wherein the first nucleic acid is covalently attached at a 5' end of the second nucleic acid, a third nucleic acid comprising a sequence encoding a de-immunized extracellular spacer, wherein the third nucleic acid sequence is covalently attached at a 3' end of the second nucleic acid, a fourth nucleic acid comprising a sequence encoding a transmembrane domain, wherein the fourth nucleic acid is covalently attached at a 3' end of the third nucleic acid, a fifth nucleic acid comprising a sequence encoding a signaling domain sequence, wherein the signaling domain comprises a 4-1BB domain, CD3-zeta domain and/or CD28-zeta domain, and wherein the fifth nucleic acid is covalently attached at a 3' end of the fourth nucleic acid, a sixth nucleic acid comprising a sequence encoding a linker, wherein the sixth nucleic acid is covalently attached at a 3' end of the fifth nucleic acid and a seventh nucleic acid comprising a sequence encoding a marker domain, wherein the seventh nucleic acid is covalently attached at a 3' end of the sixth nucleic acid, thereby having said nucleic acid encoding a chimeric antigen receptor. In some alternatives, the nucleic acid encoding a chimeric antigen receptor comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid sequence is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a 4-1BB domain, CD3-zeta domain and/or CD28-zeta domain, and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid and an eighth nucleic acid comprising a sequence encoding a marker domain, wherein the eighth nucleic acid is covalently attached at a 3' end of the seventh nucleic acid, thereby having said nucleic acid encoding a chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. In some alternatives, the vector is a viral vector. In some alternatives, the vector is a lentiviral vector, retroviral vector, gammaretroviral vectors or a foamy viral vector. In some alternatives, the vector is a transposon, integrase vector system, or an mRNA vector.

A Bi-Specific Chimeric Antigen Receptor Specific for a B Cell Specific Cell Surface Molecule and Specific for a Cell Surface Tumor Specific Molecule In some alternatives, a bi-specific chimeric antigen receptor specific for a B cell specific cell surface molecule and specific for a cell surface tumor specific molecule encoded by a nucleic acid or vector of any one of the alternatives is provided. In some alternatives, the bi-specific chimeric antigen receptor is specific for a B cell specific cell surface molecule and is specific for a cell surface tumor specific molecule, the vector comprising the nucleic acid of any one of the alternatives provided herein. In some alternatives, the nucleic acid encoding a bi-specific chimeric antigen receptor comprises a first nucleic acid sequence comprising a sequence encoding a leader sequence, a second nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the first nucleic acid is covalently attached at a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding a de-immunized extracellular spacer, wherein the fourth nucleic acid is covalently attached at a 3' end of the third nucleic acid, a fifth nucleic acid comprising a sequence encoding a transmembrane domain, wherein the fifth nucleic acid is covalently attached at a 3' end of the fourth nucleic acid, a sixth nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the sixth nucleic acid is covalently attached at a 3' end of the fifth nucleic acid, a seventh nucleic acid comprising a sequence encoding a linker, wherein the seventh nucleic acid is covalently attached at a 3' end of the sixth nucleic acid, and an eighth nucleic acid comprising a sequence encoding a marker domain, wherein the eighth nucleic acid is covalently attached at a 3' end of the seventh nucleic acid, thereby having said nucleic acid encoding a bi-specific chimeric antigen receptor. In some alternatives, the nucleic acid encoding a bi-specific chimeric antigen receptor comprises a first nucleic acid comprising a sequence encoding a leader sequence, a second nucleic acid comprising a sequence encoding a first promoter inducible by a drug, wherein the first nucleic acid is covalently attached to a 5' end of the second nucleic acid, a third nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the third nucleic acid is covalently attached at a 3' end of the second nucleic acid, a fourth nucleic acid comprising a sequence encoding an antibody or binding fragment thereof or scFv, wherein the antibody or binding fragment thereof or scFv is specific for a B cell specific cell surface molecule or is specific for a cell surface tumor specific molecule, and wherein the fourth nucleic acid is covalently attached at a 3' end of the third nucleic acid, a fifth nucleic acid comprising a sequence encoding a de-immunized extracellular spacer, wherein the fifth nucleic acid is covalently attached at a 3' end of the fourth nucleic acid, a sixth nucleic acid comprising a sequence encoding a transmembrane domain, wherein the sixth nucleic acid is covalently attached at a 3' end of the fifth nucleic acid, a seventh nucleic acid comprising a sequence encoding a signaling domain sequence, wherein the signaling domain comprises a co-stimulatory domain, wherein the co-stimulatory domain comprises a 4-1BB domain, CD3-zeta domain and/or CD28-zeta domain and wherein the seventh nucleic acid is covalently attached at a 3' end of the sixth nucleic acid, an eighth nucleic acid comprising a sequence encoding a linker, wherein the eighth nucleic acid is covalently attached at a 3' end of the seventh nucleic acid, and a ninth nucleic acid comprising a sequence encoding a marker domain, wherein the ninth nucleic acid is covalently attached at a 3' end of the eighth nucleic acid, thereby having said nucleic acid encoding a bi-specific chimeric antigen receptor. In some alternatives, the linker is a ribosome skip sequence or an IRES sequence. In some alternatives, the ribosome skip sequence is a P2A, T2A, E2A or F2A sequence. In some alternatives, the ribosome skip sequence is T2A. In some alternatives, the T2A sequence comprises an amino acid sequence set forth in SEQ ID NO: 33 and is encoded by a nucleic acid sequence set forth in SEQ ID NO: 34. In some alternatives, the linker further comprises an IRES sequence at the 5' end of the linker. In some alternatives, the first promoter is inducible by tamoxifen and/or its metabolites. In some alternatives, the first promoter is inducible by a drug. In some alternatives, the sequence encoding the transmembrane domain further comprises an IRES sequence at the 3' end of the sequence encoding the transmembrane domain. In some alternatives, the B-cell specific cell surface molecule is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the nucleic acid further comprises a polynucleotide encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the drug is a steroid, such as a ligand for the estrogen receptor. In some alternatives, the steroid is tamoxifen and/or its metabolites. In some alternatives, the cell surface tumor specific molecule is a cancer antigen. In some alternatives, the cell surface tumor specific molecule is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the spacer is an IgG4 hinge spacer. In some alternatives, the spacer comprises an amino acid sequence set forth in SEQ ID NO: 1 and is encoded by a nucleic acid sequence set forth in SEQ ID NO: 2. In some alternatives, the spacer comprises an amino acid sequence set forth in SEQ ID NO: 3 and is encoded by a nucleic acid sequence set forth in SEQ ID NO: 4. In some alternatives, the spacer comprises an amino acid sequence set forth in SEQ ID NO: 39 and is encoded by a nucleic acid sequence set forth in SEQ ID NO: 40. In some alternatives, the CD28-zeta domain comprises an amino acid sequence set forth in SEQ ID NO: 5 and is encoded by a nucleic acid sequence set forth in SEQ ID NO: 6. In some alternatives, the 4-1BB domain comprises an amino acid sequence set forth in SEQ ID NO: 7 and is encoded by a nucleic acid sequence set forth in SEQ ID NO: 8. In some alternatives, the CD3-zeta domain comprises an amino acid sequence set forth in SEQ ID NO: 9 and is encoded by a nucleic acid sequence set forth in SEQ ID NO: 10. In some alternatives, the antibody or binding fragment thereof or scFv specific for the B cell specific cell surface molecule is specific for CD19. In some alternatives, the antibody or binding fragment thereof or scFv specific for the B cell specific cell surface molecule comprises an amino sequence set forth in SEQ ID NO: 11 and is encoded by a nucleic acid sequence set forth in SEQ ID NO: 12. In some alternatives, the antibody or binding fragment thereof or scFv specific for the B cell specific cell surface molecule is specific for CD20. In some alternatives, the antibody or binding fragment thereof or scFv specific for the B cell specific cell surface molecule comprises an amino sequence set forth in SEQ ID NO: 13 and is encoded by a nucleic acid sequence set forth in SEQ ID NO: 14. In some alternatives, the antibody or binding fragment thereof or scFv specific for a cell surface tumor specific molecule is specific for L1CAM. In some alternatives, the antibody or binding fragment thereof or scFv specific for a cell surface tumor specific molecule is specific for a CE7 epitope on L1CAM. In some alternatives, the antibody or binding fragment thereof or scFv comprises an amino acid sequence set forth in SEQ ID NO: 15 and is encoded by a nucleic acid sequence set forth in SEQ ID NO: 16. In some alternatives, the antibody or binding fragment thereof or scFv specific for a cell surface tumor specific molecule is specific for ROR1. In some alternatives, the antibody or binding fragment thereof or scFv comprises an amino acid sequence set forth in SEQ ID NO: 17 and is encoded by a nucleic acid sequence set forth in SEQ ID NO: 18. In some alternatives, the antibody or binding fragment thereof or scFv specific for a cell surface tumor specific molecule is specific for EGFR 806. In some alternatives, the antibody or binding fragment thereof or scFv comprises an amino acid sequence set forth in SEQ ID NO: 19 and is encoded by a nucleic acid sequence set forth in SEQ ID NO: 20. In some alternatives, the antibody or binding fragment thereof or scFv specific for a cell surface tumor specific molecule is specific for Her2. In some alternatives, the antibody or binding fragment thereof or scFv comprises an amino acid sequence set forth in SEQ ID NO: 21 and is encoded by a nucleic acid sequence set forth in SEQ ID NO: 22. In some alternatives, the antibody or binding fragment thereof or scFv specific for a cell surface tumor specific molecule is specific for GD2. In some alternatives, the antibody or binding fragment thereof or scFv comprises an amino acid sequence set forth in SEQ ID NO: 23 and is encoded by a nucleic acid sequence set forth in SEQ ID NO: 24. In some alternatives, the antibody or binding fragment thereof or scFv specific for a cell surface tumor specific molecule is specific for EphA2 (2H4). In some alternatives, the antibody or binding fragment thereof or scFv comprises an amino acid sequence set forth in SEQ ID NO: 25 and is encoded by a nucleic acid sequence set forth in SEQ ID NO: 26. In some alternatives, the antibody or binding fragment thereof or scFv specific for a cell surface tumor specific molecule is specific for EphA2 (4H5). In some alternatives, the antibody or binding fragment thereof or scFv comprises an amino acid sequence set forth in SEQ ID NO: 27 and is encoded by a nucleic acid sequence set forth in SEQ ID NO: 28. In some alternatives, the leader sequence comprises a Granulocyte-macrophage colony-stimulating factor signal sequence. In some alternatives, the Granulocyte-macrophage colony-stimulating factor signal sequence comprises an amino acid sequence set forth in SEQ ID NO: 29 and is encoded by a nucleic acid sequence set forth in SEQ ID NO: 30. In some alternatives, the leader sequence comprises an amino acid sequence set forth in SEQ ID NO: 31 and is encoded by a nucleic acid sequence set forth in SEQ ID NO: 32. In some alternatives, the marker domain comprises Her2tG. In some alternatives, Her2tG comprises an amino acid sequence set forth in SEQ ID NO: 35 and is encoded by a nucleic acid sequence set forth in SEQ ID NO: 36. In some alternatives, the marker domain comprises EGFRt. In some alternatives, EGFRt comprises an amino acid sequence set forth in SEQ ID NO: 37 and is encoded by a nucleic acid sequence set forth in SEQ ID NO: 38. In some alternatives, the vector is a viral vector. In some alternatives, the vector is a lentiviral vector, retroviral vector, gammaretroviral vectors or a foamy viral vector. In some alternatives, the vector is a transposon, integrase vector system, or an mRNA vector.

A Cell Comprising a First and Second Chimeric Antigen Receptor or TcR

In some alternatives, a cell comprising a first and second chimeric antigen receptor or TcR is provided, wherein the first chimeric antigen receptor is specific for a ligand on a B cell, which promotes the in vivo expansion and activation of an effector cell and, wherein the second chimeric antigen receptor or TcR is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the first chimeric antigen receptor and/or the second chimeric antigen receptor or TcR are inducibly expressed in said cell. In some alternatives, expression of the first chimeric antigen receptor and/or the second chimeric antigen receptor or TcR is under the control of a regulatory element. In some alternatives, the first chimeric antigen receptor comprises an antibody or binding fragment thereof or scFv, a receptor ligand or mutant thereof, peptide, and/or polypeptide affinity molecule or binding partner. In some alternatives, the second chimeric antigen receptor or TcR comprises an antibody or binding fragment thereof or scFv, a receptor ligand or mutant thereof, peptide, and/or polypeptide affinity molecule or binding partner. In some alternatives, a first marker protein is co-expressed with the first chimeric antigen receptor and a second marker protein is co-expressed with the second chimeric antigen receptor or TcR. In some alternatives, the first marker protein co-expressed with the first chimeric antigen receptor is EGFRt and the second marker protein co-expressed with the second chimeric antigen receptor or TcR is Her2tg or first marker protein co-expressed with the first chimeric antigen receptor is Her2tg and the second marker protein co-expressed with the second chimeric antigen receptor or TcR is EGFRt. In some alternatives, the cell further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the cell expresses a soluble protein for therapy. In some alternatives, the soluble protein is a homeostatic cytokine, wherein the homeostatic cytokine is IL2, IL7, IL12 or IL15. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+ T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the first chimeric antigen receptor is specific for a ligand on a B cell, wherein the ligand on the B cell is CD19, and wherein the second chimeric antigen receptor is specific for L1CAM, and wherein the chimeric antigen receptors further comprises a 4-1 BB and CD3-zeta signaling domain. In some alternatives, the first chimeric antigen receptor is specific for a ligand on a B cell, wherein the ligand on the B cell is CD19, and wherein the second chimeric antigen receptor is specific for ROR1, and wherein the chimeric antigen receptors further comprises a 4-1 BB and CD3-zeta signaling domain.

A Cell Comprising a Bi-Specific Chimeric Antigen Receptor

In some alternatives, a cell comprising a bi-specific chimeric antigen receptor is provided, wherein the bi-specific chimeric antigen receptor comprises two binding domains, wherein a first binding domain is specific for a ligand on a B cell, which promotes the in vivo expansion and activation of the B cell and a second binding domain, wherein the second binding domain is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the first and second binding domain comprises an antibody or portion thereof, a receptor ligand or mutant thereof, peptide, and/or polypeptide affinity molecule or binding partner. In some alternatives, the cell further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the cell expresses a soluble protein for therapy. In some alternatives, the soluble protein is a homeostatic cytokine, wherein the homeostatic cytokine is IL2, IL7, IL12 or IL15. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the first binding domain is specific for a ligand on a B cell, wherein the ligand on the B cell is CD19, and wherein the second binding domain is specific for L1CAM. In some alternatives, the first binding domain is specific for a ligand on a B cell, wherein the ligand on the B cell is CD19, and wherein the second binding domain is specific for ROR1.

A Method of Making a Cell Having a Chimeric Antigen Receptor

In some alternatives, a method of making a cell having a chimeric antigen receptor is provided, wherein the method comprises introducing into a cell a first nucleic acid or a first vector comprising a polynucleotide sequence encoding a first chimeric antigen receptor that comprises a binding domain specific for a ligand on a B cell, which promotes the in vivo expansion and activation of the B cell, introducing into the cell a second nucleic acid or a second vector comprising a polynucleotide sequence encoding a second chimeric antigen receptor or TcR that comprises a binding domain specific for a ligand on a solid tumor, expanding the cell, and isolating the cell. In some alternatives, the first nucleic acid and the second nucleic acid reside on separate viral vectors. In some alternatives, the viral vectors are retroviral vectors, gammaretroviral vectors, foamy viral vector and/or lentiviral vectors. In some alternatives, the viral vectors are co-introduced into the cell as a composition comprising the viral vectors. In some alternatives, the vectors are a transposon, integrase vector system, and/or an mRNA vector. In some alternatives, expression of the first chimeric antigen receptor is linked to co-expression of EGFRt and expression of the second chimeric antigen receptor is linked to co-expression of Her2tg, or wherein expression of the first chimeric antigen receptor is linked to co-expression of Her2tg, and expression of the second chimeric antigen receptor is linked to co-expression of EGFRt. In some alternatives, the method further comprises introducing a vector comprising a sequence encoding a soluble protein into said cell. In some alternatives, the soluble protein is a homeostatic cytokine. In some alternatives, the homeostatic cytokine is IL2, IL7, IL12 or IL15. In some alternatives, the viral vectors further comprise a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the method further comprises introducing a vector comprising a sequence encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives of the method, the method further comprises stimulating the cells. In some alternatives, cells are stimulated with interleukin-2 (IL-2) for CD8 cells. In some alternatives, cells are stimulated with interleukin-7 (IL-7) for CD4 cells. In some alternatives cells are stimulated with anti-CD3/CD28 beads.

A Method of Making a Cell Having a Chimeric Antigen Receptor

In some alternatives, a method of making a cell having a chimeric antigen receptor is provided, wherein the method comprises co-delivering into a cell two vectors, wherein the first vector comprises a first nucleic acid sequence encoding a first chimeric antigen receptor that comprises a binding domain specific for a ligand on a B cell, which promotes the in vivo expansion and activation of the B cell, and a second vector wherein the second vector comprises a second polynucleotide sequence encoding a second chimeric antigen receptor or TcR that comprises a binding domain specific for a ligand on a solid tumor, expanding the cell and isolating the cell. In some alternatives, the vectors are plasmids and/or minicircle transposons. In some alternatives, the first nucleic acid and the second nucleic acid reside between a first inverted terminal repeat gene sequence and a second inverted terminal repeat gene sequence. In some alternatives, the inverted terminal repeat gene sequences are inverted repeats of a Sleeping Beauty transposon or Piggy-Bac transposons. In some alternatives, the method further comprises introducing a vector encoding the Sleeping Beauty transposase or PiggyBac transposase into the cell. In some alternatives of the method, the method further comprises stimulating the cells. In some alternatives, cells are stimulated with interleukin-2 (IL-2) for CD8 cells. In some alternatives, cells are stimulated with interleukin-7 (IL-7) for CD4 cells. In some alternatives cells are stimulated with anti-CD3/CD28 beads.

A Method of Making a Cell Having a Bi-Specific Chimeric Antigen Receptor

In some alternatives, a method of making a cell having a chimeric antigen receptor is provided, wherein the method comprises co-delivering into a cell two vectors, wherein the first vector comprises a first nucleic acid sequence encoding a first chimeric antigen receptor that comprises a binding domain specific for a ligand on a B cell, which promotes the in vivo expansion and activation of the B cell, and a second vector wherein the second vector comprises a second polynucleotide sequence encoding a second chimeric antigen receptor or TcR that comprises a binding domain specific for a ligand on a solid tumor, expanding the cell, and isolating the cell. In some alternatives, the vectors are plasmids and/or minicircle transposons. In some alternatives, the first nucleic acid and the second nucleic acid reside between a first inverted terminal repeat gene sequence and a second inverted terminal repeat gene sequence. In some alternatives, the inverted terminal repeat gene sequences are inverted repeats of a Sleeping Beauty transposon or Piggy-Bac transposons. In some alternatives, the method further comprises introducing a vector encoding the Sleeping Beauty transposase or PiggyBac transposase into the cell. In some alternatives of the method, the method further comprises stimulating the cells. In some alternatives, cells are stimulated with interleukin-2 (IL-2) for CD8 cells. In some alternatives, cells are stimulated with interleukin-7 (IL-7) for CD4 cells. In some alternatives cells are stimulated with anti-CD3/CD28 beads.

A Method of Making a Cell Having a Bi-Specific Chimeric Antigen Receptor

In some alternatives, a method of making a cell having a bi-specific chimeric antigen receptor is provided, wherein the method comprises introducing into a cell a nucleic acid comprising a polynucleotide sequence encoding a bi-specific chimeric antigen receptor that comprises a first binding domain specific for a ligand on a B cell, which promotes the in vivo expansion and activation of the B cell, and a second binding domain specific for a ligand on a solid tumor, expanding the cells and isolating the cells. In some alternatives, the polynucleotide resides on a viral vector. In some alternatives, the viral vector is a lentiviral, retroviral vector, foamy viral vector or a gammaretroviral vector. In some alternatives, the polynucleotide resides on a transposon, integrase vector system, and/or an mRNA vector. In some alternatives, the bi-specific chimeric antigen receptor is co-expressed with a marker protein. In some alternatives, the marker protein is EGFRt or Her2tg. In some alternatives, the method further comprises introducing a vector comprising a sequence encoding a soluble protein into said cell. In some alternatives, the soluble protein is a homeostatic cytokine. In some alternatives, the homeostatic cytokine is IL2, IL7, IL12 or IL15. In some alternatives, the viral vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the method further comprises introducing a vector comprising a sequence encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives of the method, the method further comprises stimulating the cells. In some alternatives, cells are stimulated with interleukin-2 (IL-2) for CD8 cells. In some alternatives, cells are stimulated with interleukin-7 (IL-7) for CD4 cells. In some alternatives cells are stimulated with anti-CD3/CD28 beads.

A Method of Making a Cell Having a Bi-Specific Chimeric Antigen Receptor

In some alternatives, a method of making a cell having a bi-specific chimeric antigen receptor is provided, wherein the method comprises introducing into a cell a vector, wherein the vector comprises a first nucleic acid encoding a bi-specific chimeric antigen receptor that comprises a first binding domain specific for a ligand on a B cell, which promotes the in vivo expansion and activation of the B cell, and a second binding domain wherein the second binding domain comprises a binding domain specific for a ligand on a solid tumor; expanding the cell and isolating the cell. In some alternatives, the vector is a plasmid or minicircle transposon. In some alternatives, the first nucleic acid resides between a first inverted terminal repeat gene sequence and a second inverted terminal repeat gene sequence. In some alternatives, the inverted terminal repeat gene sequences are inverted repeats of a Sleeping Beauty transposon or PiggyBac transposons. In some alternatives, the method further comprises introducing a vector encoding a Sleeping Beauty transposase or PiggyBac transposase into the cell. In some alternatives of the method, the method further comprises stimulating the cells. In some alternatives, cells are stimulated with interleukin-2 (IL-2) for CD8 cells. In some alternatives, cells are stimulated with interleukin-7 (IL-7) for CD4 cells. In some alternatives cells are stimulated with anti-CD3/CD28 beads.

Compositions

In some alternatives, a composition comprising any one or more of the cells of any one or more of the alternatives, is provided. In some alternatives, the cell comprises a first and second chimeric antigen receptor or TcR, wherein the first chimeric antigen receptor is specific for a ligand on a B cell, which promotes the in vivo expansion and activation of an effector cell and, wherein the second chimeric antigen receptor or TcR is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the first chimeric antigen receptor and/or the second chimeric antigen receptor or TcR are inducibly expressed in said cell. In some alternatives, expression of the first chimeric antigen receptor and/or the second chimeric antigen receptor or TcR is under the control of a regulatory element. In some alternatives, the first chimeric antigen receptor comprises an antibody or binding fragment thereof or scFv, a receptor ligand or mutant thereof, peptide, and/or polypeptide affinity molecule or binding partner. In some alternatives, the second chimeric antigen receptor or TcR comprises an antibody or binding fragment thereof or scFv, a receptor ligand or mutant thereof, peptide, and/or polypeptide affinity molecule or binding partner. In some alternatives, a first marker protein is co-expressed with the first chimeric antigen receptor and a second marker protein is co-expressed with the second chimeric antigen receptor or TcR. In some alternatives, the first marker protein co-expressed with the first chimeric antigen receptor is EGFRt and the second marker protein co-expressed with the second chimeric antigen receptor or TcR is Her2tg or first marker protein co-expressed with the first chimeric antigen receptor is Her2tg and the second marker protein co-expressed with the second chimeric antigen receptor or TcR is EGFRt. In some alternatives, the cell comprises a bi-specific chimeric antigen receptor, wherein the bi-specific chimeric antigen receptor comprises two binding domains, wherein a first binding domain is specific for a ligand on a B cell, which promotes the in vivo expansion and activation of the B cell and a second binding domain, wherein the second binding domain is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives, the cancer antigen is L1CAM. In some alternatives, the cancer antigen is ROR1. In some alternatives, the first and second binding domain comprises an antibody or portion thereof, a receptor ligand or mutant thereof, peptide, and/or polypeptide affinity molecule or binding partner. In some alternatives, the cell further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the cell expresses a soluble protein for therapy. In some alternatives, the soluble protein is a homeostatic cytokine, wherein the homeostatic cytokine is IL2, IL7, IL12 or IL15. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the first chimeric antigen receptor is specific for a ligand on a B cell, wherein the ligand on the B cell is CD19, and wherein the second chimeric antigen receptor is specific for L1CAM, and wherein the chimeric antigen receptors further comprises a 4-1 BB and CD3-zeta signaling domain. In some alternatives, the first chimeric antigen receptor is specific for a ligand on a B cell, wherein the ligand on the B cell is CD19, and wherein the second chimeric antigen receptor is specific for ROR1, and wherein the chimeric antigen receptors further comprises a 4-1 BB and CD3-zeta signaling domain. In some alternatives, the first binding domain is specific for a ligand on a B cell, wherein the ligand on the B cell is CD19, and wherein the second binding domain is specific for L1CAM. In some alternatives, the first binding domain is specific for a ligand on a B cell, wherein the ligand on the B cell is CD19, and wherein the second binding domain is specific for ROR1.

A Method of Treating, Ameliorating, or Inhibiting a Non-B Cell Related Disease in a Subject In some alternatives, a method of treating, ameliorating, or inhibiting a non-B cell related disease in a subject is provided, wherein the method comprises identifying a subject that does not have a B-cell related disease for therapy, introducing, providing, or administering any one or more of the cells of any one or more of the alternatives herein or the cells made by any one or more of the methods of any one or more of the alternatives herein or the composition of any one or more of the alternatives herein into a subject for therapy. In some alternatives, the composition comprises any one or more of the cells of any one or more of the alternatives herein or the cells made by any one or more of the methods of any one of the alternatives described herein. In some alternatives, the composition comprises CD8+ T cytotoxic lymphocyte cells and/or CD4+ T helper lymphocyte cells, wherein the CD8+ T cytotoxic lymphocyte cells are selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells and, wherein the CD4+T helper lymphocyte cells are selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the composition has a ratio of CD4+ T helper lymphocyte cells to CD8+ T lymphocytes of 1:10 to 10:1. In some alternatives, the ratio of CD4+ T helper lymphocyte cells to CD8+ T lymphocytes is 1:1. In some alternatives, the subject does not have a B-cell related disease. In some alternatives, the subject does not have B-cell lymphoma, Hodgkin's lymphomas, non-Hodgkins lymphomas, Diffuse large B cell lymphoma, Follicular lymphoma, marginal zone lymphoma, Mucosa-Associated Lymphatic Tissue lymphoma, small lymphocytic lymphoma, chronic lymphocytic leukemia, mantle cell lymphoma, Burkitt lymphoma, primary mediastinal (thymic) large B cell lymphoma, Lymphoplasmacytic lymphoma, Waldenstrom macroglobulinermia, Nodal marginal zone B cell lymphoa, splenic marginal zone lymphoma, intravascular large B cell lymphoma, Intravascular large B-cell lymphoma, Primary effusion lymphoma, Lymphomatoid granulomatosis, T cell/histiocyte-rich large B-cell lymphoma, Primary central nervous system lymphoma, Primary cutaneous diffuse large B-cell lymphoma (leg type), EBV positive diffuse large B-cell lymphoma of the elderly, Diffuse large B-cell lymphoma associated with inflammation, Intravascular large B-cell lymphoma, ALK-positive large B-cell lymphoma, ALK-positive large B-cell lymphoma, Plasmablastic lymphoma, Large B-cell lymphoma arising in HHV8-associated multicentric Castleman's disease, B-cell lymphoma, unclassifiable with features intermediate between diffuse large B-cell lymphoma and Burkitt lymphoma, B-cell lymphoma, unclassifiable with features intermediate between diffuse large B-cell lymphoma and classical Hodgkin lymphoma, or nodular lymphocyte predominant Hodgkin's lymphoma. In some alternatives, the disease is a cancer. In some alternatives, the disease is an infection, wherein the infection is a bacterial or viral infection. In some alternatives, the cancer is a solid tumor. In some alternatives, the solid tumor is selected from the group consisting of a breast cancer, brain cancer, lung cancer, liver cancer, stomach cancer, spleen cancer, colon cancer, renal cancer, pancreatic cancer, prostate cancer, uterine cancer, skin cancer, head cancer, neck cancer, sarcomas, neuroblastomas and ovarian cancer. In some alternatives, the subject has refractory and relapsed neuroblastoma. In some alternatives, the subject is identified or selected to receive a non-B cell related disease therapy, anti-cancer therapy, anti-infection therapy, antibacterial therapy, anti-viral therapy, or anti-tumoral therapy. In some alternatives, the method further comprises measuring or evaluating an inhibition of said non-B cell related disease, cancer, infection, bacterial infection, viral infection, or tumor. In some alternatives, the method further comprises introducing, providing, or administering to said subject an additional therapeutic agent, such as a chemotherapeutic agent, an antiviral agent, or an antibacterial agent or an adjunct therapy such as radiation therapy and/or surgery before, during, or after introducing, providing, or administering any one or more of the cells of any one of the alternatives described herein or the cells made by any one or more of the methods of any one of the alternatives described herein or the composition of any one of the alternatives described herein into the subject for therapy. In some alternatives, the composition comprises any one or more of the cells of any one of the alternatives described herein or the cells made by any one or more of the methods of any one of the alternatives described herein. In some alternatives, the composition comprises CD8+ T cytotoxic lymphocyte cells and/or CD4+ T helper lymphocyte cells, wherein the CD8+ T cytotoxic lymphocyte cells are selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells and, wherein the CD4+T helper lymphocyte cells are selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the composition has a ratio of CD4+ T helper lymphocyte cells to CD8+ T lymphocytes of 1:10 to 10:1. In some alternatives, the ratio of CD4+ T helper lymphocyte cells to CD8+ T lymphocytes is 1:1. In some alternatives, the composition comprises any one or more of the cells of any one or more of the alternatives. In some alternatives, the cell comprises a first and second chimeric antigen receptor or TcR, wherein the first chimeric antigen receptor is specific for a ligand on a B cell, which promotes the in vivo expansion and activation of an effector cell and, wherein the second chimeric antigen receptor or TcR is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives of the cell, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives of the cell, the cancer antigen is L1CAM. In some alternatives, the cancer antigen is ROR1. In some alternatives of the cell, the first chimeric antigen receptor and/or the second chimeric antigen receptor or TcR are inducibly expressed in said cell. In some alternatives of the cell, expression of the first chimeric antigen receptor and/or the second chimeric antigen receptor or TcR is under the control of a regulatory element. In some alternatives of the cell, the first chimeric antigen receptor comprises an antibody or binding fragment thereof or scFv, a receptor ligand or mutant thereof, peptide, and/or polypeptide affinity molecule or binding partner. In some alternatives of the cell, the second chimeric antigen receptor or TcR comprises an antibody or binding fragment thereof or scFv, a receptor ligand or mutant thereof, peptide, and/or polypeptide affinity molecule or binding partner. In some alternatives of the cell, a first marker protein is co-expressed with the first chimeric antigen receptor and a second marker protein is co-expressed with the second chimeric antigen receptor or TcR. In some alternatives, the first marker protein co-expressed with the first chimeric antigen receptor is EGFRt and the second marker protein co-expressed with the second chimeric antigen receptor or TcR is Her2tg or first marker protein co-expressed with the first chimeric antigen receptor is Her2tg and the second marker protein co-expressed with the second chimeric antigen receptor or TcR is EGFRt. In some alternatives of the cell, the cell comprises a bi-specific chimeric antigen receptor, wherein the bi-specific chimeric antigen receptor comprises two binding domains, wherein a first binding domain is specific for a ligand on a B cell, which promotes the in vivo expansion and activation of the B cell and a second binding domain, wherein the second binding domain is specific for a ligand on a tumor. In some alternatives, the ligand on a B cell is CD1d, CD5, CD19, CD20, CD21, CD22, CD23/Fc epsilon RII, CD24, CD25/IL-2 R alphaCD27/TNFRSF7, CD32, CD34, CD35, CD38, CD40 (TNFRSF5), CD44, CD45, CD45.1, CD45.2, CD54 (ICAM-1), CD69, CD72, CD79, CD80, CD84/SLAMF5, LFA-1, CALLA, BCMA, B-cell receptor (BCR), IgMs, IgD, B220/CD45R, C1q R1/CD93, CD84/SLAMF5, BAFF R/TNFRSF13C, B220/CD45R, B7-1/CD80, B7-2/CD86, TNFSF7, TNFRSF5, ENPP-1, HVEM/TNFRSF14, BLIMP1/PRDM1, CXCR4, DEP-1/CD148, or EMMPRIN/CD147. In some alternatives of the cell, the ligand on the tumor is a cancer antigen. In some alternatives, the cancer antigen is EGFR, HER2, Mesothelin, cancer testis antigens, L1CAM, o-acetylated GD2, GD2, neoantigens, Var2, glypican-2 (GPC2), HPV antigens, alphafetoprotein, carcinoembryonic antigen, CA-125, MUC-1, epithelial tumor antigen, abnormal products of ras or p53, EphA2, MAGE-A3, MAGE-A4, MAGE-C2, PRAME, SSX2, adipophilin, AIM2, ALDH1A1, BCLX, EpCAM, CS274, CPSF, cyclin D1, DKK1, ENAH, EpCAM, EphA3, EZH2, FGF5, glypican-3, G250, HLA-DOB, Hepsin, ID01, IGF2B3, IL13Ralpha2, Intestinal carboxylesterase, alpha-foetoprotein, kallikrein4, KIF20A, Lengsin, M-CSF, MCSP, mdm-2, Meloe, midkine, MMP-2, MMP-7, MUC1, MUC5AC, p53, PAX5, PBF, PRAME, PSMA, RAGE-1, RGS5, RhoC, RNF43, RUF43, FU2AS, secernin 1, SOX10, STEAP1, survivin, telomerase, TPBG, VEGF, WT1, NY-ESO-1 or ROR1. In some alternatives of the cell, the cancer antigen is L1CAM. In some alternatives, the cancer antigen is ROR1. In some alternatives, the first and second binding domain comprises an antibody or portion thereof, a receptor ligand or mutant thereof, peptide, and/or polypeptide affinity molecule or binding partner. In some alternatives, the cell further comprises a nucleic acid encoding a suicide gene system. In some alternatives of the cell, the suicide gene system is a Herpes Simplex Virus Thymidine Kinase (HSVTK)/Ganciclovir (GCV) suicide gene system or an inducible Caspase suicide gene system. In some alternatives, the cell expresses a soluble protein for therapy. In some alternatives of the cell, the soluble protein is a homeostatic cytokine, wherein the homeostatic cytokine is IL2, IL7, IL12 or IL15. In some alternatives, the cell is a CD8+ T cytotoxic lymphocyte cell selected from the group consisting of naïve CD8+ T-cells, CD8+ memory T-cells, central memory CD8+ T-cells, regulatory CD8+ T-cells, IPS derived CD8+ T-cells, effector memory CD8+ T-cells and bulk CD8+ T-cells. In some alternatives, the cell is a CD4+T helper lymphocyte cell that is selected from the group consisting of naïve CD4+ T-cells, CD4+ memory T-cells, central memory CD4+ T-cells, regulatory CD4+ T-cells, IPS derived CD4+ T-cells, effector memory CD4+ T-cells and bulk CD4+ T-cells. In some alternatives, the first chimeric antigen receptor is specific for a ligand on a B cell, wherein the ligand on the B cell is CD19, and wherein the second chimeric antigen receptor is specific for L1 CAM, and wherein the chimeric antigen receptors further comprises a 4-1 BB and CD3-zeta signaling domain. In some alternatives of the cell, the first chimeric antigen receptor is specific for a ligand on a B cell, wherein the ligand on the B cell is CD19, and wherein the second chimeric antigen receptor is specific for ROR1, and wherein the chimeric antigen receptors further comprises a 4-1 BB and CD3-zeta signaling domain. In some alternatives of the cell, the first binding domain is specific for a ligand on a B cell, wherein the ligand on the B cell is CD19, and wherein the second binding domain is specific for L1CAM. In some alternatives of the cell, the first binding domain is specific for a ligand on a B cell, wherein the ligand on the B cell is CD19, and wherein the second binding domain is specific for ROR1. In some alternatives, the method of making a cell having a chimeric antigen receptor comprises introducing into a cell a first nucleic acid or a first vector comprising a polynucleotide sequence encoding a first chimeric antigen receptor that comprises a binding domain specific for a ligand on a B cell, which promotes the in vivo expansion and activation of the B cell, introducing into the cell a second nucleic acid or a second vector comprising a polynucleotide sequence encoding a second chimeric antigen receptor or TcR that comprises a binding domain specific for a ligand on a solid tumor, expanding the cell, and isolating the cell. In some alternatives, the first nucleic acid and the second nucleic acid reside on separate viral vectors. In some alternatives, the viral vectors are retroviral vectors, gammaretroviral vectors, foamy viral vector and/or lentiviral vectors. In some alternatives, the viral vectors are co-introduced into the cell as a composition comprising the viral vectors. In some alternatives, the vectors are a transposon, integrase vector system, and/or an mRNA vector. In some alternatives, expression of the first chimeric antigen receptor is linked to co-expression of EGFRt and expression of the second chimeric antigen receptor is linked to co-expression of Her2tg, or wherein expression of the first chimeric antigen receptor is linked to co-expression of Her2tg, and expression of the second chimeric antigen receptor is linked to co-expression of EGFRt. In some alternatives, the method further comprises introducing a vector comprising a sequence encoding a soluble protein into said cell. In some alternatives, the soluble protein is a homeostatic cytokine. In some alternatives, the homeostatic cytokine is IL2, IL7, IL12 or IL15. In some alternatives, the viral vectors further comprise a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the method further comprises introducing a vector comprising a sequence encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives the method of making a cell having a chimeric antigen receptor comprises co-delivering into a cell two vectors, wherein the first vector comprises a first nucleic acid sequence encoding a first chimeric antigen receptor that comprises a binding domain specific for a ligand on a B cell, which promotes the in vivo expansion and activation of the B cell, and a second vector wherein the second vector comprises a second polynucleotide sequence encoding a second chimeric antigen receptor or TcR that comprises a binding domain specific for a ligand on a solid tumor, expanding the cell and isolating the cell. In some alternatives, the vectors are plasmids and/or minicircle transposons. In some alternatives, the first nucleic acid and the second nucleic acid reside between a first inverted terminal repeat gene sequence and a second inverted terminal repeat gene sequence. In some alternatives, the inverted terminal repeat gene sequences are inverted repeats of a Sleeping Beauty transposon or PiggyBac transposons. In some alternatives, the method further comprises introducing a vector encoding the Sleeping Beauty transposase or PiggyBac transposase into the cell. In some alternatives, the method of making a cell having a chimeric antigen receptor comprises co-delivering into a cell two vectors, wherein the first vector comprises a first nucleic acid sequence encoding a first chimeric antigen receptor that comprises a binding domain specific for a ligand on a B cell, which promotes the in vivo expansion and activation of the B cell, and a second vector wherein the second vector comprises a second polynucleotide sequence encoding a second chimeric antigen receptor or TcR that comprises a binding domain specific for a ligand on a solid tumor, expanding the cell, and isolating the cell. In some alternatives, the vectors are plasmids and/or minicircle transposons. In some alternatives, the first nucleic acid and the second nucleic acid reside between a first inverted terminal repeat gene sequence and a second inverted terminal repeat gene sequence. In some alternatives, the inverted terminal repeat gene sequences are inverted repeats of a Sleeping Beauty transposon or PiggyBac transposons. In some alternatives, the method further comprises introducing a vector encoding the Sleeping Beauty transposase or PiggyBac transposase into the cell. In some alternatives, the method of making a cell having a bi-specific chimeric antigen receptor comprises introducing into a cell a nucleic acid comprising a polynucleotide sequence encoding a bi-specific chimeric antigen receptor that comprises a first binding domain specific for a ligand on a B cell, which promotes the in vivo expansion and activation of the B cell, and a second binding domain specific for a ligand on a solid tumor, expanding the cells and isolating the cells. In some alternatives, the polynucleotide resides on a viral vector. In some alternatives, the viral vector is a lentiviral, retroviral vector, foamy viral vector or a gammaretroviral vector. In some alternatives, the polynucleotide resides on a transposon, integrase vector system, and/or an mRNA vector. In some alternatives, the bi-specific chimeric antigen receptor is co-expressed with a marker protein. In some alternatives, the marker protein is EGFRt or Her2tg. In some alternatives, the method further comprises introducing a vector comprising a sequence encoding a soluble protein into said cell. In some alternatives, the soluble protein is a homeostatic cytokine. In some alternatives, the homeostatic cytokine is IL2, IL7, IL12 or IL15. In some alternatives, the viral vector further comprises a nucleic acid encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the method further comprises introducing a vector comprising a sequence encoding a suicide gene system. In some alternatives, the suicide gene system is a Herpes Simplex Virus Thymidine Kinase (HSVTK)/Ganciclovir (GCV) suicide gene system or an inducible Caspase suicide gene system. In some alternatives, the method of making a cell having a bi-specific chimeric antigen receptor comprises introducing into a cell a vector, wherein the vector comprises a first nucleic acid encoding a bi-specific chimeric antigen receptor that comprises a first binding domain specific for a ligand on a B cell, which promotes the in vivo expansion and activation of the B cell, and a second binding domain wherein the second binding domain comprises a binding domain specific for a ligand on a solid tumor; expanding the cell and isolating the cell. In some alternatives, the vector is a plasmid or minicircle transposon. In some alternatives, the first nucleic acid resides between a first inverted terminal repeat gene sequence and a second inverted terminal repeat gene sequence. In some alternatives, the inverted terminal repeat gene sequences are inverted repeats of a Sleeping Beauty transposon or PiggyBac transposons. In some alternatives, the method further comprises introducing a vector encoding a Sleeping Beauty transposase or PiggyBac transposase into the cell.

What is claimed is:

1. A method of treating, ameliorating, or inhibiting a non-B cell cancer in a human subject, wherein the cancer comprises an EGFR+ cell, the method comprising administering to the subject a human T cell comprising:
    a first chimeric antigen receptor (CAR) capable of specifically binding to CD19, wherein the first CAR comprises a first ligand binding domain encoded by a sequence having at least 95% identity with the nucleotide sequence of SEQ ID NO: 12; and
    a second CAR capable of specifically binding to EGFR, wherein the second CAR comprises a second ligand binding domain encoded by a sequence having at least 95% identity with the nucleotide sequence of SEQ ID NO: 20, and wherein the first CAR is different from the second CAR and wherein the first CAR and second CAR each comprises an IgG4 hinge spacer domain, a CD28 transmembrane domain, an intracellular signaling domain, and a cell surface selectable marker.

2. The method of claim 1, wherein the first ligand binding domain comprises the amino acid sequence of SEQ ID NO:11.

3. The method of claim 1, wherein the second ligand binding domain comprises the amino acid sequence of SEQ ID NO:19.

4. The method of claim 1, wherein the first CAR and the second CAR each comprise an intracellular signalling domain comprising a 4-1BB domain and a CD3 zeta domain.

5. The method of claim 1, wherein the cell comprises a first polynucleotide encoding the first CAR and a first cell surface selectable marker.

6. The method of claim 5, wherein the cell comprises a second polynucleotide encoding the second CAR and a second cell surface selectable marker.

7. The method of claim 6, wherein the first or the second cell surface selectable marker is selected from a truncated HER2 (Her2tG) polypeptide or a truncated EGFR (EGFRt) polypeptide.

8. The method of claim 6, further comprising administering an antibody or antigen binding fragment thereof capable of binding to the first or the second cell surface selectable marker.

9. The method of claim 8, wherein the antibody or antigen binding fragment thereof is selected from cetuximab (ERBITUX) or trastuzumab (HERCEPTIN).

10. The method of claim 1, wherein the cell is a CD4+ T cell or a CD8+ T cell.

11. The method of claim 10, wherein the cell is a CD4+ helper T lymphocyte selected from the group consisting of a naïve CD4+ T cell, a central memory CD4+ T cell, an effector memory CD4+ T cell, and a bulk CD4+ T cell.

12. The method of claim 10, wherein the cell is a CD8+ cytotoxic T lymphocyte cell selected from the group consisting of a naïve CD8+ T cell, a central memory CD8+ T cell, an effector memory CD8+ T cell, and a bulk CD8+ T cell.

13. The method of claim 1, wherein the cell comprises a CD4+ T cell, and is administered in combination with a CD8+ T cell comprising the first CAR and the second CAR.

14. The method of claim 1, wherein the non-B cell cancer comprises a solid tumor.

15. The method of claim 1, wherein the non-B cell cancer is a breast cancer, a brain cancer, a lung cancer, a liver cancer, a stomach cancer, a spleen cancer, a colon cancer, a renal cancer, a pancreatic cancer, a prostate cancer, a uterine cancer, a skin cancer, a head cancer, a neck cancer, a sarcoma, an ovarian cancer, a neuroblastoma, a refractory neuroblastoma, or a relapsed neuroblastoma.

16. The method of claim 1, wherein the subject is a pediatric subject.

* * * * *